(12) United States Patent
Tiet et al.

(10) Patent No.: US 11,191,745 B2
(45) Date of Patent: Dec. 7, 2021

(54) SILICA NANOPARTICLE WITH AN INSOLUBLE DRUG

(71) Applicant: CITY OF HOPE, Duarte, CA (US)

(72) Inventors: Pamela Tiet, Pasadena, CA (US); Jacob Berlin, Monrovia, CA (US)

(73) Assignee: CITY OF HOPE, Duarte, CA (US)

( * ) Notice: Subject to any disclaimer, the term of this patent is extended or adjusted under 35 U.S.C. 154(b) by 0 days.

(21) Appl. No.: 16/483,212

(22) PCT Filed: Feb. 2, 2018

(86) PCT No.: PCT/US2018/016756
§ 371 (c)(1),
(2) Date: Aug. 2, 2019

(87) PCT Pub. No.: WO2018/144954
PCT Pub. Date: Aug. 9, 2018

(65) Prior Publication Data
US 2020/0316010 A1  Oct. 8, 2020

Related U.S. Application Data

(60) Provisional application No. 62/454,686, filed on Feb. 3, 2017.

(51) Int. Cl.
*A61K 31/337* (2006.01)
*A61K 9/14* (2006.01)
*A61K 47/24* (2006.01)

(52) U.S. Cl.
CPC .............. *A61K 31/337* (2013.01); *A61K 9/14* (2013.01); *A61K 47/24* (2013.01); *Y10S 977/773* (2013.01)

(58) Field of Classification Search
CPC .................................................. A61K 31/337
See application file for complete search history.

(56) References Cited

U.S. PATENT DOCUMENTS

| 6,682,761 B2 | 1/2004 | Pace et al. | |
| 2007/0259056 A1* | 11/2007 | Bowen | A61K 31/015 424/748 |
| 2010/0255103 A1 | 10/2010 | Liong et al. | |
| 2012/0045515 A1* | 2/2012 | Liu | A61K 9/5115 424/489 |
| 2012/0128777 A1 | 5/2012 | Keck et al. | |

(Continued)

FOREIGN PATENT DOCUMENTS

| WO | WO-2016/094991 A1 | 6/2016 | |
| WO | WO-2016094991 A * | 6/2016 | ............. A61K 47/30 |
| WO | WO-2017041032 A1 * | 3/2017 | ............. A61P 31/12 |

OTHER PUBLICATIONS

Google Translate. English Translation of WO2016094991A1. https://patents.google.com/patent/WO2016094991A1/en?oq=+WO+2016%2f094991+A1 accessed Nov. 25, 2020, originally published in Portuguese on Jun. 23, 2016, pp. 1-22. (Year: 2016).*

(Continued)

*Primary Examiner* — Isaac Shomer
(74) *Attorney, Agent, or Firm* — Mintz, Levin, Cohn, Ferris, Glovsky and Popeo, P.C.

(57) ABSTRACT

Disclosed herein, inter alia, are nanoparticle compositions (e.g., silica nanoparticles) including insoluble drug nanocrystals and methods of using the same for treating cancer.

18 Claims, 59 Drawing Sheets

(56) References Cited

U.S. PATENT DOCUMENTS

| | | | |
|---|---|---|---|
| 2013/0195963 A1* | 8/2013 | Serda | A61K 47/6923 424/450 |
| 2013/0287856 A1 | 10/2013 | Caprasse et al. | |
| 2014/0271884 A1 | 9/2014 | Prud'homme et al. | |
| 2014/0377175 A1 | 12/2014 | Berlin et al. | |
| 2015/0004095 A1* | 1/2015 | Finnie | A61K 9/1641 424/1.29 |
| 2015/0337006 A1 | 11/2015 | Barman et al. | |

OTHER PUBLICATIONS

Zhongdong Chen, Xiang Li, Haiyan He, Zhaohui Ren, Yong Liu, Juan Wang, Zhe Li, Ge Shen, Gaorong Han. "Mesoporous silica nanoparticles with manipulated microstructures for drug delivery." Colloids and Surfaces B: Biointerfaces 95 (2012), pp. 274-278. (Year: 2012).*

Jessica M. Rosenholm, Cecilia Sahlgren and Mika Linden. "Towards multifunctional, targeted drug delivery systems using mesoporous silica nanoparticles—opportunities & challenges." Nanoscale, vol. 2, 2010, pp. 1870-1883. (Year: 2010).*

Yang Liu, Leaf Huang, and Feng Liu. "Paclitaxel Nanocrystals for Overcoming Multidrug Resistance in Cancer." Molecular Pharmaceutics, vol. 7, No. 3, 2010, pp. 863-869. (Year: 2010).*

Yonghui Deng, Jing Wei, Zhenkun Sun and Dongyuan Zhao. "Large-pore ordered mesoporous materials templated from non-Pluronic amphiphilic block copolymers." Chemical Society Reviews, vol. 42, 2013, pp. 4054-4070. (Year: 2013).*

Zhijian Wu, Hong Xiang, Taehoon Kim, Myung-Suk Chun, Kangtaek Lee. "Surface properties of submicrometer silica spheres modified with aminopropyltriethoxysilane and phenyltriethoxysilane." Journal of Colloid and Interface Science, vol. 304 (2006), pp. 119-124. (Year: 2006).*

YP He, SQ Wang, CR Li, YM Miao, ZY Wu and BS Zou. "Synthesis and characterization of functionalized silica-coated $Fe_3O_4$ superparamagnetic nanocrystals for biological applications." Journal of Physics D: Applied Physics, vol. 38, 2005, pp. 1342-1350. (Year: 2005).*

Linlin Li et al. "Silica Nanorattle-Doxorubicin-Anchored Mesenchymal Stem Cells for Tumor-Tropic Therapy." ACS Nano, vol. 5, No. 9, 2011, pp. 7462-7470. (Year: 2011).*

Yi Lu, Yan Chen, Richard A Gemeinhart, Wei Wu & Tonglei Li. "Developing nanocrystals for cancer treatment." Nanomedicine (Lond.), 2015, Future Medicine Ltd., ISSN 1743-5889, 16 printed pages. (Year: 2015).*

International Search Report dated Mar. 28, 2018, for PCT Application No. PCT/US2018/016756, filed Feb. 2, 2018, 4 pages.

Rahman, I.A. et al. (Feb. 27, 2012). "Synthesis of Silica Nanoparticles by Sol-Gel: Size-Dependent Properties, Surface Modification, and Applications in Silica-Polymer Nanocomposites—A Review," *Journal of Nanomaterials* vol. 2021, 16 pages.

Wang, S. et al. (2011, e-published Dec. 20, 2011). "Aminopropyltriethoxysilane-mediated surface functionalization of hydroxyapatite nanoparticles: synthesis, characterization, and in vitro toxicity assay," *Int J Nanomedicine* 6:3449-3459.

Written Opinion dated Mar. 28, 2018, for PCT Application No. PCT/US2018/016756, filed Feb. 2, 2018, 6 pages.

* cited by examiner

PTX nanorods
- Zeta Potential: +43.60 mV

PTX nanorods with PEG
- Zeta Potential: +2.82 mV 6,500x magnification 30,000x magnification PTX with Cremophor+EtOH PTX nanocrystals stabilized with Pluronic F127

PTX silica nanorods

PEG-PTX silica nanorods

QA day 2 (Combined)

| Run | Mobility | Zeta Potential (mV) | Rel. Residual |
|---|---|---|---|
| 1 | 2.88 | 36.84 | 0.0125 |
| 2 | 3.08 | 39.38 | 0.0120 |
| 3 | 3.04 | 38.85 | 0.0120 |
| 4 | 3.06 | 39.16 | 0.0152 |
| 5 | 3.11 | 39.77 | 0.0094 |
| 6 | 3.22 | 41.25 | 0.0085 |
| 7 | 3.23 | 41.32 | 0.0229 |
| 8 | 3.23 | 41.36 | 0.0191 |
| 9 | 3.07 | 39.33 | 0.0149 |
| 10 | 3.12 | 39.07 | 0.0164 |
| Mean | 3.10 | 39.72 | 0.0143 |
| Std. Error | 0.03 | 0.44 | 0.0014 |
| Combined | 3.10 | 39.73 | 0.0069 |

| Group | Treatment |
|---|---|
| A | Abraxane |
| B | MSN.Paclitaxel |
| C | NP.Paclitaxel (Nanorods) |
| D | Paclitaxel Nanocrystal (F127) |
| E | Sham – No Treatment |

| Group | Treatment |
|---|---|
| A | Abraxane |
| B | MSN.Paclitaxel |
| C | NP.Paclitaxel (Nanorods) |
| D | Paclitaxel Nanocrystal (F127) |
| E | Sham – No Treatment |

$$\frac{m_{silica}}{m_{PTX}} = \frac{\rho_{silica} * V_{silica}}{\rho_{PTX} * V_{PTX}}$$

$$= \frac{\rho_{silica} * \pi * (R_1 * R_1 - R_2 * R_2) * L}{\rho_{PTX} * \pi * R_2 * R_2 * L}$$

$$= \frac{\rho_{silica} * (R_1 * R_1 - R_2 * R_2)}{\rho_{PTX} * R_2 * R_2}$$

SILICA NANOPARTICLE WITH AN INSOLUBLE DRUG

CROSS-REFERENCES TO RELATED APPLICATIONS

This application is the national stage filing under U.S.C. 371 of International Application No. PCT/US18/16756, filed Feb. 2, 2018, which claims priority to U.S. Provisional Application No. 62/454,686, filed Feb. 3, 2017, which are hereby incorporated by reference in their entirety and for all purposes.

STATEMENT AS TO RIGHTS TO INVENTIONS MADE UNDER FEDERALLY SPONSORED RESEARCH AND DEVELOPMENT

This invention was made with government support under grant number R01 CA97359 awarded by the National Institutes of Health. The government has certain rights in the invention.

BACKGROUND

Many drug candidates, such as paclitaxel, have emerged from drug discovery programs and have low solubility in water, which leads to poor bioavailability and efficacy in vivo. Nanosuspensions of insoluble drugs stabilized by surfactants, have received interest since they are formulated from pure crystalline drug and do not require the use of potentially harmful excipients. However, these nanosuspensions formulated with surfactants provide temporary stabilization, ultimately resulting in fusion and aggregation of nanocrystals over time. Disclosed herein, inter alia, are solutions to these and other problems in the art.

SUMMARY

In an aspect is provided a nanoparticle obtainable by a process including (a) mixing an insoluble drug and an amphiphilic polymer in an organic solvent; (b) removing the organic solvent, adding a solvent (e.g., water or aqueous solution), and sonicating the mixture to form a nanocrystal; and (c) mixing tetraethyl orthosilicate (TEOS), phenyltrimethoxysilane (PTMS), and hydrolyzed aminopropyltriethoxy silane (APTES) with the nanocrystal to form a nanoparticle.

In an aspect is provided a nanoparticle including an insoluble drug and silica, wherein the nanoparticle includes the insoluble drug. In embodiments, the nanoparticle includes at least about 1 wt % of the insoluble drug.

In an aspect is provided a nanoparticle including an insoluble drug, silica, and a polymer. In embodiments, the polymer is a poloxamer.

In an aspect is a cell including the nanoparticle (e.g., a nanoparticle including an insoluble drug) as described herein, including embodiments.

In an aspect is provided a nanoparticle-cell construct including a monovalent nanoparticle as described herein, including embodiments, covalently attached to a protein (e.g., a cell-surface protein) through a covalent linker.

In an aspect is provided a method of treating cancer in a patient in need of such treatment, the method including administering to a subject in need thereof a therapeutically effective amount of the nanoparticle, the cell, or the nanoparticle-cell construct, as described herein.

In an aspect is provided a nanoparticle including an insoluble drug nanocrystal, wherein the insoluble drug nanocrystal is enclosed within a silica layer.

BRIEF DESCRIPTION OF THE DRAWINGS

(FIG. 3A) PTX and Pluronic F127 are first solubilized in chloroform. The organic solvent is then evaporated under a stream of N2 and placed into a vacuum dessicator for an hour to remove residual chloroform. (FIG. 3B) Water is then added to the scintillation vial and the mixture undergoes sonication.

FIG. 11A: Empty silica nanoparticles were formed using TEOS, PTMS, and APTES. By DLS, they have a hydrodynamic diameter of 45 nm and a zeta potential of +15.07 mV. FIG. 11B: OVCAR-8 cells were treated with empty silica nanoparticles to determine toxicity after 24, 48, and 72 hours. Cell viability, measured by MTS, remained high even after 72 hours.

FIG. 21B) 15000×; FIG. 21C) Cumulative release of PTX from nanorod in DMEM medium with 10% FBS.

FIG. 23A) Correlation of PTX loading into NSCs with increasing concentration of PTX nanorod incubated with NSCs; FIG. 23B) NSC viability 24 hours after PTX nanorod loading; FIG. 23C) NSC uptake of rhodamine labeled PTX nanorod immediately after loading, phalloidin 488 labeled F-actin, rhodamine labeled nanorod, nuclei, merged image, scale bar 25 µm; FIG. 23D) NSC uptake of rhodamine labeled PTX nanorod 4 hours after loading, phalloidin 488 labeled F-actin, rhodamine labeled nanorod, nuclei, merged image, scale bar 25 µm; FIG. 23E) Cumulative release of PTX from NSC/nanorod hybrids.

FIG. 24A) NSCs migration after incubation with PTX-F127, Abraxane and PTX nanorod by Boyden chamber assay; FIG. 24B) OVCAR-8 viability after coculture with different ratios of NSC/nanorod by luciferase luminescent assay.

FIG. 25B) 1:2; FIG. 25C) 1:5 and d) 1:10 with negative staining by uranyl acetate, scale bar 0.5 µm.

FIG. 27C) size, FIG. 27D) zeta potential of PTX nanorod after storing at room temperature for one day.

FIG. 28A) TEM image of empty silica nanoparticles; FIG. 28B) Cytotoxicity of empty silica particles and equivalent PTX concentration for PTX nanorod with same amount of silica content.

FIG. 29A) Paclitaxel (PTX) loaded into mesoporous silica nanoparticles (MSN). The loaded MSNs were subsequently coated with a thin silica layer. FIG. 29B) Paclitaxel (PTX) nanorods.

FIG. 32A) Schematic of experimental procedure. FIG. 32B) Plot showing PTX release as a function of time.

FIG. 33A) Cell viability on Day 1 following treatment with F127-PTX (e.g., PTX nanocrystals) or 0.5× (PTX nanorods) at varying concentrations. FIG. 33B) Cell viability on Day 3 of treatment with F127-PTX (e.g., PTX nanocrystals) or 0.5× (PTX nanorods) at varying concentrations. FIG. 33C) Cell viability on Day 1 following treatment with Abraxane or MSN at varying concentrations. FIG. 33D) Cell viability on Day 3 following treatment with Abraxane or MSN at varying concentrations.

FIG. 34A) Neural stem cell (NSC) loading strategy. FIG. 34B) NSC viability at 24 hrs after loading with indicated composition. FIG. 34C) NSC migration after loading in Boyden chamber assay.

FIG. 35A) Normalized luminescent intensity following treatment with NSC loaded with PTX nanorod or NSC loaded with F127-PTX (e.g., PTX nanocrystals) at different NSC to Ovcar-8 ratios. FIG. 35B) Normalized luminescent intensity following treatment with NSC loaded with MSN or NSC loaded with Abraxane at different NSC to Ovcar-8 ratios.

FIG. 37A.) PTX weight calculated overtime from the cell pellet. FIG. 37B.) Total number of NSCs over time. FIG. 37C.) PTX weight normalized to 1 million (1M) NSCs over time. FIG. 37D.) PTX weight in supernatant over time.

FIG. 38A.) PTX weight calculated overtime in from the cell pellet. FIG. 38B.) Total number of NSCs over time. FIG. 38C.) PTX weight normalized to 1 million (1M) NSCs over time. FIG. 38D.) PTX weight in supernatant over time.

FIG. 39. Design of initial in vivo study at high dose. Treatment groups are as shown.

DETAILED DESCRIPTION

I. Definitions

Figure 1:
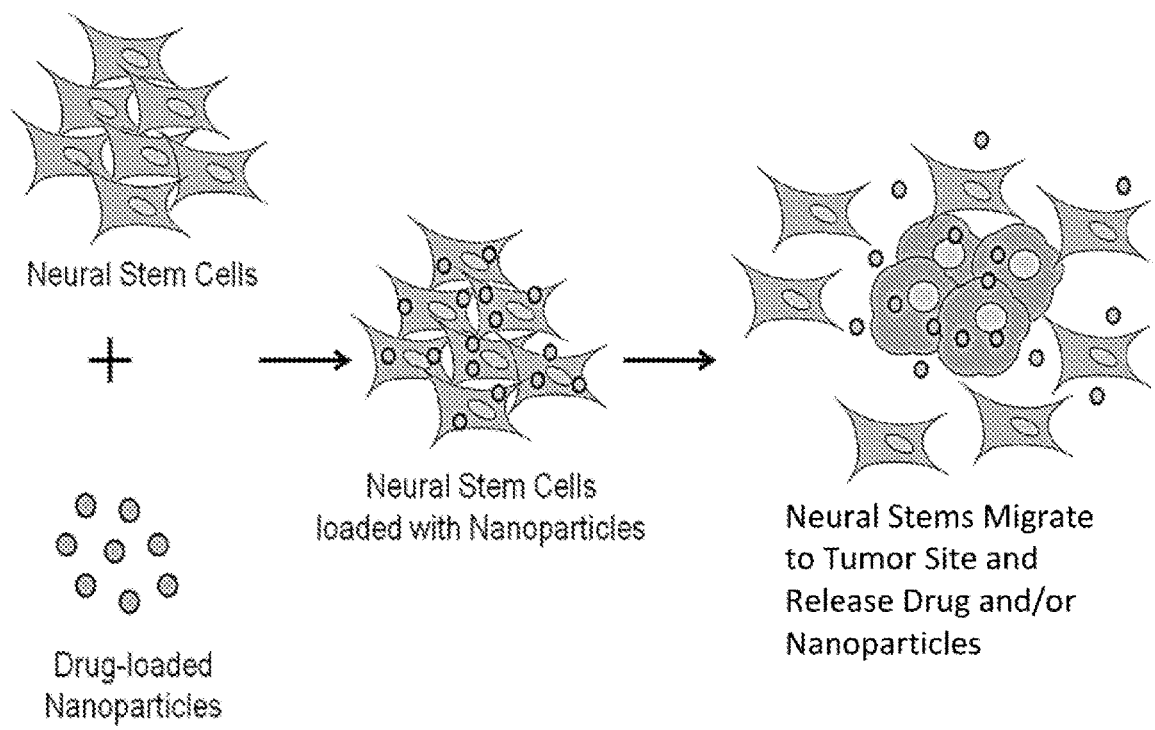
FIG. 1. Schematic for Neural Stem Cell targeted delivery. Neural stem cells will be initially loaded with drug-loaded nanoparticles. The delayed release in drug allows the Neural stem cells to migrate towards the site of the tumor. Once there, drug is released by the nanoparticle-loaded neural stem cells.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals. The alkyl may include a designated number of carbons (e.g., C$_1$-C$_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., N, S, Si, or P) may be placed at any interior position of the heteroalkyl group or at the position at which the alkyl group is attached to the remainder of the molecule. Heteroalkyl is an uncyclized chain. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH═CHO—CH$_3$, —Si(CH$_3$)$_3$, —CH$_2$—CH═N—OCH$_3$, —CH═CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

In embodiments, the term "cycloalkyl" means a monocyclic, bicyclic, or a multicyclic cycloalkyl ring system. In embodiments, monocyclic ring systems are cyclic hydrocarbon groups containing from 3 to 8 carbon atoms, where such groups can be saturated or unsaturated, but not aromatic. In embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. In embodiments, bridged monocyclic rings contain a monocyclic cycloalkyl ring where two non adjacent carbon atoms of the monocyclic ring are linked by an alkylene bridge of between one and three additional carbon atoms (i.e., a bridging group of the form (CH$_2$)$_w$, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2] nonane, bicyclo[3.3.1]nonane, and bicyclo[4.2.1]nonane. In embodiments, fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkyl is attached to the parent molecular moiety through any carbon atom contained within the monocyclic cycloalkyl ring. In embodiments, cycloalkyl groups are optionally substituted with one or two groups which are independently oxo or thia. In embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkyl is attached to the parent molecular moiety through any carbon atom contained within the base ring. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic cycloalkyl groups include, but are not limited to tetradecahydrophenanthrenyl, perhydrophenothiazin-1-yl, and perhydrophenoxazin-1-yl.

In embodiments, a cycloalkyl is a cycloalkenyl. The term "cycloalkenyl" is used in accordance with its plain ordinary meaning. In embodiments, a cycloalkenyl is a monocyclic, bicyclic, or a multicyclic cycloalkenyl ring system. In embodiments, monocyclic cycloalkenyl ring systems are cyclic hydrocarbon groups containing from 3 to 8 carbon atoms, where such groups are unsaturated (i.e., containing at least one annular carbon carbon double bond), but not aromatic. Examples of monocyclic cycloalkenyl ring systems include cyclopentenyl and cyclohexenyl. In embodiments, bicyclic cycloalkenyl rings are bridged monocyclic rings or a fused bicyclic rings. In embodiments, bridged monocyclic rings contain a monocyclic cycloalkenyl ring where two non adjacent carbon atoms of the monocyclic ring are linked by an alkylene bridge of between one and three additional carbon atoms (i.e., a bridging group of the form (CH$_2$)$_w$, where w is 1, 2, or 3). Representative examples of bicyclic cycloalkenyls include, but are not limited to, norbornenyl and bicyclo[2.2.2]oct 2 enyl. In embodiments, fused bicyclic cycloalkenyl ring systems contain a monocyclic cycloalkenyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkenyl is attached to the parent molecular moiety through any carbon atom contained within the monocyclic cycloalkenyl ring. In embodiments, cycloalkenyl groups are optionally substituted with one or two groups which are independently oxo or thia. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkenyl is attached to the parent molecular moiety through any carbon atom contained within the base ring. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a monocyclic heteroaryl, a monocyclic cycloalkyl, a monocyclic cycloalkenyl, and a monocyclic heterocyclyl.

In embodiments, a heterocycloalkyl is a heterocyclyl. The term "heterocyclyl" as used herein, means a monocyclic, bicyclic, or multicyclic heterocycle. The heterocyclyl monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The heterocyclyl monocyclic heterocycle is connected to the parent molecular moiety through any carbon atom or any nitrogen atom contained within the heterocyclyl monocyclic heterocycle. Representative examples of heterocyclyl monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The heterocyclyl bicyclic heterocycle is a monocyclic heterocycle fused to either a phenyl, a monocyclic cycloalkyl, a monocyclic cycloalkenyl, a monocyclic heterocycle, or a monocyclic heteroaryl. The heterocyclyl bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. In embodiments, heterocyclyl groups are optionally substituted with one or two groups which are independently oxo or thia. In certain embodiments, the bicyclic heterocyclyl is a 5 or 6 membered monocyclic heterocyclyl ring fused to a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia. Multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. The multicyclic heterocyclyl is attached to the parent molecular moiety through any carbon atom or nitrogen atom contained within the base ring. In embodiments, multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic heterocyclyl groups include, but are not limited to 10H-phenothiazin-10-yl, 9,10-dihydroacridin-9-yl, 9,10-dihydroacridin-10-yl, 10H-phenoxazin-10-yl, 10,11-dihydro-5H-dibenzo[b,f]azepin-5-yl, 1,2,3,4-tetrahydropyrido[4,3-g]isoquinolin-2-yl, 12H-benzo[b]phenoxazin-12-yl, and dodecahydro-1H-carbazol-9-yl.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

A fused ring heterocycloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substitutents described herein.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different. ∿

The symbol "∿" denotes the point of attachment of a chemical moiety to the remainder of a molecule or chemical formula.

The term "oxo," as used herein, means an oxygen that is double bonded to a carbon atom.

The term "alkylsulfonyl," as used herein, means a moiety having the formula —S(O$_2$)—R', where R' is a substituted or unsubstituted alkyl group as defined above. R' may have a specified number of carbons (e.g., "C$_1$-C$_4$ alkylsulfonyl").

The term "alkylarylene" as an arylene moiety covalently bonded to an alkylene moiety (also referred to herein as an alkylene linker). In embodiments, the alkylarylene group has the formula:

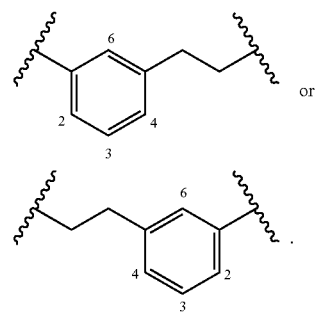

An alkylarylene moiety may be substituted (e.g. with a substituent group) on the alkylene moiety or the arylene linker (e.g. at carbons 2, 3, 4, or 6) with halogen, oxo, —N$_3$, —CF$_3$, —CCl$_3$, —CBr$_3$, —Cl$_3$, —CN, —CHO, —OH, —NH$_2$, —COOH, —CONH$_2$, —NO$_2$, —SH, —SO$_2$CH$_3$—SO$_3$H, —OSO$_3$H, —SO$_2$NH$_2$, —NHNH$_2$, —ONH$_2$, —NHC(O)NHNH$_2$, substituted or unsubstituted C$_1$-C$_5$ alkyl or substituted or unsubstituted 2 to 5 membered heteroalkyl). In embodiments, the alkylarylene is unsubstituted.

Each of the above terms (e.g., "alkyl," "heteroalkyl," "cycloalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C(O)NR"NR'"R"", —CN, —NO$_2$, —NR'SO$_2$R", —NR'C(O)R", —NR'C(O)—OR", —NR'OR", in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —$C(O)CH_3$, —$C(O)CF_3$, —$C(O)CH_2OCH_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C(O)NR"NR'"R"", —CN, —$NO_2$, —R', —$N_3$, —CH(Ph)$_2$, fluoro($C_1$-$C_4$)alkoxy, and fluoro($C_1$-$C_4$)alkyl, —NR'SO$_2$R", —NR'C(O)R", —NR'C(O)—OR", NR'R", in a number rain g from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R'", and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R'")$_d$—, where s and d are independently integers of from 0 to 3, and X' is —O—, —NR'—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$,—OCHC$_2$, —OCHBr$_2$, —OCHI$_2$, —OCHF$_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (B) alkyl, heteroalkyl, cycloalkyl, heterocycloalkyl, aryl, heteroaryl, substituted with at least one substituent selected from:
(i) oxo,
halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and
(ii) alkyl, heteroalkyl, cycloalkyl, heterocycloalkyl, aryl, heteroaryl, substituted with at least one substituent selected from:
(a)oxo,
halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and
(b) alkyl, heteroalkyl, cycloalkyl, heterocycloalkyl, aryl, heteroaryl, substituted with at least one substituent selected from: oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_5$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science* 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention. Salts tend to be more soluble in aqueous or other protonic solvents than are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Provided herein are agents (e.g. compounds, drugs, therapeutic agents) that may be in a prodrug form. Prodrugs of the compounds described herein are those compounds that readily undergo chemical changes under select physiological conditions to provide the final agents (e.g. compounds, drugs, therapeutic agents). Additionally, prodrugs can be converted to agents (e.g. compounds, drugs, therapeutic agents) by chemical or biochemical methods in an ex vivo environment. Prodrugs described herein include compounds that readily undergo chemical changes under select physiological conditions to provide agents (e.g. compounds, drugs, therapeutic agents) to a biological system (e.g. in a subject).

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those that are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this disclosure.

The compounds of the present disclosure may also contain unnatural proportions of atomic isotopes at one or more of the atoms that constitute such compounds. For example, the compounds may be radiolabeled with radioactive isotopes, such as for example tritium ($^{3}$H), iodine-125 ($^{125}$I), or carbon-14 ($^{14}$C). All isotopic variations of the compounds of the present disclosure, whether radioactive or not, are encompassed within the scope of the present disclosure.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

As used herein, the term "bioconjugate" or "bioconjugate linker" refers to the resulting association between atoms or molecules of bioconjugate reactive groups. The association can be direct or indirect. For example, a conjugate between a first bioconjugate reactive group (e.g. —NH$_2$, —COOH, —N-hydroxysuccinimide, or -maleimide) and a second bioconjugate reactive group (e.g., sulfhydryl, sulfur-containing amino acid, amine, amine sidechain containing amino acid, or carboxylate) provided herein can be direct, e.g., by covalent bond or linker (e.g. a first linker of second linker), or indirect, e.g., by non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). In embodiments, bioconjugates or bioconjugate linkers are formed using bioconjugate chemistry (i.e. the association of two bioconjugate reactive groups) including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the first bioconjugate reactive group (e.g., maleimide moiety) is covalently attached to the second bioconjugate reactive group (e.g. a sulfhydryl). In embodiments, the first bioconjugate reactive group (e.g., haloacetyl moiety) is covalently attached to the second bioconjugate reactive group (e.g. a sulfhydryl). In embodiments, the first bioconjugate reactive group (e.g., pyridyl moiety) is covalently attached to the second bioconjugate reactive group (e.g. a sulfhydryl). In embodiments, the first bioconjugate reactive group (e.g., —N-hydroxysuccinimide moiety) is covalently attached to the second bioconjugate reactive group (e.g. an amine). In embodiments, the first bioconjugate reactive group (e.g., maleimide moiety) is covalently attached to the second bioconjugate reactive group (e.g. a sulfhydryl). In embodiments, the first bioconjugate reactive group (e.g., -sulfo-N-hydroxysuccinimide moiety) is covalently attached to the second bioconjugate reactive group (e.g. an amine). The term "haloacetyl," as used herein, refers to a functional group having the formula:

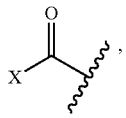

wherein X is a halogen.

A "detectable agent" or "detectable compound" is a substance detectable by appropriate means such as spectroscopic, photochemical, biochemical, immunochemical, chemical, magnetic resonance imaging, or other physical means. For example, useful detectable agents include $^{18}$F, $^{32}$P, $^{33}$P, $^{45}$Ti, $^{47}$Sc, $^{52}$Fe, $^{59}$Fe, $^{62}$Cu, $^{64}$Cu, $^{67}$Cu, $^{67}$Ga, $^{68}$Ga, $^{77}$As, $^{86}$Y, $^{90}$Y. 89Sr, $^{89}$Zr, $^{94}$Tc, $^{94}$Tc, $^{99m}$Tc, $^{99}$Mo, $^{105}$Pd, $^{105}$Rh $^{111}$Ag, $^{111}$In, $^{123}$I, $^{124}$I, $^{125}$I, $^{131}$I, $^{142}$Pr, $^{143}$Pr, $^{149}$Pm, $^{153}$Sm, $^{154-1581}$Gd, $^{161}$Tb, $^{166}$Dy, $^{166}$Ho, $^{169}$Er, $^{175}$Lu, $^{177}$Lu, $^{186}$Re, $^{188}$Re, $^{189}$Re, $^{194}$Ir, $^{198}$Au, $^{199}$Au, $^{211}$At, $^{211}$Pb, $^{212}$Bi, $^{212}$Pb, $^{213}$Bi, $^{223}$Ra, $^{225}$Ac, Cr, V, Mn, Fe, Co, Ni, Cu, La, Ce, Pr, Nd, Pm, Sm, Eu, Gd, Tb, Dy, Ho, Er, Tm, Yb, Lu, $^{32}$P, fluorophore (e.g. fluorescent dyes), electron-dense reagents, enzymes (e.g., as commonly used in an ELISA), biotin, digoxigenin, paramagnetic molecules, paramagnetic nanoparticles, ultrasmall superparamagnetic iron oxide ("USPIO") nanoparticles, USPIO nanoparticle aggregates, superparamagnetic iron oxide ("SPIO") nanoparticles, SPIO nanoparticle aggregates, monochrystalline iron oxide nanoparticles, monochrystalline iron oxide, nanoparticle contrast agents, liposomes or other delivery vehicles containing Gadolinium chelate ("Gd-chelate") molecules, Gadolinium, radioisotopes, radionuclides (e.g. carbon-11, nitrogen-13, oxygen-15, fluorine-18, rubidium-82), fluorodeoxyglucose (e.g. fluorine-18 labeled), any gamma ray emitting radionuclides, positron-emitting radionuclide, radiolabeled glucose, radiolabeled water, radiolabeled ammonia, biocolloids, microbubbles (e.g. including microbubble shells including albumin, galactose, lipid, and/or polymers; microbubble gas core including air, heavy gas(es), perfluorcarbon, nitrogen, octafluoropropane, perflexane lipid microsphere, perflutren, etc.), iodinated contrast agents (e.g. iohexol, iodixanol, ioversol, iopamidol, ioxilan, iopromide, diatrizoate, metrizoate, ioxaglate), barium sulfate, thorium dioxide, gold, gold nanoparticles, gold nanoparticle aggregates, fluorophores, two-photon fluorophores, or haptens and proteins or other entities which can be made detectable, e.g., by incorporating a radiolabel into a peptide or antibody specifically reactive with a target peptide. A detectable moiety is a monovalent detectable agent or a detectable agent capable of forming a bond with another composition.

Radioactive substances (e.g., radioisotopes) that may be used as imaging and/or labeling agents in accordance with the embodiments of the disclosure include, but are not limited to, $^{18}$F, $^{32}$P, $^{33}$P, $^{45}$Ti, $^{47}$Sc, $^{52}$Fe, $^{9}$Fe, $^{62}$Cu, $^{64}$Cu, $^{67}$Cu, $^{67}$Ga, $^{68}$Ga, $^{77}$As, $^{86}$Y, $^{90}$Y, $^{89}$Sr, $^{89}$Zr, $^{94}$Tc, $^{94}$Tc, $^{99m}$Tc, $^{99}$Mo, $^{105}$Pd, $^{105}$Rh, $^{111}$Ag, $^{111}$In, $^{123}$I, $^{124}$I, $^{125}$I, $^{131}$I, $^{142}$Pr, $^{143}$Pr, $^{149}$Pm, $^{153}$Sm, $^{154-1581}$Gd, $^{161}$Tb, $^{166}$Dy, $^{166}$Ho, $^{169}$Er, $^{175}$Lu, $^{177}$Lu, $^{86}$Re, $^{188}$Re, $^{189}$Re, $^{194}$Ir, $^{198}$Au, $^{199}$Au, $^{211}$At, $^{211}$Pb, $^{212}$Bi, $^{212}$Pb, $^{213}$Bi, $^{223}$Ra and $^{225}$Ac. Paramagnetic ions that may be used as additional imaging agents in accordance with the embodiments of the disclosure include, but are not limited to, ions of transition and lanthanide metals (e.g. metals having atomic numbers of 21-29, 42, 43, 44, or 57-71). These metals include ions of Cr, V, Mn, Fe, Co, Ni, Cu, La, Ce, Pr, Nd, Pm, Sm, Eu, Gd, Tb, Dy, Ho, Er, Tm, Yb and Lu.

Useful bioconjugate reactive groups used for bioconjugate chemistries herein include, for example:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;

(b) hydroxyl groups which can be converted to esters, ethers, aldehydes, etc.

(c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups which are capable of participating in Diels-Alder reactions such as, for example, maleimido or maleimide groups;

(e) aldehyde or ketone groups such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be converted to disulfides, reacted with acyl halides, or bonded to metals such as gold, or react with maleimides;

(h) amine or sulfhydryl groups (e.g., present in cysteine), which can be, for example, acylated, alkylated or oxidized;

(i) alkenes, which can undergo, for example, cycloadditions, acylation, Michael addition, etc;

(j) epoxides, which can react with, for example, amines and hydroxyl compounds;

(k) phosphoramidites and other standard functional groups useful in nucleic acid synthesis;
(l) metal silicon oxide bonding; and
(m) metal bonding to reactive phosphorus groups (e.g. phosphines) to form, for example, phosphate diester bonds.
(n) azides coupled to alkynes using copper catalyzed cycloaddition click chemistry.
(o) biotin conjugate can react with avidin or strepavidin to form a avidin-biotin complex or streptavidin-biotin complex.

The bioconjugate reactive groups can be chosen such that they do not participate in, or interfere with, the chemical stability of the conjugate described herein. Alternatively, a reactive functional group can be protected from participating in the crosslinking reaction by the presence of a protecting group. In embodiments, the bioconjugate comprises a molecular entity derived from the reaction of an unsaturated bond, such as a maleimide, and a sulfhydryl group.

"Analog," or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "leaving group" is used in accordance with its ordinary meaning in chemistry and refers to a moiety (e.g., atom, functional group, molecule) that separates from the molecule following a chemical reaction (e.g., bond formation, reductive elimination, condensation, cross-coupling reaction) involving an atom or chemical moiety to which the leaving group is attached, also referred to herein as the "leaving group reactive moiety", and a complementary reactive moiety (i.e. a chemical moiety that reacts with the leaving group reactive moiety) to form a new bond between the remnants of the leaving groups reactive moiety and the complementary reactive moiety. Thus, the leaving group reactive moiety and the complementary reactive moiety form a complementary reactive group pair. Non limiting examples of leaving groups include hydrogen, hydroxide, organotin moieties (e.g., organotin heteroalkyl), halogen (e.g., Br), perfluoroalkylsulfonates (e.g. triflate), tosylates, mesylates, water, alcohols, nitrate, phosphate, thioether, amines, ammonia, fluoride, carboxylate, phenoxides, boronic acid, boronate esters, and alkoxides. In embodiments, two molecules with leaving groups are allowed to contact, and upon a reaction and/or bond formation (e.g., acyloin condensation, aldol condensation, Claisen condensation, Stille reaction) the leaving groups separates from the respective molecule. In embodiments, a leaving group is a bioconjugate reactive moiety. In embodiments, at least two leaving groups (e.g., $R^1$ and $R^{13}$) are allowed to contact such that the leaving groups are sufficiently proximal to react, interact or physically touch. In embodiments, the leaving groups is designed to facilitate the reaction.

The term "protecting group" is used in accordance with its ordinary meaning in organic chemistry and refers to a moiety covalently bound to a heteroatom, heterocycloalkyl, or heteroaryl to prevent reactivity of the heteroatom, heterocycloalkyl, or heteroaryl during one or more chemical reactions performed prior to removal of the protecting group. Typically a protecting group is bound to a heteroatom (e.g., O) during a part of a multipart synthesis wherein it is not desired to have the heteroatom react (e.g., a chemical reduction) with the reagent. Following protection the protecting group may be removed (e.g., by modulating the pH). In embodiments the protecting group is an alcohol protecting group. Non-limiting examples of alcohol protecting groups include acetyl, benzoyl, benzyl, methoxymethyl ether (MOM), tetrahydropyranyl (THP), and silyl ether (e.g., trimethylsilyl (TMS)). In embodiments the protecting group is an amine protecting group. Non-limiting examples of amine protecting groups include carbobenzyloxy (Cbz), tert-butyloxycarbonyl (BOC), 9-Fluorenylmethyloxycarbonyl (FMOC), acetyl, benzoyl, benzyl, carbamate, p-methoxybenzyl ether (PMB), and tosyl (Ts).

The terms "treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, certain methods herein treat hyperproliferative disorders, such as cancer (e.g. ovarian cancer, bladder cancer, head and neck cancer, brain cancer, breast cancer, lung cancer, cervical cancer, liver cancer, colorectal cancer, pancreatic cancer, glioblastoma, neuroblastoma, rhabdomyosarcoma, osteosarcoma, renal cancer, renal cell carcinoma, non-small cell lung cancer, uterine cancer, testicular cancer, anal cancer, bile duct cancer, biliary tract cancer, gastrointestinal carcinoid tumors, esophageal cancer, gall bladder cancer, appendix cancer, small intestine cancer, stomach (gastric) cancer, urinary bladder cancer, genitourinary tract cancer, endometrial cancer, nasopharyngeal cancer, head and neck squamous cell carcinoma, or prostate cancer). For example certain methods herein treat cancer by decreasing or reducing or preventing the occurrence, growth, metastasis, or progression of cancer or by decreasing or reducing or preventing a symptom of cancer. Symptoms of cancer (e.g., ovarian cancer, bladder cancer, head and neck cancer, brain cancer, breast cancer, lung cancer, cervical cancer, liver cancer, colorectal cancer, pancreatic cancer, glioblastoma, neuroblastoma, rhabdomyosarcoma, osteosarcoma, renal cancer, renal cell carcinoma, non-small cell lung cancer, uterine cancer, testicular cancer, anal cancer, bile duct cancer, biliary tract cancer, gastrointestinal carcinoid tumors, esophageal cancer, gall bladder cancer, appendix cancer, small intestine cancer, stomach (gastric) cancer, urinary bladder cancer, genitourinary tract cancer, endometrial cancer, nasopharyngeal cancer, head and neck squamous cell carcinoma, or prostate cancer) would be known or may be determined by a person of ordinary skill in the art. The term "treating" and conjugations thereof, include prevention of an injury, pathology, condition, or disease (e.g. preventing the development of one or more symptoms of cancer (e.g. ovarian cancer, bladder cancer, head and neck cancer, brain cancer, breast cancer, lung cancer, cervical cancer, liver cancer, colorectal cancer, pancreatic cancer, glioblastoma, neuroblastoma, rhabdomyosarcoma, osteosarcoma, renal cancer, renal cell carcinoma, non-small cell lung cancer, uterine cancer, testicular cancer, anal cancer, bile duct cancer, biliary tract cancer, gastrointestinal carcinoid tumors, esophageal cancer, gall bladder cancer, appendix cancer, small intestine cancer, stomach (gastric) cancer, urinary bladder cancer, genitourinary tract cancer, endometrial cancer, nasopharyngeal cancer, head and neck squamous cell carcinoma, or prostate cancer).

As used herein, the term "cancer" refers to all types of cancer, neoplasm or malignant tumors found in mammals, including leukemia, lymphoma, carcinomas and sarcomas. Exemplary cancers that may be treated with a compound, pharmaceutical composition, or method provided herein include ovarian cancer, lymphoma, sarcoma, bladder cancer, bone cancer, brain tumor, cervical cancer, colon cancer, esophageal cancer, gastric cancer, head and neck cancer, kidney cancer, myeloma, thyroid cancer, leukemia, prostate cancer, breast cancer (e.g. ER positive, ER negative, chemotherapy resistant, herceptin resistant, HER2 positive, doxorubicin resistant, tamoxifen resistant, ductal carcinoma, lobular carcinoma, primary, metastatic), ovarian cancer, pancreatic cancer, liver cancer (e.g. hepatocellular carcinoma), lung cancer (e.g. non-small cell lung carcinoma, squamous cell lung carcinoma, adenocarcinoma, large cell lung carcinoma, small cell lung carcinoma, carcinoid, sarcoma, cisplatin resistant lung cancer, carboplatin resistant lung cancer, platinum-based compound resistant lung cancer), glioblastoma multiforme, glioma, or melanoma. Additional examples include, cancer of the thyroid, endocrine system, brain, breast, cervix, colon, head & neck, liver, kidney, lung, non-small cell lung, melanoma, mesothelioma, ovary, sarcoma, stomach, uterus or Medulloblastoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget's Disease of the Nipple, Phyllodes Tumors, Lobular Carcinoma, Ductal Carcinoma, cancer of the pancreatic stellate cells, cancer of the hepatic stellate cells, or prostate cancer. In embodiments "cancer" refers to a cancer resistant to an anti-cancer therapy (e.g. treatment with an anti-cancer agent).

The term "sarcoma" generally refers to a tumor which is made up of a substance like the embryonic connective tissue and is generally composed of closely packed cells embedded in a fibrillar or homogeneous substance. Sarcomas that may be treated with a compound, pharmaceutical composition, or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "carcinoma" refers to a malignant new growth made up of epithelial cells tending to infiltrate the surrounding tissues and gives rise to metastases. Exemplary carcinomas that may be treated with a compound, pharmaceutical composition, or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, ductal carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lobular carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tubular carcinoma, tuberous carcinoma, verrucous carcinoma, or carcinoma villosum.

An "effective amount" is an amount sufficient to accomplish a stated purpose (e.g. achieve the effect for which it is administered, treat a disease, reduce enzyme activity, increase enzyme activity, reduce protein function, reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug or prodrug is an amount of a drug or prodrug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

The term "associated" or "associated with" in the context of a substance or substance activity or function associated with a disease (e.g. cancer, ovarian cancer, bladder cancer, head and neck cancer, brain cancer, breast cancer, lung cancer, cervical cancer, liver cancer, colorectal cancer, pancreatic cancer, glioblastoma, neuroblastoma, rhabdomyosarcoma, osteosarcoma, renal cancer, renal cell carcinoma, non-small cell lung cancer, uterine cancer, testicular cancer, anal cancer, bile duct cancer, biliary tract cancer, gastrointestinal carcinoid tumors, esophageal cancer, gall bladder cancer, appendix cancer, small intestine cancer, stomach (gastric) cancer, urinary bladder cancer, genitourinary tract cancer, endometrial cancer, nasopharyngeal cancer, head and neck squamous cell carcinoma, or prostate cancer) means that the disease is caused by (in whole or in part), or a symptom of the disease is caused by (in whole or in part) the substance or substance activity or function. As used herein, what is described as being associated with a disease, if a causative agent, could be a target for treatment of the disease. For example cancer may be treated with a composition (e.g. compound, composition, nanoparticle, or conjugate, all as described herein) effective for inhibiting DNA replication.

"Control" or "control experiment" or "standard control" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects.

"Contacting" is used in accordance with its plain ordinary meaning and refers to the process of allowing at least two distinct species (e.g. chemical compounds including biomolecules, or cells) to become sufficiently proximal to react, interact or physically touch. It should be appreciated, however, that the resulting reaction product can be produced directly from a reaction between the added reagents or from an intermediate from one or more of the added reagents which can be produced in the reaction mixture. The term "contacting" may include allowing two species to react, interact, or physically touch, wherein the two species may be a compound as described herein and a protein or enzyme. In some embodiments, contacting includes allowing a compound described herein to interact with a protein.

As defined herein, the term "inhibition", "inhibit", "inhibiting" and the like in reference to a protein-inhibitor (e.g. antagonist) interaction means negatively affecting (e.g. decreasing) the level of activity or function of the protein relative to the level of activity or function of the protein in the absence of the inhibitor. In embodiments, inhibition refers to a decrease in DNA replication or transcription. In some embodiments inhibition refers to reduction of a disease or symptoms of disease (e.g. cancer, ovarian cancer, bladder cancer, head and neck cancer, brain cancer, breast cancer, lung cancer, cervical cancer, liver cancer, colorectal cancer, pancreatic cancer, glioblastoma, neuroblastoma, rhabdomyosarcoma, osteosarcoma, renal cancer, renal cell carcinoma, non-small cell lung cancer, uterine cancer, testicular cancer, anal cancer, bile duct cancer, biliary tract cancer, gastrointestinal carcinoid tumors, esophageal cancer, gall bladder cancer, appendix cancer, small intestine cancer, stomach (gastric) cancer, urinary bladder cancer, genitourinary tract cancer, endometrial cancer, nasopharyngeal cancer, head and neck squamous cell carcinoma, or prostate cancer). Thus, inhibition may include, at least in part, partially or totally blocking stimulation, decreasing, preventing, or delaying activation, or inactivating, desensitizing, or down-regulating signal transduction or enzymatic activity or the amount of a protein.

As defined herein, the term "activation", "activate", "activating" and the like in reference to a protein-activator (e.g. agonist) interaction means positively affecting (e.g. increasing) the activity or function of the protein relative to the activity or function of the protein in the absence of the activator (e.g. compound described herein). Thus, activation may include, at least in part, partially or totally increasing stimulation, increasing or enabling activation, or activating, sensitizing, or up-regulating signal transduction or enzymatic activity or the amount of a protein decreased in a disease. Activation may include, at least in part, partially or totally increasing stimulation, increasing or enabling activation, or activating, sensitizing, or up-regulating signal transduction or enzymatic activity or the amount of a protein.

The term "modulator" refers to a composition that increases or decreases the level of a target molecule or the function of a target molecule.

"Patient" or "subject in need thereof" or "subject" refers to a living organism suffering from or prone to a disease or condition that can be treated by administration of a compound or pharmaceutical composition or by a method, as provided herein. Non-limiting examples include humans, other mammals, bovines, rats, mice, dogs, monkeys, goat, sheep, cows, deer, and other non-mammalian animals. In some embodiments, a patient is human. In some embodiments, a subject is human.

"Disease" or "condition" refer to a state of being or health status of a patient or subject capable of being treated with a compound, pharmaceutical composition, or method provided herein. In embodiments, the disease is cancer. In embodiments, the disease is ovarian cancer, bladder cancer, head and neck cancer, brain cancer, breast cancer, lung cancer, cervical cancer, liver cancer, colorectal cancer, pancreatic cancer, glioblastoma, neuroblastoma, rhabdomyosarcoma, osteosarcoma, renal cancer, renal cell carcinoma, non-small cell lung cancer, uterine cancer, testicular cancer, anal cancer, bile duct cancer, biliary tract cancer, gastrointestinal carcinoid tumors, esophageal cancer, gall bladder cancer, appendix cancer, small intestine cancer, stomach (gastric) cancer, urinary bladder cancer, genitourinary tract cancer, endometrial cancer, nasopharyngeal cancer, head and neck squamous cell carcinoma, or prostate cancer.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, parenteral, intraperitoneal, intramuscular, intralesional, intrathecal, intracranial, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies. The compound of the invention can be administered alone or can be coadministered to the patient. Coadministration is meant to include simultaneous or sequential administration of the compound individually or in combination (more than one compound or agent). Thus, the preparations can also be combined, when desired, with other active substances (e.g. to reduce metabolic degradation, to increase degradation of a prodrug and release of the drug, detectable agent). The compositions of the present invention can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., *Gao Pharm. Res.* 12:857-863, 1995); or, as microspheres for oral administration (see, e.g., Eyles, *J. Pharm. Pharmacol.* 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions of the present invention can also be delivered as nanoparticles.

Pharmaceutical compositions provided by the present invention include compositions wherein the active ingredient (e.g. compounds described herein, including embodiments or examples) may be contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., reducing, eliminating, or slowing the progression of disease symptoms. Determination of a therapeutically effective amount of a compound of the invention is well within the capabilities of those skilled in the art, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated, kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to affect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

The compounds described herein can be used in combination with one another, with other active agents (e.g. anti-cancer agents) known to be useful in treating a disease described herein (e.g. ovarian cancer, bladder cancer, head and neck cancer, brain cancer, breast cancer, lung cancer, cervical cancer, liver cancer, colorectal cancer, pancreatic cancer, glioblastoma, neuroblastoma, rhabdomyosarcoma, osteosarcoma, renal cancer, renal cell carcinoma, non-small cell lung cancer, uterine cancer, testicular cancer, anal cancer, bile duct cancer, biliary tract cancer, gastrointestinal carcinoid tumors, esophageal cancer, gall bladder cancer, appendix cancer, small intestine cancer, stomach (gastric) cancer, urinary bladder cancer, genitourinary tract cancer, endometrial cancer, nasopharyngeal cancer, head and neck squamous cell carcinoma, or prostate cancer), or with adjunctive agents that may not be effective alone, but may contribute to the efficacy of the active agent.

In some embodiments, co-administration includes administering one active agent within 0.5, 1, 2, 4, 6, 8, 10, 12, 16, 20, or 24 hours of a second active agent (e.g. anti-cancer agent). Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another.

"Anti-cancer agent" is used in accordance with its plain ordinary meaning and refers to a composition (e.g. compound, drug, antagonist, inhibitor, modulator) having antineoplastic properties or the ability to inhibit the growth or proliferation of cells. In some embodiments, an anti-cancer agent is a chemotherapeutic. In some embodiments, an anti-cancer agent is an agent identified herein having utility in methods of treating cancer. In some embodiments, an anti-cancer agent is an agent approved by the FDA or similar regulatory agency of a country other than the USA, for treating cancer. Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethlymelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds or platinum containing agents (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; daclixamab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin Il (including recombinant interleukin II, or rIL.sub.2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol™ (i.e. paclitaxel), Taxotere™, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), Vincristine sulfate, Cryptophycin 52 (i.e. LY-355703), Vitilevuamide, Tubulysin A, Canadensol, Centaureidin (i.e. NSC-106969), Oncocidin A1 (i.e. BTO-956 and DIME), Fijianolide B, Laulimalide, Narcosine (also known as NSC-5366), Nascapine, Hemiasterlin, Vanadocene acetylacetonate, Monsatrol, Inanocine (i.e. NSC-698666), Eleutherobins (such as Desmethyleleutherobin, Desaetyleleutherobin, Isoeleutherobin A, and Z-Eleutherobin), Caribaeoside, Caribaeolin, Halichondrin B, Diazonamide A, Taccalonolide A, Diozostatin, (−)-Phenylahistin (i.e. NSCL-96F037), Myoseverin B, Resverastatin phosphate sodium, steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., *Bacillus* Calmette-Guerin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), radioimmunotherapy (e.g., anti-CD20 monoclonal antibody conjugated to $^{111}$In, 90 or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, hormonal therapies, or the like.

"Analog" and "analogue" are used interchangeably and are used in accordance with their plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound, including isomers thereof. Accordingly, an analog is a compound that is similar or comparable in function and appearance but not in structure or origin to a reference compound.

As used herein, the term "about" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about means the specified value.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature. Sulfur-containing amino acids refers to naturally occurring and synthetic amino acids comprising sulfur, e.g., methionine, cysteine, homocysteine, and taurine.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., spodoptera) and human cells. Cells may be useful when they are naturally nonadherent or have been treated not to adhere to surfaces, for example by trypsinization.

A "neural stem cell" as used herein, refers to a self-renewing multipotent cell capable of generating cells of the nervous system (e.g., neurons, astrocytes, and oligodendrocytes). In embodiments, a neural stem cell is a tropic stem cell that can self-renew and give rise to differentiated progenitor cells, such as HB1.F3 neural stem cells.

A "nanoparticle," as used herein, is a particle wherein the longest dimension is less than or equal to 1000 nanometers. The longest dimension of the nanoparticle may be referred to herein as the length of the nanoparticle. The shortest dimension of the nanoparticle may be referred to herein refer as the width of the nanoparticle.

Nanoparticles may be composed of any appropriate material. Nanoparticles may be composed of at least two materials. In embodiments, one material forms the core of the nanoparticle, also referred to herein as a nanoparticle core, and a second material that forms a shell, also referred to herein as a layer (e.g., silica layer) or nanoparticle shell, that encapsulates (e.g., surround, encloses) the core (e.g., nanoparticle core). For example, nanoparticle cores may include appropriate metals and metal oxides thereof (e.g., a metal nanoparticle core), carbon (e.g., an organic nanoparticle core) silicon and oxides thereof (e.g., a silicon nanoparticle core) or boron and oxides thereof (e.g., a boron nanoparticle core), or mixtures thereof. In embodiments, the nanoparticle core includes a solid. In embodiments, the nanoparticle core is a solid. In embodiments, the nanoparticle core includes an amorphous solid. In embodiments, the nanoparticle core is an amorphous solid. In embodiments, the nanoparticle core includes a crystalline solid. In embodiments, the nanoparticle core is a crystalline solid. In embodiments, the nanoparticle core includes a nanocrystal. In embodiments, the nanoparticle core is a nanocrystal. In embodiments, the nanoparticle core includes an insoluble drug. In embodiments, the insoluble drug is in the form of a solid. In embodiments, the insoluble drug is in the form of an amorphous solid. In embodiments, the insoluble drug is in the form of a crystalline solid. In embodiments, the insoluble drug is in the form of a nanocrystal.

Nanoparticles come in different shapes and sizes. In embodiments, the nanoparticle has the shape of a sphere, rod, cube, triangular, hexagonal, cylinder, spherocylinder, or ellipsoid. In embodiments, the nanoparticle has the shape of a rod.

An "inorganic nanoparticle" refers to a nanoparticle including an inorganic layer (i.e. a layer with inorganic components (e.g. metal, silica). In embodiments, the inorganic layer does not include carbon. The inorganic layer may enclose (e.g., surround, encapsulate, envelope) a nanoparticle core. An inorganic layer may alternatively be referred to herein as a shell. For example, an inorganic layer may refer to a layer including a metal and/or metal oxide thereof (e.g., gold nanoparticle, iron nanoparticle), silicon and/or oxides thereof (e.g., a silica nanoparticle), or titanium and oxides thereof (e.g., titanium dioxide nanoparticle). In embodiments, the nanoparticle as described herein, including embodiments thereof, is an inorganic nanoparticle. In embodiments, the inorganic nanoparticle is a silica nanoparticle (i.e. a nanoparticle including a silica layer (i.e., a layer without carbon including silica). The inorganic nanoparticle may be a metal nanoparticle. When the nanoparticle is a metal, the metal may be titanium, zirconium, gold, silver, platinum, cerium, arsenic, iron, aluminum or silicon. The metal nanoparticle may be titanium, zirconium, gold, silver, or platinum and appropriate metal oxides thereof. In embodiments, the nanoparticle is titanium oxide, zirconium oxide, cerium oxide, arsenic oxide, iron oxide, aluminum oxide, or silicon oxide. The metal oxide nanoparticle may be titanium oxide or zirconium oxide. The nanoparticle may be titanium. The nanoparticle may be gold. In embodiments, the metal nanoparticle is a gold nanoparticle. In embodiments, the inorganic nanoparticle may further include a moiety which contains carbon. The term "inorganic layer" refers to a contiguous portion of an inorganic nanoparticle including inorganic components. Likewise, a "silica layer" refers to a contiguous portion of an inorganic nanoparticle including silica. In embodiments, a silica layer does not include carbon. In embodiments, the silica layer is at least 80%, 85%, 90%, 95%, 96%, 97%, 98%, 99% or 100% silica. In embodiments, the silica layer is at least 80% silica. In embodiments, the silica layer is at least 85% silica. In embodiments, the silica layer is at least 90% silica. In embodiments, the silica layer is at least 95% silica. In embodiments, the silica layer is at least 96% silica. In embodiments, the silica layer is at least 97% silica. In embodiments, the silica layer is at least 98% silica. In embodiments, the silica layer is at least 99% silica. In embodiments, the silica layer is 100% silica.

The term "silica" is used according to its plain and ordinary meaning and refers to a composition (e.g. a solid composition such as a crystal, nanoparticle, or nanocrystal) containing oxides of silicon such as Si atoms (e.g., in a tetrahedral coordination) with 4 oxygen atoms surrounding a central Si atom. As described supra, nanoparticles may be composed of at least two distinct materials, one material (e.g., insoluble drug) forms the core (e.g., nanoparticle core) and the other material (e.g., silica) forms the shell, also known as a layer (e.g., silica layer), surrounding (e.g., enclosing, encapsulating, enveloping) the core. When the shell includes Si atoms, the nanoparticle may be referred to as a silica nanoparticle. A silica nanoparticle may refer to a particle including a matrix of silicon-oxygen bonds wherein the longest dimension is typically less than or equal to 1000 nanometers. In embodiments, the silica nanoparticle is not a mesoporous silica nanoparticle. In embodiments, the silica nanoparticle is not a mesoporous silica nanoparticle including a silica layer. In embodiments, the silica nanoparticle does not form part of a silica network.

A functionalized silica nanoparticle, as used herein, may refer to the post hoc conjugation (i.e. conjugation after the formation of the silica nanoparticle) of a moiety to the hydroxyl surface of a nanoparticle. For example, a silica nanoparticle may be further functionalized to include additional atoms (e.g., nitrogen) or chemical entities (e.g., polymeric moieties or bioconjugate groups). For example, when the silica nanoparticle is further functionalized with a nitrogen containing compound, one of the surface oxygen atoms surrounding the Si atom may be replaced with a nitrogen containing moiety.

The term "polymeric" or "polymer" refers to a molecule including repeating subunits (e.g., polymerized monomers). For example, polymeric molecules may be based upon polyethylene glycol (PEG), poly[amino(1-oxo-1,6-hexanediyl)], poly(oxy-1,2-ethanediyloxycarbonyl-1,4-phenylenecarbonyl), tetraethylene glycol (TEG), polyvinylpyrrolidone (PVP), poly(xylene), or poly(p-xylylene). See, for example, "Chemistry of Protein Conjugation and Cross-Linking" Shan S. Wong CRC Press, Boca Raton, Fla., USA, 1993; "BioConjugate Techniques" Greg T. Hermanson Academic Press, San Diego, Calif., USA, 1996; "Catalog of Polyethylene Glycol and Derivatives for Advanced PEGylation, 2004" Nektar Therapeutics Inc, Huntsville, Ala., USA, which are incorporated by reference in their entirety for all purposes.

The term "poloxamer" is used in accordance with its meaning in the art of polymer chemistry and refers to a triblock copolymer composed of a central hydrophobic block (e.g., polyoxypropylene) flanked by two hydrophilic blocks (e.g., polyoxyethylene). Poloxamers, may be customized by adjusting the degree of hydrophobicity and/or hydrophilicity by extending or retracting the length of the blocks. Non-limiting examples of poloxamers include poloxamer 407, poloxamer 188, poloxamer 127, or poloxamer 388. Certain poloxamers are understood to be safe for use in humans, see for example Singh-Joy and McLain (Int J Toxicol. 2008; 27 Suppl 2:93-128) which is incorporated by reference in its entirety for all purposes.

The term "polymerizable monomer" is used in accordance with its meaning in the art of polymer chemistry and refers to a compound that may covalently bind chemically to other monomer molecules (such as other polymerizable monomers that are the same or different) to form a polymer.

The term "branched polymer" is used in accordance with its meaning in the art of polymer chemistry and refers to a molecule including repeating subunits, wherein at least one repeating subunit (e.g., polymerizable monomer) is covalently bound to an additional subunit substituent (e.g., resulting from a reaction with a polymerizable monomer). For example a branched polymer has the formula:

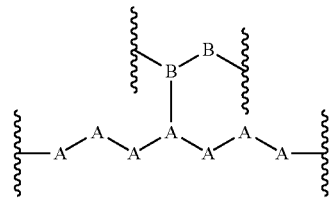

wherein 'A' is the first repeating subunit and 'B' is the second repeating subunit. In embodiments, the first repeating subunit (e.g., polyethylene glycol) is optionally different from the second repeating subunit (e.g., polymethylene glycol).

The term "block copolymer" is used in accordance with its ordinary meaning and refers to two or more portions (e.g., blocks) of polymerized monomers linked by a covalent bond. In embodiments, a block copolymer is a repeating pattern of polymers. In embodiments, the block copolymer includes two or more monomers in a periodic (e.g., repeating pattern) sequence. For example, a diblock copolymer has the formula: -B-B-B-B-B-B-A-A-A-A-A-, where 'B' is a first subunit and 'A' is a second subunit covalently bound together. A triblock copolymer therefore is a copolymer with three distinct blocks, two of which may be the same (e.g., -A-A-A-A-A-B-B-B-B-B-A-A-A-A-A-) or all three are different (e.g., -A-A-A-A-A-B-B-B-B-B-C-C-C-C-C-) where 'A' is a first subunit, 'B' is a second subunit, and 'C' is a third subunit, covalently bound together.

The term "amphiphilic polymer" as used herein refers to a polymer containing both hydrophilic and hydrophobic portions. In embodiments, the hydrophilic to hydrophobic portions are present in a 1 to 1 mass ratio. In embodiments, the hydrophilic to hydrophobic portions are present in a 1 to 2 mass ratio. In embodiments, the hydrophilic to hydrophobic portions are present in a 1 to 5 mass ratio. In embodiments, the hydrophilic to hydrophobic portions are present in a 2 to 1 mass ratio. In embodiments, the hydrophilic to hydrophobic portions are present in a 5 to 1 mass ratio. An amphiphilic polymer may be a diblock or triblock copolymer. In embodiments, the amphiphilic polymer may include two hydrophilic portions (e.g., blocks) and one hydrophobic portion (e.g., block). In embodiments, the hydrophilic block to hydrophobic to hydrophilic ratio is 1 to 1 to 1. In embodiments, the hydrophilic block to hydrophobic to hydrophilic ratio is 1.8 to 1 to 1.8. In embodiments, the hydrophilic block to hydrophobic to hydrophilic ratio is 2 to 1 to 2. In embodiments, the hydrophilic block to hydrophobic to hydrophilic ratio is 1 to 1 to 2.

The term "insoluble drug" used herein refers to a therapeutic agent that has low solubility in water. For example, low solubility in water refers to the solubility of a compound which is about 0.0005 mg/mL to about 10 mg/mL soluble in water. In embodiments, low solubility refers to the solubility of a compound which is less than about 10 mg/mL soluble in water. In embodiments, low solubility refers to the solubility of a compound which is less than about 1 mg/mL soluble in water. In embodiments, low solubility refers to the solubility of a compound which is about 1 µg/mL soluble in water. In embodiments, low solubility refers to the solubility of paclitaxel in water. Solubility is used in accordance with its ordinary meaning and refers to the maximum quantity of solute that can dissolve in a certain quantity of solvent (e.g., water) at standard experimental conditions. Insoluble drugs therefore, are considered to have low solubility in water at standard laboratory conditions (e.g., 25° C. and 1atm). Non-limiting examples of insoluble drugs include paclitaxel, docetaxel, amphotericin B, artemisinin, atovaquone, camptothecin, rapamycin, aprepitant, thymectacin, fenofibrate, budesonide, or insulin, see for example additional examples as described in Rabinow, Nature Reviews Drug Discovery 3, 785-796 (September 2004) and Yi et al (Nanomedicine (Long.) 10(16) 2537-2552, 2015), which are incorporated by reference in their entirety for all purposes. The solubility of an agent is related to the lipophilicity as measured by its partition coefficient. In embodiments, the insoluble drug forms a nanoscrystal.

A "therapeutic agent" as used herein refers to an agent (e.g., compound or composition) that when administered to a subject will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms or the intended therapeutic effect, e.g., treatment or amelioration of an injury, disease, pathology or condition, or their symptoms including any objective or subjective parameter of treatment such as abatement; remission; diminishing of symptoms or making the injury, pathology or condition more tolerable to the patient; slowing in the rate of degeneration or decline; making the final point of degeneration less debilitating; or improving a patient's physical or mental well-being.

The term "organic solvent" as used herein is used in accordance with its ordinary meaning in chemistry and refers to a solvent which includes carbon. Non-limiting examples of organic solvents include acetic acid, acetone, acetonitrile, benzene, 1-butanol, 2-butanol, 2-butanone, t-butyl alcohol, carbon tetrachloride, chlorobenzene, chloroform, cyclohexane, 1,2-dichloroethane, diethylene glycol, diethyl ether, diglyme (diethylene glycol, dimethyl ether), 1,2-dimethoxyethane (glyme, DME), dimethylformamide (DMF), dimethyl sulfoxide (DMSO), 1,4-dioxane, ethanol, ethyl acetate, ethylene glycol, glycerin, heptane, hexamethylphosphoramide (HMPA), hexamethylphosphorous, triamide (HMPT), hexane, methanol, methyl t-butyl ether (MTBE), methylene chloride, N-methyl-2-pyrrolidinone (NMP), nitromethane, pentane, petroleum ether (ligroine), 1-propanol, 2-propanol, pyridine, tetrahydrofuran (THF), toluene, triethyl amine, o-xylene, m-xylene, or p-xylene. In embodiments, the organic solvent is or includes chloroform, dichloromethane, methanol, ethanol, tetrahydrofuran, or dioxane.

The term "sonicating" as used herein refers to the process of applying sound energy to agitate particles in a sample. In situ, sonicating is applied using a sonicator such as an ultrasonic bath or an ultrasonic probe. In embodiments, the sound energy is at least 20 kHz. In embodiments, the sound energy is greater than 20 kHz. In embodiments, the sound energy is about 20 to about 40 kHz.

The term "macrolide" is used in accordance with its ordinary meaning in chemistry, and refers to a macrocyclic lactone ring to which one or more deoxy sugars is attached. Non-limiting examples of macrolides include erythromycin, clarithromycin, fidaxomicin, or azithromycin.

The term "steroid" is used in accordance with its plain ordinary meaning and refers to a a class of tetracyclic compounds with, three cyclohexane and one cyclopentane ring arranged with the structural formula:

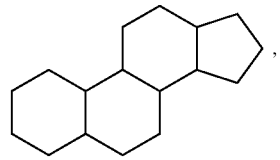 [SMILES: C1CCC2C(C1)CCC1C3CCCC3CCC21]

which is optionally substituted and may include one or more points of non-saturation (i.e. double bonds) within one or more of the rings. Steroids can vary in the number of functional groups or methyl groups attached to the rings, or differ in the level of saturation within the rings. Additional non limiting examples of steroids include cholesterol, cholic acid, progesterone, testosterone, or estradiol.

The term "nanocrystal" is used in accordance with their ordinary meaning and refer a solid material wherein constituents, (e.g., atoms) are arranged in a highly ordered (e.g., repetitive, periodic) lattice and wherein the longest dimension is less than or equal to 1000 nanometers.

II. Compositions, Constructs, and Cells

In an aspect is provided a nanoparticle including an insoluble drug and silica, wherein the nanoparticle includes the insoluble drug. In embodiments, the nanoparticle is an inorganic nanoparticle. In embodiments, the nanoparticle is a silica nanoparticle. In embodiments, the nanoparticle includes at least about 1 wt % of the insoluble drug. In embodiments, the nanoparticle includes about 1 to about 99.9 wt % of the insoluble drug. In embodiments, the nanoparticle includes about 50 to about 95 wt % of the insoluble drug. In embodiments, the nanoparticle includes about 80 to about 90 wt % of the insoluble drug. In embodiments, the nanoparticle includes greater than about 20 wt % of the insoluble drug. In embodiments, the nanoparticle includes less than about 20 wt % of the insoluble drug. In embodiments, the nanoparticle includes about 20 wt % of the insoluble drug. In embodiments, the nanoparticle includes 3 wt % of the insoluble drug. In embodiments, the nanoparticle includes about 19 wt % of the insoluble drug. In embodiments, the insoluble drug is in the form of a nanocrystal. In embodiments, the nanoparticle does not include any active pharmaceutical ingredient other than the insoluble drug. In embodiments, the properties of the nanoparticle include one or more of the properties identified herein for all other nanoparticle aspects and embodiments thereof.

In an aspect is provided a nanoparticle including an insoluble drug, silica, and a polymer. In embodiments, the nanoparticle is an inorganic nanoparticle. In embodiments, the nanoparticle is a silica nanoparticle. In embodiments, the insoluble drug is in the form of a nanocrystal. In embodiments, the polymer is an amphiphilic polymer. In embodiments, the amphiphilic polymer is a block (e.g., diblock or triblock) copolymer. In embodiments, the amphiphilic polymer is a diblock copolymer. In embodiments, the amphiphilic polymer is a triblock copolymer. In embodiments, the polymer is a poloxamer. In embodiments, the polymer is poloxamer 407 (e.g., a triblock copolymer consisting of a central hydrophobic block of polypropylene glycol flanked by two hydrophilic blocks of polyethylene glycol, wherein the approximate lengths of the two PEG blocks is 101 polymerized monomers while the approximate length of the propylene glycol block is approximately 56 polymerized monomers). In embodiments, the polymer is polyvinylpyrrolidone. In embodiments, the nanoparticle does not include any active pharmaceutical ingredient other than said insoluble drug. In embodiments, the properties of the nanoparticle includes one or more of the properties identified herein for all other nanoparticle aspects and embodiments thereof.

In another aspect is provided a nanoparticle obtainable by a process including (a) mixing an insoluble drug and an amphiphilic polymer in an organic solvent thereby forming a reaction mixture (e.g. in a reaction vessel); (b) removing the organic solvent from the reaction mixture (e.g. from the reaction vessel), adding a solvent (e.g., water or aqueous solution) to the reaction mixture to form an aqueous reaction mixture, and sonicating the aqueous reaction mixture to form a nanocrystal; and (c) mixing tetraethyl orthosilicate (TEOS), phenyltrimethoxysilane (PTMS), and hydrolyzed aminopropyltriethoxy silane (APTES) with the nanocrystal to form a nanoparticle. In embodiments, the process further includes isolating the nanoparticle from the reaction mixture formed by step (c). In embodiments, the isolating of the nanoparticle includes the use of a sucrose gradient solution. In embodiments, hydrolyzed aminopropyltriethoxy silane refers to aminopropyltriethoxy silane in water. In embodiments, hydrolyzed aminopropyltriethoxy silane refers to aminopropyltriethoxy silane which has undergone hydrolysis, for example

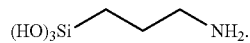

In embodiments, step (c) does not include NH$_4$OH or NaOH. In embodiments, step (c) does not include NaOH. In embodiments, step (c) does not include NH$_4$OH. In embodiments, the nanoparticle obtainable by a process further includes isolating the nanoparticle following step (c). In embodiments, the removing of the organic solvent removes most (i.e. more the 50%, 60%, 70%, 80%, 90%, 95%, 96%, 97%, 98%, or 99%, or removing all (100%)) of the organic solvent from the reaction mixture. In embodiments, the adding of the solvent is performed after the removing of the organic solvent. In embodiments, the properties of the nanoparticle obtainable by this process include one or more of the properties identified herein for all other nanoparticle aspects, including embodiments thereof.

In embodiments, the organic solvent of part (a) is or includes acetic acid, acetone, acetonitrile, benzene, 1-butanol, 2-butanol, 2-butanone, t-butyl alcohol, carbon tetrachloride, chlorobenzene, chloroform, cyclohexane, 1,2-dichloroethane, diethylene glycol, diethyl ether, diglyme (diethylene glycol, dimethyl ether), 1,2-dimethoxyethane (glyme, DME), dimethylformamide (DMF), dimethyl sulfoxide (DMSO), 1,4-dioxane, ethanol, ethyl acetate, ethylene glycol, glycerin, heptane, hexamethylphosphoramide (IMPA), hexamethylphosphorous, triamide (HMPT), hexane, methanol, methyl t-butyl ether (MTBE), methylene chloride, N-methyl-2-pyrrolidinone (NMP), nitromethane, pentane, petroleum ether (ligroine), 1-propanol, 2-propanol, pyridine, tetrahydrofuran (THF), toluene, triethyl amine, o-xylene, m-xylene, or p-xylene. In embodiments, the organic solvent is or includes chloroform, dichloromethane, methanol, ethanol, tetrahydrofuran, or dioxane. In embodiments, the organic solvent is chloroform, dichloromethane, methanol, ethanol, tetrahydrofuran, or dioxane. In embodiments, the organic solvent is or includes chloroform. In embodiments, the solvent in part (b) is or includes chloroform, dichloromethane, methanol, ethanol, tetrahydrofuran, dioxane, or water. In embodiments, the solvent in part (b) includes a salt.

In embodiments, the mass ratio of TEOS to PTMS is about 1 to 1 to about 5 to 1. In embodiments, the mass ratio of TEOS to PTMS is about 1 to 1 to about 3 to 1. In embodiments, the mass ratio of TEOS to PTMS is about 1 to 1 to about 2 to 1. In embodiments, the mass ratio of TEOS to PTMS is about 1 to 1 to about 1.5 to 1. In embodiments, the mass ratio of TEOS to PTMS is about 1 to 1. In embodiments, the mass ratio of TEOS to PTMS is about 1.1 to 1. In embodiments, the mass ratio of TEOS to PTMS is about 1.2 to 1. In embodiments, the mass ratio of TEOS to PTMS is about 1.3 to 1. In embodiments, the mass ratio of TEOS to PTMS is about 1.4 to 1. In embodiments, the mass ratio of TEOS to PTMS is about 1.5 to 1. In embodiments, the mass ratio of TEOS to PTMS is about 1.6 to 1. In embodiments, the mass ratio of TEOS to PTMS is about 1.7 to 1. In embodiments, the mass ratio of TEOS to PTMS is about 1.8 to 1. In embodiments, the mass ratio of TEOS to PTMS is about 1.9 to 1. In embodiments, the mass ratio of TEOS to PTMS is about 2 to 1.

In embodiments, the mass ratio of PTMS to the insoluble drug is about 50 to 1. In embodiments, the mass ratio of PTMS to the insoluble drug is about 40 to 1. In embodiments, the mass ratio of PTMS to the insoluble drug is about 30 to 1. In embodiments, the mass ratio of PTMS to the insoluble drug is about 20 to 1. In embodiments, the mass ratio of PTMS to the insoluble drug is about 10 to 1. In embodiments, the mass ratio of PTMS to the insoluble drug is about 5 to 1. In embodiments, the mass ratio of PTMS to the insoluble drug is about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 to 1. In embodiments, the mass ratio of PTMS to the insoluble drug is about 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 to 1. In embodiments, the mass ratio of PTMS to the insoluble drug is about 30, 31, 32, 33, 34, 35, 36, 37, 38, 39, 40, 41, 42, 43, 44, 45, 46, 47, 48, 49, or about 50 to 1.

In embodiments, the mass ratio of PTMS to the insoluble drug is about 32, 33, 34, 35, 36, 37, 38, 39, 40, 41, or about 42 to 1. In embodiments, the mass ratio of PTMS to the insoluble drug is about 32 to 1. In embodiments, the mass ratio of PTMS to the insoluble drug is about 42 to 1.

In embodiments, the insoluble drug has a solubility of about 0.0005 mg/mL to about 10 mg/mL in water. In embodiments, the insoluble drug has a solubility of less than about 0.5 µg/mL in water. In embodiments, the insoluble drug has a solubility of less than about 0.1 µg/mL in water. In embodiments, the insoluble drug has a solubility of less than about 0.2 µg/mL in water. In embodiments, the insoluble drug has a solubility of less than about 1 µg/mL in water. In embodiments, the insoluble drug has a solubility of less than about 2.5 µg/mL in water. In embodiments, the insoluble drug has a solubility of less than about 3 µg/mL in water. In embodiments, the insoluble drug has a solubility of less than about 5 µg/mL in water. In embodiments, the insoluble drug has a solubility of less than about 10 µg/mL in water. In embodiments, the insoluble drug has a solubility of less than about 20 µg/mL in water. In embodiments, the insoluble drug has a solubility of less than about 50 µg/mL in water. In embodiments, the insoluble drug has a solubility of less than about 80 µg/mL in water. In embodiments, the insoluble drug has a solubility of less than about 0.1 mg/mL in water. In embodiments, the insoluble drug has a solubility of less than about 0.2 mg/mL in water. In embodiments, the insoluble drug has a solubility of less than about 2.5 mg/mL in water. In embodiments, the insoluble drug has a solubility of less than about 3 mg/mL in water. In embodiments, the insoluble drug has a solubility of less than about 5 mg/mL in water. In embodiments, the insoluble drug has a solubility of less than about 10 mg/mL in water. In embodiments, the insoluble drug has a solubility of less than about 20 mg/mL in water. In embodiments, the insoluble drug has a solubility of less than about 50 mg/mL in water. In embodiments, the insoluble drug has a solubility of less than about 80 mg/mL in water.

In embodiments, the insoluble drug has a solubility of about 0.5 µg/mL to about 10 mg/mL in water. In embodiments, the insoluble drug has a solubility of about 0.1 µg/mL to about 1 mg/mL in water. In embodiments, the insoluble drug has a solubility of about 50 to about 100 µg/mL in water. In embodiments, the insoluble drug has a solubility of about 0.5 µg/mL in water. In embodiments, the insoluble drug has a solubility of about 0.1 µg/mL in water. In embodiments, the insoluble drug has a solubility of about 0.2 µg/mL in water. In embodiments, the insoluble drug has a solubility of about 1 µg/mL in water. In embodiments, the insoluble drug has a solubility of about 2.5 µg/mL in water. In embodiments, the insoluble drug has a solubility of about 3 µg/mL in water. In embodiments, the insoluble drug has a solubility of about 5 µg/mL in water. In embodiments, the insoluble drug has a solubility of about 10 µg/mL in water. In embodiments, the insoluble drug has a solubility of about 20 µg/mL in water. In embodiments, the insoluble drug has a solubility of about 50 µg/mL in water. In embodiments, the insoluble drug has a solubility of about 80 µg/mL in water. In embodiments, the insoluble drug has a solubility of about 0.1 mg/mL in water. In embodiments, the insoluble drug has a solubility of about 0.2 mg/mL in water. In embodiments, the insoluble drug has a solubility of about 2.5 mg/mL in water. In embodiments, the insoluble drug has a solubility of about 3 mg/mL in water. In embodiments, the insoluble drug has a solubility of about 5 mg/mL in water. In embodiments, the insoluble drug has a solubility of about 10 mg/mL in water. In embodiments, the insoluble drug has a solubility of about 20 mg/mL in water. In embodiments, the insoluble drug has a solubility of about 50 mg/mL in water. In embodiments, the insoluble drug has a solubility of about 80 mg/mL in water. It is understood the solubility referred to within the disclosure is measured at standard laboratory conditions (e.g., 25° C. and 1atm). In embodiments, the insoluble drug may be referred to as having poor or very poor solubility in water (e.g., less than about 55 mg/mL). In embodiments, an insoluble drug has the solubility of paclitaxel in water. In embodiments, an insoluble drug has the solubility of camptothecin in water.

In embodiments, low solubility refers to the solubility of a compound which is less than about 0.6 mg/mL soluble in water. In embodiments, low solubility refers to the solubility of a compound which is less than about 0.5 mg/mL soluble in water. In embodiments, low solubility refers to the solubility of a compound which is less than about 0.1 mg/mL soluble in water. In embodiments, low solubility refers to the solubility of a compound which is less than about 0.01 mg/mL soluble in water.

In embodiments, the insoluble drug is a macrolide, steroid, or terpene. In embodiments, the insoluble drug is a macrolide. In embodiments, the insoluble drug is a steroid (e.g., corticosteroid). In embodiments, the insoluble drug is a terpene. In embodiments, the insoluble drug includes a terpene. In embodiments, the insoluble drug is griseofulvin, verapamil, sirolimus, dexmethylphenidate hydrochloride, morphine sulfate, methylphenidate hydrochloride, diltiazem, tizanidine hydrochloride, aprepitant, fenofibrate, nabilone, megestrol acetate, fenofibrate, naproxen sodium, theophylline, paliperidone palmitate, 2-methoxyestradiol, guanylhydrazone, paclitaxel, or thymectacin. In embodiments, the insoluble drug is carbamazepine, megestrol acetate, paliperidone palmitate, insulin, ketoprofen, azithromycin, albendazole, tarazepide, griseofulvin, mitotane, cilostazol, aphidicolin, buparvaquone, fenofibrate, cytokine inhibitor, emend, rapamune, probucol, danazol, naproxen, loviride, clofazimine, oridonin, ascorbyl palmitate, dihydroartemisinin, omeprazole, thymectacin, paclitaxel, hydrocortisone, prednisolone, hexadecadrol, budesonide, fluticasone, or busulfan. In embodiments, the insoluble drug is a taxane. In embodiments, the insoluble drug is paclitaxel. In embodiments, the insoluble drug is camptothecin or paclitaxel. In embodiments, the insoluble drug is camptothecin.

In an aspect is a cell including the nanoparticle (e.g., a nanoparticle including an insoluble drug) as described herein, including embodiments. Thus, in embodiments, the properties of the nanoparticle include one or more of the properties identified herein for all other nanoparticle aspects and embodiments thereof. In embodiments, the cell is a tumor tropic cell, macrophage, stem cell (e.g., neural, mesenchymal), or T-cell. In embodiments, the cell is neural stem cell, a mesenchymal stem cell, a mesenchymal stromal cell, a hematopoetic stem cell, T-lymphocyte, a macrophage, or a liver stem cell. In embodiments, the cell is a neural stem cell. In embodiments, the cell is genetically modified. In embodiments, the cell is a genetically modified stem cell. In embodiments, the cell is a genetically modified neural stem cell. In embodiments, the neural stem cell is a human HB1.F3 stem cell. In embodiments, the nanoparticle is within the cell. In embodiments, the nanoparticle is incorporated within the cell via the enhanced permeability and retention (EPR) effect.

In an aspect is provided a nanoparticle-cell construct including a monovalent nanoparticle covalently attached to a protein (e.g., a cell-surface protein) through a covalent linker. In embodiments, the protein is attached to the cell and is a cell surface protein. In embodiments, the protein includes a sulfur-containing amino acid. In embodiments, the protein includes methionine, cysteine, homocysteine, or taurine. In embodiments, the protein includes a sulfhydryl moiety. In embodiments of the nanoparticle-cell construct, the nanoparticle includes an insoluble drug. In embodiments of the nanoparticle-cell construct, the nanoparticle includes an insoluble drug and an amphiphilic polymer (e.g., poloxamer 407). The monovalent nanoparticle may be a monovalent form of a nanoparticle described in any aspect set forth herein, including embodiments thereof. Thus, in embodiments, the properties of the monovalent nanoparticle include one or more of the properties identified herein for all other nanoparticle aspects and embodiments thereof.

In embodiments, the protein is a cell surface protein. A cell surface protein refers to a protein at the surface of a cell. In embodiments, the cell surface protein is a transmembrane protein. In embodiments, the protein is in contact with the extracellular matrix (e.g., extracellular matrix associated with a cancer cell or in contact with a cancer cell). In embodiments, the protein is in contact with a tumor. In embodiments, the tumor includes stromal cells, immune cells, proteins, and extracellular matrix generated by those cells. In embodiments, immune cells, stromal cells, proteins associated with the immune cells, proteins associated with the stromal cells, and the extracellular matrix generated from immune cells and stromal cells form part of a tumor.

In embodiments, the covalent linker has the formula: -$L^2$-$X^1$-$L^1$-$X^2$-$L^3$- (Ia) or -$L^2$-$X^2$-$L^3$- (Ib). $X^1$ and $X^2$ are independently a bioconjugate linker or a bond, wherein one of $X^1$ or $X^2$ is a bioconjugate linker. $L^1$ is independently a polymeric linker. $L^2$ is independently a bond, or a linker that includes: —$NR^{1a}$—, —O—, —S—, —C(O)—, —C(O)O—, —S(O)—, —S(O)$_2$—, —$NR^{1a}$C(O)—, —C(O)$NR^{1b}$—, —C(O)(CH$_2$)$_{z1}$—, —$NR^{1a}$C(O)O—, —$NR^{1a}$C(O)$NR^{1b}$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $L^3$ is independently a bond, —$NR^{2a}$—, —O—, —S—, —C(O)—, —C(O)O—, —S(O)—, —S(O)$_2$—, —$NR^{2a}$C(O)—, —C(O)$NR^{2b}$—, —C(O)(CH$_2$)$_{z2}$—, —$NR^{2a}$C(O)O—, —$NR^{2a}$C(O)$NR^{2b}$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $R^{1a}$, $R^{2a}$, $R^{1b}$, and $R^{2b}$ are independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NINH$_2$, —ONH$_2$, —NHC=(O)NHNH$_2$, —NHC=(O)NH$_2$, —NHSO$_2$H, —NHC=(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; the symbols z1 and z2 are independently an integer from 1 to 10. In embodiments, $R^{1a}$, $R^{2a}$, $R^{1b}$, and $R^{2b}$ are independently hydrogen, halogen, —CF$_3$, —CN, —OH, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; the symbols z1 and z2 are independently an integer from 1 to 10. In formula (Ib), $X^2$ is a bioconjugate linker. In embodiments, the covalent linker is (Ib) and $X^2$ a bioconjugate linker. In embodiments, the covalent linker is (Ia) and $X^1$ a bioconjugate linker. In embodiments, the nanoparticle-cell construct includes a plurality of covalent linkers. In embodiments, the plurality of covalent linkers are chemically identical to one another. In embodiments, the plurality of covalent linkers are chemically different from one another.

Non-limiting examples of bioconjugate linkers include

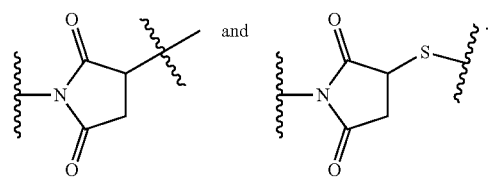 [SMILES: *C1CC(=O)N(*)C1=O ; *SC1CC(=O)N(*)C1=O]

In embodiments, the bioconjugate linker is

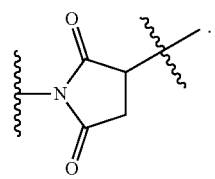 [SMILES: *C1CC(=O)N(*)C1=O]

In embodiments, the bioconjugate linker is

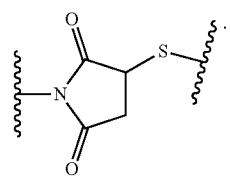 [SMILES: *SC1CC(=O)N(*)C1=O]

Non-limiting examples of bioconjugate reactive groups include —NH2, —COOH,

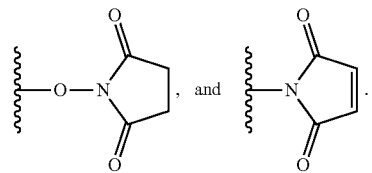 [SMILES: *ON1C(=O)CCC1=O ; *N1C(=O)C=CC1=O]

In embodiments, the bioconjugate reactive group is

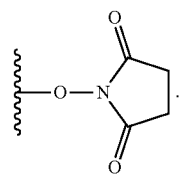 [SMILES: *ON1C(=O)CCC1=O]

In embodiments, the bioconjugate reactive group is

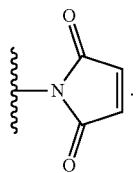

In embodiments, $L^2$ is independently a bond, —NR$^{1a}$—, —O—, —S—, —C(O)—, —C(O)O—, —S(O)—, —S(O)$_2$—, —NR$^{1a}$C(O)—, —C(O)NR$^{1b}$—, —C(O)(CH$_2$)$_{z1}$—, —NR$^{1a}$C(O)O—, —NR$^{1a}$C(O)NR$^{1b}$-substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, $L^2$ has the formula -L$^{2A}$-L$^{2B}$-L$^{2A}$ and L$^{2B}$ are independently a bond, —NR$^{1a}$—, —O—, —S—, —C(O)—, —C(O)O—, —S(O)—, —S(O)$_2$—, —NR$^{1a}$C(O)—, —C(O)NR$^{1b}$—, —C(O)(CH$_2$)$_{z1}$—, —NR$^{1a}$C(O)O—, —NR$^{1a}$C(O)NR$^{1b}$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^{2A}$ is a substituted (e.g., substituted with a substituent group, a size-limited substituent group, or lower substituent group) or unsubstituted alkylene, substituted (e.g., substituted with a substituent group, a size-limited substituent group, or lower substituent group) or unsubstituted heteroalkylene, substituted (e.g., substituted with a substituent group, a size-limited substituent group, or lower substituent group) or unsubstituted cycloalkylene, substituted (e.g., substituted with a substituent group, a size-limited substituent group, or lower substituent group) or unsubstituted heterocycloalkylene, substituted (e.g., substituted with a substituent group, a size-limited substituent group, or lower substituent group) or unsubstituted arylene, or substituted (e.g., substituted with a substituent group, a size-limited substituent group, or lower substituent group) or unsubstituted heteroarylene. In embodiments, $L^{2B}$ is a substituted (e.g., substituted with a substituent group, a size-limited substituent group, or lower substituent group) or unsubstituted alkylene, substituted (e.g., substituted with a substituent group, a size-limited substituent group, or lower substituent group) or unsubstituted heteroalkylene, substituted (e.g., substituted with a substituent group, a size-limited substituent group, or lower substituent group) or unsubstituted cycloalkylene, substituted (e.g., substituted with a substituent group, a size-limited substituent group, or lower substituent group) or unsubstituted heterocycloalkylene, substituted (e.g., substituted with a substituent group, a size-limited substituent group, or lower substituent group) or unsubstituted arylene, or substituted (e.g., substituted with a substituent group, a size-limited substituent group, or lower substituent group) or unsubstituted heteroarylene. In embodiments, $L^{2A}$ and $L^{2B}$ are independently an unsubstituted alkylene, unsubstituted heteroalkylene, unsubstituted cycloalkylene, unsubstituted heterocycloalkylene, unsubstituted arylene, or unsubstituted heteroarylene.

In embodiments, the nanoparticle is further covalently attached to one or more nanoparticle substituents. In embodiments, the nanoparticle further includes one or more nanoparticle substituents. In embodiments, the nanoparticle substituent includes a polymeric moiety. In embodiments, the polymeric moiety is a polyethylene glycol moiety.

In embodiments, the nanoparticle substituent is independently: -L$^2$-X$^1$—R$^3$ formula (i); -L$^2$-X$^1$-L$^1$-X$^3$ formula (ii); or -L$^2$-X$^3$ formula (iii). L$^1$, L$^2$, and X$^1$ are as defined herein and are optionally different. R$^3$ is independently a polymeric moiety. X$^3$ is independently a bioconjugate reactive group. In embodiments, one or more of L$^1$, L$^2$, X$^1$, and X$^3$ are the same.

In embodiments, $L^1$ is a linear polymeric linker. In embodiments, $L^1$ is a branched polymeric linker. In embodiments, a nanoparticle includes multiple, optionally different, $L^1$ linkers and each $L^1$ linker is independently a linear or branched polymeric linker. In embodiments, $L^1$ is branched with 3 to 10 branches. In embodiments, when $L^1$ is branched, $L^1$ is includes one bioconjugate reactive group. In embodiments, when $L^1$ is branched, $L_1$ includes a plurality of bioconjugate reactive groups.

In embodiments, $L^1$ is divalent polyethylene glycol. In embodiments, $L^1$ is divalent-PEG$_{400}$-SH. In embodiments, $L^1$ is divalent-PEG$_{1000}$-SH. In embodiments, $L^1$ is divalent-PEG$_{2000}$-SH. In embodiments, $L^1$ is divalent-PEG$_{5000}$-SH. It will be understood that the immediately preceding divalent PEG-SH groups may be bonded to a separate moiety through the terminal thiol group where the bond between sulfur and hydrogen is replaced with a bond between sulfur and another moiety. In embodiments, $L^1$ is divalent-TFP-(PEG$_{11}$)$_3$. It will be understood that the immediately preceding divalent TFP-PEG groups may be bonded to a separate moiety through the tetrafluorophenyl (TFP) ester group wherein the bond is between the tetrafluorophenyl ester and another moiety. In embodiments, $L^1$ is divalent NHS-(PEG$_{24}$)$_3$. It will be understood that the immediately preceding divalent NSH-PEG groups may be bonded to a separate moiety through the N-hydroxysuccinimide group where the bond is between N-hydroxysuccinimide and another moiety. In embodiments, $L^1$ is divalent polyethylene glycol with an average molecular weight of about 400 g/mol, 484 g/mol, 1000 g/mol, 1450 g/mol, 1500 g/mol, 2000 g/mol, or 5000 g/mol. In embodiments, $L^1$ is divalent polyethylene glycol with an average molecular weight of about 400 g/mol, 484 g/mol, 1000 g/mol, 1450 g/mol, 1500 g/mol, 2000 g/mol, or 5000 g/mol within +/−10, 20, 30, 40, or 50 of the average molecular weight.

In embodiments, $L^1$ is divalent polyethylene glycol with an average molecular weight of about 400 g/mol. In embodiments, $L^1$ is divalent polyethylene glycol with an average molecular weight of about 484 g/mol. In embodiments, $L^1$ is divalent polyethylene glycol with an average molecular weight of about 484 g/mol per arm. In embodiments, $L^1$ is divalent polyethylene glycol with an average molecular weight of about 1000 g/mol. In embodiments, Li is divalent polyethylene glycol with an average molecular weight of about 1450 g/mol. In embodiments, $L^1$ is divalent polyethylene glycol with an average molecular weight of about 1500 g/mol. In embodiments, $L^1$ is divalent polyethylene glycol with an average molecular weight of about 2000 g/mol. In embodiments, $L^1$ is divalent polyethylene glycol with an average molecular weight of about 5000 g/mol.

A person of ordinary skill in the art will understand when a variable (e.g., moiety or linker) of a compound or of a compound genus (e.g., a genus described herein) is described by a name or formula of a standalone compound with all valencies filled, the unfilled valence(s) of the variable will be dictated by the context in which the variable is used. For example, when a variable of a compound as described herein is connected (e.g., bonded) to the remainder of the compound through a single bond, that variable is understood to represent a monovalent form (i.e., capable of forming a single bond due to an unfilled valence) of a standalone compound (e.g., if the variable is named "methane" in an embodiment but the variable is known to be attached by a single bond to the remainder of the compound, a person of ordinary skill in the art would understand that the variable is actually a monovalent form of methane, i.e., methyl or —CH). Likewise, for a linker variable (e.g., $L^1$, $L^2$, or $L^3$ as described herein), a person of ordinary skill in the art will understand that the variable is the divalent form of a standalone compound (e.g., if the variable is assigned to "PEG" or "polyethylene glycol" in an embodiment but the variable is connected by two separate bonds to the remainder of the compound, a person of ordinary skill in the art would understand that the variable is a divalent (i.e., capable of forming two bonds through two unfilled valences) form of PEG instead of the standalone compound PEG).

In embodiments, $L^1$ is a polymeric linker further including substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^1$ is a polymeric linker further including unsubstituted alkylene, unsubstituted heteroalkylene, unsubstituted cycloalkylene, unsubstituted heterocycloalkylene, unsubstituted arylene, or unsubstituted heteroarylene.

In embodiments, $L^2$ is independently a bond, $-NR^{1a}-$, $-O-$, $-S-$, $-C(O)-$, $-C(O)O-$, $-S(O)-$, $-S(O)_2-$, $-NR^{1a}C(O)-$, $-C(O)NR^{1b}-$, $-C(O)(CH_2)_{z1}-$, $-NR^{1a}C(O)O-$, $-NR^{1a}C(O)NR^{1b}$-substituted or unsubstituted alkylene (e.g. $C_1$-$C_8$ alkylene, $C_1$-$C_6$ alkylene, or $C_1$-$C_4$ alkylene), substituted or unsubstituted heteroalkylene (e.g. 2 to 10 membered heteroalkylene, 2 to 8 membered heteroalkylene, 4 to 8 membered heteroalkylene, 2 to 6 membered heteroalkylene, or 2 to 4 membered heteroalkylene), substituted or unsubstituted cycloalkylene (e.g. $C_3$-$C_8$ cycloalkylene, $C_4$-$C_8$ cycloalkylene, or $C_5$-$C_6$ cycloalkylene), substituted or unsubstituted heterocycloalkylene (e.g. 3 to 8 membered heterocycloalkylene, 4 to 8 membered heterocycloalkylene, or 5 to 6 membered heterocycloalkylene), substituted or unsubstituted arylene (e.g. $C_6$-$C_{10}$ arylene or $C_6$ arylene), or substituted or unsubstituted heteroarylene (e.g. 5 to 10 membered heteroarylene, 5 to 9 membered heteroarylene, or 5 to 6 membered heteroarylene).

In embodiments, $L^2$ has the formula:

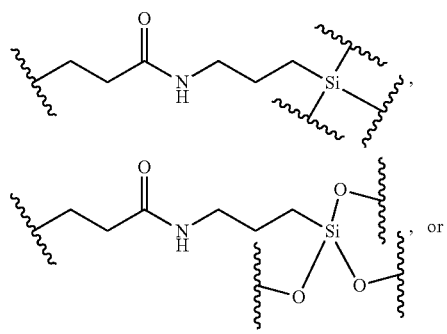

In embodiments, $L^2$ has the formula:

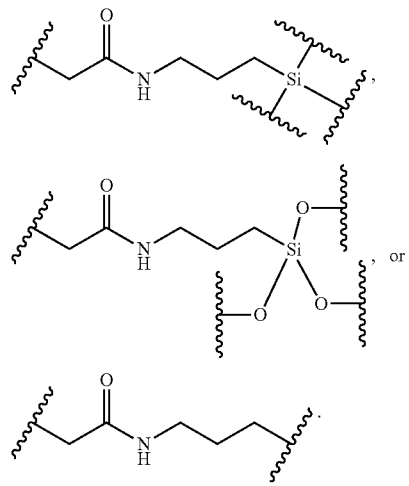

In embodiments, $L^2$ has the formula:

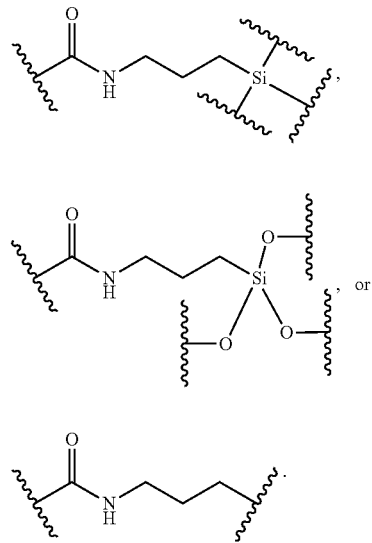

In embodiments, $L^2$ has the formula:

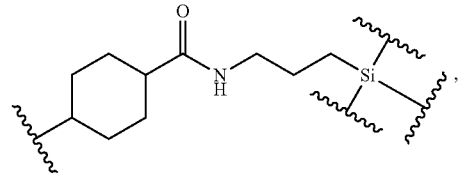

53

-continued

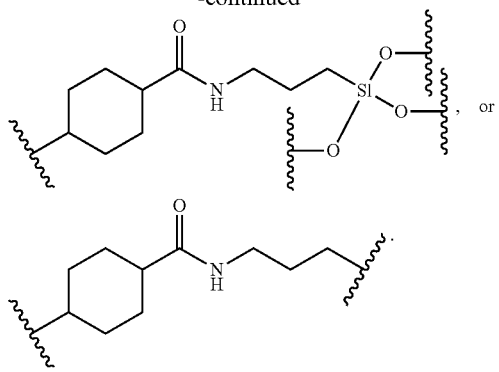, or

In embodiments, L² has the formula:

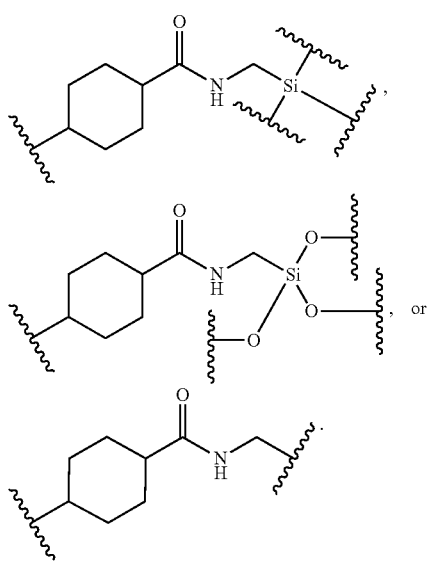

In embodiments, L² has the formula:

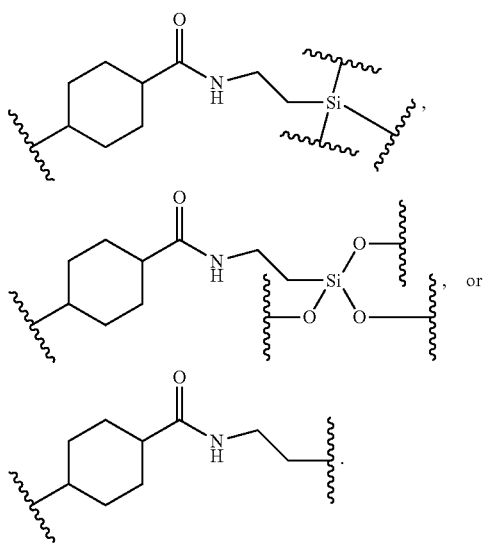

54

In embodiments, L² has the formula:

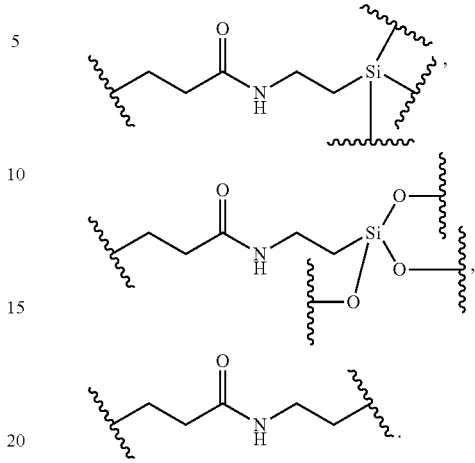

In embodiments, L² is independently a bond, —NR$^{1a}$—, —O—, —S—, —C(O)—, —C(O)O—, —S(O)—, —S(O)$_2$—, —NR$^{1a}$C(O)—, —C(O)NR$^{1b}$—, —C(O)(CH$_2$)$_{z1}$—, —NR$^{1a}$C(O)O—, —NR$^{1a}$C(O)NR$^{1b}$—, R$^4$-substituted or unsubstituted alkylene (e.g. C$_1$-C$_8$ alkylene, C$_1$-C$_6$ alkylene, or C$_1$-C$_4$ alkylene), R$^4$-substituted or unsubstituted heteroalkylene (e.g. 2 to 10 membered heteroalkylene, 2 to 8 membered heteroalkylene, 4 to 8 membered heteroalkylene, 2 to 6 membered heteroalkylene, or 2 to 4 membered heteroalkylene), R$^4$-substituted or unsubstituted cycloalkylene (e.g. C$_3$-C$_8$ cycloalkylene, C$_4$-C$_8$ cycloalkylene, or C$_5$-C$_6$ cycloalkylene), R$^4$-substituted or unsubstituted heterocycloalkylene (e.g. 3 to 8 membered heterocycloalkylene, 4 to 8 membered heterocycloalkylene, or 5 to 6 membered heterocycloalkylene), R$^4$-substituted or unsubstituted arylene (e.g. C$_6$-C$_{10}$ arylene or C$_6$ arylene), or R$^4$-substituted or unsubstituted heteroarylene (e.g. 5 to 10 membered heteroarylene, 5 to 9 membered heteroarylene, or 5 to 6 membered heteroarylene). In embodiments, L² is independently a bond, —NR$^{1a}$—, —O—, —S—, —C(O)—, —C(O)O—, —S(O)—, —S(O)$_2$—, NR$^{1a}$C(O)—, —C(O)NR$^{1b}$—, —C(O)(CH$_2$)$_{z1}$—, —NR$^{1a}$C(O)O—, —NR$^{1a}$C(O)NR$^{1b}$—, unsubstituted alkylene (e.g. C$_1$-C$_8$ alkylene, C$_1$-C$_6$ alkylene, or C$_1$-C$_4$ alkylene), unsubstituted heteroalkylene (e.g. 2 to 10 membered heteroalkylene, 2 to 8 membered heteroalkylene, 4 to 8 membered heteroalkylene, 2 to 6 membered heteroalkylene, or 2 to 4 membered heteroalkylene), unsubstituted cycloalkylene (e.g. C$_3$-C$_8$ cycloalkylene, C$_4$-C$_8$ cycloalkylene, or C$_5$-C$_6$ cycloalkylene), unsubstituted heterocycloalkylene (e.g. 3 to 8 membered heterocycloalkylene, 4 to 8 membered heterocycloalkylene, or 5 to 6 membered heterocycloalkylene), unsubstituted arylene (e.g. C$_6$-C$_{10}$ arylene or C$_6$ arylene), or unsubstituted heteroarylene (e.g. 5 to 10 membered heteroarylene, 5 to 9 membered heteroarylene, or 5 to 6 membered heteroarylene).

R$^4$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O) NHNH$_2$, —NHC=(O) NH$_2$, —NHSO$_2$H, —NHC=(O)H, —NHC(O)—OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, R$^5$-substituted or unsubstituted alkyl (e.g. $C_1$-$C_8$ alkyl, $C_1$-$C_6$ alkyl, or $C_1$-$C_4$ alkyl), $R^5$-substituted or unsubstituted heteroalkyl (e.g. 2 to 8 membered heteroalkyl, 2 to 6 membered heteroalkyl, or 2 to 4 membered heteroalkyl), $R^5$-substituted or unsubstituted cycloalkyl (e.g. $C_3$-$C_8$ cycloalkyl, $C_4$-$C_8$ cycloalkyl, or $C_5$-$C_6$ cycloalkyl), $R^5$-substituted or unsubstituted heterocycloalkyl (e.g. 3 to 8 membered heterocycloalkyl, 4 to 8 membered heterocycloalkyl, or 5 to 6 membered heterocycloalkyl), $R^5$-substituted or unsubstituted aryl (e.g. $C_6$-$C_{10}$ aryl or $C_6$ aryl), or $R^5$-substituted or unsubstituted heteroaryl (e.g. 5 to 10 membered heteroaryl, 5 to 9 membered heteroaryl, or 5 to 6 membered heteroaryl).

In embodiments, $L^3$ is independently a bond, —$NR^{2a}$—, —O—, —S—, —C(O)—, —C(O)O—, —S(O)—, —S(O)$_2$—, —$NR^{2a}$C(O)—, —C(O)$NR^{2b}$—, —C(O)(CH$_2$)$_{z2}$—, —$NR^{2a}$C(O)O—, —$NR^{2a}$C(O)$NR^{2b}$—, substituted or unsubstituted alkylene (e.g. $C_1$-$C_8$ alkylene, $C_1$-$C_6$ alkylene, or $C_1$-$C_4$ alkylene), substituted or unsubstituted heteroalkylene (e.g. 2 to 10 membered heteroalkylene, 2 to 8 membered heteroalkylene, 4 to 8 membered heteroalkylene, 2 to 6 membered heteroalkylene, or 2 to 4 membered heteroalkylene), substituted or unsubstituted cycloalkylene (e.g. $C_3$-$C_8$ cycloalkylene, $C_4$-$C_8$ cycloalkylene, or $C_5$-$C_6$ cycloalkylene), substituted or unsubstituted heterocycloalkylene (e.g. 3 to 8 membered heterocycloalkylene, 4 to 8 membered heterocycloalkylene, or 5 to 6 membered heterocycloalkylene), substituted or unsubstituted arylene (e.g. $C_6$-$C_{10}$ arylene or $C_6$ arylene), or substituted or unsubstituted heteroarylene (e.g. 5 to 10 membered heteroarylene, 5 to 9 membered heteroarylene, or 5 to 6 membered heteroarylene).

In embodiments, $L^3$ is independently a bond, —$NR^{2a}$—, —O—, —S—, —C(O)—, —C(O)O—, —S(O)—, —S(O)$_2$—, —$NR^{2a}$C(O)—, —C(O)$NR^{2b}$—, —C(O)(CH$_2$)$_{z2}$—, —$NR^{2a}$C(O)O—, —$NR^{2a}$C(O)$NR^{2b}$—, $R^6$-substituted or unsubstituted alkylene (e.g. $C_1$-$C_8$ alkylene, $C_1$-$C_6$ alkylene, or $C_1$-$C_4$ alkylene), $R^6$-substituted or unsubstituted heteroalkylene (e.g. 2 to 10 membered heteroalkylene, 2 to 8 membered heteroalkylene, 4 to 8 membered heteroalkylene, 2 to 6 membered heteroalkylene, or 2 to 4 membered heteroalkylene), $R^6$-substituted or unsubstituted cycloalkylene (e.g. $C_3$-$C_8$ cycloalkylene, $C_4$-$C_8$ cycloalkylene, or $C_5$-$C_6$ cycloalkylene), $R^6$-substituted or unsubstituted heterocycloalkylene (e.g. 3 to 8 membered heterocycloalkylene, 4 to 8 membered heterocycloalkylene, or 5 to 6 membered heterocycloalkylene), $R^6$-substituted or unsubstituted arylene (e.g. $C_6$-$C_{10}$ arylene or $C_6$ arylene), or $R^6$-substituted or unsubstituted heteroarylene (e.g. 5 to 10 membered heteroarylene, 5 to 9 membered heteroarylene, or 5 to 6 membered heteroarylene).

$R^6$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F $R^7$-substituted or unsubstituted alkyl (e.g. $C_1$-$C_8$ alkyl, $C_1$-$C_6$ alkyl, or $C_1$-$C_4$ alkyl), $R^7$-substituted or unsubstituted heteroalkyl (e.g. 2 to 8 membered heteroalkyl, 2 to 6 membered heteroalkyl, or 2 to 4 membered heteroalkyl), $R^7$-substituted or unsubstituted cycloalkyl (e.g. $C_3$-$C_8$ cycloalkyl, $C_4$-$C_8$ cycloalkyl, or $C_5$-$C_6$ cycloalkyl), $R^7$-substituted or unsubstituted heterocycloalkyl (e.g. 3 to 8 membered heterocycloalkyl, 4 to 8 membered heterocycloalkyl, or 5 to 6 membered heterocycloalkyl), $R^7$-substituted or unsubstituted aryl (e.g. $C_6$-$C_{10}$ aryl or $C_6$ aryl), or $R^7$-substituted or unsubstituted heteroaryl (e.g. 5 to 10 membered heteroaryl, 5 to 9 membered heteroaryl, or 5 to 6 membered heteroaryl).

$R^5$ and $R^7$ are independently oxo, halogen, —F, —Cl, —Br, —I, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl or $C_6$ aryl), or unsubstituted heteroaryl (e.g. 5 to 10 membered heteroaryl, 5 to 9 membered heteroaryl, or 5 to 6 membered heteroaryl).

In embodiments, $R^{1a}$, $R^{2a}$, $R^{1b}$, and $R^{2b}$ are independently hydrogen, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)OH, —NHOH, —OCF$_3$, —OCHF$_2$, substituted or unsubstituted alkyl (e.g. $C_1$-$C_8$ alkyl, $C_1$-$C_6$ alkyl, or $C_1$-$C_4$ alkyl), substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), substituted or unsubstituted cycloalkyl (e.g. $C_3$-$C_8$ cycloalkyl, $C_4$-$C_8$ cycloalkyl, or $C_5$-$C_6$ cycloalkyl), substituted or unsubstituted heterocycloalkyl (e.g. 3 to 8 membered heterocycloalkyl, 4 to 8 membered heterocycloalkyl, or 5 to 6 membered heterocycloalkyl), substituted or unsubstituted aryl (e.g. $C_6$-$C_{10}$ aryl or $C_6$ aryl), or substituted or unsubstituted heteroaryl (e.g. 5 to 10 membered heteroaryl, 5 to 9 membered heteroaryl, or 5 to 6 membered heteroaryl). In embodiments, $R^{1a}$, $R^{2a}$, $R^{1b}$, and $R^{2b}$ are independently hydrogen, halogen, —CF$_3$, —CN, —OH, —COOH, —CONH$_2$, substituted or unsubstituted alkyl (e.g. $C_1$-$C_8$ alkyl, $C_1$-$C_6$ alkyl, or $C_1$-$C_4$ alkyl), substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), substituted or unsubstituted cycloalkyl (e.g. $C_3$-$C_8$ cycloalkyl, $C_4$-$C_8$ cycloalkyl, or $C_5$-$C_6$ cycloalkyl), substituted or unsubstituted heterocycloalkyl (e.g. 3 to 8 membered heterocycloalkyl, 4 to 8 membered heterocycloalkyl, or 5 to 6 membered heterocycloalkyl), substituted or unsubstituted aryl (e.g. $C_6$-$C_{10}$ aryl or $C_6$ aryl), or substituted or unsubstituted heteroaryl (e.g. 5 to 10 membered heteroaryl, 5 to 9 membered heteroaryl, or 5 to 6 membered heteroaryl).

In embodiments, $R^{1a}$ is independently hydrogen, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —OCF$_3$, —OCHF$_2$, $R^8$-substituted or unsubstituted alkyl (e.g. $C_1$-$C_8$ alkyl, $C_1$-$C_6$ alkyl, or $C_1$-$C_4$ alkyl), $R^8$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^8$-substituted or unsubstituted cycloalkyl (e.g. $C_3$-$C_8$ cycloalkyl, $C_4$-$C_8$ cycloalkyl, or $C_5$-$C_6$ cycloalkyl), $R^8$-substituted or unsubstituted heterocycloalkyl (e.g. 3 to 8 membered heterocycloalkyl, 4 to 8 membered heterocycloalkyl, or 5 to 6 membered heterocycloalkyl), $R^8$-substituted or unsubstituted aryl (e.g. $C_6$-$C_{10}$ aryl or $C_6$ aryl), or $R^8$-substituted or unsubstituted heteroaryl (e.g. 5 to 10 membered heteroaryl, 5 to 9 membered heteroaryl, or 5 to 6 membered heteroaryl). In embodiments, $R^{1a}$ is independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCF_3$, —$OCHF_2$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl or $C_6$ aryl), or unsubstituted heteroaryl (e.g. 5 to 10 membered heteroaryl, 5 to 9 membered heteroaryl, or 5 to 6 membered heteroaryl).

$R^8$ is independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCF_3$, —$OCHF_2$, $R^9$-substituted or unsubstituted alkyl (e.g. $C_1$-$C_8$ alkyl, $C_1$-$C_6$ alkyl, or $C_1$-$C_4$ alkyl), $R^9$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^9$-substituted or unsubstituted cycloalkyl (e.g. $C_3$-$C_8$ cycloalkyl, $C_4$-$C_8$ cycloalkyl, or $C_5$-$C_6$ cycloalkyl), $R^9$-substituted or unsubstituted heterocycloalkyl (e.g. 3 to 8 membered heterocycloalkyl, 4 to 8 membered heterocycloalkyl, or 5 to 6 membered heterocycloalkyl), $R^9$-substituted or unsubstituted aryl (e.g. $C_6$-$C_{10}$ aryl or $C_6$ aryl), or $R^9$-substituted or unsubstituted heteroaryl (e.g. 5 to 10 membered heteroaryl, 5 to 9 membered heteroaryl, or 5 to 6 membered heteroaryl).

In embodiments, $R^{1b}$ is independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCF_3$, —$OCHF_2$, $R^{10}$-substituted or unsubstituted alkyl (e.g. $C_1$-$C_8$ alkyl, $C_1$-$C_6$ alkyl, or $C_1$-$C_4$ alkyl), $R^{10}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{10}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{10}$-substituted or unsubstituted heterocycloalkyl (e.g. 3 to 8 membered heterocycloalkyl, 4 to 8 membered heterocycloalkyl, or 5 to 6 membered heterocycloalkyl), $R^{10}$-substituted or unsubstituted aryl (e.g. $C_6$-$C_{10}$ aryl or $C_6$ aryl), or $R^{10}$-substituted or unsubstituted heteroaryl (e.g. 5 to 10 membered heteroaryl, 5 to 9 membered heteroaryl, or 5 to 6 membered heteroaryl). In embodiments, $R^{1b}$ is independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCF_3$, —$OCHF_2$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl or $C_6$ aryl), or unsubstituted heteroaryl (e.g. 5 to 10 membered heteroaryl, 5 to 9 membered heteroaryl, or 5 to 6 membered heteroaryl).

$R^{10}$ is independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCF_3$, —$OCHF_2$, $R^{11}$-substituted or unsubstituted alkyl (e.g. $C_1$-$C_8$ alkyl, $C_1$-$C_6$ alkyl, or $C_1$-$C_4$ alkyl), $R^{11}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{11}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{11}$-substituted or unsubstituted heterocycloalkyl (e.g. 3 to 8 membered heterocycloalkyl, 4 to 8 membered heterocycloalkyl, or 5 to 6 membered heterocycloalkyl), $R^{11}$-substituted or unsubstituted aryl (e.g. $C_6$-$C_{10}$ aryl or $C_6$ aryl), or $R^{11}$-substituted or unsubstituted heteroaryl (e.g. 5 to 10 membered heteroaryl, 5 to 9 membered heteroaryl, or 5 to 6 membered heteroaryl).

In embodiments, $R^2$ is independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCF_3$, —$OCHF_2$ $R^{12}$-substituted or unsubstituted alkyl (e.g. $C_1$-$C_8$ alkyl, $C_1$-$C_6$ alkyl, or $C_1$-$C_4$ alkyl), $R^{12}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{12}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{12}$-substituted or unsubstituted heterocycloalkyl (e.g. 3 to 8 membered heterocycloalkyl, 4 to 8 membered heterocycloalkyl, or 5 to 6 membered heterocycloalkyl), $R^{12}$-substituted or unsubstituted aryl (e.g. $C_6$-$C_{10}$ aryl or $C_6$ aryl), or R12-substituted or unsubstituted heteroaryl (e.g. 5 to 10 membered heteroaryl, 5 to 9 membered heteroaryl, or 5 to 6 membered heteroaryl). In embodiments, $R^2$ is independently hydrogen, halogen, —$CF_3$, —CN, —OH, —$NH_2$, —COOH, —$CONH_2$, —$NO_2$, —SH, —$S_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCF_3$, —$OCHF_2$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl or $C_6$ aryl), or unsubstituted heteroaryl (e.g. 5 to 10 membered heteroaryl, 5 to 9 membered heteroaryl, or 5 to 6 membered heteroaryl).

$R^{12}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)OH, —NHOH, —$OCF_3$, —$OCHF_2$, $R^{13}$-substituted or unsubstituted alkyl (e.g. $C_1$-$C_8$ alkyl, $C_1$-$C_6$ alkyl, or $C_1$-$C_4$ alkyl), $R^{13}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{13}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{13}$-substituted or unsubstituted heterocycloalkyl (e.g. 3 to 8 membered heterocycloalkyl, 4 to 8 membered heterocycloalkyl, or 5 to 6 membered heterocycloalkyl), $R^{13}$-substituted or unsubstituted aryl (e.g. $C_6$-$C_{10}$ aryl or $C_6$ aryl), or $R^{13}$-substituted or unsubstituted heteroaryl (e.g. 5 to 10 membered heteroaryl, 5 to 9 membered heteroaryl, or 5 to 6 membered heteroaryl).

In embodiments, $R^{2b}$ is independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)OH, —NHOH, —$OCF_3$, —$OCHF_2R^{14}$-substituted or unsubstituted alkyl (e.g. $C_1$-$C_8$ alkyl, $C_1$-$C_6$ alkyl, or $C_1$-$C_4$ alkyl), $R^{14}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{14}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{14}$-substituted or unsubstituted heterocycloalkyl (e.g. 3 to 8 membered heterocycloalkyl, 4 to 8 membered heterocycloalkyl, or 5 to 6 membered heterocycloalkyl), $R^{14}$-substituted or unsubstituted aryl (e.g. $C_6$-$C_{10}$ aryl or $C_6$ aryl), or R14-substituted or unsubstituted heteroaryl (e.g. 5 to 10 membered heteroaryl, 5 to 9 membered heteroaryl, or 5 to 6 membered heteroaryl). In embodiments, $R^{2b}$ is independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)OH, —NHOH, —$OCF_3$, —$OCHF_2$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl or $C_6$ aryl), or unsubstituted heteroaryl (e.g. 5 to 10 membered heteroaryl, 5 to 9 membered heteroaryl, or 5 to 6 membered heteroaryl).

$R^{14}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)OH, —NHOH, —$OCF_3$, —$OCHF_2$, $R^{15}$-substituted or unsubstituted alkyl (e.g. $C_1$-$C_8$ alkyl, $C_1$-$C_6$ alkyl, or $C_1$-$C_4$ alkyl), $R^{15}$-substituted or unsubstituted heteroalkyl (e.g. 2 to 10 membered heteroalkyl, 2 to 8 membered heteroalkyl, 4 to 8 membered heteroalkyl, or 2 to 4 membered heteroalkyl), $R^{15}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{15}$-substituted or unsubstituted heterocycloalkyl (e.g. 3 to 8 membered heterocycloalkyl, 4 to 8 membered heterocycloalkyl, or 5 to 6 membered heterocycloalkyl), $R^{15}$-substituted or unsubstituted aryl (e.g. $C_6$-$C_{10}$ aryl or $C_6$ aryl), or $R^{15}$-substituted or unsubstituted heteroaryl (e.g. 5 to 10 membered heteroaryl, 5 to 9 membered heteroaryl, or 5 to 6 membered heteroaryl).

In embodiments, $R^9$, R, $R^{13}$, $R^{15}$ are independently oxo, halogen, —F, —Cl, —Br, —I, —$CF_3$, —$CCl_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O) $NH_2$, —$NHSO_2H$, —NHC═(O)H, —NHC(O)—OH, —NHOH, —$OCF_3$, —$OCHF_2$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl or $C_6$ aryl), or unsubstituted heteroaryl (e.g. 5 to 10 membered heteroaryl, 5 to 9 membered heteroaryl, or 5 to 6 membered heteroaryl).

In embodiments, $R^3$ is monovalent polyethylene glycol (PEG). In embodiments, $R^3$ is monovalent $PEG_{400}$-SH. In embodiments, $R^3$ is monovalent $PEG_{1000}$-SH. In embodiments, $R^3$ is monovalent $PEG_{2000}$-SH. In embodiments, $R^3$ is monovalent $PEG_{5000}$-SH. It will be understood that the immediately preceding divalent PEG-SH groups may be bonded to a separate moiety through the terminal thiol group where the bond between sulfur and hydrogen is replaced with a bond between sulfur and another moiety. In embodiments, $R^3$ is monovalent TFP-$(PEG_{11})_3$. It will be understood that the immediately preceding monovalent TFP-PEG groups may be bonded to a separate moiety through the tetrafluorophenyl (TFP) ester group where the bond is between the tetrafluorophenyl ester and another moiety. In embodiments, $R^3$ is monovalent NHS-$(PEG_{24})_3$. It will be understood that the immediately preceding monovalent NSH-PEG groups may be bonded to a separate moiety through the N-hydroxysuccinimide group where the bond is between N-hydroxysuccinimide and another moiety. In embodiments, $R^3$ is a monovalent polyethylene glycol with an average molecular weight of about 400 g/mol, 484 g/mol, 1000 g/mol, 1450 g/mol, 1500 g/mol, 2000 g/mol, or 5000 g/mol. In embodiments, $R^3$ is a monovalent polyethylene glycol with an average molecular weight of about 400 g/mol. In embodiments, $R^3$ is a monovalent polyethylene glycol with an average molecular weight of about 484 g/mol. In embodiments, $R^3$ is a monovalent polyethylene glycol with an average molecular weight of about 484 g/mol per arm. In embodiments, $R^3$ is a monovalent polyethylene glycol with an average molecular weight of about 1000 g/mol. In embodiments, $R^3$ is a monovalent polyethylene glycol with an average molecular weight of about 1450 g/mol. In embodiments, $R^3$ is a monovalent polyethylene glycol with an average molecular weight of about 1500 g/mol. In embodiments, $R^3$ is a monovalent polyethylene glycol with an average molecular weight of about 2000 g/mol. In embodiments, $R^3$ is a monovalent polyethylene glycol with an average molecular weight of about 5000 g/mol.

In embodiments, —$X^2$— has the formula:

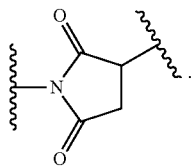 [SMILES: *C1CC(=O)N(*)C1=O]

In embodiments, —$X^2$-$L^3$- has the formula:

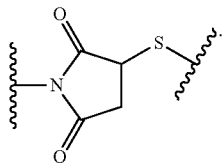 [SMILES: *SC1CC(=O)N(*)C1=O]

In embodiments, $X^3$ is —$NH_2$, —COOH, —N-hydroxysuccinimide, or maleimide. In embodiments, $X^3$ is

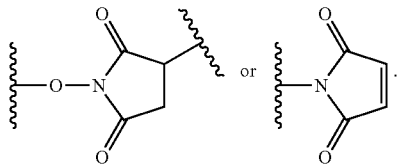 [SMILES: *ON1C(=O)CC(*)C1=O ; *N1C(=O)C=CC1=O]

In embodiments, $X^3$ is -haloacetyl (eg., iodoacetyl, bromoacetyl, or chloroacetyl). In embodiments, $X^3$ is pyridyl. In embodiments, $X^3$ is maleimide. In embodiments, $X^3$ is —N-hydroxysuccinimide. In embodiments, $X^3$ is —COOH. In embodiments, $X^3$ is —$NH_2$.

In embodiments, z1 is independently 10. In embodiments, z1 is independently 9. In embodiments, z1 is independently 8. In embodiments, z1 is independently 7. In embodiments, z1 is independently 6. In embodiments, z1 is independently 5. In embodiments, z1 is independently 4. In embodiments, z1 is independently 3. In embodiments, z1 is independently 2. In embodiments, z1 is independently 1. In embodiments, z2 is independently 10. In embodiments, z2 is independently 9. In embodiments, z2 is independently 8. In embodiments, z2 is independently 7. In embodiments, z2 is independently 6. In embodiments, z2 is independently 5. In embodiments, z2 is independently 4. In embodiments, z2 is independently 3. In embodiments, z2 is independently 2. In embodiments, z2 is independently 1.

In embodiments, the nanoparticle-cell construct has the formula:

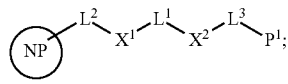

wherein NP is a nanoparticle and $P^1$ is a protein optionally attached to a cell (e.g., a stem cell). $L^2$, $X^1$, $L^1$, $X^2$, and $L^3$ are as described herein. In embodiments, the protein is attached to a cell and is a cell surface protein.

In embodiments, the nanoparticle is further covalently attached to one or more nanoparticle substituents. In embodiments, the nanoparticle substituent includes a polymeric moiety. In embodiments, the polymeric moiety is a polyethylene glycol moiety. In embodiments, the nanoparticle substituents occupy about 5%, 10%, 15%, 20%, 25%, 40%, 50%, 60%, 75%, 80%, 90%, 95%, 99%, or about 100% of the nanoparticle surface.

In embodiments, the nanoparticle includes a plurality of nanoparticle substituents of the formula (i) and a plurality of nanoparticle substituents of the formula (ii), and not formula (iii). In embodiments, the nanoparticle includes a plurality of nanoparticle substituents of the formula (i) and a plurality of nanoparticle substituents of the formula (iii), and not formula (ii). In embodiments, the nanoparticle includes a plurality of nanoparticle substituents of the formula (ii) and a plurality of nanoparticle substituents of the formula (iii), and not formula (i). In embodiments, the nanoparticle includes a plurality of nanoparticle substituents of the formula (i), and not formula (ii) or formula (iii). In embodiments, the nanoparticle includes a plurality of nanoparticle substituents of the formula (ii), and not formula (i) or formula (iii). In embodiments, the nanoparticle includes a plurality of nanoparticle substituents of the formula (iii), and not formula (i) or formula (ii).

In embodiments, the nanoparticle includes a plurality of nanoparticle substituents of the formula (i) and a plurality of nanoparticle substituents of the formula (ii) in a ratio of about 50:50 to about 80:20. In embodiments, the ratio of a plurality of nanoparticle substituents of the formula (i) and a plurality of substituents of the formula (ii) is about 50:50, 51:49, 52:48, 53:47, 54:46, 55:45, 56:44, 57:43, 58:42, 59:41, 60:40, 61:39, 62:38, 63:37, 64:36, 65:35, 66:34, 67:33, 68:32, 69:31, 70:30, 71:29, 72:28, 73:27, 74:26, 75:25, 76:24, 77:23, 78:22, 79:21, or 80:20.

In embodiments, the nanoparticle includes a plurality of nanoparticle substituents of the formula (i) and a plurality of nanoparticle substituents of the formula (iii) in a ratio of about 50:50 to about 80:20. In embodiments, the ratio of a plurality of nanoparticle substituents of the formula (i) and a plurality of substituents of the formula (iii) is about 50:50, 51:49, 52:48, 53:47, 54:46, 55:45, 56:44, 57:43, 58:42, 59:41, 60:40, 61:39, 62:38, 63:37, 64:36, 65:35, 66:34, 67:33, 68:32, 69:31, 70:30, 71:29, 72:28, 73:27, 74:26, 75:25, 76:24, 77:23, 78:22, 79:21, or 80:20.

In embodiments, the nanoparticle includes a plurality of nanoparticle substituents of the formula (ii) and a plurality of nanoparticle substituents of the formula (iii) in a ratio of about 50:50 to about 80:20. In embodiments, the ratio of a plurality of nanoparticle substituents of the formula (ii) and a plurality of nanoparticle substituents of the formula (iii) is about 50:50, 51:49, 52:48, 53:47, 54:46, 55:45, 56:44, 57:43, 58:42, 59:41, 60:40, 61:39, 62:38, 63:37, 64:36, 65:35, 66:34, 67:33, 68:32, 69:31, 70:30, 71:29, 72:28, 73:27, 74:26, 75:25, 76:24, 77:23, 78:22, 79:21, or 80:20.

In embodiments, the linker is formed by a conjugation or bioconjugation reaction combining a first reactant moiety covalently bonded to the polymeric linker and a second reactant moiety covalently bonded to a protein. In such embodiments, the composition formed by such conjugation or bioconjugation reaction (including compounds or nanoparticles as described herein) to a cell may be referred to as a nanoparticle-cell construct.

In embodiments, the mass ratio of insoluble drug to amphiphilic polymer is about 1 to 1 to about 1 to 20. In embodiments, the mass ratio of insoluble drug to amphiphilic polymer is about 1 to 1 to about 1 to 10. In embodiments, the mass ratio of insoluble drug to amphiphilic polymer is about 1 to 1 to about 1 to 5. In embodiments, the mass ratio of insoluble drug to amphiphilic polymer is about 1 to 1 or 1 to 5. In embodiments, the mass ratio of insoluble drug to amphiphilic polymer is about 1 to 1. In embodiments, the mass ratio of insoluble drug to amphiphilic polymer is about 1 to 5.

In embodiments, the mass ratio of insoluble drug to amphiphilic polymer is about 1 to 1. In embodiments, the mass ratio of insoluble drug to amphiphilic polymer is about 1 to 2. In embodiments, the mass ratio of insoluble drug to amphiphilic polymer is about 1 to 2.5. In embodiments, the mass ratio of insoluble drug to amphiphilic polymer is about 1 to 3. In embodiments, the mass ratio of insoluble drug to amphiphilic polymer is about 1 to 4. In embodiments, the mass ratio of insoluble drug to amphiphilic polymer is about 1 to 5. In embodiments, the mass ratio of insoluble drug to amphiphilic polymer is about 1 to 6. In embodiments, the mass ratio of insoluble drug to amphiphilic polymer is about 1 to 7. In embodiments, the mass ratio of insoluble drug to amphiphilic polymer is about 1 to 8. In embodiments, the mass ratio of insoluble drug to amphiphilic polymer is about 1 to 9. In embodiments, the mass ratio of insoluble drug to amphiphilic polymer is about 1 to 10. In embodiments, the mass ratio of insoluble drug to amphiphilic polymer is about 1 to 11. In embodiments, the mass ratio of insoluble drug to amphiphilic polymer is about 1 to 12. In embodiments, the mass ratio of insoluble drug to amphiphilic polymer is about 1 to 13. In embodiments, the mass ratio of insoluble drug to amphiphilic polymer is about 1 to 14. In embodiments, the mass ratio of insoluble drug to amphiphilic polymer is about 1 to 15. In embodiments, the mass ratio of insoluble drug to amphiphilic polymer is about 1 to 16. In embodiments, the mass ratio of insoluble drug to amphiphilic polymer is about 1 to 17. In embodiments, the mass ratio of insoluble drug to amphiphilic polymer is about 1 to 18. In embodiments, the mass ratio of insoluble drug to amphiphilic polymer is about 1 to 19. In embodiments, the mass ratio of insoluble drug to amphiphilic polymer is about 1 to 20.

In embodiments, the average longest dimension of the nanoparticle is from about 10 nm to about 1000 nm. In embodiments, the average longest dimension of the nanoparticle is from about 60 nm to about 940 nm. In embodiments, the average longest dimension of the nanoparticle is from about 10 nm to about 900 nm. In embodiments, the average longest dimension of the nanoparticle is from about 10 nm to about 800 nm. In embodiments, the average longest dimension of the nanoparticle is from about 10 nm to about 700 nm. In embodiments, the average longest dimension of the nanoparticle is from about 100 nm to about 400 nm. In embodiments, the average longest dimension of the nanoparticle is from about 200 nm to about 500 nm. In embodiments, the average longest dimension of the nanoparticle is from about 300 nm to about 500 nm. In embodiments, the average longest dimension of the nanoparticle is from about 500 nm to about 1000 nm. In embodiments, the average longest dimension of the nanoparticle is from about 400 nm to about 800 nm.

In embodiments, the average longest dimension of the nanoparticle is from about 10 nm to about 600 nm. In embodiments, the average longest dimension of the nanoparticle is from about 10 nm to about 500 nm. In embodiments, the average longest dimension of the nanoparticle is from about 10 nm to about 300 nm. In embodiments, the average longest dimension of the nanoparticle is from about 10 nm to about 100 nm. In embodiments, the average longest dimension of the nanoparticle is from about 10 nm to about 90 nm. In embodiments, the average longest dimension of the nanoparticle is from about 10 nm to about 80 nm. In embodiments, the average longest dimension of the nanoparticle is from about 10 nm to about 70 nm. In embodiments, the average longest dimension of the nanoparticle is from about 10 nm to about 60 nm. In embodiments, the average longest dimension of the nanoparticle is from about 10 nm to about 50 nm. In embodiments, the average longest dimension of the nanoparticle is from about 25 nm to about 75 nm. In embodiments, the average longest dimension of the nanoparticle is from about 40 nm to about 60 nm. In embodiments, the average longest dimension of the nanoparticle is from about 45 nm to about 55 nm. In embodiments, the average longest dimension of the nanoparticle is about 51 nm.

In embodiments, the average longest dimension of the nanoparticle is from about 200 nm to about 250 nm. In embodiments, the average longest dimension of the nanoparticle is from about 400 nm to about 600 nm. In embodiments, the average longest dimension of the nanoparticle is from about 430 nm to about 530 nm.

In embodiments, the average longest dimension of the nanoparticle is from about 100 nm to about 400 nm. In embodiments, the average longest dimension of the nanoparticle is about 170 nm to 270 nm. In embodiments, the average longest dimension of the nanoparticle is about 10 nm, 15 nm, 20 nm, 25 nm, 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, 150 nm, 155 nm, 160 nm, 165 nm, 170 nm, 175 nm, 180 nm, 185 nm, 190 nm, 195 nm, 200 nm, 205 nm, 210 nm, 215 nm, 220 nm, 225 nm, 230 nm, 235 nm, 240 nm, 245 nm, 250 nm, 255 nm, 260 nm, 265 nm, 270 nm, 275 nm, 280 nm, 285 nm, 290 nm, 295 nm, 300 nm, 305 nm, 310 nm, 315 nm, 320 nm, 325 nm, 330 nm, 335 nm, 340 nm, 345 nm, 350 nm, 355 nm, 360 nm, 365 nm, 370 nm, 375 nm, 380 nm, 385 nm, 390 nm, 395 nm, 400 nm, 405 nm, 410 nm, 415 nm, 420 nm, 425 nm, 430 nm, 435 nm, 440 nm, 445 nm, 450 nm, 455 nm, 460 nm, 465 nm, 470 nm, 475 nm, 480 nm, 485 nm, 490 nm, 495 nm, 500 nm, 505 nm, 510 nm, 515 nm, 520 nm, 525 nm, 530 nm, 535 nm, 540 nm, 545 nm, 550 nm, 555 nm, 560 nm, 565 nm, 570 nm, 575 nm, 580 nm, 585 nm, 590 nm, 595 nm, or 600 nm. In embodiments, the average shortest dimension of the nanoparticle is about 10 nm.

In embodiments, the average longest dimension of the nanoparticle is from about 600 nm, 605 nm, 610 nm, 615 nm, 620 nm, 625 nm, 630 nm, 635 nm, 640 nm, 645 nm, 650 nm, 655 nm, 660 nm, 665 nm, 670 nm, 675 nm, 680 nm, 685 nm, 690 nm, 695 nm, 700 nm, 705 nm, 710 nm, 715 nm, 720 nm, 725 nm, 730 nm, 735 nm, 740 nm, 745 nm, 750 nm, 755 nm, 760 nm, 765 nm, 770 nm, 775 nm, 780 nm, 785 nm, 790 nm, 795 nm, 800 nm, 805 nm, 810 nm, 815 nm, 820 nm, 825 nm, 830 nm, 835 nm, 840 nm, 845 nm, 850 nm, 855 nm, 860 nm, 865 nm, 870 nm, 875 nm, 880 nm, 885 nm, 890 nm, 895 nm, 900 nm, 905 nm, 910 nm, 915 nm, 920 nm, 925 nm, 930 nm, 935 nm, 940 nm, 945 nm, 950 nm, 955 nm, 960 nm, 965 nm, 970 nm, 975 nm, 980 nm, 985 nm, 990 nm, 995 nm or about 1000 nm.

In embodiments, the average longest dimension of the nanoparticle is less than about 1000 nm. In embodiments, the average longest dimension of the nanoparticle is less than about 900 nm. In embodiments, the average longest dimension of the nanoparticle is less than about 800 nm. In embodiments, the average longest dimension of the nanoparticle is less than about 700 nm. In embodiments, the average longest dimension of the nanoparticle is less than about 600 nm. In embodiments, the average longest dimension of the nanoparticle is less than about 500 nm. In embodiments, the average longest dimension of the nanoparticle is less than about 400 nm. In embodiments, the average longest dimension of the nanoparticle is less than about 300 nm. In embodiments, the average longest dimension of the nanoparticle is less than about 200 nm. In embodiments, the average longest dimension of the nanoparticle is less than about 100 nm. In embodiments, the average longest dimension of the nanoparticle is less than about 90 nm. In embodiments, the average longest dimension of the nanoparticle is less than about 80 nm. In embodiments, the average longest dimension of the nanoparticle is less than about 70 nm. In embodiments, the average longest dimension of the nanoparticle is less than about 60 nm. In embodiments, the average longest dimension of the nanoparticle is less than about 50 nm. In embodiments, the average longest dimension of the nanoparticle is less than about 40 nm. In embodiments, the average longest dimension of the nanoparticle is less than about 30 nm. In embodiments, the average longest dimension of the nanoparticle is less than about 20 nm. In embodiments, the average longest dimension of the nanoparticle is less than about 10 nm.

In embodiments, the average longest dimension of the nanoparticle is less than about 10 nm, 15 nm, 20 nm, 25 nm, 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, 150 nm, 155 nm, 160 nm, 165 nm, 170 nm, 175 nm, 180 nm, 185 nm, 190 nm, 195 nm, 200 nm, 205 nm, 210 nm, 215 nm, 220 nm, 225 nm, 230 nm, 235 nm, 240 nm, 245 nm, 250 nm, 255 nm, 260 nm, 265 nm, 270 nm, 275 nm, 280 nm, 285 nm, 290 nm, 295 nm, 300 nm, 305 nm, 310 nm, 315 nm, 320 nm, 325 nm, 330 nm, 335 nm, 340 nm, 345 nm, 350 nm, 355 nm, 360 nm, 365 nm, 370 nm, 375 nm, 380 nm, 385 nm, 390 nm, 395 nm, 400 nm, 405 nm, 410 nm, 415 nm, 420 nm, 425 nm, 430 nm, 435 nm, 440 nm, 445 nm, 450 nm, 455 nm, 460 nm, 465 nm, 470 nm, 475 nm, 480 nm, 485 nm, 490 nm, 495 nm, 500 nm, 505 nm, 510 nm, 515 nm, 520 nm, 525 nm, 530 nm, 535 nm, 540 nm, 545 nm, 550 nm, 555 nm, 560 nm, 565 nm, 570 nm, 575 nm, 580 nm, 585 nm, 590 nm, 595 nm, or 600 nm. In embodiments, the average shortest dimension of the nanoparticle is about 10 nm.

In embodiments, the average longest dimension of the nanoparticle is less than about 600 nm, 605 nm, 610 nm, 615 nm, 620 nm, 625 nm, 630 nm, 635 nm, 640 nm, 645 nm, 650 nm, 655 nm, 660 nm, 665 nm, 670 nm, 675 nm, 680 nm, 685 nm, 690 nm, 695 nm, 700 nm, 705 nm, 710 nm, 715 nm, 720 nm, 725 nm, 730 nm, 735 nm, 740 nm, 745 nm, 750 nm, 755 nm, 760 nm, 765 nm, 770 nm, 775 nm, 780 nm, 785 nm, 790 nm, 795 nm, 800 nm, 805 nm, 810 nm, 815 nm, 820 nm, 825 nm, 830 nm, 835 nm, 840 nm, 845 nm, 850 nm, 855 nm, 860 nm, 865 nm, 870 nm, 875 nm, 880 nm, 885 nm, 890 nm, 895 nm, 900 nm, 905 nm, 910 nm, 915 nm, 920 nm, 925 nm, 930 nm, 935 nm, 940 nm, 945 nm, 950 nm, 955 nm, 960 nm, 965 nm, 970 nm, 975 nm, 980 nm, 985 nm, 990 nm, 995 nm or about 1000 nm.

In embodiments, the average longest dimension of the nanoparticle is less than 1000 nm. In embodiments, the average longest dimension of the nanoparticle is less than 900 nm. In embodiments, the average longest dimension of the nanoparticle is less than 800 nm. In embodiments, the average longest dimension of the nanoparticle is less than 700 nm. In embodiments, the average longest dimension of the nanoparticle is less than 600 nm. In embodiments, the average longest dimension of the nanoparticle is less than 500 nm. In embodiments, the average longest dimension of the nanoparticle is less than 400 nm. In embodiments, the average longest dimension of the nanoparticle is less than 300 nm. In embodiments, the average longest dimension of the nanoparticle is less than 200 nm. In embodiments, the average longest dimension of the nanoparticle is less than 100 nm. In embodiments, the average longest dimension of the nanoparticle is less than 90 nm. In embodiments, the average longest dimension of the nanoparticle is less than 80 nm. In embodiments, the average longest dimension of the nanoparticle is less than 70 nm. In embodiments, the average longest dimension of the nanoparticle is less than 60 nm. In embodiments, the average longest dimension of the nanoparticle is less than 50 nm. In embodiments, the average longest dimension of the nanoparticle is less than 40 nm. In embodiments, the average longest dimension of the nanoparticle is less than 30 nm. In embodiments, the average longest dimension of the nanoparticle is less than 20 nm. In embodiments, the average longest dimension of the nanoparticle is less than 10 nm.

In embodiments, the average longest dimension of the nanoparticle is less than 10 nm, 15 nm, 20 nm, 25 nm, 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, 150 nm, 155 nm, 160 nm, 165 nm, 170 nm, 175 nm, 180 nm, 185 nm, 190 nm, 195 nm, 200 nm, 205 nm, 210 nm, 215 nm, 220 nm, 225 nm, 230 nm, 235 nm, 240 nm, 245 nm, 250 nm, 255 nm, 260 nm, 265 nm, 270 nm, 275 nm, 280 nm, 285 nm, 290 nm, 295 nm, 300 nm, 305 nm, 310 nm, 315 nm, 320 nm, 325 nm, 330 nm, 335 nm, 340 nm, 345 nm, 350 nm, 355 nm, 360 nm, 365 nm, 370 nm, 375 nm, 380 nm, 385 nm, 390 nm, 395 nm, 400 nm, 405 nm, 410 nm, 415 nm, 420 nm, 425 nm, 430 nm, 435 nm, 440 nm, 445 nm, 450 nm, 455 nm, 460 nm, 465 nm, 470 nm, 475 nm, 480 nm, 485 nm, 490 nm, 495 nm, 500 nm, 505 nm, 510 nm, 515 nm, 520 nm, 525 nm, 530 nm, 535 nm, 540 nm, 545 nm, 550 nm, 555 nm, 560 nm, 565 nm, 570 nm, 575 nm, 580 nm, 585 nm, 590 nm, 595 nm, or 600 nm. In embodiments, the average shortest dimension of the nanoparticle is about 10 nm.

In embodiments, the average longest dimension of the nanoparticle is less than 600 nm, 605 nm, 610 nm, 615 nm, 620 nm, 625 nm, 630 nm, 635 nm, 640 nm, 645 nm, 650 nm, 655 nm, 660 nm, 665 nm, 670 nm, 675 nm, 680 nm, 685 nm, 690 nm, 695 nm, 700 nm, 705 nm, 710 nm, 715 nm, 720 nm, 725 nm, 730 nm, 735 nm, 740 nm, 745 nm, 750 nm, 755 nm, 760 nm, 765 nm, 770 nm, 775 nm, 780 nm, 785 nm, 790 nm, 795 nm, 800 nm, 805 nm, 810 nm, 815 nm, 820 nm, 825 nm, 830 nm, 835 nm, 840 nm, 845 nm, 850 nm, 855 nm, 860 nm, 865 nm, 870 nm, 875 nm, 880 nm, 885 nm, 890 nm, 895 nm, 900 nm, 905 nm, 910 nm, 915 nm, 920 nm, 925 nm, 930 nm, 935 nm, 940 nm, 945 nm, 950 nm, 955 nm, 960 nm, 965 nm, 970 nm, 975 nm, 980 nm, 985 nm, 990 nm, 995 nm or about 1000 nm.

In embodiments, the longest dimension of the nanoparticle is from about 10 nm to about 1000 nm. In embodiments, the longest dimension of the nanoparticle is from about 60 nm to about 940 nm. In embodiments, the longest dimension of the nanoparticle is from about 10 nm to about 900 nm. In embodiments, the longest dimension of the nanoparticle is from about 10 nm to about 800 nm. In embodiments, the longest dimension of the nanoparticle is from about 10 nm to about 700 nm. In embodiments, the longest dimension of the nanoparticle is from about 100 nm to about 400 nm. In embodiments, the longest dimension of the nanoparticle is from about 200 nm to about 500 nm. In embodiments, the longest dimension of the nanoparticle is from about 300 nm to about 500 nm. In embodiments, the longest dimension of the nanoparticle is from about 500 nm to about 1000 nm. In embodiments, the longest dimension of the nanoparticle is from about 400 nm to about 800 nm.

In embodiments, the longest dimension of the nanoparticle is from about 10 nm to about 600 nm. In embodiments, the longest dimension of the nanoparticle is from about 10 nm to about 500 nm. In embodiments, the longest dimension of the nanoparticle is from about 10 nm to about 300 nm. In embodiments, the longest dimension of the nanoparticle is from about 10 nm to about 100 nm. In embodiments, the longest dimension of the nanoparticle is from about 10 nm to about 90 nm. In embodiments, the longest dimension of the nanoparticle is from about 10 nm to about 80 nm. In embodiments, the longest dimension of the nanoparticle is from about 10 nm to about 70 nm. In embodiments, the longest dimension of the nanoparticle is from about 10 nm to about 60 nm. In embodiments, the longest dimension of the nanoparticle is from about 10 nm to about 50 nm. In embodiments, the longest dimension of the nanoparticle is from about 25 nm to about 75 nm. In embodiments, the longest dimension of the nanoparticle is from about 40 nm to about 60 nm. In embodiments, the longest dimension of the nanoparticle is from about 45 nm to about 55 nm. In embodiments, the longest dimension of the nanoparticle is about 51 nm.

In embodiments, the longest dimension of the nanoparticle is from about 200 nm to about 250 nm. In embodiments, the longest dimension of the nanoparticle is from about 400 nm to about 600 nm. In embodiments, the longest dimension of the nanoparticle is from about 430 nm to about 530 nm.

In embodiments, the longest dimension of the nanoparticle is from about 100 nm to about 400 nm. In embodiments, the longest dimension of the nanoparticle is about 170 nm to about 270 nm. In embodiments, the longest dimension of the nanoparticle is about 10 nm, 15 nm, 20 nm, 25 nm, 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, 150 nm, 155 nm, 160 nm, 165 nm, 170 nm, 175 nm, 180 nm, 185 nm, 190 nm, 195 nm, 200 nm, 205 nm, 210 nm, 215 nm, 220 nm, 225 nm, 230 nm, 235 nm, 240 nm, 245 nm, 250 nm, 255 nm, 260 nm, 265 nm, 270 nm, 275 nm, 280 nm, 285 nm, 290 nm, 295 nm, 300 nm, 305 nm, 310 nm, 315 nm, 320 nm, 325 nm, 330 nm, 335 nm, 340 nm, 345 nm, 350 nm, 355 nm, 360 nm, 365 nm, 370 nm, 375 nm, 380 nm, 385 nm, 390 nm, 395 nm, 400 nm, 405 nm, 410 nm, 415 nm, 420 nm, 425 nm, 430 nm, 435 nm, 440 nm, 445 nm, 450 nm, 455 nm, 460 nm, 465 nm, 470 nm, 475 nm, 480 nm, 485 nm, 490 nm, 495 nm, 500 nm, 505 nm, 510 nm, 515 nm, 520 nm, 525 nm, 530 nm, 535 nm, 540 nm, 545 nm, 550 nm, 555 nm, 560 nm, 565 nm, 570 nm, 575 nm, 580 nm, 585 nm, 590 nm, 595 nm, or 600 nm. In embodiments, the average shortest dimension of the nanoparticle is about 10 nm.

In embodiments, the longest dimension of the nanoparticle is from about 600 nm, 605 nm, 610 nm, 615 nm, 620 nm, 625 nm, 630 nm, 635 nm, 640 nm, 645 nm, 650 nm, 655 nm, 660 nm, 665 nm, 670 nm, 675 nm, 680 nm, 685 nm, 690 nm, 695 nm, 700 nm, 705 nm, 710 nm, 715 nm, 720 nm, 725 nm, 730 nm, 735 nm, 740 nm, 745 nm, 750 nm, 755 nm, 760 nm, 765 nm, 770 nm, 775 nm, 780 nm, 785 nm, 790 nm, 795 nm, 800 nm, 805 nm, 810 nm, 815 nm, 820 nm, 825 nm, 830 nm, 835 nm, 840 nm, 845 nm, 850 nm, 855 nm, 860 nm, 865 nm, 870 nm, 875 nm, 880 nm, 885 nm, 890 nm, 895 nm, 900 nm, 905 nm, 910 nm, 915 nm, 920 nm, 925 nm, 930 nm, 935 nm, 940 nm, 945 nm, 950 nm, 955 nm, 960 nm, 965 nm, 970 nm, 975 nm, 980 nm, 985 nm, 990 nm, 995 nm or about 1000 nm.

In embodiments, the longest dimension of the nanoparticle is less than about 1000 nm. In embodiments, the longest dimension of the nanoparticle is less than about 900 nm. In embodiments, the longest dimension of the nanoparticle is less than about 800 nm. In embodiments, the longest dimension of the nanoparticle is less than about 700 nm. In embodiments, the longest dimension of the nanoparticle is less than about 600 nm. In embodiments, the longest dimension of the nanoparticle is less than about 500 nm. In embodiments, the longest dimension of the nanoparticle is less than about 400 nm. In embodiments, the longest dimension of the nanoparticle is less than about 300 nm. In embodiments, the longest dimension of the nanoparticle is less than about 200 nm. In embodiments, the longest dimension of the nanoparticle is less than about 100 nm. In embodiments, the longest dimension of the nanoparticle is less than about 90 nm. In embodiments, the longest dimension of the nanoparticle is less than about 80 nm. In embodiments, the longest dimension of the nanoparticle is less than about 70 nm. In embodiments, the longest dimension of the nanoparticle is less than about 60 nm. In embodiments, the longest dimension of the nanoparticle is less than about 50 nm. In embodiments, the longest dimension of the nanoparticle is less than about 40 nm. In embodiments, the longest dimension of the nanoparticle is less than about 30 nm. In embodiments, the longest dimension of the nanoparticle is less than about 20 nm. In embodiments, the longest dimension of the nanoparticle is less than about 10 nm.

In embodiments, the longest dimension of the nanoparticle is less than about 10 nm, 15 nm, 20 nm, 25 nm, 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, 150 nm, 155 nm, 160 nm, 165 nm, 170 nm, 175 nm, 180 nm, 185 nm, 190 nm, 195 nm, 200 nm, 205 nm, 210 nm, 215 nm, 220 nm, 225 nm, 230 nm, 235 nm, 240 nm, 245 nm, 250 nm, 255 nm, 260 nm, 265 nm, 270 nm, 275 nm, 280 nm, 285 nm, 290 nm, 295 nm, 300 nm, 305 nm, 310 nm, 315 nm, 320 nm, 325 nm, 330 nm, 335 nm, 340 nm, 345 nm, 350 nm, 355 nm, 360 nm, 365 nm, 370 nm, 375 nm, 380 nm, 385 nm, 390 nm, 395 nm, 400 nm, 405 nm, 410 nm, 415 nm, 420 nm, 425 nm, 430 nm, 435 nm, 440 nm, 445 nm, 450 nm, 455 nm, 460 nm, 465 nm, 470 nm, 475 nm, 480 nm, 485 nm, 490 nm, 495 nm, 500 nm, 505 nm, 510 nm, 515 nm, 520 nm, 525 nm, 530 nm, 535 nm, 540 nm, 545 nm, 550 nm, 555 nm, 560 nm, 565 nm, 570 nm, 575 nm, 580 nm, 585 nm, 590 nm, 595 nm, or 600 nm. In embodiments, the average shortest dimension of the nanoparticle is about 10 nm.

In embodiments, the longest dimension of the nanoparticle is less than about 600 nm, 605 nm, 610 nm, 615 nm, 620 nm, 625 nm, 630 nm, 635 nm, 640 nm, 645 nm, 650 nm, 655 nm, 660 nm, 665 nm, 670 nm, 675 nm, 680 nm, 685 nm, 690 nm, 695 nm, 700 nm, 705 nm, 710 nm, 715 nm, 720 nm, 725 nm, 730 nm, 735 nm, 740 nm, 745 nm, 750 nm, 755 nm, 760 nm, 765 nm, 770 nm, 775 nm, 780 nm, 785 nm, 790 nm, 795 nm, 800 nm, 805 nm, 810 nm, 815 nm, 820 nm, 825 nm, 830 nm, 835 nm, 840 nm, 845 nm, 850 nm, 855 nm, 860 nm, 865 nm, 870 nm, 875 nm, 880 nm, 885 nm, 890 nm, 895 nm, 900 nm, 905 nm, 910 nm, 915 nm, 920 nm, 925 nm, 930 nm, 935 nm, 940 nm, 945 nm, 950 nm, 955 nm, 960 nm, 965 nm, 970 nm, 975 nm, 980 nm, 985 nm, 990 nm, 995 nm or about 1000 nm.

In embodiments, the longest dimension of the nanoparticle is less than 1000 nm. In embodiments, the longest dimension of the nanoparticle is less than 900 nm. In embodiments, the longest dimension of the nanoparticle is less than 800 nm. In embodiments, the longest dimension of the nanoparticle is less than 700 nm. In embodiments, the longest dimension of the nanoparticle is less than 600 nm. In embodiments, the longest dimension of the nanoparticle is less than 500 nm. In embodiments, the longest dimension of the nanoparticle is less than 400 nm. In embodiments, the longest dimension of the nanoparticle is less than 300 nm. In embodiments, the longest dimension of the nanoparticle is less than 200 nm. In embodiments, the longest dimension of the nanoparticle is less than 100 nm. In embodiments, the longest dimension of the nanoparticle is less than 90 nm. In embodiments, the longest dimension of the nanoparticle is less than 80 nm. In embodiments, the longest dimension of the nanoparticle is less than 70 nm. In embodiments, the longest dimension of the nanoparticle is less than 60 nm. In embodiments, the longest dimension of the nanoparticle is less than 50 nm. In embodiments, the longest dimension of the nanoparticle is less than 40 nm. In embodiments, the longest dimension of the nanoparticle is less than 30 nm. In embodiments, the longest dimension of the nanoparticle is less than 20 nm. In embodiments, the longest dimension of the nanoparticle is less than 10 nm.

In embodiments, the longest dimension of the nanoparticle is less than 10 nm, 15 nm, 20 nm, 25 nm, 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, 150 nm, 155 nm, 160 nm, 165 nm, 170 nm, 175 nm, 180 nm, 185 nm, 190 nm, 195 nm, 200 nm, 205 nm, 210 nm, 215 nm, 220 nm, 225 nm, 230 nm, 235 nm, 240 nm, 245 nm, 250 nm, 255 nm, 260 nm, 265 nm, 270 nm, 275 nm, 280 nm, 285 nm, 290 nm, 295 nm, 300 nm, 305 nm, 310 nm, 315 nm, 320 nm, 325 nm, 330 nm, 335 nm, 340 nm, 345 nm, 350 nm, 355 nm, 360 nm, 365 nm, 370 nm, 375 nm, 380 nm, 385 nm, 390 nm, 395 nm, 400 nm, 405 nm, 410 nm, 415 nm, 420 nm, 425 nm, 430 nm, 435 nm, 440 nm, 445 nm, 450 nm, 455 nm, 460 nm, 465 nm, 470 nm, 475 nm, 480 nm, 485 nm, 490 nm, 495 nm, 500 nm, 505 nm, 510 nm, 515 nm, 520 nm, 525 nm, 530 nm, 535 nm, 540 nm, 545 nm, 550 nm, 555 nm, 560 nm, 565 nm, 570 nm, 575 nm, 580 nm, 585 nm, 590 nm, 595 nm, or 600 nm. In embodiments, the average shortest dimension of the nanoparticle is about 10 nm.

In embodiments, the longest dimension of the nanoparticle is less than 600 nm, 605 nm, 610 nm, 615 nm, 620 nm, 625 nm, 630 nm, 635 nm, 640 nm, 645 nm, 650 nm, 655 nm, 660 nm, 665 nm, 670 nm, 675 nm, 680 nm, 685 nm, 690 nm, 695 nm, 700 nm, 705 nm, 710 nm, 715 nm, 720 nm, 725 nm, 730 nm, 735 nm, 740 nm, 745 nm, 750 nm, 755 nm, 760 nm, 765 nm, 770 nm, 775 nm, 780 nm, 785 nm, 790 nm, 795 nm, 800 nm, 805 nm, 810 nm, 815 nm, 820 nm, 825 nm, 830 nm, 835 nm, 840 nm, 845 nm, 850 nm, 855 nm, 860 nm, 865 nm, 870 nm, 875 nm, 880 nm, 885 nm, 890 nm, 895 nm, 900 nm, 905 nm, 910 nm, 915 nm, 920 nm, 925 nm, 930 nm, 935 nm, 940 nm, 945 nm, 950 nm, 955 nm, 960 nm, 965 nm, 970 nm, 975 nm, 980 nm, 985 nm, 990 nm, 995 nm or about 1000 nm.

In embodiments, the aspect ratio (i.e., the width divided by the length) of the nanoparticle is about 0.2, 0.3, 0.4, 0.5, 0.6, 0.7, 0.8, 0.9, 0.10, 0.11, 0.12, 0.13, 0.14, 0.15, 0.16, 0.17, 0.18, 0.19, 0.20, 0.21, 0.22, 0.23, 0.24, 0.25, 0.26, 0.27, 0.28, 0.29, 0.30, 0.31, 0.32, 0.33, 0.34, 0.35, 0.36, 0.37, 0.38, 0.39, 0.40, 0.41, 0.42, 0.43, 0.44, 0.45, 0.46, 0.47, 0.48, 0.49, 0.50, 0.51, 0.52, 0.53, 0.54, 0.55, 0.56, 0.57, 0.58, 0.59, 0.60, 0.61, 0.62, 0.63, 0.64, 0.65, 0.66, 0.67, 0.68, 0.69, 0.70, 0.71, 0.72, 0.73, 0.74, 0.75, 0.76, 0.77, 0.78, 0.79, 0.80, 0.81, 0.82, 0.83, 0.84, 0.85, 0.86, 0.87, 0.88, 0.89, 0.90, 0.91, 0.92, 0.93, 0.94, 0.95, 0.96, 0.97, 0.98, 0.99, or about 1.0.

In embodiments, the nanoparticle includes about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or about 99.9 wt % of the insoluble drug. In embodiments, the insoluble drug is paclitaxel. In embodiments, the nanoparticle further includes an amphiphilic polymer. In embodiments, the amphiphilic polymer is poloxamer 407.

In embodiments, the nanoparticle is obtainable by the process including the steps of (a) mixing an insoluble drug and an amphiphilic polymer in an organic solvent thereby forming a reaction mixture (e.g. in a reaction vessel); (b) removing the organic solvent from the reaction mixture (e.g. from the reaction vessel), adding a solvent (e.g., water or aqueous solution) to the reaction mixture to form an aqueous reaction mixture, and sonicating the aqueous reaction mixture to form a nanocrystal; and (c) mixing tetraethyl orthosilicate (TEOS), phenyltrimethoxysilane (PTMS), and hydrolyzed aminopropyltriethoxy silane (APTES) with the nanocrystal to form a nanoparticle. In embodiments, the nanoparticle obtainable by the process further includes isolating the nanoparticle from the reaction mixture formed by step (c). In embodiments, the isolating of the nanoparticle includes differential centrifugation. In embodiments, the isolating of the nanoparticle includes the use of a density gradient solution. In embodiments, the isolating of the nanoparticle includes the use of a sucrose gradient solution. In embodiments, the isolating of the nanoparticle includes centrifugation. In embodiments, the isolating includes centrifugation at 3600 rpm for about 35 minutes. In embodiments, nanoparticle obtainable by the process further includes isolating the nanoparticle following step (c). In embodiments, the removing of the organic solvent removes most (i.e. more the 50%, 60%, 70%, 80%, 90%, 95%, 96%, 97%, 98%, 99%, or removes 100%) of the organic solvent from the reaction mix. In embodiments, the adding of the solvent is performed after the removing of the organic solvent. In embodiments, the properties of the nanoparticle obtainable by this process include one or more of the properties identified herein for all other nanoparticle aspects, including embodiments thereof.

In embodiments, the organic solvent of part (a) is or includes acetic acid, acetone, acetonitrile, benzene, 1-butanol, 2-butanol, 2-butanone, t-butyl alcohol, carbon tetrachloride, chlorobenzene, chloroform, cyclohexane, 1,2-dichloroethane, diethylene glycol, diethyl ether, diglyme (diethylene glycol, dimethyl ether), 1,2-dimethoxyethane (glyme, DME), dimethylformamide (DMF), dimethyl sulfoxide (DMSO), 1,4-dioxane, ethanol, ethyl acetate, ethylene glycol, glycerin, heptane, hexamethylphosphoramide (IMPA), hexamethylphosphorous, triamide (HMPT), hexane, methanol, methyl t-butyl ether (MTBE), methylene chloride, N-methyl-2-pyrrolidinone (NMP), nitromethane, pentane, petroleum ether (ligroine), 1-propanol, 2-propanol, pyridine, tetrahydrofuran (THF), toluene, triethyl amine, o-xylene, m-xylene, or p-xylene. In embodiments, the organic solvent is or includes chloroform, dichloromethane, methanol, ethanol, tetrahydrofuran, or dioxane. In embodiments, the organic solvent is chloroform, dichloromethane, methanol, ethanol, tetrahydrofuran, or dioxane. In embodiments, the organic solvent is or includes chloroform. In embodiments, the solvent in part (b) is or includes chloroform, dichloromethane, methanol, ethanol, tetrahydrofuran, dioxane, or water. In embodiments, the solvent in part (b) includes a salt.

In embodiments, the sucrose gradient includes at least two different concentrations of sucrose. In embodiments, the sucrose gradient includes at least three different concentrations of sucrose. In embodiments, the sucrose gradient includes at least four different concentrations of sucrose. In embodiments, the sucrose gradient includes at least five different concentrations of sucrose. In embodiments, the sucrose gradient includes five different concentrations of sucrose, wherein the percentage of sucrose in water are given as 18%, 21%, 24%, 27%, and 30%. In embodiments, the sucrose gradient includes five different concentrations of sucrose, wherein the percentage of sucrose in water are given as 10%, 20%, 30%, 40%, and 50%.

In embodiments, step (b) includes sonicating for at least 100 minutes. In embodiments, step (b) includes sonicating for at least 90 minutes. In embodiments, step (b) includes sonicating for at least 85 minutes. In embodiments, step (b) includes sonicating for about 100 minutes. In embodiments, step (b) includes sonicating for about 90 minutes. In embodiments, step (b) includes sonicating for about 85 minutes. In embodiments, step (b) includes sonicating for about 80 minutes. In embodiments, step (b) includes sonicating for about 75 minutes. In embodiments, step (b) includes sonicating for about 70 minutes. In embodiments, step (b) includes sonicating for about 65 minutes. In embodiments, step (b) includes sonicating for about 60 minutes. In embodiments, step (b) includes sonicating for about 55 minutes. In embodiments, step (b) includes sonicating for about 50 minutes. In embodiments, step (b) includes sonicating for about 40 minutes. In embodiments, step (b) includes sonicating for about 30 minutes. In embodiments, step (b) includes sonicating for about 25 minutes. In embodiments, step (b) includes sonicating for about 20 minutes. In embodiments, step (b) includes sonicating for about 15 minutes. In embodiments, step (b) includes sonicating for about 10 minutes. In embodiments, step (b) includes sonicating for about 5 minutes. In embodiments, step (b) includes sonicating in periodic amounts (e.g., sonicating for 5 minutes and resting for 15 minutes or sonicating for 5 minutes and resting for 10 minutes). In embodiments, step (b) includes sonicating in about 5 minute intervals for a total of about 25 sonicating minutes, including 60 total minutes of resting intervals. In embodiments, step (b) includes sonicating in about 5 minute intervals for a total of about 15 sonicating minutes, including about 30 total minutes of resting interval.

In embodiments, step (c) stirs for at least 1 hour. In embodiments, step (c) stirs for at least 2 hours. In embodiments, step (c) stirs for at least 3 hours. In embodiments, step (c) stirs for at least 4 hours. In embodiments, step (c) stirs for at least 6 hours. In embodiments, step (c) stirs for at least 12 hours. In embodiments, step (c) stirs for at least 16 hours. In embodiments, step (c) stirs for about 1 hour. In embodiments, step (c) stirs for about 2 hours. In embodiments, step (c) stirs for about 3 hours. In embodiments, step (c) stirs for about 4 hours. In embodiments, step (c) stirs for about 6 hours. In embodiments, step (c) stirs for about 12 hours. In embodiments, step (c) stirs for about 16 hours.

In embodiments, the nanoparticle obtainable by the process including the steps of (a) mixing an insoluble drug (e.g., paclitaxel) and an amphiphilic polymer (e.g., poloxamer 407) in an organic solvent (e.g., chloroform) and vortexed using a vortex mixer. In embodiments, following step (a), nitrogen gas is used to evaporate the organic solvent (e.g., chloroform). In embodiments, the reaction from step (a) is placed in a vacuum with a drying agent (e.g., drierite) for about an hour. Following the removal of the organic solvent (e.g., using nitrogen gas or in a vacuum with a drying agent), water is vortexed with a vortex mixer with the reactants from step (a) (e.g., the reacted amphiphilic polymer and insoluble drug) for about 20 minutes. In embodiments, step (b) includes sonicating at periodic intervals (e.g., 5 minutes sonicating, 15 minutes of not sonicating) to form a nanocrystal. In embodiments, step (c) includes mixing TEOS and PTMS, followed by the addition of APTES which was diluted in water. In embodiments, step (c) mixes for about 6 hours. In embodiments, step (c) mixes for about 8 hours. In embodiments, step (c) mixes for about 10 hours. In embodiments, step (c) mixes for about 12 hours. In embodiments, step (c) mixes for about 14 hours. In embodiments, step (c) mixes for about 16 hours. In embodiments, step (c) mixes for about 18 hours. In embodiments, step (c) mixes for about 20 hours. In embodiments, step (c) mixes for about 22 hours. In embodiments, step (c) mixes for about 24 hours. In embodiments, following step (c), the reaction is centrifuged (e.g., for about 20 minutes at 14,000×g) and washed with water. In embodiments, the reaction is washed about three times.

In embodiments, the nanoparticle obtainable by the process described herein further includes isolating the nanoparticle. In embodiments, the isolating of the nanoparticle includes centrifugation. In embodiments, the centrifugation occurs at 20,000×g for 10 minutes. Following centrifugation, the nanoparticles may be washed with water (e.g., milliQ water) up to or greater than 3 times. In embodiments, the isolating of the nanoparticle includes differential centrifugation. One of ordinary skill in the art would understand if differential centrifugation (e.g., sucrose gradient is used in combination with centrifugation) is used to isolate the nanoparticles, separation of the nanoparticles occurs on the basis of particle size (e.g., nanoparticles of different sizes in the sucrose suspension will sediment at different rates). In embodiments, the isolating of the nanoparticle includes the use of a density gradient solution. In embodiments, the isolating of the nanoparticle includes the use of a sucrose gradient solution. In embodiments, the isolating of the nanoparticle includes centrifugation. In embodiments, the isolating includes centrifugation at 3600×rpm for about 35 minutes. Following centrifugation, the nanoparticles of interest (e.g., a specific size) may be extracted (e.g., using a pipette) from at least one layer (e.g., distinct concentration of sucrose).

In an aspect is provided a nanoparticle including an insoluble drug nanocrystal, wherein the insoluble drug nanocrystal is enclosed within a silica layer. In embodiments, the insoluble drug nanocrystal is a macrolide nanocrystal, steroid nanocrystal, or terpene nanocrystal. In embodiments, the insoluble drug nanocrystal is a macrolide nanocrystal. In embodiments, the insoluble drug nanocrystal is a steroid nanocrystal. In embodiments, the insoluble drug nanocrystal is a terpene nanocrystal. In embodiments, the insoluble drug nanocrystal is a taxane nanocrystal. In embodiments, the insoluble drug nanocrystal is a paclitaxel nanocrystal. In embodiments, the nanoparticle does not include any active pharmaceutical ingredient other than the insoluble drug. In embodiments, the properties of the nanoparticle include one or more of the properties identified herein for all other nanoparticle aspects and embodiments thereof.

The silica layer may be engineered (e.g., by altering the ratio of starting materials (e.g., PTMS, TEOS, APTES) or duration of mixing) to have a specific thickness. Thickness of a layer, as referred to herein, is defined as the distance from the inner surface of the layer, which contacts (interfaces) with the insoluble drug nanocrystal (which may also be referred to herein as a nanoparticle core), to the outer surface of the layer (the surface that interfaces with a non-silica layer and/or the environment outside of the nanoparticle), which interfaces with the external environment (e.g., external medium). Layer thickness may be approximately uniform (e.g. no more than 25% variation, 20% variation, 15% variation, 10% variation, 5% variation, 4% variation, 3% variation, 2% variation or 1% variation) over (around) the insoluble drug nanocrystal. Alternatively, the layer thickness may be non-uniform over the insoluble drug nanocrystal. In embodiments, the layer thickness is determined by transmission electron microscopy (TEM).

In embodiments, the silica layer is from about 1 nm to about 100 nm thick. In embodiments, the silica layer is from about 5 nm to about 100 nm thick. In embodiments, the silica layer is from about 10 nm to about 100 nm thick. In embodiments, the silica layer is from about 20 nm to about 100 nm thick. In embodiments, the silica layer is from about 10 nm to about 90 nm thick. In embodiments, the silica layer is from about 10 nm to about 80 nm thick. In embodiments, the silica layer is from about 20 nm to about 80 nm thick. In embodiments, the silica layer is from about 20 nm to about 70 nm thick. In embodiments, the silica layer is from about 20 nm to about 60 nm thick. In embodiments, the silica layer is from about 20 nm to about 50 nm thick. In embodiments, the silica layer is from about 20 nm to about 40 nm thick. In embodiments, the silica layer is from about 30 nm to about 40 nm thick. In embodiments, the silica layer is at least 1, 5, 10, 20, 30, 40, 50, 60, 70, 80, 90, or 100 nm thick. In embodiments, the silica layer is about 1, 5, 10, 20, 30, 40, 50, 60, 70, 80, 90, or 100 nm thick. In embodiments, the silica layer is about 35 nm thick. In embodiments, the silica layer is, on average, about 35 nm thick. In embodiments, these thicknesses are approximately uniform around the insoluble drug nanocrystal (e.g. no more than 25% variation, 20% variation, 15% variation, 10% variation, 5% variation, 4% variation, 3% variation, 2% variation or 1% variation)

In embodiments, the silica layer is maximally (i.e. the maximum thickness of the silica layer around the drug nanocrystal) from about 1 nm to about 100 nm thick. In embodiments, the silica layer is maximally from about 5 nm to about 100 nm thick. In embodiments, the silica layer is maximally from about 10 nm to about 100 nm thick. In embodiments, the silica layer is maximally from about 20 nm to about 100 nm thick. In embodiments, the silica layer is maximally from about 10 nm to about 90 nm thick. In embodiments, the silica layer is maximally from about 10 nm to about 80 nm thick. In embodiments, the silica layer is maximally from about 20 nm to about 80 nm thick. In embodiments, the silica layer is maximally from about 20 nm to about 70 nm thick. In embodiments, the silica layer is maximally from about 20 nm to about 60 nm thick. In embodiments, the silica layer is maximally from about 20 nm to about 50 nm thick. In embodiments, the silica layer is maximally from about 20 nm to about 40 nm thick. In embodiments, the silica layer is maximally from about 30 nm to about 40 nm thick. In embodiments, the silica layer is maximally 1, 5, 10, 20, 30, 40, 50, 60, 70, 80, 90, or 100 nm thick. In embodiments, the silica layer is maximally about 1, 5, 10, 20, 30, 40, 50, 60, 70, 80, 90, or 100 nm thick. In embodiments, the silica layer is maximally about 35 nm thick. In embodiments, the silica layer is, on average, maximally about 35 nm thick.

The silica layer may include components other than silica. For example, the silica layer may include components from steps involved in formation of the insoluble drug nanocrystal (e.g., step (a)). Thus, in embodiments, the silica layer further includes a polymer (e.g. an amphiphilic polymer). In embodiments, the polymer (e.g., amphiphilic polymer) is a triblock polymer. In embodiments, the triblock polymer is poloxamer 407.

In embodiments, the nanoparticle has a length (i.e., longest dimension) less than or equal to 1000 microns. In embodiments, the nanoparticle has a length (i.e., longest dimension) less than or equal to 900 microns. In embodiments, the nanoparticle has a length (i.e., longest dimension) less than or equal to 800 microns. In embodiments, the nanoparticle has a length (i.e., longest dimension) less than or equal to 700 microns. In embodiments, the nanoparticle has a length (i.e., longest dimension) less than or equal to 600 microns. In embodiments, the nanoparticle has a length (i.e., longest dimension) less than or equal to 500 microns. In embodiments, the nanoparticle has a length (i.e., longest dimension) less than or equal to 400 microns. In embodiments, the nanoparticle has a length (i.e., longest dimension) less than or equal to 300 microns. In embodiments, the nanoparticle has a length (i.e., longest dimension) less than or equal to 200 microns. In embodiments, the nanoparticle has a length (i.e., longest dimension) less than or equal to 100 microns. In embodiments, the nanoparticle has a length (i.e., longest dimension) less than or equal to 75 microns. In embodiments, the nanoparticle has a length (i.e., longest dimension) less than or equal to 50 microns. In embodiments, the nanoparticle has a length (i.e., longest dimension) less than or equal to 25 microns.

In embodiments, the nanoparticle has a length (i.e., longest dimension) of about 1000 microns. In embodiments, the nanoparticle has a length (i.e., longest dimension) of about 900 microns. In embodiments, the nanoparticle has a length (i.e., longest dimension) of about 800 microns. In embodiments, the nanoparticle has a length (i.e., longest dimension) of about 800 microns. In embodiments, the nanoparticle has a length (i.e., longest dimension) of about 700 microns. In embodiments, the nanoparticle has a length (i.e., longest dimension) of about 600 microns. In embodiments, the nanoparticle has a length (i.e., longest dimension) of about 500 microns. In embodiments, the nanoparticle has a length (i.e., longest dimension) of about 400 microns. In embodiments, the nanoparticle has a length (i.e., longest dimension) of about 300 microns. In embodiments, the nanoparticle has a length (i.e., longest dimension) of about 200 microns. In embodiments, the nanoparticle has a length (i.e., longest dimension) of about 100 microns. In embodiments, the nanoparticle has a length (i.e., longest dimension) of about 75 microns. In embodiments, the nanoparticle has a length (i.e., longest dimension) of about 50 microns. In embodiments, the nanoparticle has a length (i.e., longest dimension) of about 25 microns.

In embodiments, the nanoparticle has a length (i.e., longest dimension) from about 50 nm to about 900 nm. In embodiments, the nanoparticle has a length (i.e., longest dimension) from about 100 nm to about 800 nm. In embodiments, the nanoparticle has a length (i.e., longest dimension) from about 100 nm to about 700 nm. In embodiments, the nanoparticle has a length (i.e., longest dimension) from about 100 nm to about 600 nm. In embodiments, the nanoparticle has a length (i.e., longest dimension) from about 100 nm to about 500 nm. In embodiments, the nanoparticle has a length (i.e., longest dimension) from about 150 nm to about 450 nm. In embodiments, the nanoparticle has a length (i.e., longest dimension) from about 200 nm to about 450 nm. In embodiments, the nanoparticle has a length (i.e., longest dimension) from about 250 nm to about 450 nm. In embodiments, the nanoparticle has a length (i.e., longest dimension) from about 300 nm to about 400 nm.

In embodiments, the nanoparticle has a width (i.e., shortest dimension) from about 10 nm to about 200 nm. In embodiments, the nanoparticle has a width (i.e., shortest dimension) from about 15 nm to about 150 nm. In embodiments, the nanoparticle has a width (i.e., shortest dimension) from about 20 nm to about 100 nm. In embodiments, the nanoparticle has a width (i.e., shortest dimension) from about 30 nm to about 100 nm. In embodiments, the nanoparticle has a width (i.e., shortest dimension) from about 40 nm to about 100 nm. In embodiments, the nanoparticle has a width (i.e., shortest dimension) from about 40 nm to about 90 nm. In embodiments, the nanoparticle has a width (i.e., shortest dimension) from about 50 nm to about 90 nm. In embodiments, the nanoparticle has a width (i.e., shortest dimension) from about 50 nm to about 80 nm. In embodiments, the nanoparticle has a width (i.e., shortest dimension) from about 60 nm to about 80 nm. In embodiments, the nanoparticle has a width (i.e., shortest dimension) from about 70 nm to about 80 nm.

The silica layer of the nanoparticle may affect the electrical charge of the nanoparticle. One way of characterizing the charge of a nanoparticle is to determine its zeta potential. "Zeta potential" as used herein refers to the potential difference that exists between the surface of a particle (e.g., nanoparticle) and the liquid medium in which it is dispersed (e.g., water). Zeta potential may be used as an indication of stability of a suspended system. In embodiments, the nanoparticle has a zeta potential from about 10 mV to about 100 mV. In embodiments, the nanoparticle has a zeta potential from about 10 mV to about 90 mV. In embodiments, the nanoparticle has a zeta potential from about 10 mV to about 80 mV. In embodiments, the nanoparticle has a zeta potential from about 10 mV to about 70 mV. In embodiments, the nanoparticle has a zeta potential from about 10 mV to about 60 mV. In embodiments, the nanoparticle has a zeta potential from about 10 mV to about 50 mV. In embodiments, the nanoparticle has a zeta potential from about 10 mV to about 45 mV. In embodiments, the nanoparticle has a zeta potential from about 15 mV to about 45 mV. In embodiments, the nanoparticle has a zeta potential from about 20 mV to about 45 mV. In embodiments, the nanoparticle has a zeta potential from about 30 mV to about 40 mV. In embodiments, the nanoparticle has a zeta potential of about 35. In embodiments, zeta potential is determined by dynamic light scatter analysis.

In embodiments, the insoluble drug nanocrystal is at least 1 wt %, 2 wt %, 3 wt %, 4 wt %, 5 wt %, 10 wt %, 12 wt %, 13 wt %, 14 wt %, 15 wt %, 16 wt %, 17 wt %, 18 wt %, 19 wt %, 20 wt %, 25 wt % 30 wt %, 35 wt %, 40 wt % 45 wt % 50 wt % 55 wt %, 60 wt %, 65 wt %, 70 wt % 75 wt % 80 wt %, 85 wt %, 90 wt % 95 wt %, 96 wt %, 97 wt %, 98 wt % or 99 wt % of the nanoparticle. Thus, in embodiments, the insoluble drug nanocrystal weight percentage is 1, 2, 3, 4, 5, 10, 12, 13, 14, 15, 16, 17, 18, 19, 20, 25, 30, 35, 40, 45, 50, 55, 60, 65, 70, 75, 80, 85, 90, 95, 96, 97, 98 or 99% of the nanoparticle. In embodiments, the insoluble drug nanocrystal weight percentage is about 1, 2, 3, 4, 5, 10, 12, 13, 14, 15, 16, 17, 18, 19, 20, 25, 30, 35, 40, 45, 50, 55, 60, 65, 70, 75, 80, 85, 90, 95, 66, 97, 98, or 99% of the nanoparticle. In embodiments, the insoluble drug nanocrystal weight percentage is at least 5% of the nanoparticle. In embodiments, the insoluble drug nanocrystal weight percentage is at least 10% of the nanoparticle. In embodiments, the insoluble drug nanocrystal weight percentage is at least 15% of the nanoparticle. In embodiments, the insoluble drug nanocrystal weight percentage is at least 16% of the nanoparticle. In embodiments, the insoluble drug nanocrystal weight percentage is at least 17% of the nanoparticle. In embodiments, the insoluble drug nanocrystal weight percentage is at least 18% of the nanoparticle. In embodiments, the insoluble drug nanocrystal weight percentage is at least 19% of the nanoparticle. In embodiments, the insoluble drug nanocrystal weight percentage is at least 20% of the nanoparticle. In embodiments, the insoluble drug nanocrystal weight percentage is at least 25% of the nanoparticle. In embodiments, the insoluble drug nanocrystal weight percentage is at least 30% of the nanoparticle. In embodiments, the insoluble drug nanocrystal weight percentage is about 5% of the nanoparticle. In embodiments, the insoluble drug nanocrystal weight percentage is about 10% of the nanoparticle. In embodiments, the insoluble drug nanocrystal weight percentage is about 15% of the nanoparticle. In embodiments, the insoluble drug nanocrystal weight percentage is about 16% of the nanoparticle. In embodiments, the insoluble drug nanocrystal weight percentage is about 17% of the nanoparticle. In embodiments, the insoluble drug nanocrystal weight percentage is about 18% of the nanoparticle. In embodiments, the insoluble drug nanocrystal weight percentage is about 19% of the nanoparticle. In embodiments, the insoluble drug nanocrystal weight percentage is about 20% of the nanoparticle. In embodiments, the insoluble drug nanocrystal weight percentage is about 25% of the nanoparticle. In embodiments, the insoluble drug nanocrystal weight percentage is about 30% of the nanoparticle. In embodiments, the insoluble drug nanocrystal weight percentage is 5% of the nanoparticle. In embodiments, the insoluble drug nanocrystal weight percentage is 10% of the nanoparticle. In embodiments, the insoluble drug nanocrystal weight percentage is 15% of the nanoparticle. In embodiments, the insoluble drug nanocrystal weight percentage is 16% of the nanoparticle. In embodiments, the insoluble drug nanocrystal weight percentage is 17% of the nanoparticle. In embodiments, the insoluble drug nanocrystal weight percentage is 18% of the nanoparticle. In embodiments, the insoluble drug nanocrystal weight percentage is 19% of the nanoparticle. In embodiments, the insoluble drug nanocrystal weight percentage is 20% of the nanoparticle. In embodiments, the insoluble drug nanocrystal weight percentage is 25% of the nanoparticle. In embodiments, the insoluble drug nanocrystal weight percentage is 30% of the nanoparticle. In embodiments, the insoluble drug nanocrystal weight percentage is 35% of the nanoparticle. In embodiments, the insoluble drug nanocrystal weight percentage is 40% of the nanoparticle. In embodiments, the insoluble drug nanocrystal weight percentage is 45% of the nanoparticle. In embodiments, the insoluble drug nanocrystal weight percentage is 50% of the nanoparticle. In embodiments, the insoluble drug nanocrystal weight percentage is 60% of the nanoparticle. In embodiments, the insoluble drug nanocrystal weight percentage is 70% of the nanoparticle. In embodiments, the insoluble drug nanocrystal weight percentage is 80% of the nanoparticle. In embodiments, the insoluble drug nanocrystal weight percentage is 90% of the nanoparticle. In embodiments, the insoluble drug nanocrystal weight percentage is 95% of the nanoparticle. In embodiments, the insoluble drug nanocrystal weight percentage is 99% of the nanoparticle. Drug wt % of the nanoparticle may be calculated using the following equations:

$$\frac{m_{silica}}{m_{PTX}} = \frac{\rho_{silica} * V_{silica}}{\rho_{PTX} * V_{PTX}}$$
$$= \frac{\rho_{silica} * \pi * (R_1 * R_1 - R_2 * R_2) * L}{\rho_{PTX} * \pi * R_2 * R_2 * L}$$
$$= \frac{\rho_{silica} * (R_1 * R_1 - R_2 * R_2)}{\rho_{PTX} * R_2 * R_2}$$

Figure 43:
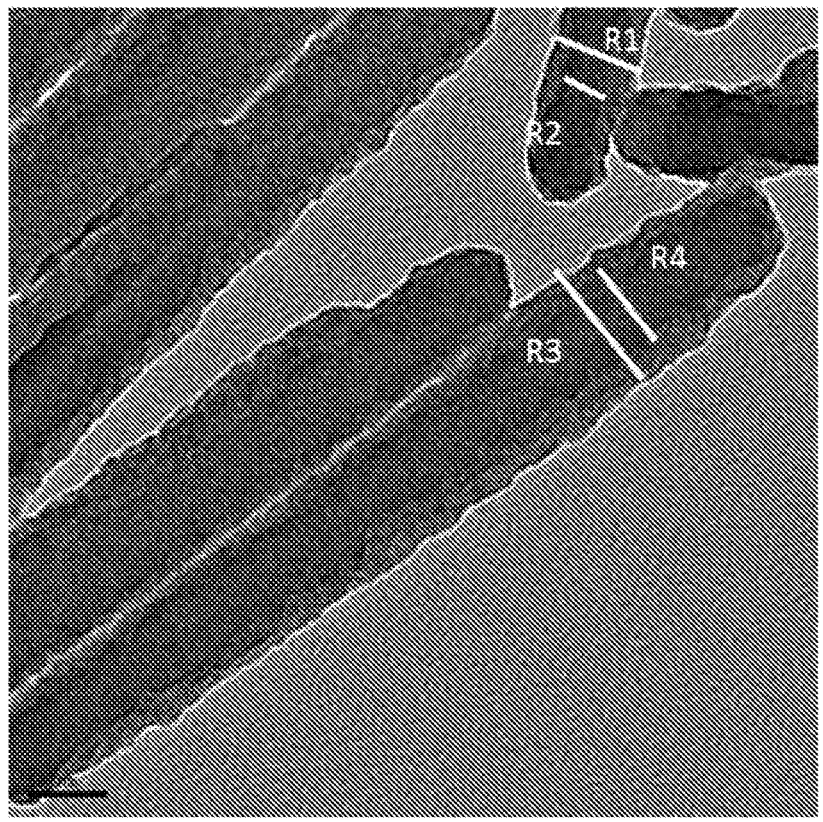
FIG. 43. Calculation of theoretical drug loading. R1=61.5 nm R2=30 nm; 2.2*(30.75^2-15^2)/1.4*(15^2)=5.03; Loading 16.6%. R3=90 nm R4=47 nm; 2.2*(45^2 23.5^2)/1.4*(23.5^2)=4.2; Loading 19.3%.

See also FIG. 43. In embodiments, drug wt is determined by High Performance Liquid chromatography (HPLC). For example, the insoluble drug nanocrystal wt % may be calculated by dividing the weight of insoluble drug as measured by HPLC by the total weight of the nanoparticle measured by weighing lyophilized nanoparticle. In embodiments, drug wt % is determined by thermogravimetric analysis (TGA). For example, the insoluble drug nanocrystal wt % may be calculated by determining net weight loss (insoluble drug loaded nanoparticle final weight minus unloaded nanoparticle final weigh measured by TGA) and dividing by the total weight of PTX loaded nanoparticle (as measured by TGA).

It is contemplated that the nanoparticles provided herein, including embodiments thereof, may be loaded into or onto cells (e.g., tumor tropic cells (e.g., neural stem cells)) to facilitate delivery of the nanoparticle payload (e.g., insoluble drug) to specific tissues or organs (e.g., tumor). Thus, the aspects, and embodiments thereof, described herein regarding nanoparticle cell conjugates and nanoparticles within cells are equally applicable to the nanoparticle aspect here. Therefore, in an aspect is provided a cell including the nanoparticle (also referred to herein as a silica nanoparticle) as described herein, including embodiments, thereof. It should be understood that when a cell includes the nanoparticle as described herein, including embodiments thereof, the nanoparticle may be inside of the cell (e.g., in the cytoplasm, nucleus, or other cellular organelle) or associated (e.g, covalently linked bound or non-covalently bound) to the cell surface (e.g., through a cell surface protein).

In embodiments, the cell is a tumor tropic cell, macrophage, stem cell (e.g., neural, mesenchymal), or T-cell. In embodiments, the cell is neural stem cell, a mesenchymal stem cell, a mesenchymal stromal cell, a hematopoetic stem cell, T-lymphocyte, a macrophage, or a liver stem cell. In embodiments, the cell is a neural stem cell. In embodiments, the cell is genetically modified. In embodiments, the cell is a genetically modified stem cell. In embodiments, the cell is a genetically modified neural stem cell. In embodiments, the neural stem cell is a human HB1.F3 stem cell. In embodiments, the nanoparticle as provided herein, including embodiments thereof, is located inside the cell (e.g., in the cytoplasm). In embodiments, the nanoparticle as provided herein, including embodiments thereof, is covalently bound to the surface of the cell through a linker as described herein. In embodiments, the nanoparticle as provided herein, including embodiments thereof, is non-covalently bound to the surface of the cell.

The nanoparticle described herein, including embodiments thereof, may be referred to herein as a siNC, nanorod, nanoparticle, or silica nanoparticle. These terms may be used interchangeably. For example, as seen in the Examples, the nanoparticle including a paclitaxel nanocrystal and a silica layer is referred to as a nanorod, PTX nanorod, PTX-nanorod, or PTX-siNC. These terms are all considered to encompass the embodied invention.

III. Pharmaceutical Compositions

In another aspect, is provided a pharmaceutical composition including a pharmaceutically acceptable excipient and a nanoparticle, cell, or nanoparticle-cell construct, as described herein, including embodiments.

The compositions (e.g., nanoparticle, cell, or nanoparticle-cell construct) of the present invention can be prepared and administered in a wide variety of oral, parenteral and topical dosage forms. Oral preparations include tablets, pills, powder, dragees, capsules, liquids, lozenges, cachets, gels, syrups, slurries, suspensions, etc., suitable for ingestion by the patient. The compositions (e.g., nanoparticle, cell, or nanoparticle-cell construct) of the present invention can also be administered by injection, that is, intravenously, intramuscularly, intracutaneously, subcutaneously, intraduodenally, or intraperitoneally. Also, the compositions (e.g., nanoparticle, cell, or nanoparticle-cell construct) described herein can be administered by inhalation, for example, intranasally. Additionally, the compositions (e.g., nanoparticle, cell, or nanoparticle-cell construct) of the present invention can be administered transdermally. It is also envisioned that multiple routes of administration (e.g., intramuscular, oral, transdermal) can be used to administer the compositions (e.g., nanoparticle, cell, or nanoparticle-cell construct) of the invention. Accordingly, the present invention also provides pharmaceutical compositions including a pharmaceutically acceptable excipient and one or more compositions (e.g., nanoparticle, cell, or nanoparticle-cell construct) of the invention.

Pharmaceutical compositions provided by the present invention include compositions wherein the active ingredient is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., modulating the activity of a target molecule, and/or reducing, eliminating, or slowing the progression of cancer symptoms. Determination of a therapeutically effective amount of a composition (e.g., nanoparticle, cell, or nanoparticle-cell construct) of the invention is well within the capabilities of those skilled in the art, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated (e.g., cancer, ovarian cancer, bladder cancer, head and neck cancer, brain cancer, breast cancer, lung cancer, cervical cancer, liver cancer, colorectal cancer, pancreatic cancer, glioblastoma, neuroblastoma, rhabdomyosarcoma, osteosarcoma, renal cancer, renal cell carcinoma, non-small cell lung cancer, uterine cancer, testicular cancer, anal cancer, bile duct cancer, biliary tract cancer, gastrointestinal carcinoid tumors, esophageal cancer, gall bladder cancer, appendix cancer, small intestine cancer, stomach (gastric) cancer, urinary bladder cancer, genitourinary tract cancer, endometrial cancer, nasopharyngeal cancer, head and neck squamous cell carcinoma, or prostate cancer), kind of concurrent treatment, complications from the disease being treated or other health-related problems. Other therapeutic regimens or agents can be used in conjunction with the methods and compositions (e.g., nanoparticle, cell, or nanoparticle-cell construct) described herein. Adjustment and manipulation of established dosages (e.g., frequency and duration) are well within the ability of those skilled in the art.

The ratio between toxicity and therapeutic effect for a particular compositions (e.g., nanoparticle, cell, or nanoparticle-cell construct) is its therapeutic index and can be expressed as the ratio between $LD_{50}$ (the amount of compositions (e.g., nanoparticle, cell, or nanoparticle-cell construct) lethal in 50% of the population) and $ED_{50}$ (the amount of compositions (e.g., nanoparticle, cell, or nanoparticle-cell construct) effective in 50% of the population). Compositions (e.g., nanoparticle, cell, or nanoparticle-cell construct) that exhibit high therapeutic indices are preferred. Therapeutic index data obtained from cell culture assays and/or animal studies can be used in formulating a range of dosages for use in humans. The dosage of such compositions (e.g., nanoparticle, cell, or nanoparticle-cell construct) preferably lies within a range of plasma concentrations that include the $ED_{50}$ with little or no toxicity. The dosage may vary within this range depending upon the dosage form employed and the route of administration utilized. See, e.g. Fingl et al., In: THE PHARMACOLOGICAL BASIS OF THERAPEUTICS, Ch. 1, p. 1, 1975. The exact formulation, route of administration and dosage can be chosen by the individual physician in view of the patient's condition and the particular method in which the composition (e.g., nanoparticle, cell, or nanoparticle-cell construct) is used.

The neutral forms of the compositions (e.g., nanoparticle, cell, or nanoparticle-cell construct) may be regenerated by contacting the salt with a base or acid and isolating the parent compound in the conventional manner. The parent form of the composition (e.g., nanoparticle, cell, or nanoparticle-cell construct) differs from the various salt forms in certain physical properties, such as solubility in polar solvents, but otherwise the salts are equivalent to the parent form of the composition (e.g., nanoparticle, cell, or nanoparticle-cell construct) for the purposes of the present invention.

Certain compositions described herein of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

In another embodiment, the compositions of the present invention are useful for parenteral administration, such as intravenous (IV) administration or administration into a body cavity or lumen of an organ. The formulations for administration will commonly include a solution of the compositions of the present invention dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of the compositions of the present invention in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The compositions (e.g., nanoparticle, cell, or nanoparticle-cell construct) described herein can be used in combination with one another, with other active agents known to be useful in treating cancer (e.g. ovarian cancer, bladder cancer, head and neck cancer, brain cancer, breast cancer, lung cancer, cervical cancer, liver cancer, colorectal cancer, pancreatic cancer, glioblastoma, neuroblastoma, rhabdomyosarcoma, osteosarcoma, renal cancer, renal cell carcinoma, non-small cell lung cancer, uterine cancer, testicular cancer, anal cancer, bile duct cancer, biliary tract cancer, gastrointestinal carcinoid tumors, esophageal cancer, gall bladder cancer, appendix cancer, small intestine cancer, stomach (gastric) cancer, urinary bladder cancer, genitourinary tract cancer, endometrial cancer, nasopharyngeal cancer, head and neck squamous cell carcinoma, or prostate cancer), or with adjunctive agents that may not be effective alone, but may contribute to the efficacy of the active agent.

In embodiments, the nanoparticles, cells, or nanoparticle-cell constructs described herein can be co-administered with conventional chemotherapeutic agents including alkylating agents (e.g., cyclophosphamide, ifosfamide, chlorambucil, busulfan, melphalan, mechlorethamine, uramustine, thiotepa, nitrosoureas, etc.), anti-metabolites (e.g., 5-fluorouracil, azathioprine, methotrexate, leucovorin, capecitabine, cytarabine, floxuridine, fludarabine, gemcitabine, pemetrexed, raltitrexed, etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), other platinum-based compounds (e.g. cisplatin, oxaloplatin, carboplatin, a second platinum-based compound described herein), and the like.

The nanoparticles, cells, or nanoparticle-cell constructs or drugs described herein can also be co-administered with conventional hormonal therapeutic agents including, but not limited to, steroids (e.g., dexamethasone), finasteride, aromatase inhibitors, tamoxifen, and gonadotropin-releasing hormone agonists (GnRH) such as goserelin.

In a further embodiment, the nanoparticles, cells, or nanoparticle-cell constructs or drugs described herein can be co-administered with conventional radiotherapeutic agents including, but not limited to, radionuclides such as $^{7}$Sc, $^{64}$Cu, $^{67}$Cu, $^{89}$Sr, $^{86}$Y, $^{87}$Y, $^{90}$Y, $^{105}$Rh, $^{111}$Ag, $^{111}$In, $^{117m}$Sn, $^{149}$Pm, $^{153}$Sm, $^{166}$Ho, $^{177}$Lu, $^{186}$Re, $^{188}$Re, $^{211}$At, and $^{212}$Bi, optionally conjugated to antibodies directed against tumor antigens.

The pharmaceutical compositions of the present invention may be sterilized by conventional, well-known sterilization techniques or may be produced under sterile conditions. Aqueous solutions can be packaged for use or filtered under aseptic conditions and lyophilized, the lyophilized preparation being combined with a sterile aqueous solution prior to administration. The compositions can contain pharmaceutically acceptable auxiliary substances as required to approximate physiological conditions, such as pH adjusting and buffering agents, tonicity adjusting agents, wetting agents, and the like, e.g., sodium acetate, sodium lactate, sodium chloride, potassium chloride, calcium chloride, sorbitan monolaurate, and triethanolamine oleate.

Formulations suitable for oral administration can comprise: (a) liquid solutions, such as an effective amount of a packaged nanoparticles, cells, or nanoparticle-cell constructs or drug suspended in diluents, e.g., water, saline, or PEG 400; (b) capsules, sachets, or tablets, each containing a predetermined amount of a nanoparticles, cells, or nanoparticle-cell constructs or drug, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise a nanoparticles, cells, or nanoparticle-cell constructs or drug in a flavor, e.g., sucrose, as well as pastilles comprising the polypeptide or peptide fragment in an inert base, such as gelatin and glycerin or sucrose and acacia emulsions, gels, and the like, containing, in addition to the polypeptide or peptide, carriers known in the art.

The nanoparticles, cells, or nanoparticle-cell constructs or drug (e.g., anti-cancer agent) of choice, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Suitable formulations for rectal administration include, for example, suppositories, which comprises an effective amount of a packaged nanoparticles, cells, or nanoparticle-cell constructs or drug with a suppository base. Suitable suppository bases include natural or synthetic triglycerides or paraffin hydrocarbons. In addition, it is also possible to use gelatin rectal capsules which contain a combination of the nanoparticles, cells, or nanoparticle-cell constructs or drug of choice with a base, including, for example, liquid triglycerides, polyethylene glycols, and paraffin hydrocarbons.

Formulations suitable for parenteral administration, such as, for example, by intraarticular (in the joints), intravenous, intramuscular, intratumoral, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Injection solutions and suspensions can also be prepared from sterile powders, granules, and tablets. In the practice of the present invention, compositions can be administered, for example, by intravenous infusion, orally, topically, intraperitoneally, intravesically, or intrathecally. Parenteral administration, oral administration, and intravenous administration are the preferred methods of administration. The formulations of compositions (e.g., nanoparticle, cell, or nanoparticle-cell construct) can be presented in unit-dose or multi-dose sealed containers, such as ampoules and vials.

The pharmaceutical preparation is preferably in unit dosage form. In such form the preparation is subdivided into unit doses containing appropriate quantities of the active component, e.g., nanoparticles, cells, or nanoparticle-cell constructs or drug. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents

IV. Methods of Treatment

In an aspect is provided a method of treating cancer in a patient in need of such treatment, the method including administering to a subject in need thereof a therapeutically effective amount of the nanoparticle, the cell, or the nanoparticle-cell construct, as described herein. In embodiments, the method is administering to a subject in need thereof a therapeutically effective amount of the nanoparticle as described herein. In embodiments, the method is administering to a subject in need thereof a therapeutically effective amount of the cell as described herein. In embodiments, the method is administering to a subject in need thereof a therapeutically effective amount of the nanoparticle-cell construct as described herein.

In embodiments, the cancer is ovarian cancer, bladder cancer, head and neck cancer, brain cancer, breast cancer, lung cancer, cervical cancer, liver cancer, colorectal cancer, pancreatic cancer, glioblastoma, neuroblastoma, rhabdomyosarcoma, osteosarcoma, renal cancer, renal cell carcinoma, non-small cell lung cancer, uterine cancer, testicular cancer, anal cancer, bile duct cancer, biliary tract cancer, gastrointestinal carcinoid tumors, esophageal cancer, gall bladder cancer, appendix cancer, small intestine cancer, stomach (gastric) cancer, urinary bladder cancer, genitourinary tract cancer, endometrial cancer, nasopharyngeal cancer, head and neck squamous cell carcinoma, or prostate cancer. In embodiments, the cancer is ovarian cancer, bladder cancer, head and neck cancer, prostate cancer, brain cancer, breast cancer, lung cancer, cervical cancer, liver cancer, bone cancer, or spinal cancer. In embodiments, the cancer is ovarian cancer.

V. Methods of Making

In another aspect is a method of making a nanoparticle including the steps of (a) mixing an insoluble drug and an amphiphilic polymer in an organic solvent; (b) removing the organic solvent, adding a solvent (e.g., water or aqueous solution), and sonicating the mixture to form a nanocrystal; and (c) mixing tetraethyl orthosilicate (TEOS), phenyltrimethoxysilane (PTMS), and hydrolyzed aminopropyltriethoxy silane (APTES) with the nanocrystal to form a nanoparticle. In embodiments, the method further includes isolating the nanoparticle from the reaction mixture formed by step (c). In embodiments, the method further includes isolating the nanoparticle following step (c).

In embodiments, the organic solvent of part (a) is or includes acetic acid, acetone, acetonitrile, benzene, 1-butanol, 2-butanol, 2-butanone, t-butyl alcohol, carbon tetrachloride, chlorobenzene, chloroform, cyclohexane, 1,2-dichloroethane, diethylene glycol, diethyl ether, diglyme (diethylene glycol, dimethyl ether), 1,2-dimethoxyethane (glyme, DME), dimethylformamide (DMF), dimethyl sulfoxide (DMSO), 1,4-dioxane, ethanol, ethyl acetate, ethylene glycol, glycerin, heptane, hexamethylphosphoramide (HMPA), hexamethylphosphorous, triamide (HMPT), hexane, methanol, methyl t-butyl ether (MTBE), methylene chloride, N-methyl-2-pyrrolidinone (NMP), nitromethane, pentane, petroleum ether (ligroine), 1-propanol, 2-propanol, pyridine, tetrahydrofuran (THF), toluene, triethyl amine, o-xylene, m-xylene, or p-xylene. In embodiments, the organic solvent is or includes chloroform, dichloromethane, methanol, ethanol, tetrahydrofuran, or dioxane. In embodiments, the organic solvent is chloroform, dichloromethane, methanol, ethanol, tetrahydrofuran, or dioxane. In embodiments, the organic solvent is or includes chloroform. In embodiments, the solvent in part (b) is or includes chloroform, dichloromethane, methanol, ethanol, tetrahydrofuran, dioxane, or water. In embodiments, the solvent in part (b) includes a salt.

In embodiments, the sucrose gradient includes at least two different concentrations of sucrose. In embodiments, the sucrose gradient includes at least three different concentrations of sucrose. In embodiments, the sucrose gradient includes at least four different concentrations of sucrose. In embodiments, the sucrose gradient includes at least five different concentrations of sucrose. In embodiments, the sucrose gradient includes five different concentrations of sucrose, wherein the percentage of sucrose in water are given as 18%, 21%, 24%, 27%, and 30%. In embodiments, the sucrose gradient includes five different concentrations of sucrose, wherein the percentage of sucrose in water are given as 10%, 20%, 30%, 40%, and 50%.

In embodiments, step (b) includes sonicating for at least 100 minutes. In embodiments, step (b) includes sonicating for at least 90 minutes. In embodiments, step (b) includes sonicating for at least 85 minutes. In embodiments, step (b) includes sonicating for at least a total of 25 minutes. In embodiments, step (b) includes sonicating for about 100 minutes. In embodiments, step (b) includes sonicating for about 90 minutes. In embodiments, step (b) includes sonicating for about 85 minutes. In embodiments, step (b) includes sonicating for about 80 minutes. In embodiments, step (b) includes sonicating for about 75 minutes. In embodiments, step (b) includes sonicating for about 70 minutes. In embodiments, step (b) includes sonicating for about 65 minutes. In embodiments, step (b) includes sonicating for about 60 minutes. In embodiments, step (b) includes sonicating for about 55 minutes. In embodiments, step (b) includes sonicating for about 50 minutes. In embodiments, step (b) includes sonicating for about 40 minutes. In embodiments, step (b) includes sonicating for about 35 minutes. In embodiments, step (b) includes sonicating for about 30 minutes. In embodiments, step (b) includes sonicating for about 25 minutes. In embodiments, step (b) includes sonicating for about 20 minutes. In embodiments, step (b) includes sonicating for about 15 minutes. In embodiments, step (b) includes sonicating for about 10 minutes. In embodiments, step (b) includes sonicating for about 5 minutes. In embodiments, step (b) includes sonicating in periodic amounts (e.g., sonicating for a variable time interval and resting for a variable time interval). In embodiments, step (b) includes sonicating in periodic amounts (e.g., sonicating for 5 minutes and resting for 15 minutes, somicating for 5 minutes and resting for 10 minutes). In embodiments, step (b) includes sonicating in about 5 minute intervals for a total of about 25 sonicating minutes, including 60 total minutes of resting intervals. In embodiments, step (b) includes sonicating in about 5 minute intervals for a total of about 15 sonicating minutes, including 30 total minutes of resting intervals.

In embodiments, step (c) stirs for at least 1 hour. In embodiments, step (c) stirs for at least 2 hours. In embodiments, step (c) stirs for at least 3 hours. In embodiments, step (c) stirs for at least 4 hours. In embodiments, step (c) stirs for at least 6 hours. In embodiments, step (c) stirs for at least 12 hours. In embodiments, step (c) stirs for at least 16 hours. In embodiments, step (c) stirs for about 1 hour. In embodiments, step (c) stirs for about 2 hours. In embodiments, step (c) stirs for about 3 hours. In embodiments, step (c) stirs for about 4 hours. In embodiments, step (c) stirs for about 6 hours. In embodiments, step (c) stirs for about 12 hours. In embodiments, step (c) stirs for about 16 hours.

In embodiments, the method of making a nanoparticle including the steps of (a) mixing an insoluble drug (e.g., paclitaxel) and an amphiphilic polymer (e.g., poloxamer 407) in an organic solvent (e.g., chloroform) and vortexed using a vortex mixer. In embodiments, following step (a), nitrogen gas is used to evaporate the organic solvent (e.g., chloroform). In embodiments, the reaction from step (a) is placed in a vacuum with a drying agent (e.g., drierite) for about an hour. Following the removal of the organic solvent (e.g., using nitrogen gas or in a vacuum with a drying agent), water is vortexed with a vortex mixer with the reactants from step (a) (e.g., the reacted amphiphilic polymer and insoluble drug) for about 20 minutes. In embodiments, step (b) includes sonicating at periodic intervals (e.g., 5 minutes sonicating, 15 minutes of not sonicating) to form a nanocrystal. In embodiments, step (c) includes mixing TEOS and PTMS, followed by the addition of APTES which was diluted in water. In embodiments, step (c) mixes for about 16 hours. In embodiments, following step (c), the reaction is centrifuged (e.g., for about 20 minutes at 14,000×g) and washed with water. In embodiments, the reaction is washed about three times.

In embodiments, the method of making further includes isolating the nanoparticle. In embodiments, the isolating of the nanoparticle includes centrifugation. In embodiments, the centrifugation occurs at 20,000×g for 10 minutes. Following centrifugation, the nanoparticles may be washed with water (e.g., milliQ water) up to or greater than 3 times. In embodiments, the isolating of the nanoparticle includes differential centrifugation. One of ordinary skill in the art would understand if differential centrifugation (e.g., sucrose gradient is used in combination with centrifugation) is used to isolate the nanoparticles, separation of the nanoparticles occurs on the basis of particle size (e.g., nanoparticles of different sizes in the sucrose suspension will sediment at different rates). In embodiments, the isolating of the nanoparticle includes the use of a density gradient solution. In embodiments, the isolating of the nanoparticle includes the use of a sucrose gradient solution. In embodiments, the isolating of the nanoparticle includes centrifugation. In embodiments, the isolating includes centrifugation at 3600× rpm for about 35 minutes. Following centrifugation, the nanoparticles of interest (e.g., a specific size) may be extracted (e.g., using a pipette) from at least one layer (e.g., distinct concentration of sucrose).

EXAMPLES

Example 1. Paclitaxel Nanosuspensions Stabilized by Organosilanes for Neural Stem Cell Loading Many drug candidates, such as Paclitaxel, that have emerged from drug discovery programs are water-insoluble, which leads to poor bioavabilability in vivo. To address the issue of solubility, various formulations of Paclitaxel have been developed, such as Taxol (solubilized in Cremophor and ethanol), Abraxane (stabilized by albumin), and Paclitaxel nanosuspensions. Nanosuspensions of Paclitaxel stabilized by surfactants, such as Pluronic F127, have received interest since they are formulated from pure crystalline drug and do not require the use of toxic excipients. However, these nanosuspensions formulated with surfactants provide temporary stabilization, resulting in fusion/aggregation of nanocrystals over time. We have developed a method to coat the individual nanocrystals with a silica shell to ensure long term stabilization and delayed release of Paclitaxel over time (e.g., for targeted delivery using tumor-tropic Neural Stem Cells as a cell carrier). Neural Stem Cells (NSCs) have demonstrated inherent tumor tropic properties (e.g. to ovarian cancer cells) in vitro and in vivo following intraperitoneal administration. However, NSCs generally do not intrinsically have anti-tumor efficacy. As NSC-based therapy moves into the clinic, there is a need to develop complementary techniques to enable targeted delivery of chemotherapeutics by NSCs.

Ovarian cancer is the leading cause of gynecologic cancer mortality in women in the US and each year ~20,000 women are diagnosed with it.[1] In 2013, of the 20,927 women in the US diagnosed with ovarian cancer, 14, 276 (68.2%) women died due to the disease.[2] The five-year survival rate remains at only 30%. The lack of validated screening programs and the absence of symptoms during the early stages of ovarian cancer contribute to the difficulty of early diagnosis. Because of this, many patients are diagnosed at an advanced stage of the disease with 60-70% of patients already at stage III or IV. Tumor debulking and chemotherapy using platinum- and taxane-based drugs are the current standard of treatment for patients.[1-4] However, alternate formulations of Paclitaxel are needed to increase aqueous solubility and reduce side effects due to toxic excipients used to solubilize the drug.

Paclitaxel (PTX) is a taxane-based drug that is effective against solid tumors, such as ovarian and breast cancer. It was first isolated in 1962 from the bark of the Pacific Yew tree. The mechanism of action of this drug involves tubulin stabilization by binding to the beta subunit of tubulin. Since PTX promotes the polymerization of tubulin, this stabilization of the microtubules prevents mitotic cell division from occurring. This leads to arrest at the G2/M phase of the cell cycle, triggering apoptosis.[6]

Since PTX has poor aqueous solubility, it is mixed in a 1:1 ratio of Cremophor (castor oil) and ethanol in order to solubilize the drug and further diluted with saline for systemic administration (Taxol). Many side effects are seen with Cremophor such as anaphylactic shock, hypersensitivity reactions, rashes, peripheral neuropathy, neutropenia, etc. Due to the high risk of hypersensitivity, patients are pretreated with corticosteroids or antihistamines. When PTX is systemically administered, more than 90% of the drug is bound to plasma proteins, such as lipoproteins, glycoproteins, and albumin. PTX is mainly metabolized in the liver by cytochrome P450 and the majority is eliminated by bile excretion.[7] In order to improve bioavailability, pharmacokinetics, solubility, and efficacy, novel nanoparticle drug formulations are currently being explored.

Abraxane is another commercially available formulation of Paclitaxel. It is stabilized by human serum albumin proteins (most abundant plasma protein found in the blood), which increases solubility of the drug in saline. Abraxane is produced through high-pressure homogenization generating particles with a diameter of ~130 nm.[8] Since albondin, a 60 kD glycoprotein (gp60) receptor, and SPARC (secreted protein, acidic and rich in cysteine) are known to have albumin-binding properties and are overexpressed in certain tumors, it is postulated that albumin-bound PTX is actively uptaken into tumor cells.[9] Due to the stabilization by albumin, there was an increase in aqueous solubility as well as in blood half-life (19 hours). The maximum tolerated dose of Abraxane increased in patients, while toxicity decreased compared to Taxol. However, there was no significant difference between the overall survival and efficacy of patients administered Abraxane or Taxol.[8, 10-12]

Systemic administration of chemotherapeutics, such as Paclitaxel (Taxol and Abraxane), causes many off-target toxicities to major organs and healthy tissues.[13,14] In the case of Abraxane, which uses albumin instead of Cremophor, hypersensitivity issues are reduced, however patients still experience side effects such as neutropenia or neuropathy caused by off-target toxicity. To address this issue of non-specificity, many nanoparticle drug delivery systems have been developed consisting of liposomes, micelles, polymeric nanoparticles, silica, etc. They can be used to package hydrophobic drugs without the use of toxic excipients (Taxol). Due to the varied composition and ease in tunability, drug-loaded nanoparticles are being investigated for use in the treatment of various tumors (targeted and passive manner). Here, we discuss the aspects of tumor physiology and the enhanced permeability and retention effect as well as common nanoparticle formulations used in drug delivery. We also investigate various nanoformulations of Paclitaxel and a novel delivery system using Neural Stem Cells as a cell carrier to potentially deliver chemotherapeutics specifically to the tumor site (e.g., ovarian cancer).

During the initial stages of tumor growth, cells retrieve nutrients in a diffusion-limited manner.[15] Due to the rapid replication of tumor cells, angiogenesis is initiated at tumor sites in order to meet the increasing demand of nutrients. This rapid growth in vasculature results in malformed blood vessels with incomplete endothelial linings and fenestrations.[16,17] Because of this, tumors are extremely heterogenous. They contain both regions of dense vasculature allowing for accessible blood supply and nutrients as well as hypoxic/necrotic regions with little to no vasculature. In addition to leaky vessels, tumors have a poor lymphatic drainage system, which causes accumulation and retention of macromolecules in the tumor for extended periods of time.[13,17,18] These two tumor physiological factors contribute to the phenomenon known as enhanced permeability and retention (EPR) effect. This phenomenon was first observed with drugs, lipids, and macromolecules larger than 50 kDa retained at the tumor site.[13,19]

Considering the tumor physiology, the EPR effect allows nanoparticles to exploit the vasculature and impaired lymphatic system in order to passively target drug-loaded nanoparticles to the tumor. The fenestrations in the malformed vessels allow nanoparticles to extravasate out of the vessels, while the poor lymphatic drainage prevents nanoparticles from being cleared from the tumor.[13] Nanoparticles are, therefore, able to accumulate and be retained in the tumor site. Many nanoparticles rely heavily on the EPR effect for passive targeting, however, nanoparticles can also be functionalized to have targeting ligands, such as antibodies, proteins, or aptamers, to selectively bind to antigens or receptors overexpressed by tumor cells.[14]

The various material composition and ease in synthesis of nanoparticles allow for these carriers to be engineered for specific drug delivery applications. The most common nanoparticle structures include liposomes, micelles, polymeric nanoparticles, silica nanoparticles, and nanosuspensions.[14,16] This section will delve into the various types of nanoparticles used for drug delivery as well as the most advanced examples representative of each particle type.

Liposomes are nanoparticles that are composed of amphiphilic molecules such as cholesterol or phospholipids. These molecules are non-toxic, non-immunogenic, and biodegradable. Their amphiphilic nature (polar and non-polar moieties) allows the molecules to form lipid layers that self-assemble into closed vesicles (unilamellar or multilamellar), allowing drugs to be encapsulated within.[20] Liposomes can be functionalized with poly(ethylene glycol) (PEG) to prolong circulation in the blood stream, avoiding uptake by macrophages.[17,21] Doxil and DaunoXome are two commercially available liposomal drug formulations approved by the FDA for cancer therapy. Doxil was the first FDA approved PEGylated biodegradable liposome developed to encapsulate doxorubicin for the treatment of solid tumors. DaunoXome uses a liposomal formula for daunorubicin delivery.[16,20,21]

Micelles are also composed of amphiphilic molecules, such as diblock and triblock copolymers (PEG-poly(L-aspartate), PEG-poly(L-glutamate), PLGA-PPO-PLGA, PEG-PPO-PEG, etc.). They self-assemble into nanostructures consisting of a hydrophobic core and hydrophilic exterior shell when the amphiphilic polymer has exceeded the critical micelle concentration (CMC).[22] They are able to encapsulate poorly water soluble drugs, due to the hydrophobic core of the micelle. Many of the diblock and triblock copolymers used are biodegradable and biocompatible, allowing for full renal clearance of the micelles over time. The hydrophilic PEG prevents opsonization of serum proteins, prolonging circulation of micelles in the body.[14,17,23] Current micellar drug delivery vehicles in phase III clinical trials include Genexol-PM (PEG-poly(D,L-lactide) and NK105 (PEG-poly(aspartate) for the treatment of breast cancer.[24-26]

Polymeric Nanoparticles can be composed of single polymer chains such as polyesters (PGA, PLA, PLGA), PLGA copolymers (PLGA-PEG), polycaprolactones, chitosan, polyamides, hyaluronic acid, or dextran.[27] PLGA is the most widely used biodegradable polymer in formulating nanoparticles. PLGA is FDA approved for use in humans since it can undergo hydrolysis in the body to form lactic and glycolic acid in the body, both which are non-toxic. PLGA particles have been engineered by different methods, including oil-in-water emulsion methods and nanoprecipitation using an anti-solvent.[28,29] Eligard is an FDA approved PLGA nanoparticle used for the delivery of leuprolide for the treatment prostate cancer.[30]

Silica nanoparticles are being explored in drug delivery due to their biocompatibility (generally regarded as safe by FDA) and scalability. They are synthesized from silica precursors such as tetraethyl orthosilicate (TEOS). The size and porosity of silica nanoparticles can be tuned as well. The Stober method involves using a combination of water, alcohol, TEOS, and ammonia to produce nonporous silica nanoparticles.[31,32] Mesoporous silica nanoparticles are can be created by using the Stober method plus added surfactant such as cetyl trimethylammonium bromide (CTAB). CTAB removal by washing of the silica nanoparticles generates pores. Porosity can be tuned depending on the concentration and type of surfactant used. Surface modifications can be easily made as well for PEGylation or drug loading.[33] There are many silica nanoparticles currently in preclinical studies.[34]

Nanosuspensions/nanocrystals are an attractive form of drug delivery since they are produced from pure drug crystals. Hydrophobic drugs, such as Paclitaxel, require solubilization in harsh organic solvents that can cause severe side effects such as hypersensitivity or nephrotoxicity. Nanocrystals on the other hand are produced by milling, sonication, or high-pressure homogenization of whole crystalline drugs (top-down approach). A bottom-up approach involves dissolving the hydrophobic drug and a stabilizing surfactant in an organic solvent, then evaporating it with a stream of $N_2$ to create a thin film. An anti-solvent ($H_2O$) is then used to immerse the film. This creates a super-saturated drug solution that leads to nucleation/growth of crystals, which can be further broken down by sonication.[35] Triblock copolymers, such as Pluronic F127 (PEG-PPO-PEG) are used to stabilize drug nanocrystals to prevent aggregation and fusion of particles. The majority of drug nanocrystals that are commercially available are geared towards oral administration, however, Paclitaxel nanocrystals for systemic administration are in phase II clinical trials.[30]

For poloxamers described herein, for example poloxamer 407 also referred to by its tradename herein as Pluronic F127, the first digit (or two digits in a three-digit number) in the numerical designation, multiplied by 300, indicates the approximate molecular weight of the hydrophobic portion of the polymer; and the last digit multiplied by 10 gives the approximate percentage polyoxyethylene content (e.g., 12 indicates a polyoxypropylene molecular mass of 3,600 g/mol and a 70% polyoxyethylene content).

There are various methods of encapsulating and loading Paclitaxel into nanoparticles for drug delivery (liposomes, micelles, polymeric nanoparticles, silica, drug nanosuspensions, etc.). For example, Genexol-PM.

Genexol-PM, is a polymeric micelle formulation of PTX which was approved for the treatment of breast cancer in Korea in 2007. It is composed of PEG and poly(D,L-lactic acid).[36] A 3-fold increase in maximum tolerated dose was seen when Genexol-PM was administered intravenously in mice. Despite PTX concentration being 2-3 times higher in the tumor, the liver, spleen, kidneys, lungs, and heart also experienced the same increase in drug concentration (nonspecific toxicity). Phase II studies of Genexol-PM demonstrated promising results with high response rates in breast cancer patients and is currently under Phase III clinical trials.[24,37]

In order to reduce side effects, improve solubility of PTX without the use of toxic excipients, and increase drug loading, many groups have turned toward developing PTX nanosuspensions/nanocrystals. Nanosuspensions are generated by wet/dry milling or sonication.[35] They are typically stabilized by surfactants or block copolymers such as Pluronic F-127 (PEG-PPO-PEG). However, stability issues arise from these formulations. The overuse of surfactant (exceeding the critical micelle concentration) generates micelles (over the CMC). When an insufficient amount of surfactant is used, nanocrystals are prone to fusing and mass aggregation. Even with the optimal amount of surfactant covering the nanocrystals, they are temporarily stable and will still undergo fusion/aggregation over time.[38]

Attempts at stabilizing PTX nansuspensions have led to variations in formulations such as 3-LG (globular protein) coated PTX nanocrystals[39] and covalently-bound PEG-PTX nanocrystals, in which succinic anhydride is used as a linker. However, these various formulations yielded polydisperse populations of PTX nanocrystals and saw minimal to no improvement in mice compared to Taxol. These formulations also do not address the underlying issue of specific, targeted delivery.

Despite the various compositions of nanoparticles, only a handful of drug-loaded nanoparticles have been FDA-approved. The underlying issue continues to be limited uptake in the tumor. The majority of the drug in nanoparticle delivery systems accumulate in the liver, spleen, and kidneys due in large part to the mononuclear phagocyte system. Many of the frequent issues that plague nanoparticle drug delivery systems include limited drug loading, high manufacturing costs, difficulties in scaling up, instability of nanoparticles, and premature leakage of encapsulated drug. All of these factors contribute to the limited success of FDA approved nanoparticles.

In order to improve biodistribution and provide an efficacious dose of drug at the tumor site, a different route of delivery must be explored. One way to improve targeted delivery is by using cell carriers that have a propensity to migrate towards tumors or specific organs. Tumor tropic- or organotropic-cell carriers such as stem cells (Mesenchymal/Neural Stem Cells), T-cells, or macrophages, can be loaded with therapeutic nanoparticles for targeted delivery.[40-45] Past studies have confirmed that Neural Stem Cells (NSCs) can selectively migrate to various tumor types, such as glioma, breast cancer, or more recently ovarian cancer.[44] They have previously been loaded with doxorubicin loaded mesoporous silica nanoparticles and were injected contralateral to the tumor (glioma). Migration of the NSCs to the tumor was observed after 4 hours, while distribution of the released drug throughout the tumor was observed after 72 hours.[45] By using NSCs as a cell carrier, we hope to alleviate the issue of off-target toxicities, while increasing intratumoral distribution of the therapeutic payload (FIG. 1). We have developed monodisperse PTX nanosuspensions stabilized by a silica shell (e.g., for Neural Stem Cell (NSC) loading). The silica shell allows for controlled (e.g., delayed) release of PTX, while maintaining viability of the NSCs. This controlled release will allow NSCs to migrate to the tumor site without undergoing apoptosis. In this study, the synthesis of PTX silica nanocrystals (PTX-siNCs) and cell viability are explored.

Example 2. Stabilization of Paclitaxel Using Pluronic F127

Figure 2:
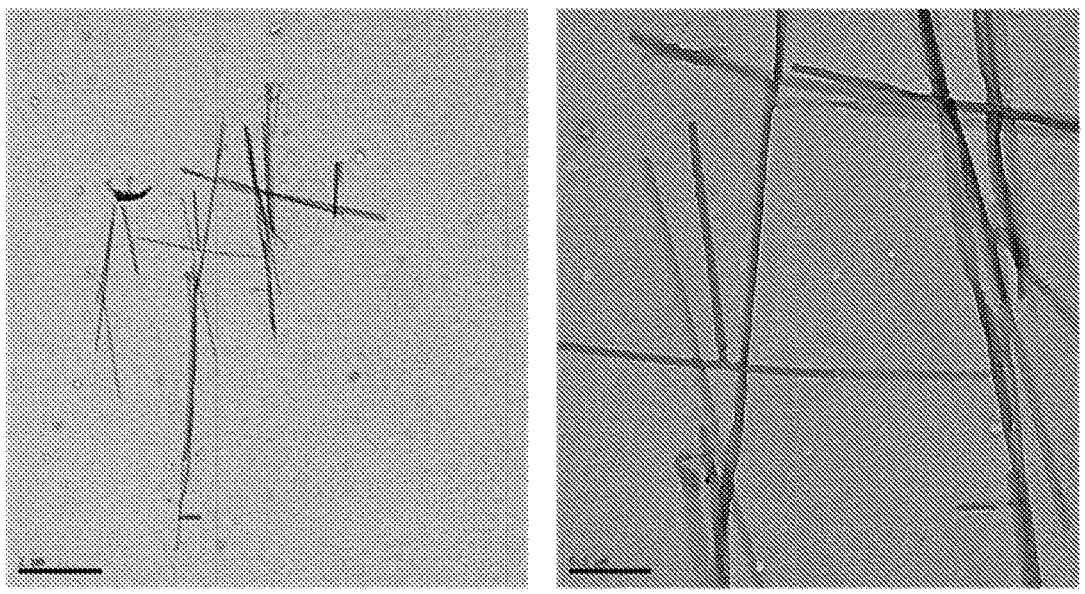
FIG. 2. Whole crystalline PTX structures. PTX was stained with uranyl acetate and imaged by TEM (6500×, 1500× magnification). PTX structures are on the order of micrometers. For reference, the scale bar on the left column corresponds to 2 µm, whereas the scale bar on the right column corresponds to 0.5 µm.
Figure 3A:
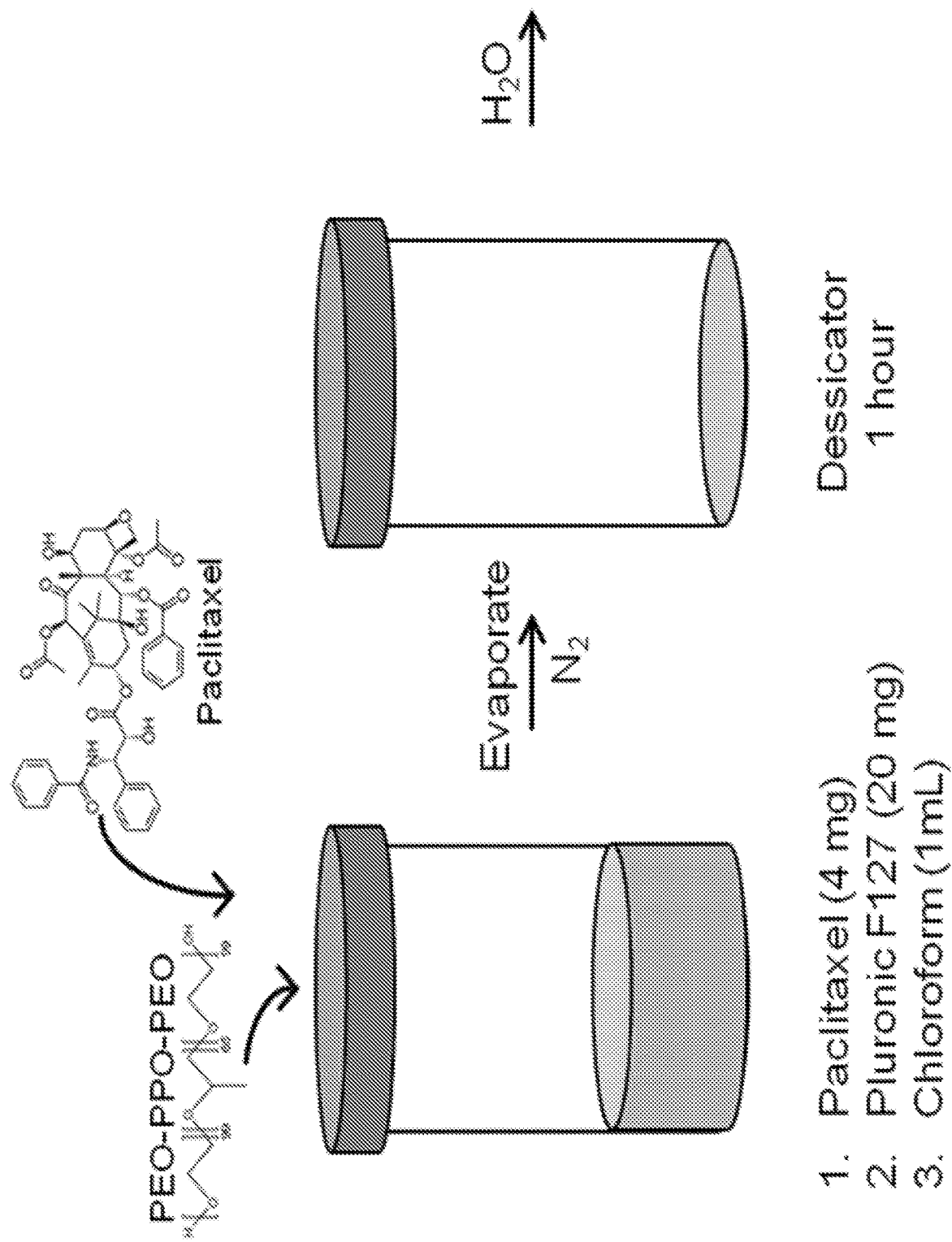
FIGS. 3A-3B. Overview of synthetic scheme providing temporary stabilization of PTX nanocrystals using Pluronic F127.
Figure 3B:
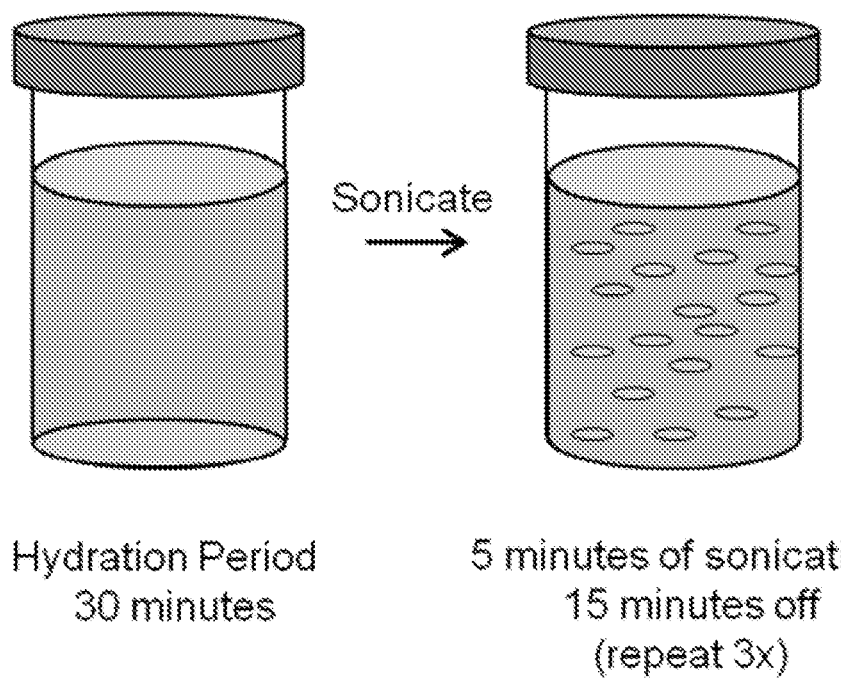
Figure 4:
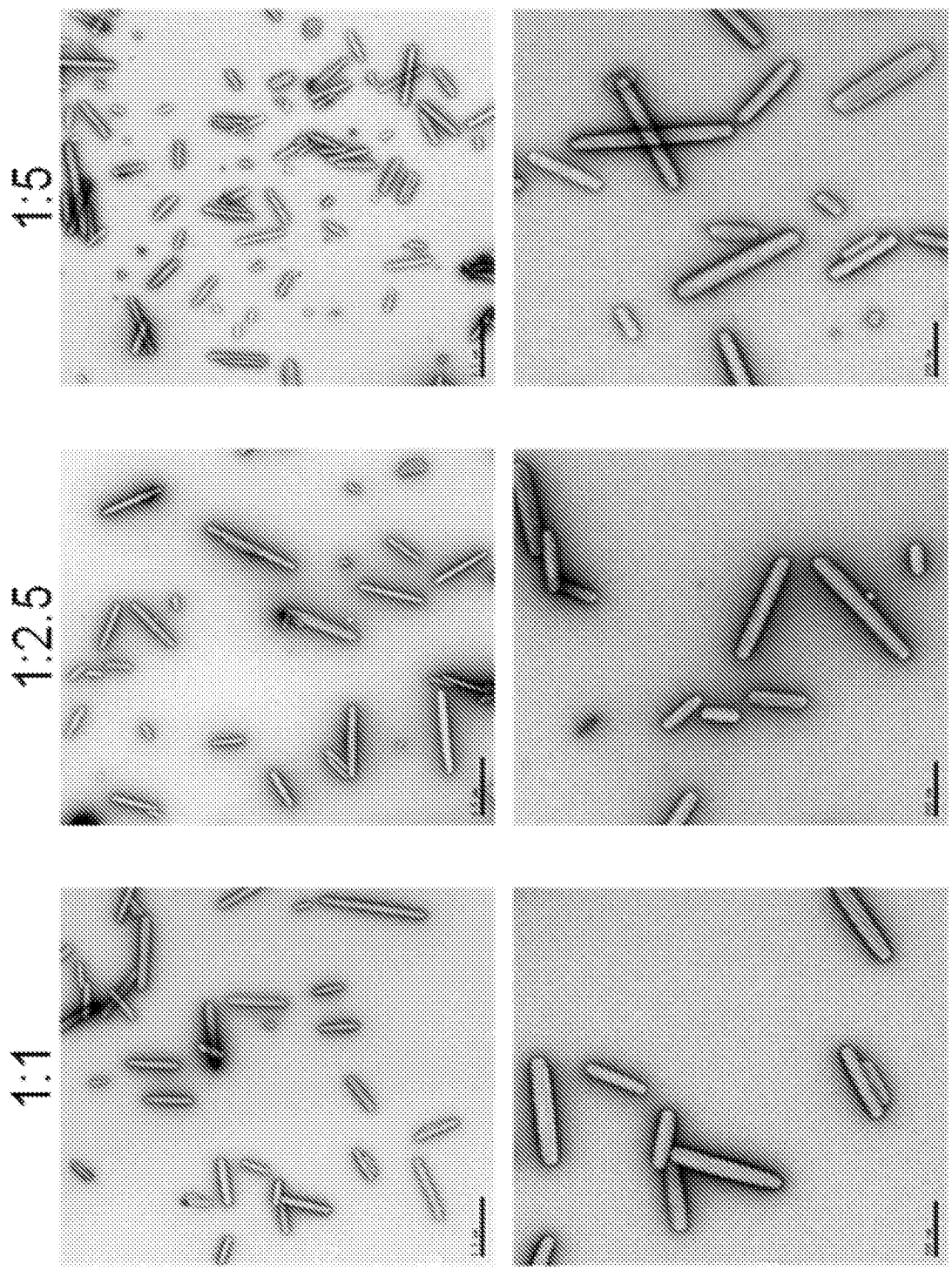
FIG. 4. PTX nanocrystal stabilization using various amounts of Pluronic F127. PTX and Pluronic were used in varying ratios (1:1, 1:2.5, and 1:5) to create PTX nanosuspensions. Nanocrystals were stained with uranyl acetate before TEM imaging (top 6500×, bottom 15000× magnification). For reference, the scale bar on the top row corresponds to 0.5 µm, whereas the scale bar on the bottom row corresponds to 200 nm.
Figure 5:
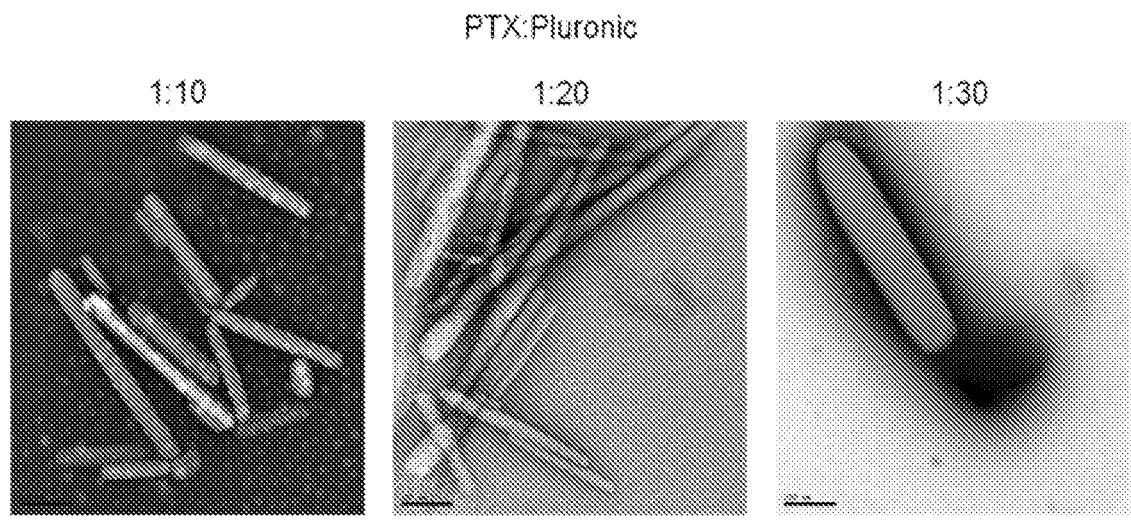
FIG. 5. Critical Micelle Concentration of Pluronic F127. PTX and Pluronic used above a 1:10 ratio (w/w) generated micelles. Nanocrystals were polydisperse. Nanocrystals were stained with uranyl acetate before TEM imaging (15000× magnification). For reference, the scale bar corresponds to 200 nm.

PTX exists in a crystalline form and is insoluble in aqueous solutions. TEM images were taken of PTX which shows the micron size and inhomogeneity of the crystals (FIG. 2). Before imaging, PTX first had to be stained with 2% uranyl acetate to make samples electron dense. Nanosuspensions were generated by first dissolving Paclitaxel and Pluronic F127 in chloroform. The organic solvent was then evaporated and placed in a vacuum with drierite for 1 hour. Antisolvent ($H_2O$) was added to the scintillation vial and placed on a shaker for 30 minutes (hydration period). The mixture was then sonicated to produce the PTX nanosuspensions stabilized by Pluronic F127 (FIG. 3). To determine the critical micelle concentration of Paclitaxel stabilized with Pluronic F127, 1:1, 1:2.5, 1:5, 1:10, 1:20, and 1:30 ratio (w/w) of PTX to Pluronic F127 was used (FIG. 4). PTX nanocrystals were stained with 2% uranyl acetate and imaged using TEM. Nanocrystal length was measured using ImageJ. The 1:1 and 1:2.5 ratio (w/w) yielded polydisperse PTX nanocrystals ranging from 64-940 nm. When PTX and Pluronic F127 was used at a 1:5 ratio (w/w), fairly monodisperse PTX nanocrystals were created. By further increasing Pluronic F127 (1:10, 1:20, and 1:30 ratio of PTX to Pluronic F127 (w/w), the critical micelle concentration was exceeded and micelles were visible in the background of the TEM image (FIG. 5). At these three conditions, the PTX nanocrystals proved to be very unstable and polydisperse.

TABLE 1

PTX and Pluronic were used in varying ratios (1:1, 1:2.5, 1:5) to create PTX nanosuspensions, corresponding to FIG. 4.

| PTX:Pluronic (w/w) | 1:1 | 1:2.5 | 1:5 |
|---|---|---|---|
| Average | 314.35 nm | 236.61 nm | 268 nm |
| STD | 153.54 nm | 118.131 nm | 146 nm |
| Max | 940 nm | 536.296 nm | 886 nm |
| Min | 96 nm | 63.64 nm | 58 nm |

Figure 6:
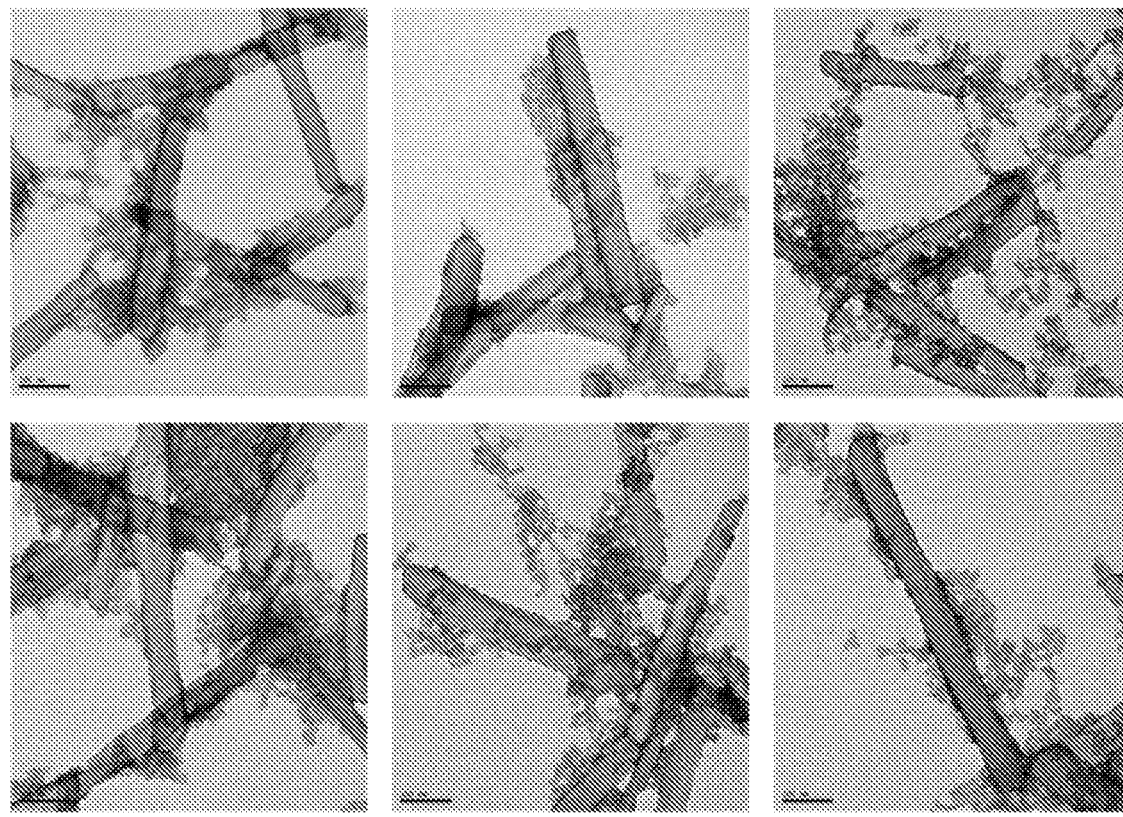
FIG. 6. TEM images of silica networks formed around PTX-siNCs using TEOS and NaOH methods. The addition of TEOS and NaOH caused spontaneous networks of silica to form in solution. The silica networks trapped many of the PTX-siNCs, causing aggregation. (30,000× magnification). For reference, the scale bar corresponds to 100 nm.
Figure 7:
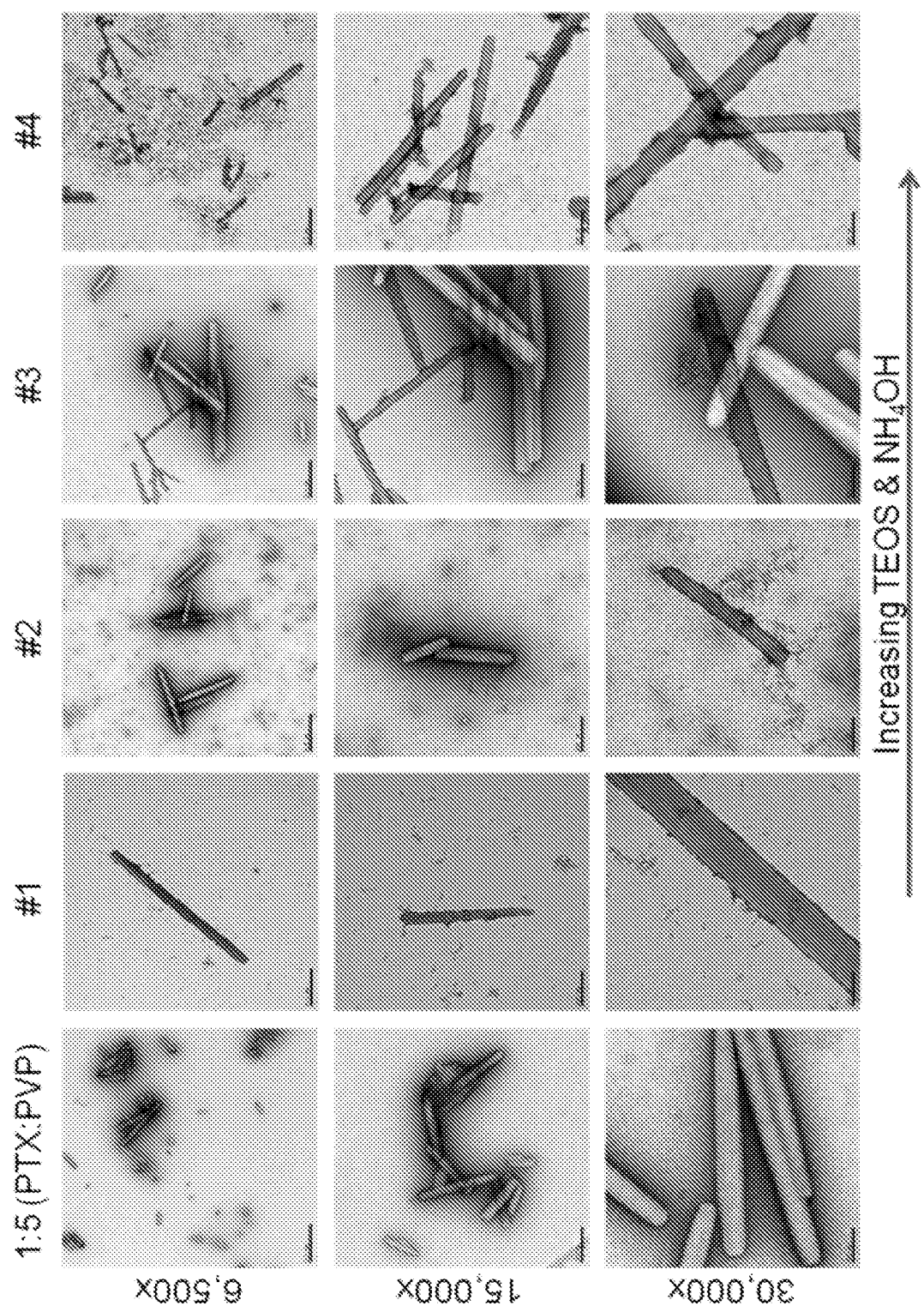
FIG. 7. TEM images of silica growth using PVP-stabilized PTX-siNCs. PTX and PVP used at a ratio of 1:5 (w/w) were used to create nanocrystals. TEOS and NH4OH were used in increasing amounts. Silica networks formed in solution, however, patchy layers of silica grew on the PTX surface. For reference, the scale bar on the top row corresponds to 0.5 µm, whereas the scale bar on the middle row corresponds to 200 nm, and the scale bar on the bottom row corresponds to 100 nm.

After establishing stabilization of PTX nanocrystals using PTX and Pluronic F127 at a 1:5 ratio (w/w), we attempted to grow a silica shell around the crystalline structures using tetraethyl orthosilicate (TEOS) and NaOH. Spontaneous networks of silica formed causing mass agglomeration of the PTX nanocrystals (FIG. 6). PTX nanocrystals were only partially covered in silica. In an attempt to use the nanocrystals as a template for silica growth, other surfactants (PVP) were used as well. Increasing amounts of TEOS and $NH_4OH$ were added to PVP-stabilized PTX at a 1:5 ratio (w/w) to form silica shells, however, networks of silica formed in solution and only a patchy layer of silica formed around the nanocrystals (FIG. 7). Despite increasing the amount of TEOS, no uniform layer was formed. From this initial attempt, it was seen that TEOS had very little affinity for the PTX nanocrystals, causing spontaneous networks of silica to form in solution instead.

Figure 8:
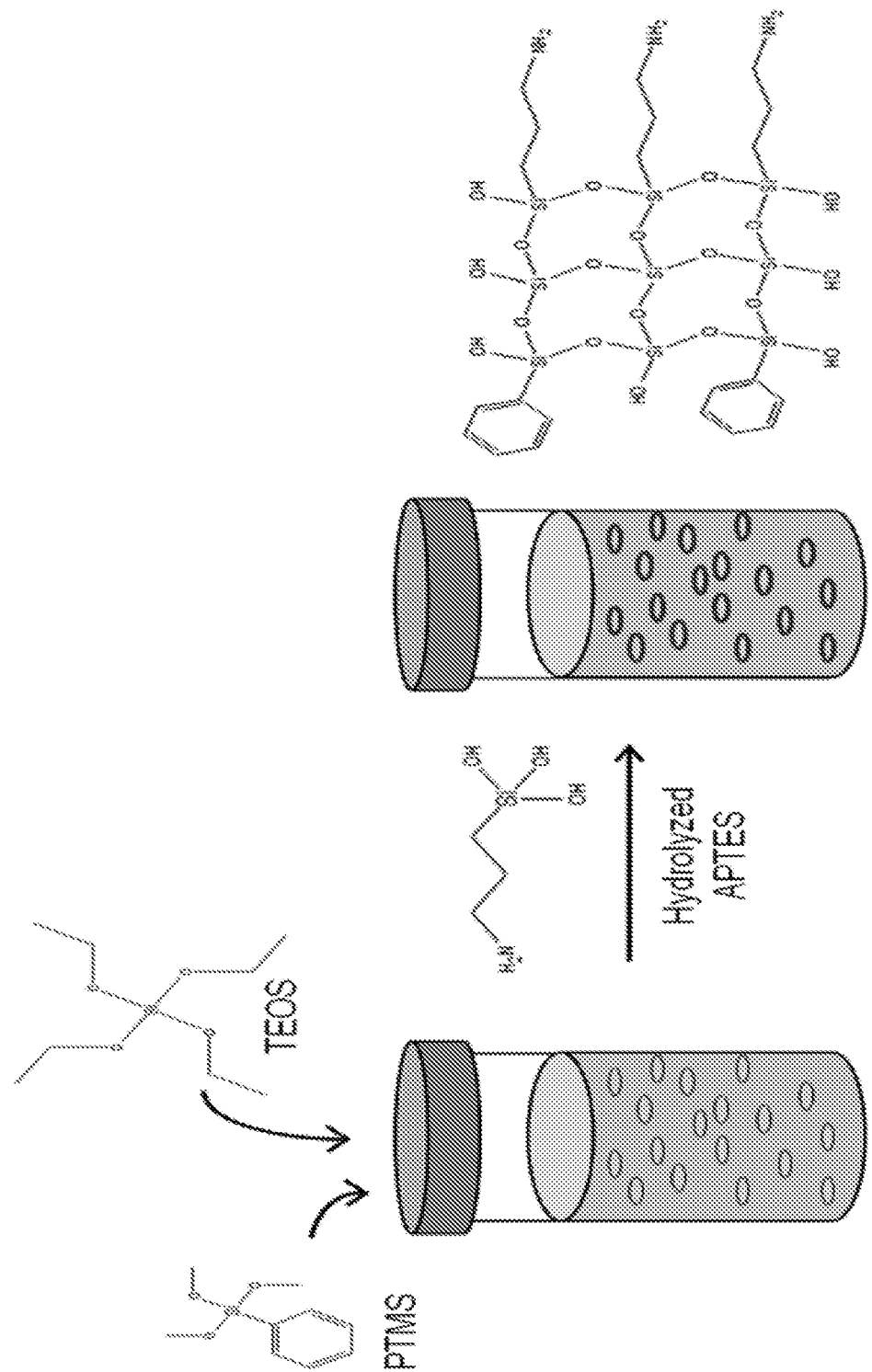
FIG. 8. Schematic for silica growth around PTX-siNCs using organosilanes. A combination of PTMS and TEOS were used in silica formation. APTES was added four hours later as the base catalyst. TEOS=Tetraethyl orthosilicate; PTMS=Phenyltrimethoxy silane; APTES=Aminopropyltriethoxy silane.
Figure 9:
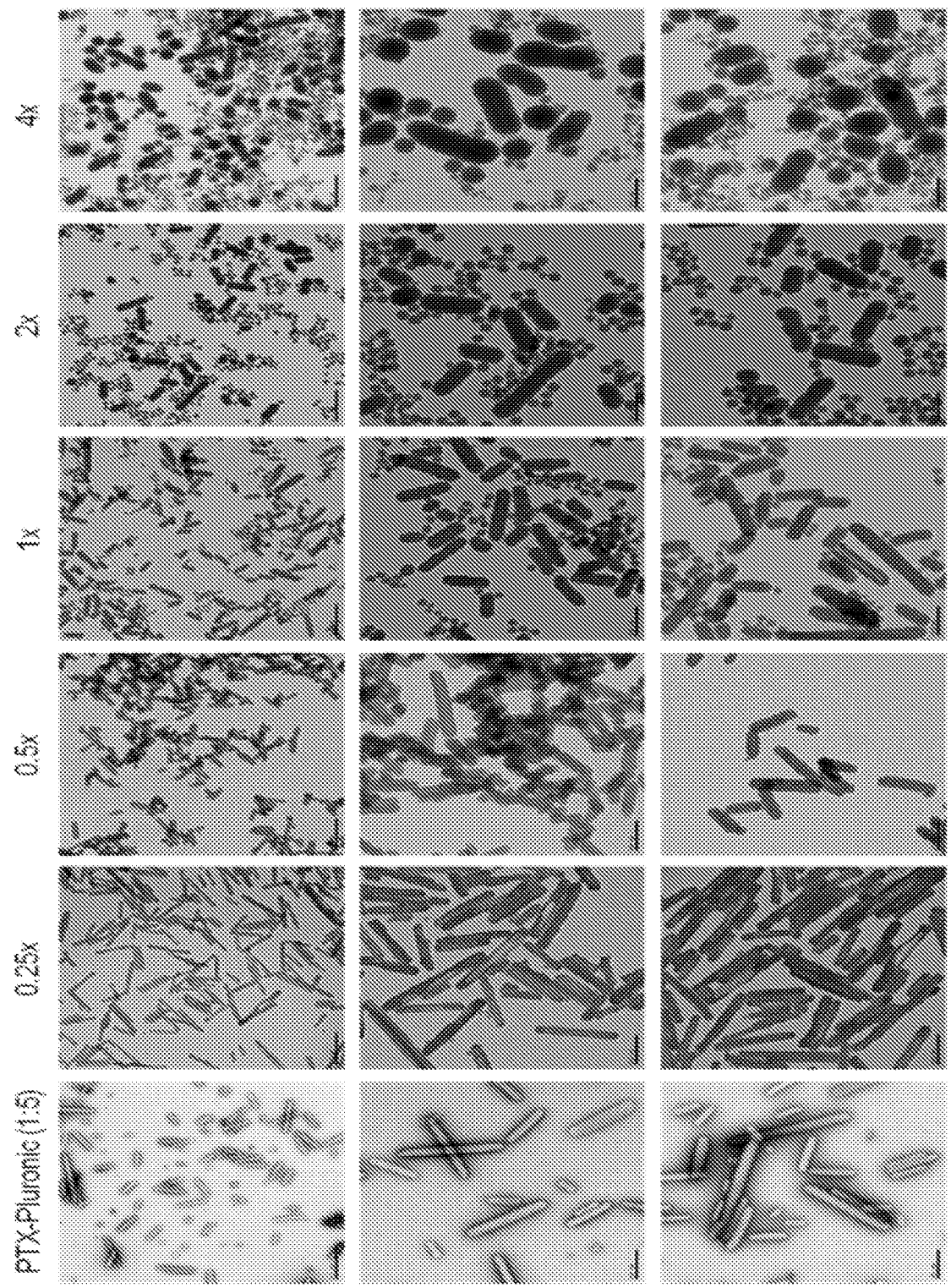
FIG. 9. PTX-siNCs stabilized by various silica shells. The silica shell was controlled by the amount of the silica precursors used. The amount of Paclitaxel was kept constant at 4.68 µmoles. 4×PTX-siNC conditions yielded the thickest silica shell at 70.54 nm. At 0.25× conditions, the silica shell was not fully uniform and was not able to be measured. (top row 6500×, bottom rows 15000× magnification). For reference, the scale bar on the top row corresponds to 0.5 µm, whereas the scale bar on the middle and bottom rows corresponds to 200 nm.

In order to form a uniform silica shell around the PTX nanocrystals, the oil-in-water emulsion method, mentioned in Example 3, was modified. It was thought that the phenyl groups from the PTMS would have higher affinity for the PTX nanocrystals, displacing the Pluronic F127 from the surface. Varying amounts of PTMS and TEOS were added to the aqueous solution of PTX nanocrystals and allowed to stir for 4 hours. Preactivated APTES (hydrolyzed) was used as a base to catalyze the reaction (FIG. 8). The reaction mixture was allowed to stir overnight for 16 hours. The nanocrystals were washed three times in $H_2O$ and then imaged by TEM. Because the particles were coated in silica (electron dense), they were not stained with uranyl acetate. By varying the amount of silica precursors used (PTX kept constant), we were able to control the shell thickness (FIG. 9). The largest shell size was seen in the 4×PTX-siNC condition that had a thickness of ~70 nm. For the 1× and 2×PTX-siNC conditions at which intermediate concentrations of silanes were used, the silica shell ranged from 33-50 nm in thickness. As we decreased the amount of silica precursors we can create extremely thin layers of silica shell. The silica shell thickness was measured to be 28.88 nm for the 0.5×PTX-siNC condition. For the 0.25× condition, the silica was so thin, that it was not able to be measured. At this concentration, the PTX nanocrystals are not uniformly covered as well. The combination of TEOS, PTMS, and APTES proved to be successful in creating uniform silica shells. This suggests that the phenyl groups from the PTMS were able to non-covalently associate with the hydrophobic PTX nanocrystal surface, which served as a template for silica growth.

TABLE 2

PTX-siNCs stabilized by various silica shells; data corresponds to FIG. 9.

|  | 0.25× | 0.5× | 1× | 2× | 4× |
|---|---|---|---|---|---|
| PTMS (μmol) | 50.21 | 100.42 | 200.84 | 401.66 | 803.32 |
| TEOS (μmol) | 33.59 | 67.18 | 134.36 | 268.71 | 537.42 |
| APTES (μmol) | 50 | 100 | 200 | 400 | 800 |
| Shell thickness (nm) | N/A | 28.88 | 33.18 | 50.27 | 70.54 |

Figure 10:
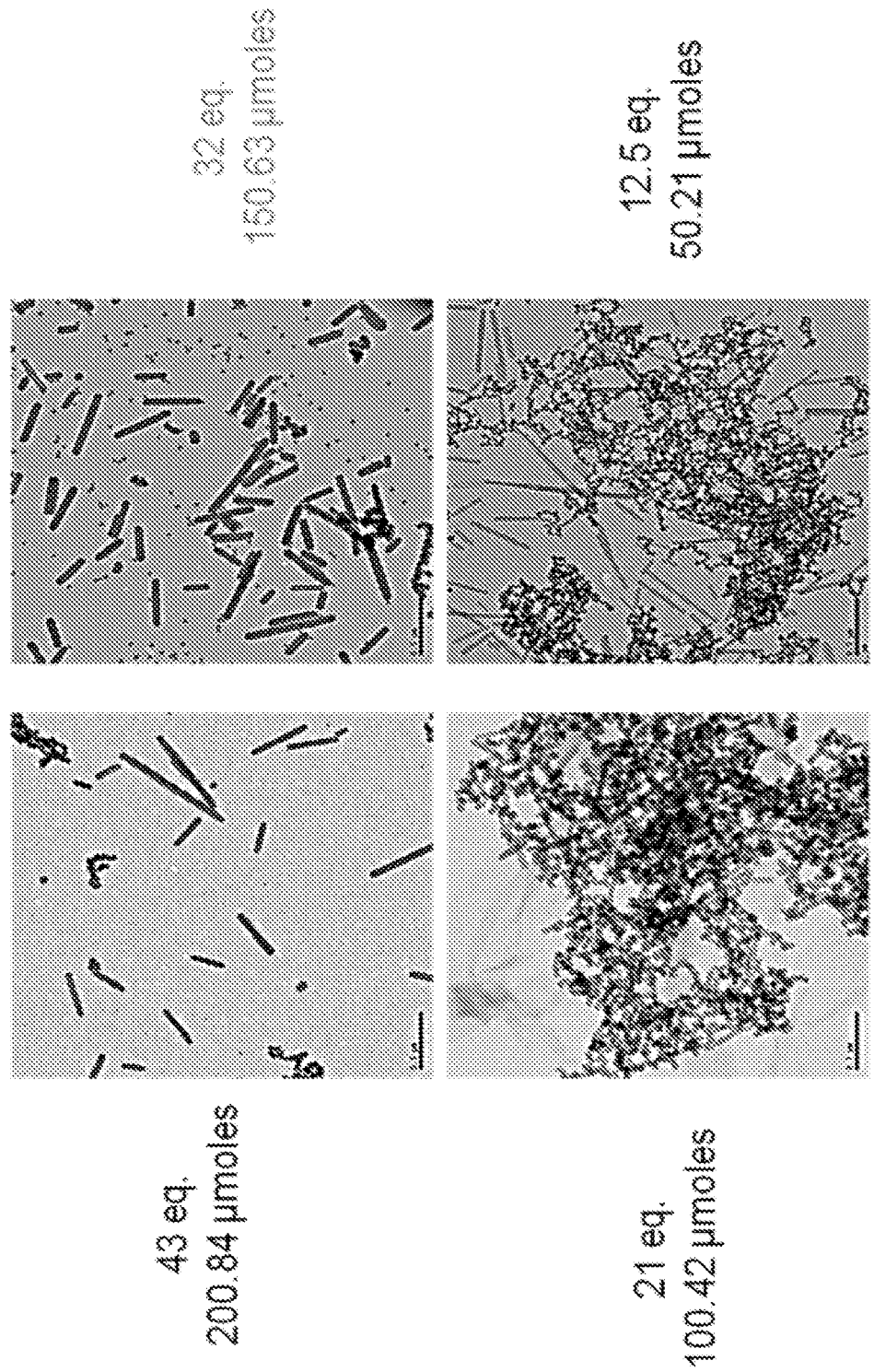
FIG. 10. Reduction of PTMS in silica formation. Various amounts of PTMS were used to determine the minimum needed for proper silica formation around PTX siNCs (1×PTX-siNCs). PTX was kept constant at 4.68 µmoles (1 eq.). Using 32 eq. of PTMS yielded particles with uniform silica formation. Further reduction in PTMS caused spontaneous silica networks to form. For reference, the scale bar corresponds to 0.5 µm.

Organosilanes, such as PTMS, are typically used to coat surfaces for anti-microbial purposes. Since PTMS could prove toxic to mammalian cells, we reduced the amount of PTMS used in the synthesis. In order to produce 1×PTX-siNCs, 42 eq. PTMS was used to form a silica shell around PTX (1 eq.). We were able to determine that this could be decreased to 32 eq. PTMS. This is the absolute minimum needed in order to form a uniform silica shell (FIG. 10). If PTMS was reduced further, spontaneous networks of silica formed. This further suggests that that the phenyl groups associate with the PTX nanocrystals (template) for uniform formation of a silica shell.

Figure 11A:
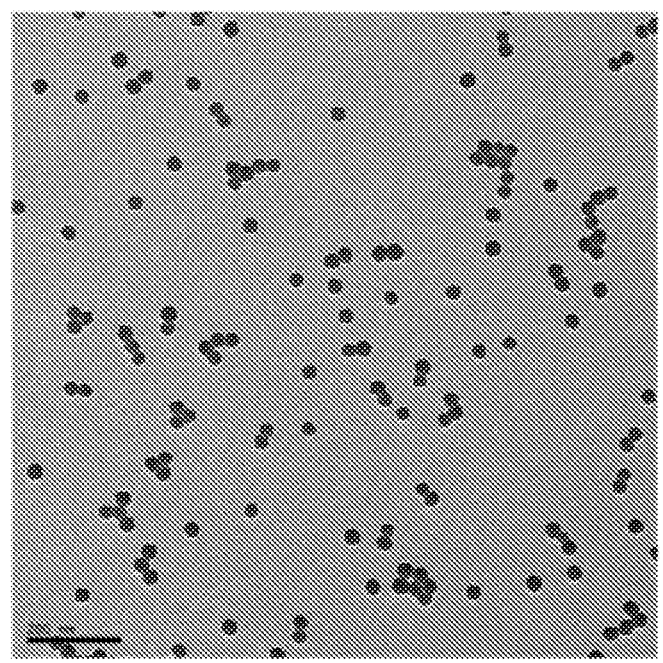
FIGS. 11A-11B. Characterization of empty control silica nanoparticles.
Figure 11B:
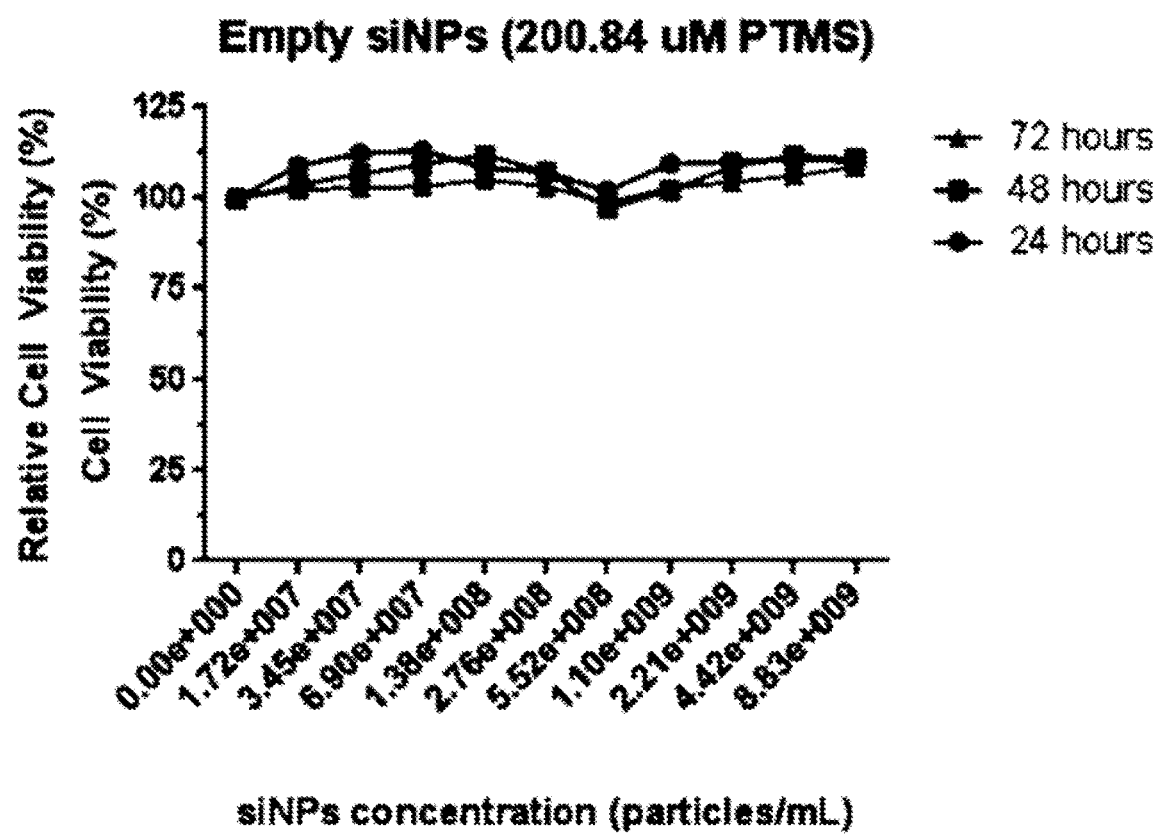

In order to definitively determine the toxicity of PTMS, empty silica nanoparticles were made and tested in OVCAR-8 cells. In order to create geometrically similar empty control nanoparticles similar to PTX-siNCs, gold nanorods (template) with CTAB would have to be used. CTAB requires numerous washing steps in methanol. This protocol was not pursued since residual CTAB remaining in silica nanoparticles could prove toxic to cells. Instead, control nanoparticles were synthesized by suspending 20 mg Pluronic F127 with 14 mL $H_2O$ followed by vortexing to create micelles. TEOS and PTMS were then added to the mixture, which was allowed to stir for 4 hours. Hydrolyzed APTES was then added and the mixture was stirred overnight (16 hours). Nanoparticles were washed 3 times in $H_2O$ and then imaged by TEM. These control silica nanoparticles were spherical in shape, however, they contain the same amount of PTMS used as in the 1×PTX-siNC preparation (FIG. 11A). The diameter of the nanoparticles were 45 nm and the zeta potential was +15.07 mV. Nanosight was also used to measure the concentration of nanoparticles. Control nanoparticles were used to treat cells to determine if the silica formed from organosilanes were toxic. OVCAR-8 cells were treated with various concentrations of control nanoparticles and viability was measured by MTS after 24, 48, and 72 hours (FIG. 11B). OVCAR-8 cells maintained high viability even after 72 hours, demonstrating that the amount of PTMS used in silica nanoparticles is non-toxic to cells. Due to this, the amount of PTMS used in PTX-siNCs was not reduced in further experiments. This study demonstrates that empty control silica nanoparticles were non-toxic to cells. Further studies that need to be conducted include creating control silica nanoparticles that contain the same amount of PTMS as the 4×PTX-siNCs.

Before treating cells with PTX-siNCs, a monodisperse population of particles needed to be isolated. The crude mixture consisted of PTX-siNCs of various sizes as well as spherical nanoparticles. Many of the existing sucrose gradient protocols are directed towards gold nanoparticles or gold nanorods, which are much denser than silica. However, we were able to modify a method used to isolate tobacco mosaic viruses of various aspect ratios.[46] The gradient consisted of various concentrations of sucrose (2 mL of 18%, 21%, 24%, 27%, and 30%) which were slowly layered onto each other.

Figure 12:
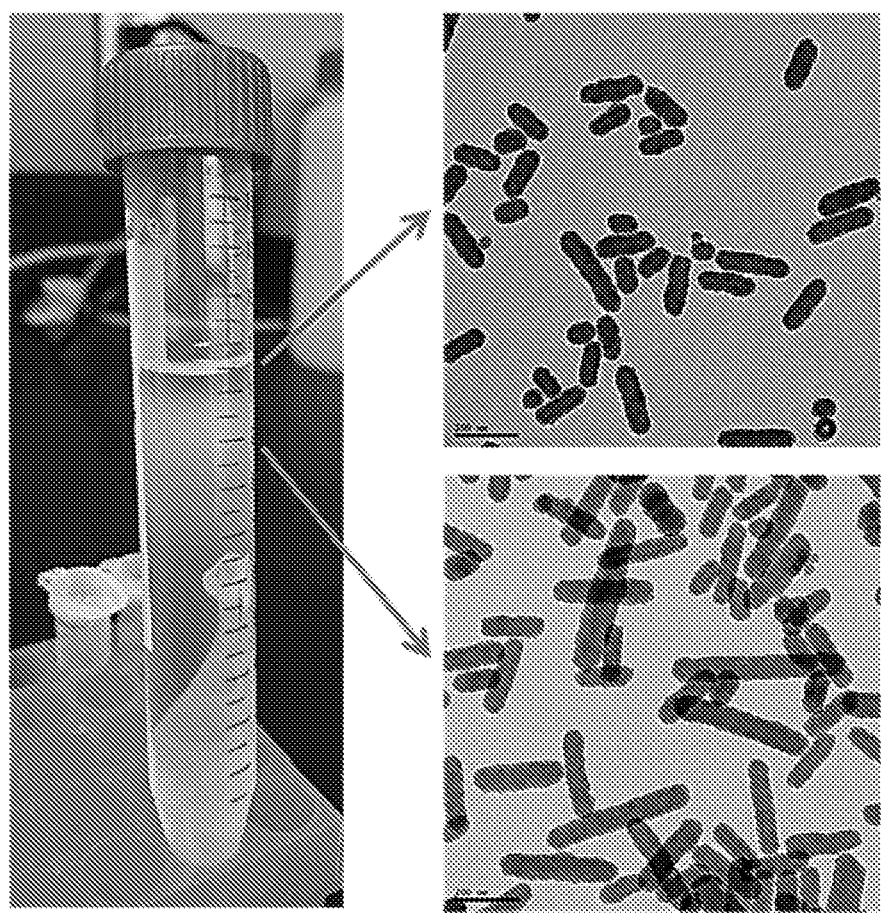
FIG. 12. Isolation of distinct populations of PTX-siNCs. A sucrose gradient (18%, 21%, 24%, 27%, and 30%) was used to isolate two populations of PTX-siNCs.
Figure 13:
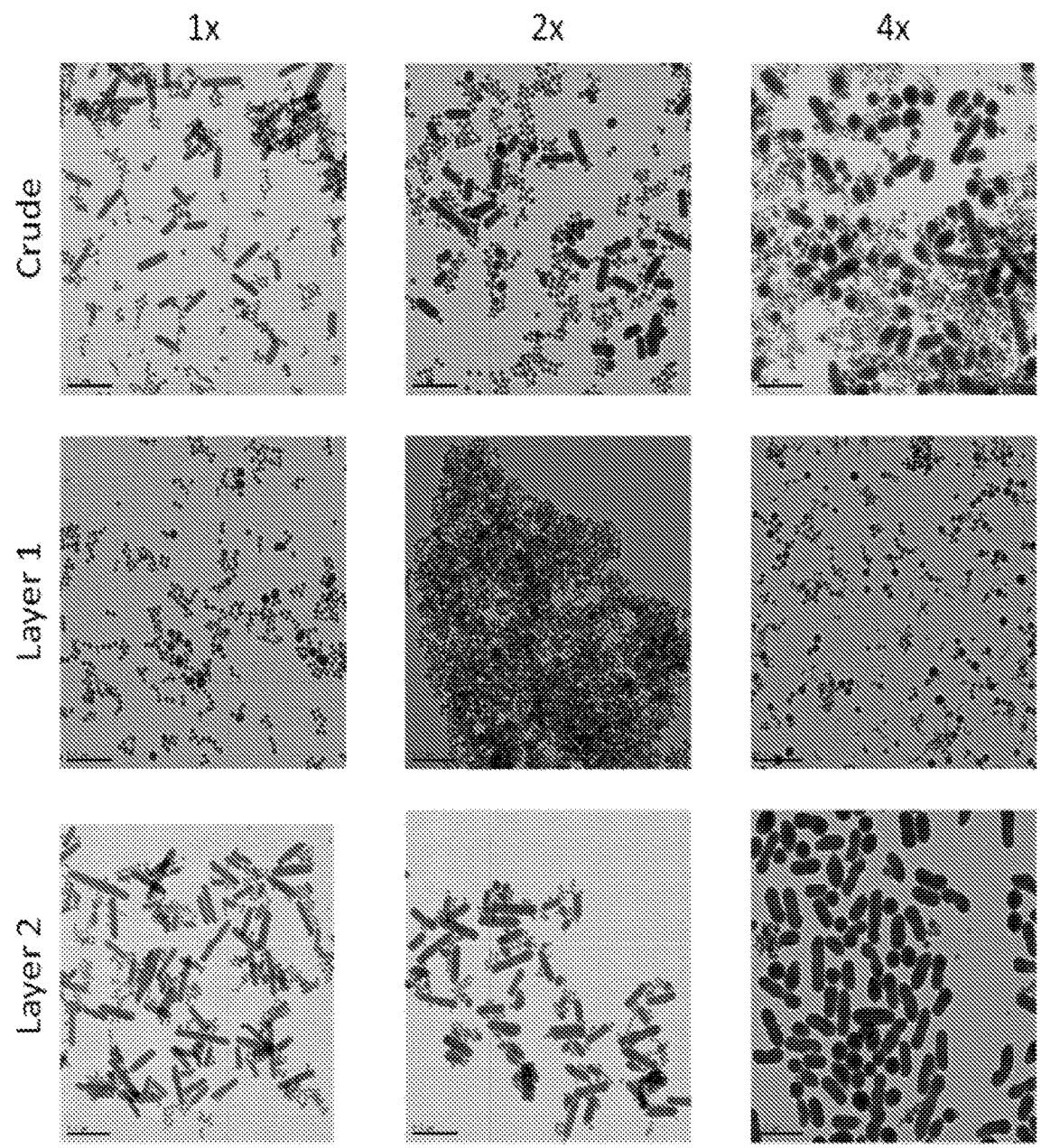
FIG. 13. Various layers of sucrose gradient isolation. The sucrose gradient method allows for the isolation of monodisperse PTX-siNCs. For the 1× and 2×PTX-siNC conditions, there is some carry-over of spherical nanoparticles. However, for the 4×PTX-siNC condition, pure siNCs can be isolated with minimal carry-over of spherical nanoparticles.
Figure 14:
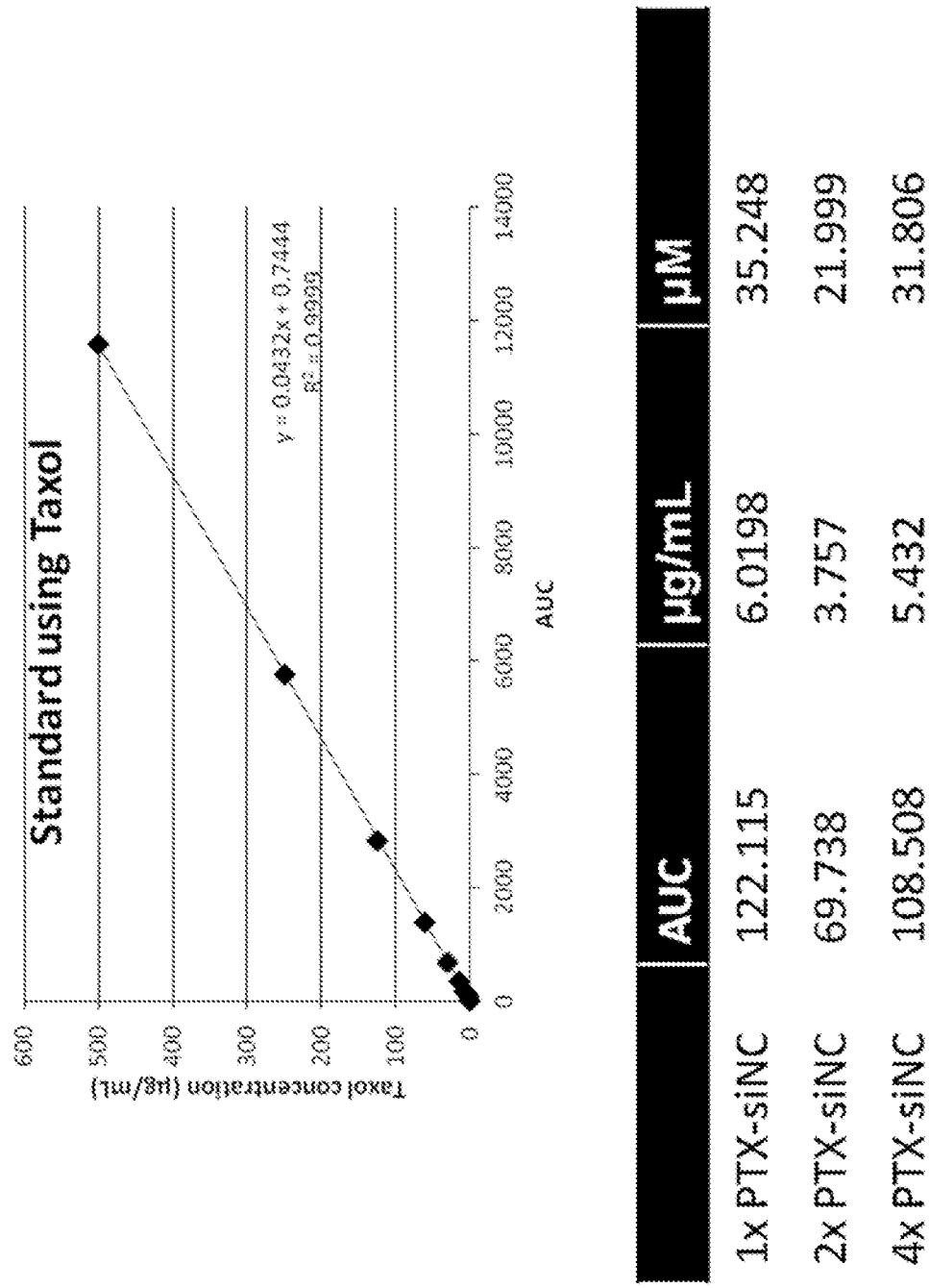
FIG. 14. Quantification of PTX. A standard curve of PTX was generated using Taxol. After one round of isolation using the sucrose gradient, PTX-siNCs were washed and then dissolved in HF and neutralized with sodium bicarbonate. The solution was then extracted with ethyl acetate before injection onto the LC-MS.
Figure 15A:
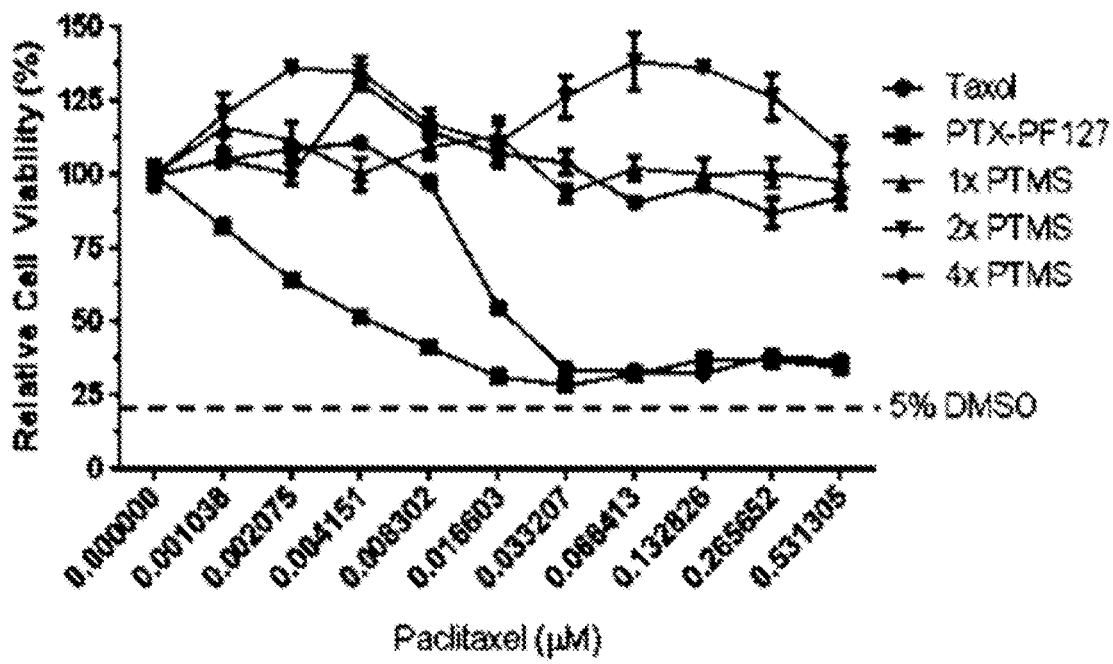
FIGS. 15A-15D. Treatment of OVCAR-8 and NSC viability with PTX-siNCs. OVCAR-8 (FIGS. 15A-15B) and NSCs (FIGS. 15C-15D) were treated with Taxol, PTX-PF127, 1×, 2×, and 4×PTX-siNCs. Viability was measured by MTS after 24 (FIGS. 15A and 15C) and 48 (FIGS. 15B and 15D) hours. PTX-PF127 greatly reduced viability after 24 hours. However, OVCAR-8 and NSCs had high viability after 24 hours when treated with the various PTX-siNCs. After 48 hours, viability was reduced.
Figure 15B:
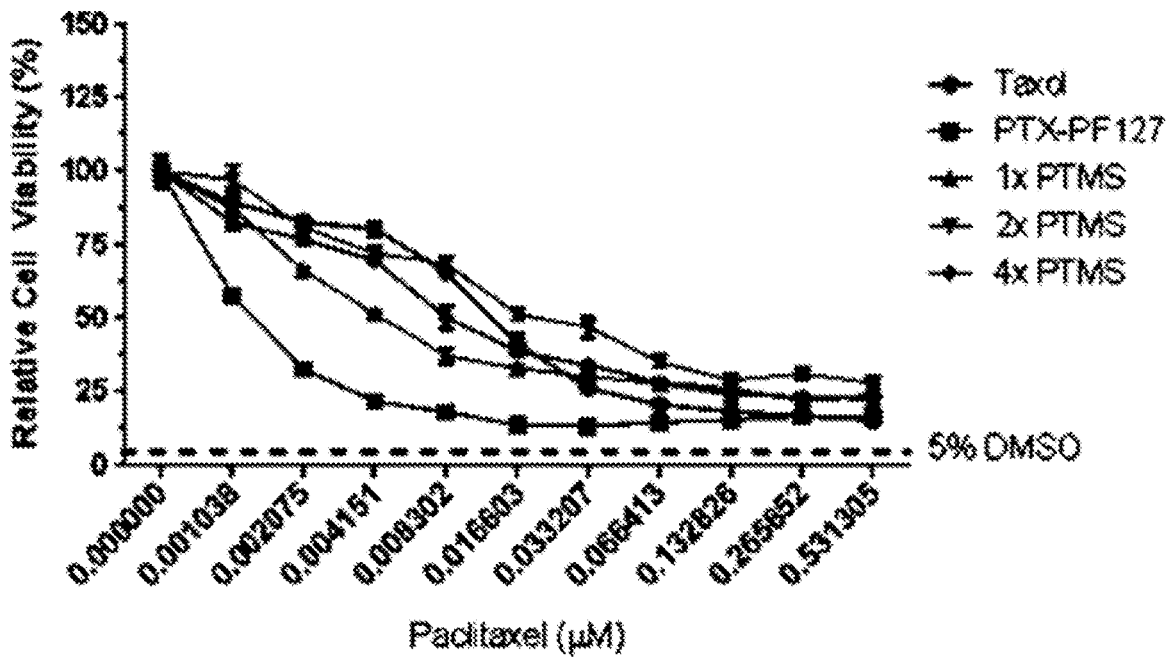
Figure 15C:
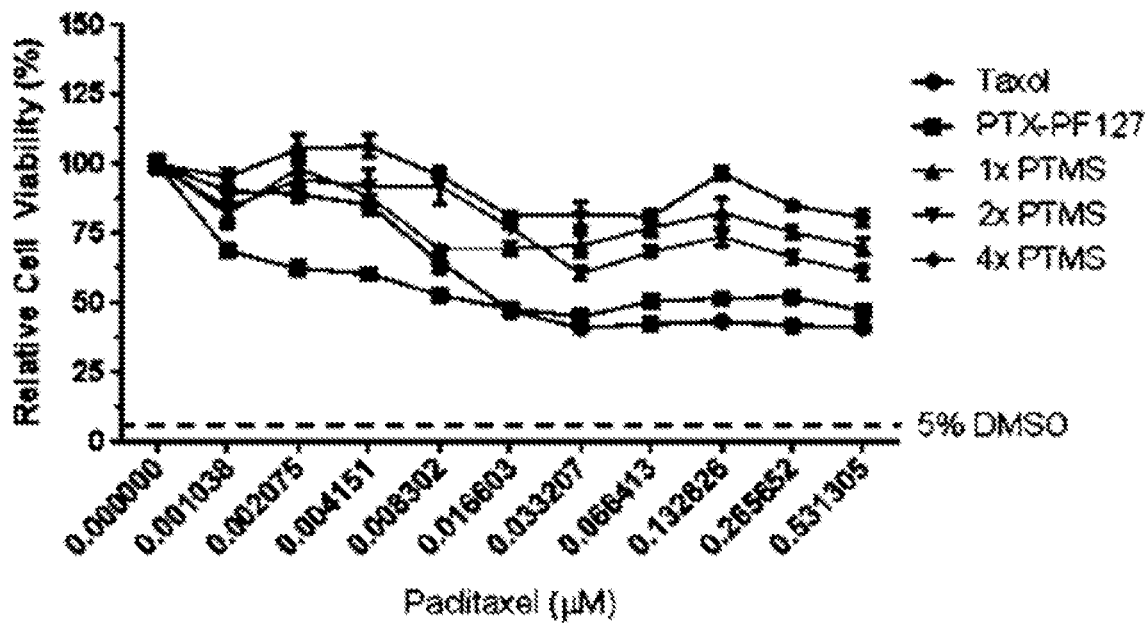
Figure 15D:
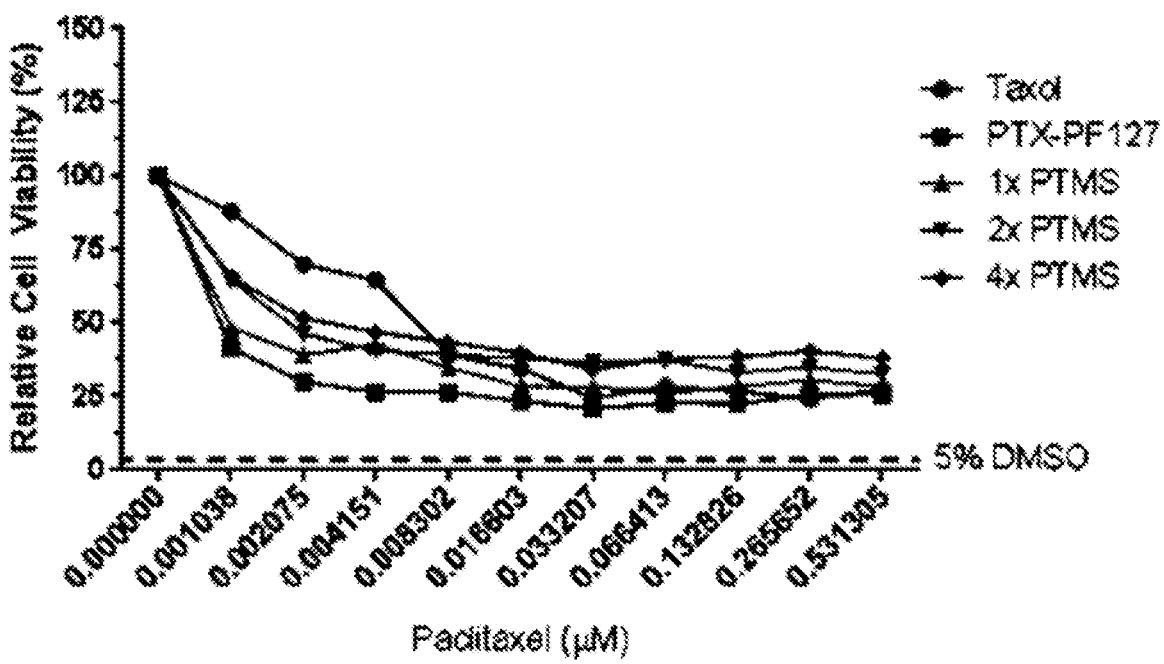

The PTX-siNCs (750 μL) were then added last and the gradient was centrifuged at 3600×g for 35 minutes. Layers were collected and washed 3× in $H_2O$ before imaging by TEM. Images were then analyzed by ImageJ. From the 1×PTX-siNC condition, two distinct populations were able to be isolated (approximately 200 nm, approximately 500 nm) (FIG. 12). The larger PTX-siNCs were used in further experiments since more could be isolated in one round of gradient isolation compared to the small population PTX-siNCs. This method was also applied to the 2× and 4×PTX-siNCs. The sucrose gradient proved to be successful in isolating a single population of PTX-siNCs. The upper layers contained mostly spherical nanoparticles. For the 1× and 2×PTX-siNCs, residual spherical nanoparticles carried through in layer 2, however, we were able to isolate pure PTX-siNCs in the 4× condition (FIG. 13). The amount of PTX was then measured for each PTX-siNC condition (FIG. 14). HF was used to dissolve the silica, which was then neutralized with sodium bicarbonate. An ethyl acetate extraction was performed prior to injection on the LC-MS.

Since a goal is to load Neural Stem Cells with PTX-siNCs for the treatment of ovarian cancer, OVCAR-8 and NSCs were used. These cells were treated with Taxol, PTX stabilized with Pluronic F127 (PTX-PF127), 1× PTX-siNCs, 2×PTX-siNCs, and 4×PTX-siNCs for 24 and 48 hours to determine viability (FIGS. 15A-15D). The $IC_{50}$ of Taxol for OVCAR-8 and NSCs after 24 hours was 0.0166 μM. However, the $IC_{50}$ of OVCAR-8 cells treated with PTX-PF127 was 0.0041 μM. Surprisingly, the lowest concentration of PTX-PF127 used (0.001 μM) caused viability to be reduced to 85% Viability of OVCAR-8 cells was further reduced in a dose dependent manner. In NSCs, the $IC_{50}$ of PTX-PF127 was 0.0166 μM (plateau). Previous research has demonstrated that Pluronic F127 can interact with the cell membrane to inhibit ABC transporters, such as P-glycoprotein, by suppressing the ATPase activity of the transporter. Due to this interaction, Pluronic F127 can sensitize multi-drug resistant cells to PTX by 2-3 orders of magnitude.[47] There was no reduction in viability when we compared the 1×, 2×, and 4×PTX-siNC treatments in OVCAR-8 at all concentrations used after 24 hours, however, after 48 hours the viability drastically decreased (dose-dependent curve). The 1×, 2×, and 4×PTX-siNCs had a similar profile to the Taxol control, which suggests that most of the PTX is released regardless of shell thickness. In OVCAR-8 cells, Taxol treated cells had an $IC_{50}$ of 0.0166 μM, 1×PTX-siNC treated cells had an $IC_{50}$ of 0.0041 μM, 2×PTX-siNC treated cells had an $IC_{50}$ of 0.0166, and 4×PTX-siNC treated cells had an $IC_{50}$ of 0.008 μM. In NSCs, the 4×PTX-siNCs had higher cell viability compared to the 1× and 2× conditions at all concentrations of PTX at 24 hours. After 48 hours, a reduction in viability was seen in all conditions. In NSCs (48 hours), Taxol treated cells had an $IC_{50}$ of 0.008 µM, 1×PTX-siNC treated cells had an $IC_{50}$ of 0.001 µM, and 2× and 4×PTX-siNC treated cells had an $IC_{50}$ of 0.0021 µM. Overall, the 4×PTX-siNCs are a promising nanoparticle candidate due to the ease in isolation of a monodisperse population of 4×PTX-siNCs. These 4×PTX-siNCs were not cytotoxic to cells after 24 hours and delayed release of the encapsulated drug. Cell viability studies will need to be repeated. The data shown here suggests that PTX-siNCs could be used for NSC loading for targeted delivery.

Figure 16:
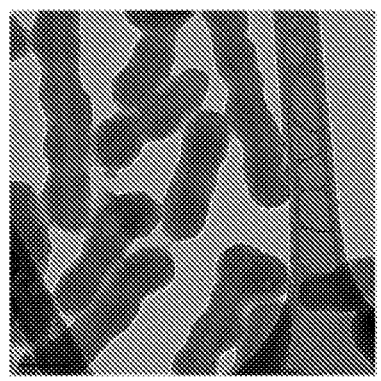
FIG. 16. Surface functionalization of PTX-siNCs. PTX-siNCs can be further functionalized due to the presence of primary amines on the surface. PTX-siNCs were functionalized with PEG and analyzed by zeta potential. PEGylated PTX-siNCs had a zeta potential of +2.82 mV (neutral surface). For reference, the scale bar corresponds to 100 nm.
Figure 16:
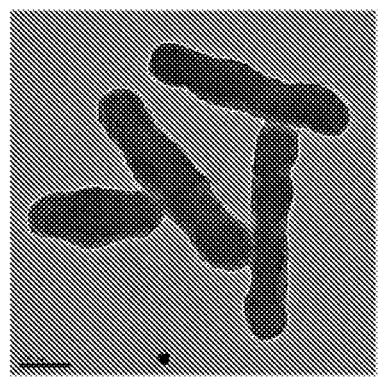

PTX-siNCs can be further functionalized due to the primary amines (APTES) on the surface of the silica. PEG-NHS-ester was functionalized onto PTX-siNCs (FIG. 16) then washed 3× in $H_2O$ before TEM imaging. Zeta potential was used to confirm full PEGylation of the surface. 2×-PTX-siNCs had a zeta potential of +43.60 mV. After neutralization of the surface with PEG, the functionalized nanoparticles experienced a reduction in charge (+2.82 mV). In the future, we plan on tracking PTX-siNCs in vitro, by functionalizing AF-488 TFP-ester onto the PTX-siNC surface. Another ligand of interest includes PEG-Maleimide for exterior loading of NSCs.

Off-target toxicities are seen in conventional chemotherapy resulting in a low percentage of free drug actually reaching the tumor. Drug delivery using nanoparticles has been extensively explored, however, much of the drug predominantly accumulates in the liver, spleen, and kidneys after systemic administration. Here we present data on the development of PTX nanocrystals coated with silica. After 24 hours, cells treated with 4×PTX-siNCs are still fully viable, however, after 48 hours, we see a drastic reduction in viability, which is postulated to be due to the release of PTX. Further studies need to be conducted to fully characterize the release kinetics of PTX from silica nanocrystals. Also, NSC-loading and cell migration experiments will need to be conducted to determine the maximum amount of PTX-siNCs that can be loaded onto cells while preserving cell functionality. Coculture experiments with PTX-siNC loaded NSCs and OVCAR-8 cells will have to be performed as well to confirm that PTX is able to be released from the nanocrystals and affect the viability of OVCAR-8 cells.

All materials were used as supplied. Tetraethylorthosilicate (TEOS), phenyltrimethoxy silane (PTMS), aminopropyltriethoxy silane (APTES), ammonium hydroxide, Pluronic F-127, Cremophor EL, and sucrose were purchased from Sigma Aldrich. Paclitaxel (PTX) was purchased from Ark Pharm. OVCAR-8 and NSCs were obtained from Dr. Karen Aboody's lab.

Formation of Nanosuspensions.

Paclitaxel (4 mg) and Pluronic F127 (20 mg) were both measured out and combined in a 20 mL scintillation vial. Chloroform (1 mL) was added to the scintillation vial and vortexed to completely solubilize Paclitaxel and Pluronic F127. A steady stream of nitrogen was used to evaporate the chloroform. This formed a dry film on the bottom of the vial. In order to ensure complete evaporation, the vial was placed in a vacuum with drierite for 1 hour. MilliQ $H_2O$ (14 mL) was added to the vial and vortexed. This was placed on a shaker for 20 minutes and vortexed. Qsonica cup sonicator (amplitude=100) was used to sonicate the mixture to form the nanosuspension. Pulse-on time was 5 minutes and pulse-off time was set to 15 minutes for a total and this was repeated two more times for a total of 45 minutes of process time. To verify formation of nanocrystals, the solution was imaged by TEM. 4 uL of the solution was removed and placed on a 300-mesh copper grid. After 30 seconds, it was blotted off and stained with 2% uranyl acetate. After 30 seconds, uranyl acetate was blotted off and allowed to dry. The grid was imaged by TEM (FEI Tecnai T12) to visualize Paclitaxel nanocrystals stabilized by Pluronic F127. After sonication, TEOS (30 µL, 200.8 µmoles) and PTMS (37.5 µL, 134.3 µmoles) was added to the nanosuspension and stirred for 4 hours. APTES (700 µL) was diluted with 375 µL of milliQ $H_2O$ in order to have a final concentration of 2.8 M. Hydrolyzed APTES (71.8 µL, 200 µmoles) was immediately added to the mixture. The mixture turned white after a minute. It was allowed to stir overnight (16 hours). The silica nanosuspensions were centrifuged at 14,000×g for 20 minutes and washed with milliQ $H_2O$ three times. In order to visualize the silica shell grown around the nanocrystals, TEM was used. The grid was charged initially before pipetting 4 µL of the nanosuspension onto the grid. It was dried in an oven at 60° C. for 5 minutes before imaging. In order to grow larger shells of silica, the amount of TEOS, PTMS, and APTES were increased by 2× and 4×-fold. In order to measure shell thickness, the width of the PTX nanocrystals stabilized by Pluronic F127 was subtracted from the width of the silica-coated nanocrystals (ImageJ).

Additional Synthetic Procedure to Make Lx PTX Silica Nanocrystals.

Paclitaxel (4 mg) and Pluronic F127 (20 mg) were both measured out and combined in a 20 mL scintillation vial. Chloroform (1 mL) was added to the scintillation vial and vortexed to completely solubilize Paclitaxel and Pluronic F127. A steady stream of nitrogen was used to evaporate the chloroform. This formed a dry film on the bottom of the vial. In order to ensure complete evaporation, the vial was placed in a vacuum with drierite for 1 hour. MilliQ $H_2O$ (14 mL) was added to the vial and vortexed. This was placed on a shaker for 20 minutes and vortexed. Qsonica cup sonicator (amplitude=100) was used to sonicate the mixture to form the nanosuspension. Pulse-on time was 5 minutes and pulse-off time was set to 15 minutes (rest period). This was repeated for a total pulse on-time of 25 minutes (entire process time is 85 minutes). To verify formation of nanocrystals, the solution was imaged by TEM. 4 uL of the solution was removed and placed on a 300-mesh copper grid. After 30 seconds, it was blotted off and stained with 2% uranyl acetate. After 30 seconds, uranyl acetate was blotted off and allowed to dry. The grid was imaged by TEM (FEI Tecnai T12) to visualize Paclitaxel nanocrystals stabilized by Pluronic F127. After sonication, TEOS (30 µL, 200.8 µmoles) and PTMS (37.5 µL, 134.3 µmoles) was added to the nanosuspension and stirred for 3 hours. APTES (700 µL) was diluted with 375 µL of milliQ $H_2O$ in order to have a final concentration of 2.8 M. Hydrolyzed APTES (71.8 µL, 200 µmoles) was immediately added to the mixture. The mixture turned white after a minute. It was allowed to stir overnight (16 hours). The silica nanosuspensions were centrifuged at 14,000×g for 20 minutes and washed with milliQ $H_2O$ three times. In order to visualize the silica shell grown around the nanocrystals, TEM was used. The grid was charged initially before pipetting 4 µL of the nanosuspension onto the grid. It was dried in an oven at 60° C. for 5 minutes before imaging. In order to grow larger shells of silica, the amount of TEOS, PTMS, and APTES were increased by 2× and 4×-fold. In order to measure shell thickness, the width of the PTX nanocrystals stabilized by Pluronic F127 was subtracted from the width of the silica-coated nanocrystals (ImageJ).

Sucrose gradient separation for 1× and 2×PTX silica nanocrystals. In order to isolate empty or spherical particles from PTX-silica nanocrystals, a sucrose gradient was used.

The gradient consisted of five different layers, each containing 2 mL of 18%, 21%, 24%, 27%, and 30% sucrose solution in a 15 mL conical tube. PTX-silica nanocrystals (750 µL) was added to the top layer slowly. The gradient was centrifuged at 3600×rpm for 35 minutes. The top layer (1 mL) consisted of spherical silica nanoparticles and small PTX-silica nanocrystals. The second layer (800 µL) contained the nanocrystals of interest (200-500 nm). The other layers were discarded since they contain aggregated nanocrystals or nanocrystals that are larger than 500 nm. PTX-silica nanocrystals were centrifuged at 14,000×g for 20 minutes and washed with milliQ $H_2O$ three times. PTX-silica nanocrystals were imaged by TEM to ensure complete isolation from spherical silica nanoparticles and aggregates.

Sucrose gradient separation for 4×PTX silica nanocrystals. In order to isolate empty or spherical particles from PTX-silica nanocrystals, a sucrose gradient was used. The gradient consisted of five different layers, each containing 2 mL of 10%, 20%, 30%, 40%, and 50% sucrose solution in a 15 mL conical tube. PTX-silica nanocrystals (750 µL) was added to the top layer slowly. The gradient was centrifuged at 3600×rpm for 35 minutes. The top layer (1.5 mL) consisted of spherical silica nanoparticles and small PTX-silica nanocrystals. The second layer (1 mL) contained the nanocrystals of interest (200-500 nm). The other layers were discarded since they contain aggregated nanocrystals or nanocrystals that are larger than 500 nm. PTX-silica nanocrystals were centrifuged at 14,000×g for 20 minutes and washed with milliQ $H_2O$ three times. PTX-silica nanocrystals were imaged by TEM to ensure complete isolation from spherical silica nanoparticles and aggregates. To synthesize the 4×PTX silica nanocrystals, we quadrupled the volumes of all the silanes mentioned in the methods, for the 2× we doubled the volume of silanes. Thus it is possible to control the silica shell thickness depending on the experimental conditions.

Isolating Single Populations of PTX-Silica Nanocrystals.

In order to isolate empty or spherical particles from PTX-silica nanocrystals, a sucrose gradient was used. The gradient consisted of five different layers, each containing 2 mL of 18%, 21%, 24%, 27%, and 30% sucrose solution in a 15 mL conical tube. PTX-silica nanocrystals (750 µL) was added to the top layer slowly. The gradient was centrifuged at 3600×rpm for 35 minutes. The top layer (500 µL) consisted of spherical silica nanoparticles and small PTX-silica nanocrystals. The second layer (800 µL) contained the nanocrystals of interest (200-500 nm). The other layers were discarded since they contain aggregated nanocrystals or nanocrystals that are larger than 500 nm. PTX-silica nanocrystals were centrifuged at 14,000×g for 20 minutes and washed with milliQ $H_2O$ three times. PTX-silica nanocrystals were imaged by TEM to ensure complete isolation from spherical silica nanoparticles and aggregates.

Quantification of PTX in PTX-Silica Nanocrystals.

PTX-silica nanocrystals (20 µL) were dissolved using HF (2 µL) for 30 minutes in an eppendorf tube. It was neutralized with sodium bicarbonate (6 mg) and calcium chloride (4 mg). 2 µL was removed from the solution and used to measure the pH on a pH strip to ensure neutralization of the HF. Ethyl acetate (50 µL) was added to the solution for extraction of the PTX from the aqueous phase. 20 µL of ethyl acetate was removed and mixed with 80 µL of acetonitrile before injection onto the LC-MS.

Treatment of Cells Using PTX-siNCs.

OVCAR-8 (RPMI, 10% FBS, 1% L-glutamine, and 1% penicillin-streptomycin) and NSCs (DMEM, 10% FBS, 1% L-glutamine, and 1% penicillin-streptomycin) were seeded in 96-well plates (4000 cells/well, 100 µL media). They were incubated at 37° C. for 16 hours before treatment. All dilutions of Taxol, PTX stabilized by Pluronic F127, and PTX-siNCs were done in media. After treatment, cells were incubated for 24, 48, and 72 hours. At each time point, cell viability was measured by MTS (20 µL) which was added into every well. The cells were allowed to incubate at 37° C. for another hour. The absorbance at 490 nm was then measured using a plate reader.

Functionalization of PTX-siNCs with PEG.

PEG-NHS-ester (20 mg) was measured and resuspended in 400 µL $H_2O$. 1 mL sodium bicarbonate (0.1M) was added to PTX-siNCs (30 µM). 400 µL of PEG-NHS-ester was then added to PTX-siNCs. This was then placed on the shaker for 1 hour. PTX-siNCs were washed 3× in $H_2O$. PTX-siNCs were then imaged by TEM and the surface charge was measured by zeta potential.

In order to address non-specificity of chemotherapeutics, we have developed a novel PTX-siNC potentially to be used NSC loading for targeted drug delivery. The organosilanes used to create PTX-siNCs proved to be non-toxic to cells. We also developed a method to isolate monodisperse populations of PTX-siNCs. In cell viability studies, it was demonstrated that PTX-siNCs were able to retain their payload up to 24 hours, which is sufficient time for NSC migration to occur. PTX-siNCs can also be functionalized with various ligands, such as PEG. Further investigations need to be done to determine the maximum amount of PTX-siNCs that can be loaded onto NSCs, while allowing migration to occur. Cytotoxic coculture studies also need to be conducted to determine if PTX-siNCs loaded onto NSCs are able to affect neighboring OVCAR-8 cells. Overall, the preliminary data provides evidence that the PTX-siNC are stable and may be used for NSC loading for targeted drug delivery.

Example 3. Synthesis of Silica Nanoparticles Using Oil-in-Water Emulsion

Figure 17:
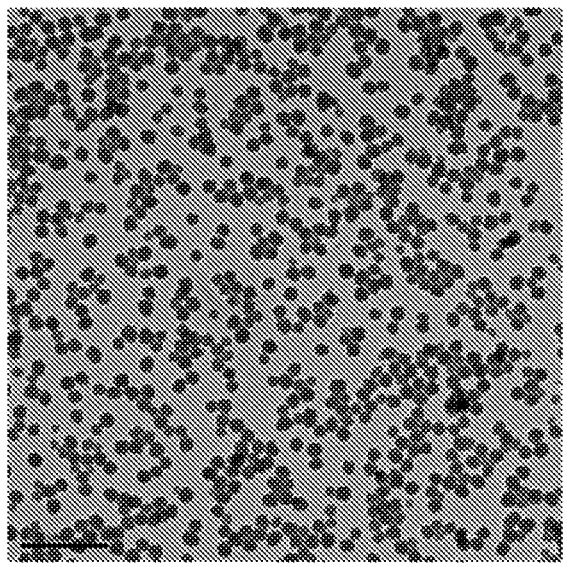
FIG. 17. Oil-in-water silica nanoparticles. Nanoparticles formulated from oil-in-water emulsions were produced (approximately 68 nm in diameter). For reference, the scale bar on the left column corresponds to 0.5 µm, whereas the scale bar on the right column corresponds to 100 nm.
Figure 17:
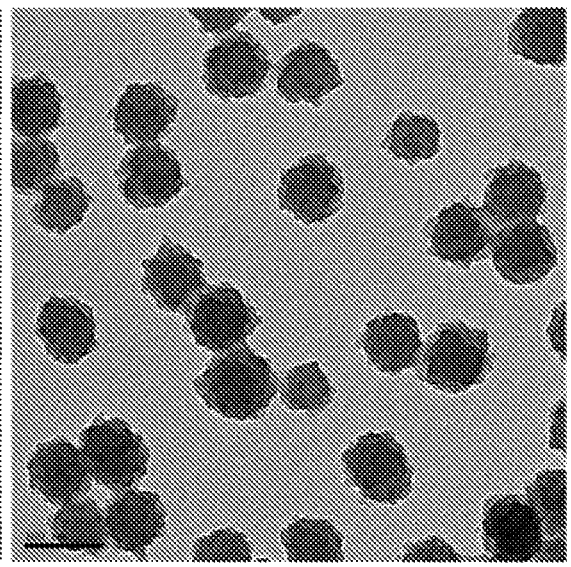
Figure 18:
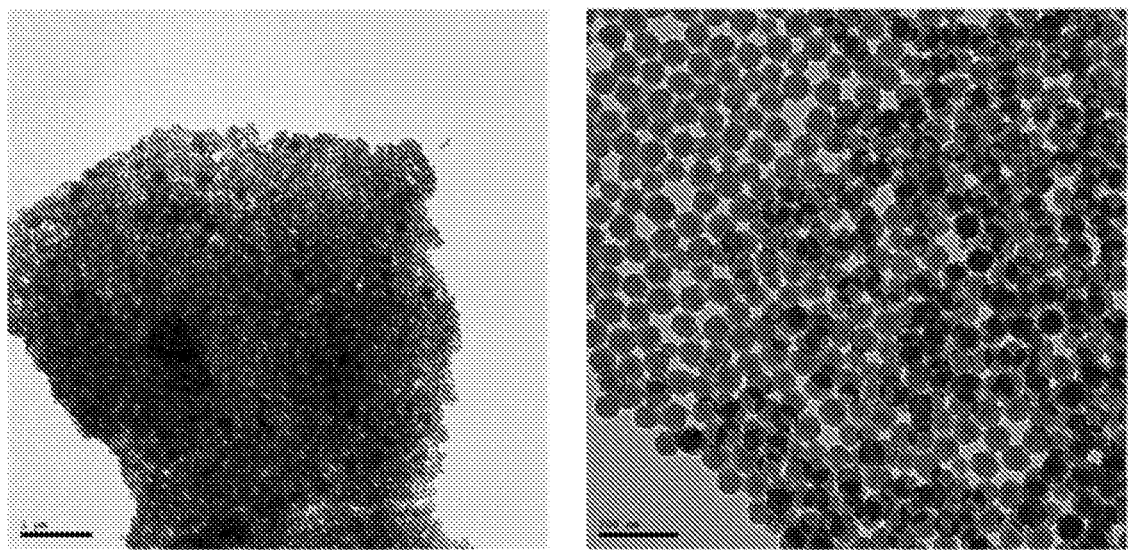
FIG. 18. Aggregation of lyophilized oil-in-water silica nanoparticles. Oil-in-water silica nanoparticles were lyophilized. Particles were aggregated upon resuspension in water. (left 4400× magnification, right 15000× magnification). For reference, the scale bar on the left column corresponds to 1 µm, whereas the scale bar on the right column corresponds to 200 nm.
Figure 19A:
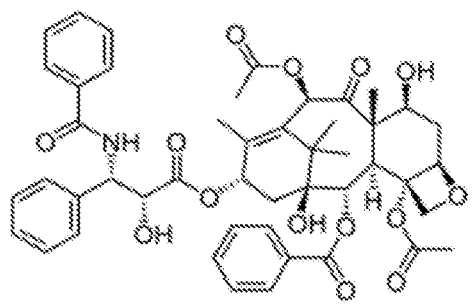
FIGS. 19A-19G. PTX (Cremophor+EtOH), PTX-PF127, 2×PTX-siNCs, and PEG-PTX-siNCs (FIG. 19A). OVCAR-8 (FIGS. 19B, 19D, 19F) and Neural Stem Cells (NSCs) (FIGS. 19C, 19E, 19G) were used. The Pluronic stabilized PTX-siNCs had a drastically lower IC50. Pluronic block copolymers are known to be sensitizers of multidrug resistant cancer cells by interacting with Pgp proteins (known efflux pumps). PTX-siNCs and PEG-PTX-siNCs behave similarly and seem to cause a slower delay in the release of the drug during the first 24 hours, especially seen in NSCs. For reference, the scale bar in FIG. 19A, the scale bar corresponds to 100 nm.
Figure 19A:
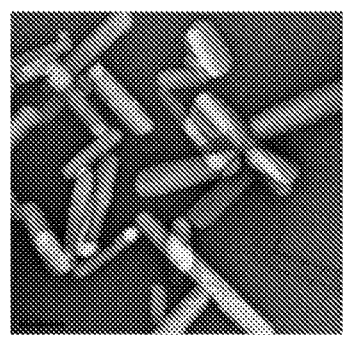
Figure 19A:
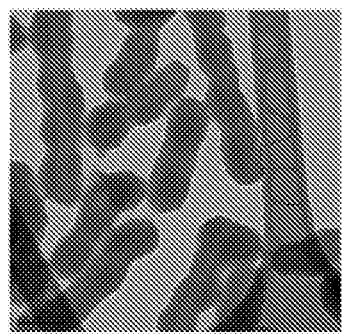
Figure 19A:
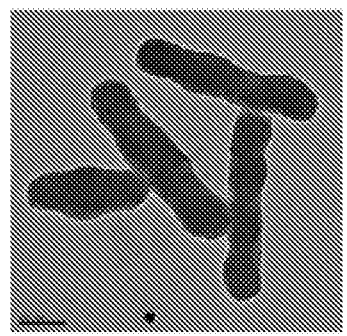
Figure 19B:
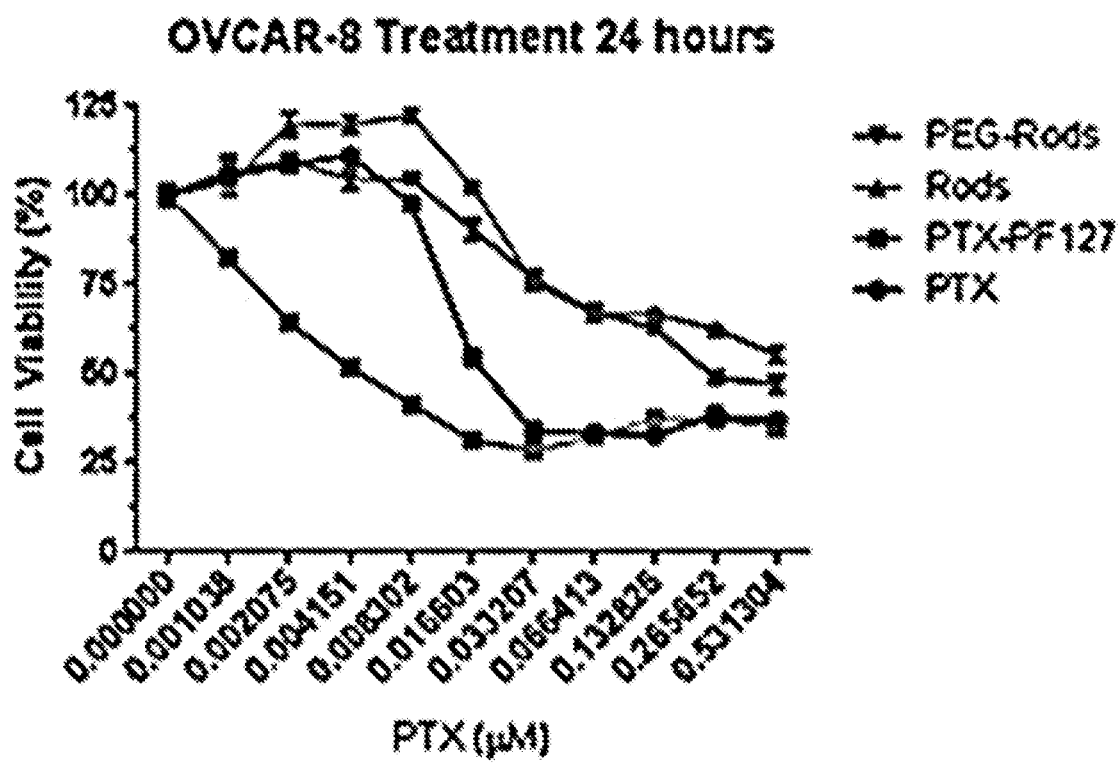
Figure 19C:
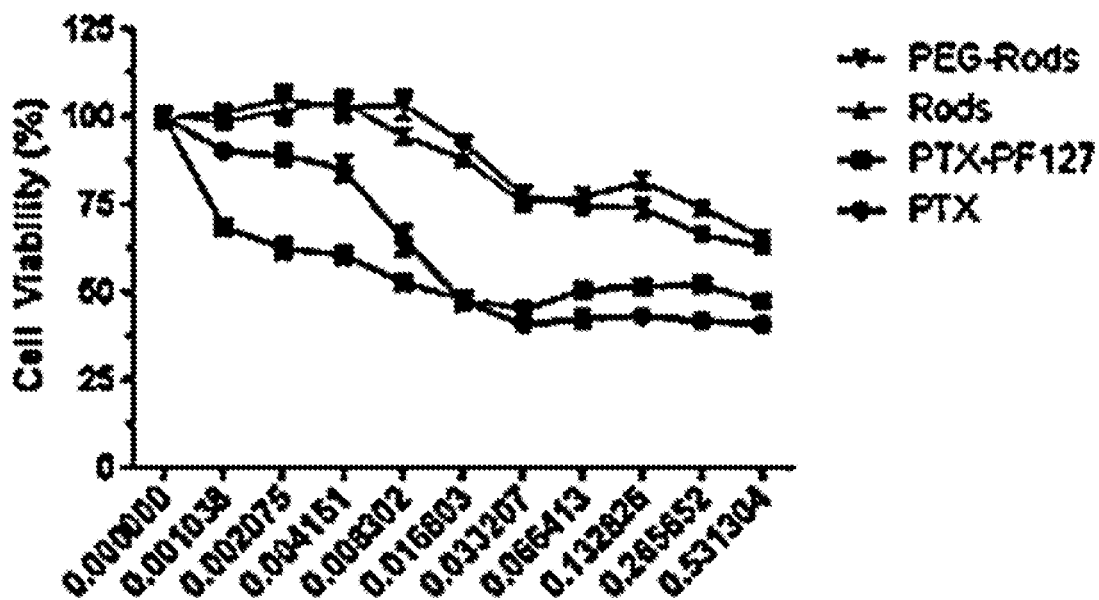
Figure 19D:
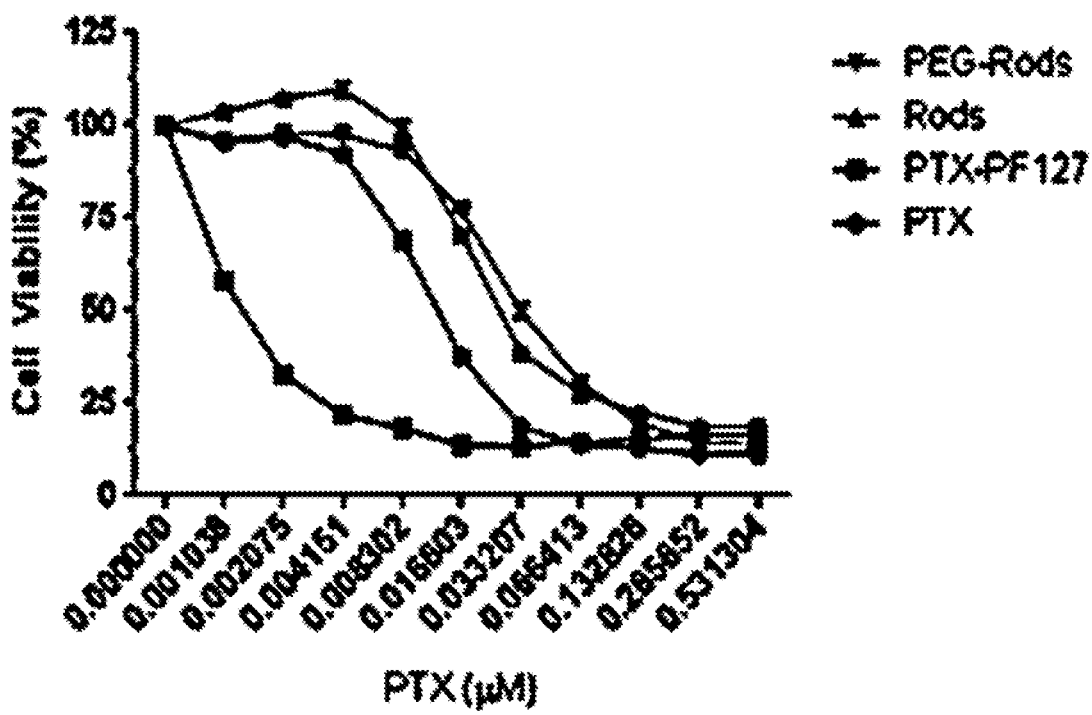
Figure 19E:
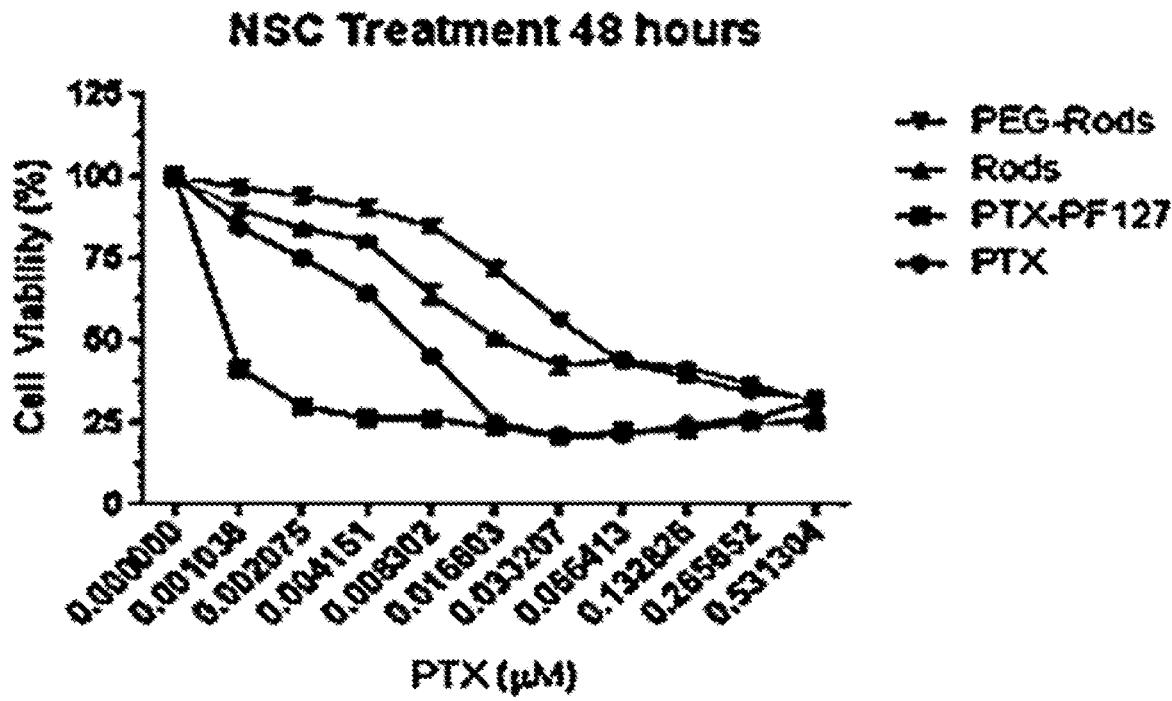
Figure 19F:
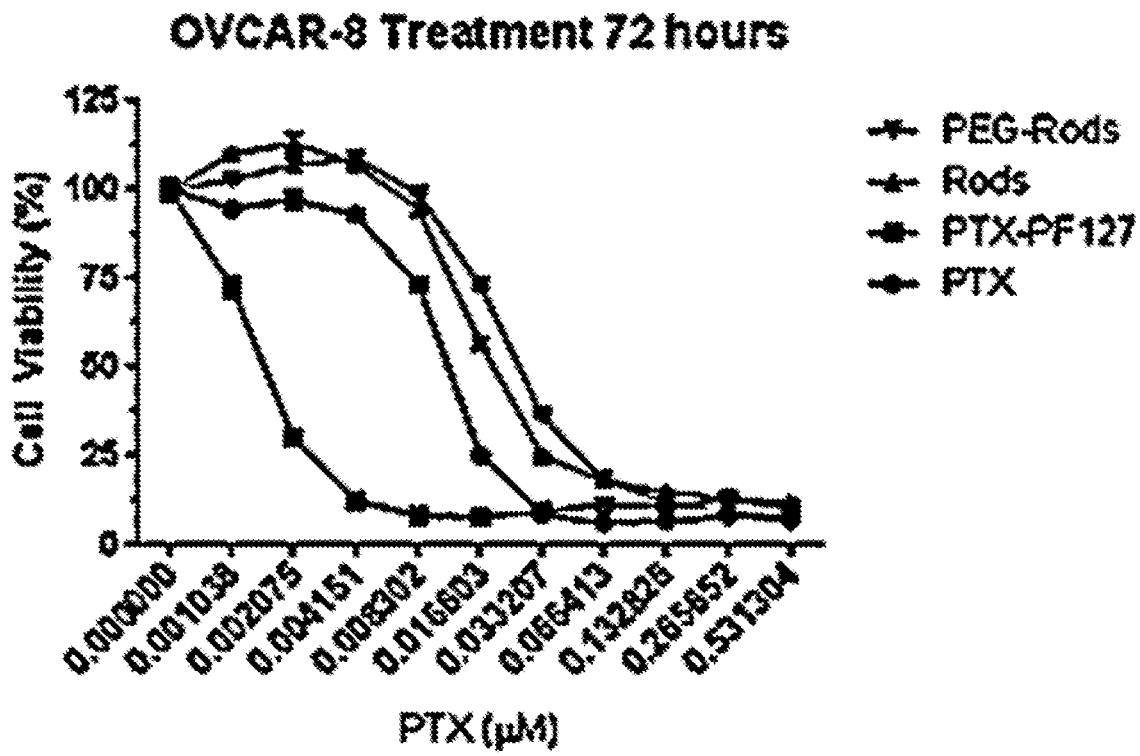
Figure 19G:
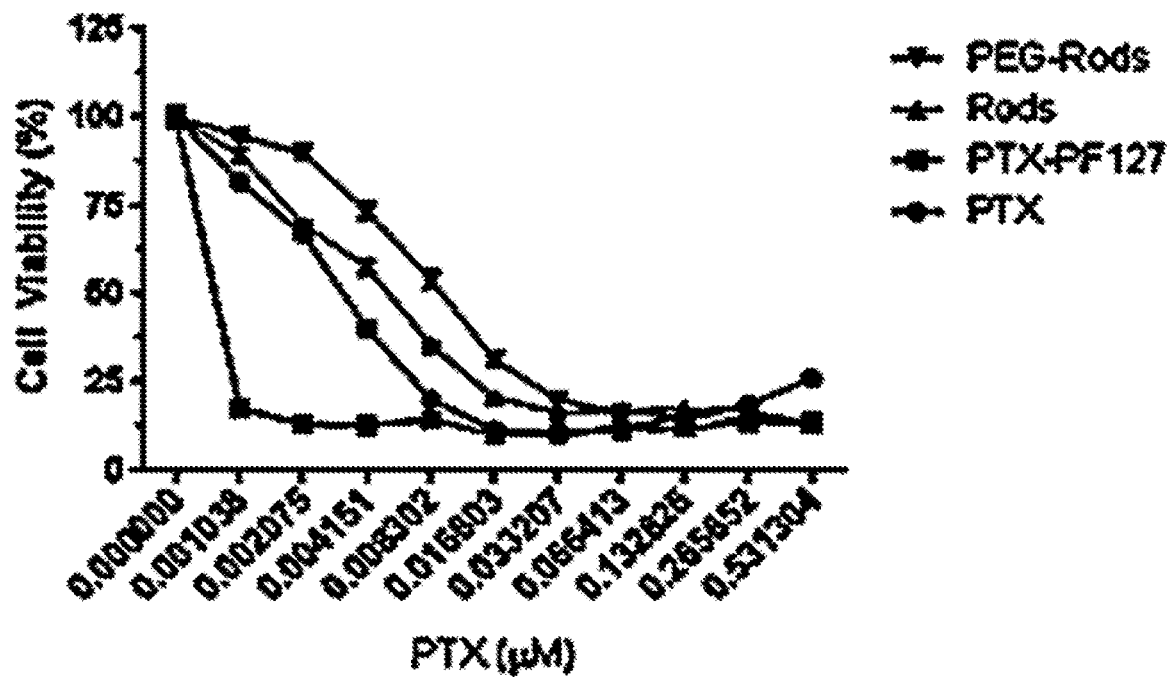

Initial attempts at growing a silica shell using standard procedures, such as TEOS and NaOH, yielded spontaneous networks of silica. Due to this, we explored alternate methods of loading PTX into silica nanoparticles. Oil-in-water emulsion methods were investigated to produce PTX-loaded silica nanoparticles. (Kong, L.; Uedono, A.; Smith, S. V.; Yamashita, Y.; Chironi, I. *Journal of Sol-Gel Science and Technology* 2012, 64, 309) Tergitol NP-9 (8 mL) was first added to 100 mL of water in a round-bottom flask and stirred for 1 hour to create the emulsion. Phenyltrimethoxysilane (PTMS) and TEOS were added and stirred for 30 minutes. Chloroform (1 mL) was then added to the emulsion and stirred for 4 hours. In order to create PTX-loaded silica nanoparticles, 40 mg PTX were solubilized in 1 mL chloroform initially and then added to the emulsion. The phenyl groups on PTMS are able to associate with the chloroform droplets in the emulsion. Lastly, hydrolyzed aminopropyltriethoxysilane (APTES) was added to the emulsion and the mixture was allowed to stir overnight (16 hours). Preactivation by hydrolyzing APTES is necessary. The hydroxyl groups on APTES can readily undergo condensation reaction to create siloxanes with the existing TEOS and PTMS. By TEM, the nanoparticles appear to have a rough exterior and have a diameter of approximately 68 nm (FIG. 17). Initial attempts at loading these particles with PTX resulted in extremely low loading (~2% loading of initial 40 mg PTX). These nanoparticles also proved to be unstable in solution and aggregated within several days. For long-term storage purposes, these nanoparticles were lyophilized, however, they were not able to be resuspended in H$_2$O and continued to be in an aggregated state even after sonication (FIG. 18).

Example 4. Paclitaxel in Treating Ovarian Cancer

Ovarian cancer is the leading cause of gynecologic cancer mortality that afflicts ~20,000 women per year in the United States.[1] Unfortunately, more than 75% of patients are diagnosed at an advanced stage with widespread metastatic disease within the peritoneal cavity.[2] The current standard of care consists of tumor debulking and chemotherapy, specifically platinum- and taxane-based drugs.[3-6] Paclitaxel (PTX), a taxane-based drug has proven to be quite effective when administered into the intraperitoneal (IP) cavity combined with cisplatin. However, due to solubility, Paclitaxel is formulated containing 6 mg PTX/mL of Cremophor EL (polyoxyl 35 castor oil) and dehydrated alcohol (1:1, v/v) (Taxol). The use of these excipients can be quite toxic and can cause ~30% of patients to experience hypersensitivity reactions.[7] Therefore, alternative formulations of PTX are still highly desirable.

With the fast development of nanotechnology over the past decades, various nanocarriers such as albumin, liposome, micelles, and mesoporous silica have been widely explored to enhance PTX solubility, improve PTX release profile, decrease its side effects, and passively or actively target to tumor sites.[8,9] Abraxane, one of the most successful nanoformulation of PTX, was approved by the FDA in 2005. When administered to patients, it increased the maximum tolerated dose while limiting the side effects as seen in Taxol.[10,11] However, the preparation of Abraxane requires high-pressure homogenization of PTX in the presence of human serum albumin, resulting in high costs of the dosage form.[12] Despite alleviating the hypersensitivity issues leading to higher tolerated doses, no significant difference was seen between the overall survival and efficacy of patients administered either Abraxane or Taxol.[13-15]

Many of the previous nanosuspension formulations also do not address the underlying issue of specific, targeted delivery. Although many of them have been designed to either passively target the tumor site by the EPR effect or actively target it by ligands, the majority of nanoparticles still accumulate in the liver, kidney and spleen.[16,17] One way to improve targeted delivery is by using cell carriers that have a propensity to migrate towards tumors or specific organs. Tumor tropic- or organotropic-cell carriers such as stem cells (Mesenchymal/Neural Stem Cells), T-cells, or macrophages, can be loaded with therapeutic nanoparticles for targeted delivery.[18] We have previously shown that the clonal human HB1.F3 neural stem cell (NSC) line is tumor tropic and selectively migrates to a number of malignant solid tumors, including glioma, neuroblastoma, and metastatic breast carcinoma.[19-21] These NSCs have been shown to penetrate hypoxic tumor regions, overcoming high interstitial pressures and stiff extracellular matrices.[22] Localization of NSCs to the tumor was observed after 1 hour, while distribution of the released drug throughout the tumor was observed after 4 days.[6] However, to the best of our knowledge, there is no report of using NSCs to distribute PTX for reducing tumor burden.

In this study, we developed a novel PTX nanoformulation suitable for NSC loading. Liu et al. previously reported using Pluronic F127 as the sole excipient to temporarily stabilize PTX nanocrystals. This PTX nanoformulation showed high drug loading, excellent antitumor activity, low toxicity, and ease in scale-up/manufacturing.[23] Despite using the optimal amount of surfactant to stabilize the nanocrystals, they ultimately will undergo fusion and aggregation over time.[7] Herein, we further modified the nanocrystal by growing a silica shell to form PTX-nanorods (NR) which are increasingly more stable than Pluronic F127 PTX nanocrystals and has improved loading to NSCs.

Results

Nanorod Synthesis and Characterization.

Figure 20:
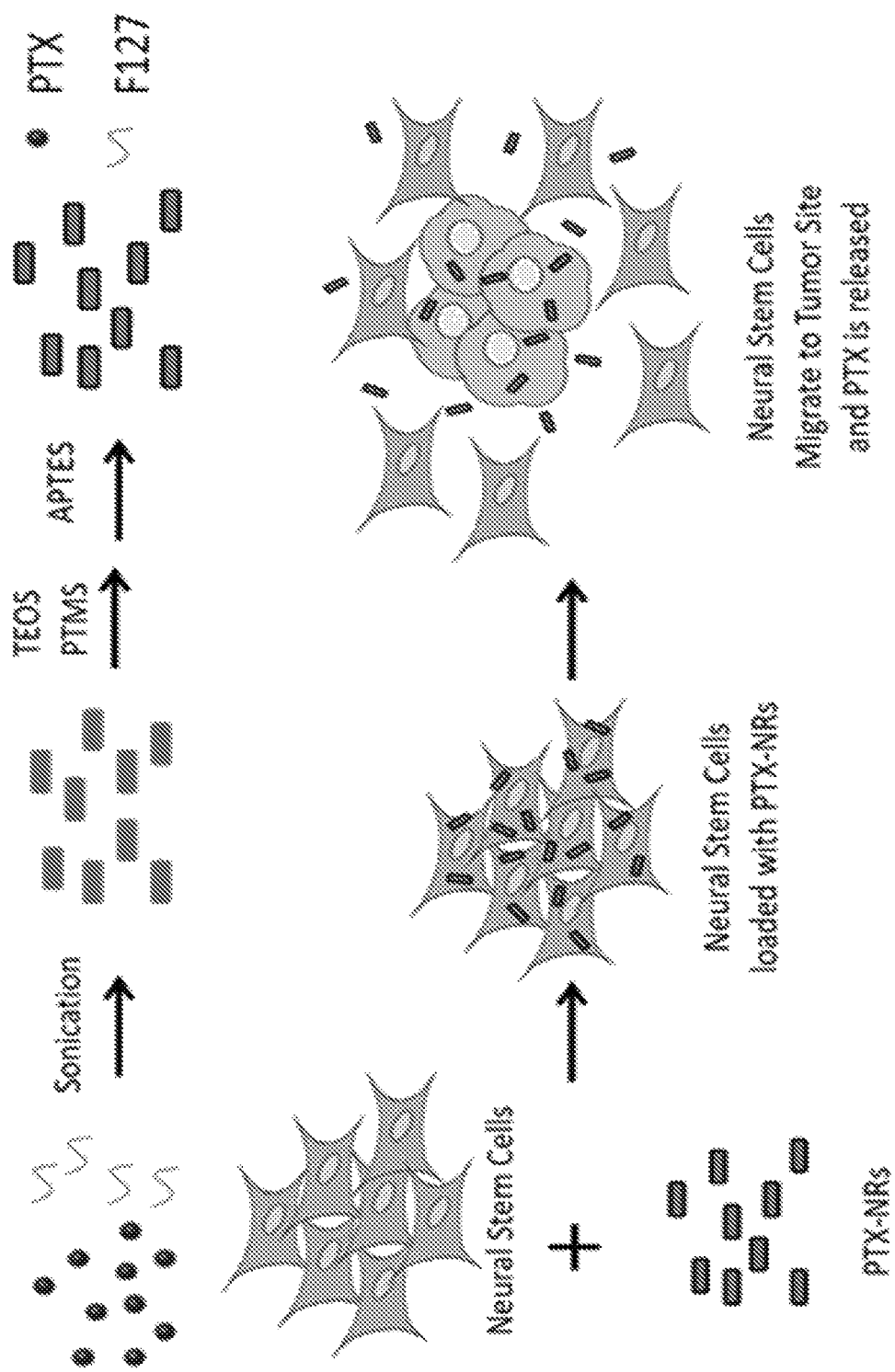
FIG. 20. Scheme of PTX-nanorod synthesis, neural stem cell loading of PTX-nanorod and ovarian cancer targeted delivery.
Figure 21A:
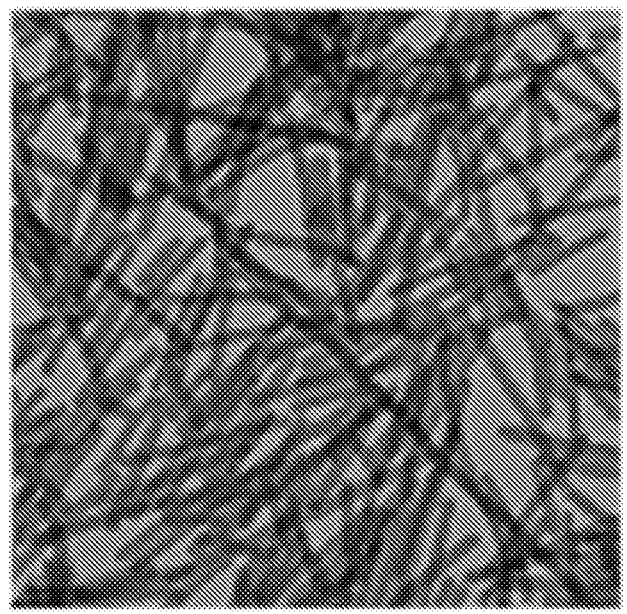
FIGS. 21A-21C. TEM image of PTX nanorod FIG. 21A) 11000×.
Figure 21B:
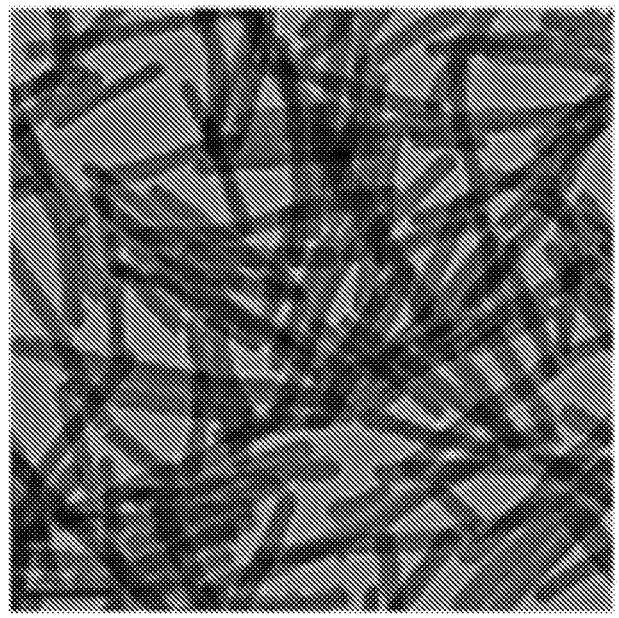
Figure 21:
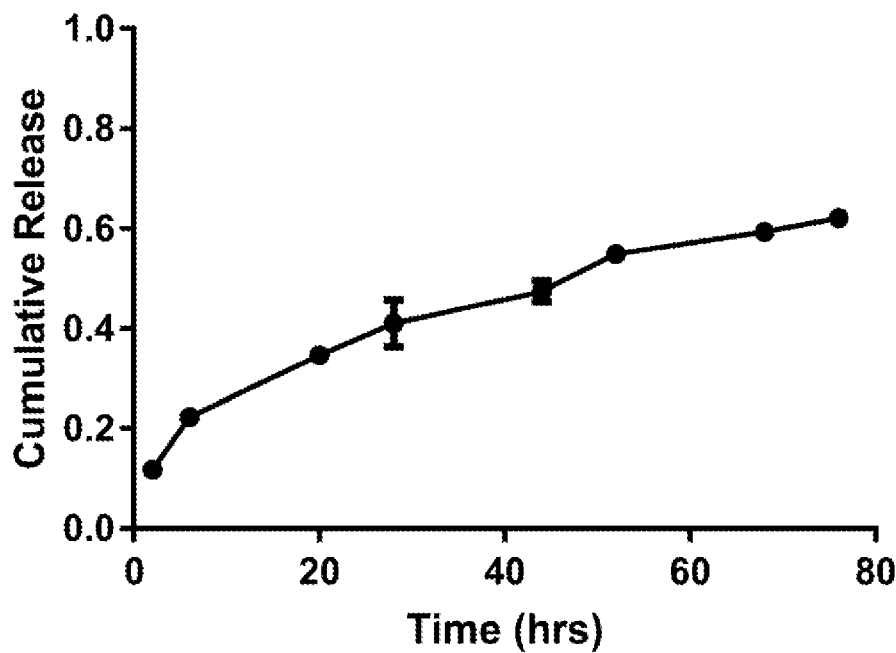
Figure 26:
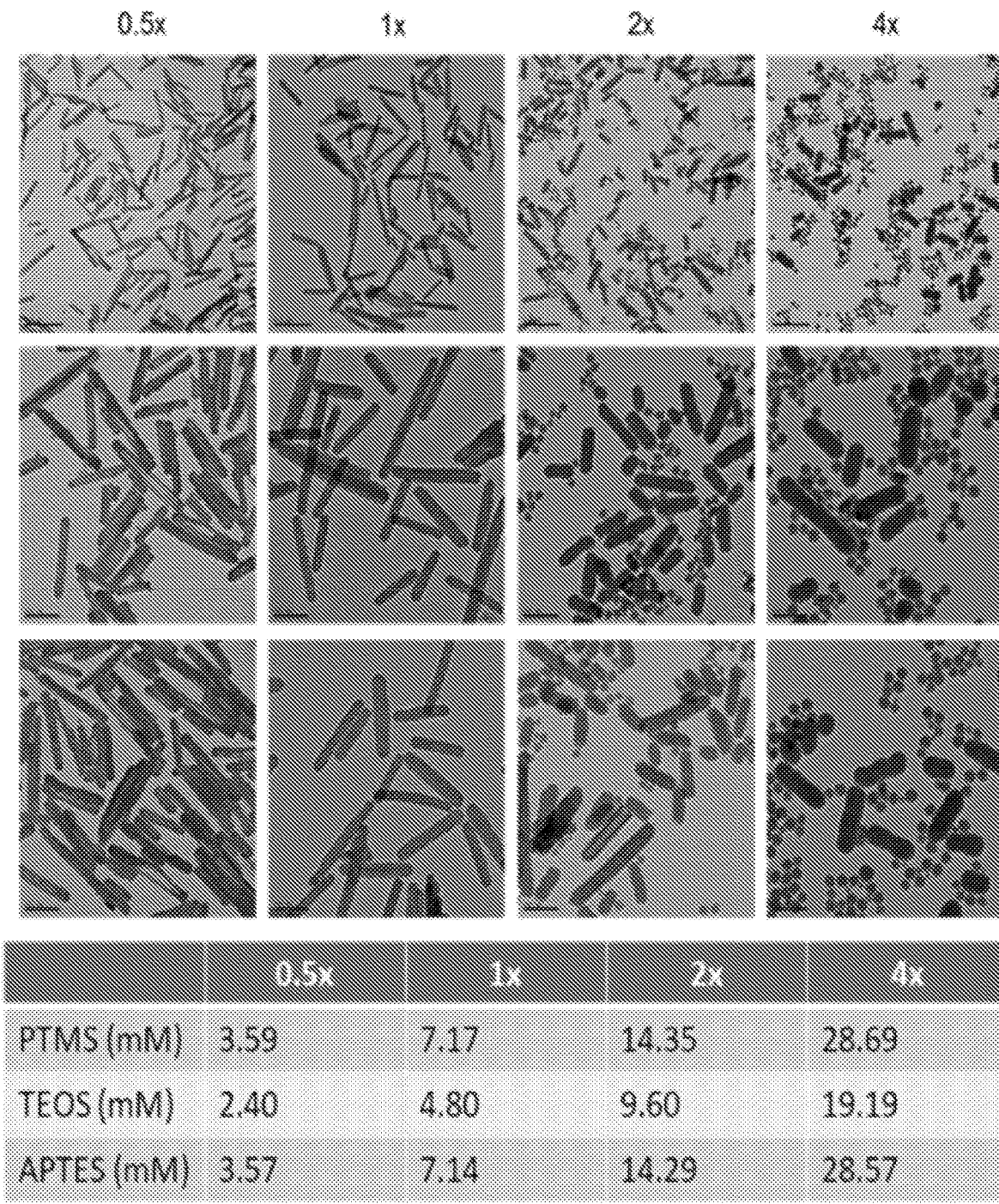
FIG. 26. TEM image of PTX nanorod prepared at different silica precursor concentrations.
Figure 27A:
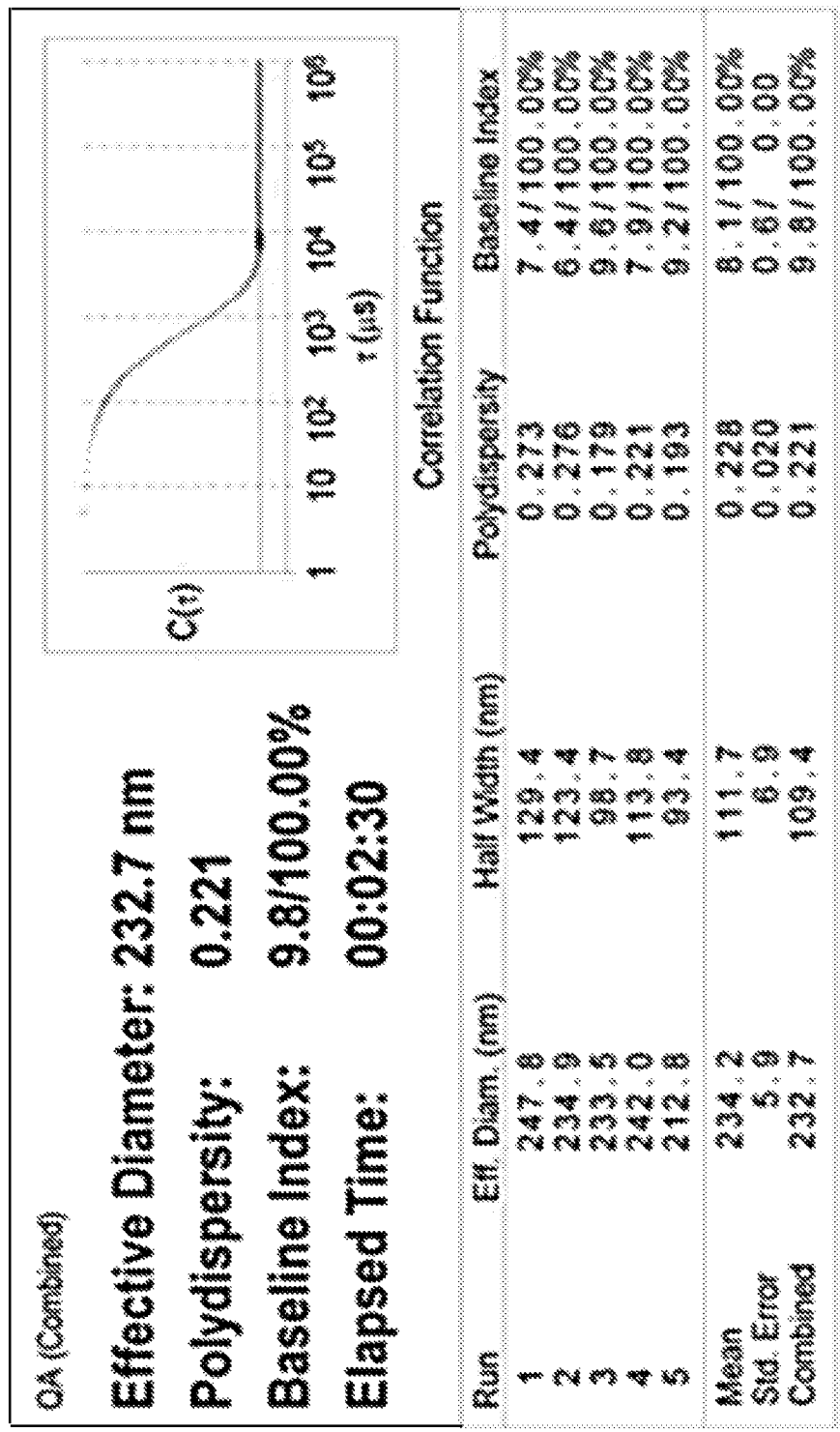
FIGS. 27A-27D. DLS measurement of FIG. 27A) size, FIG. 27B) zeta potential of PTX nanorod immediately after preparation.
Figure 27B:
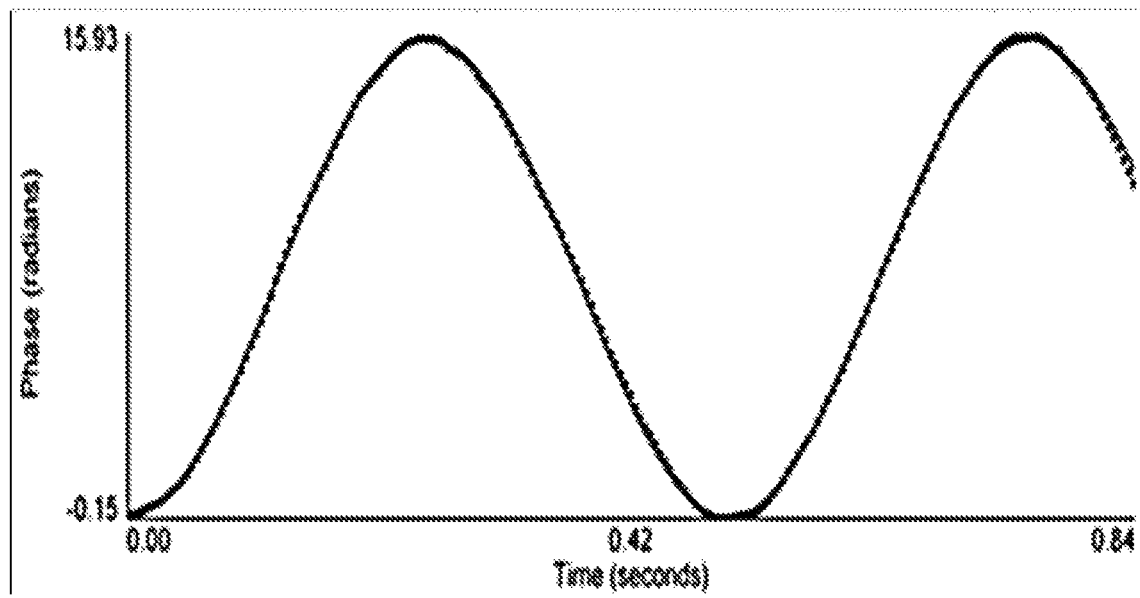
Figure 27C:
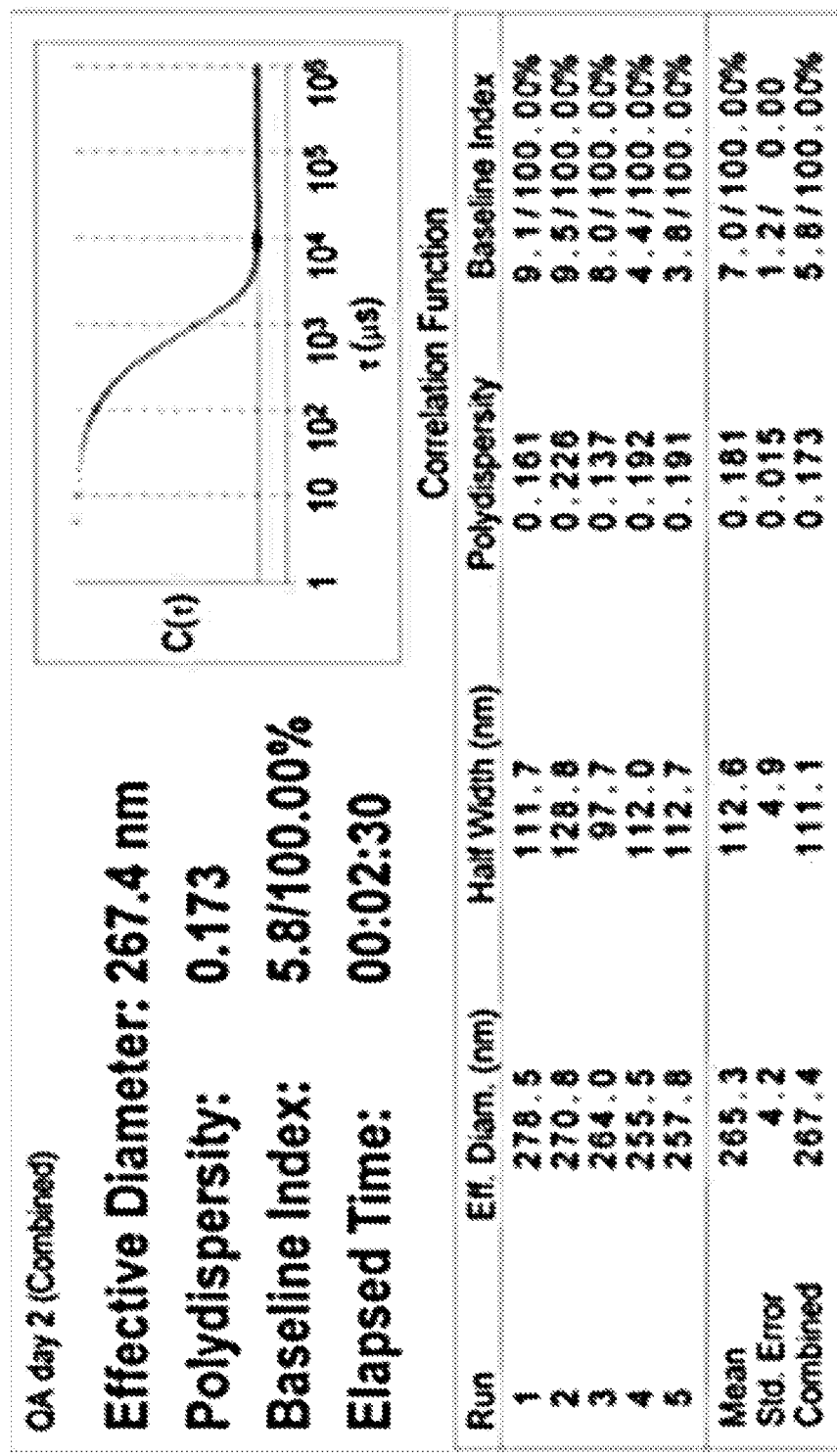
Figure 27D:
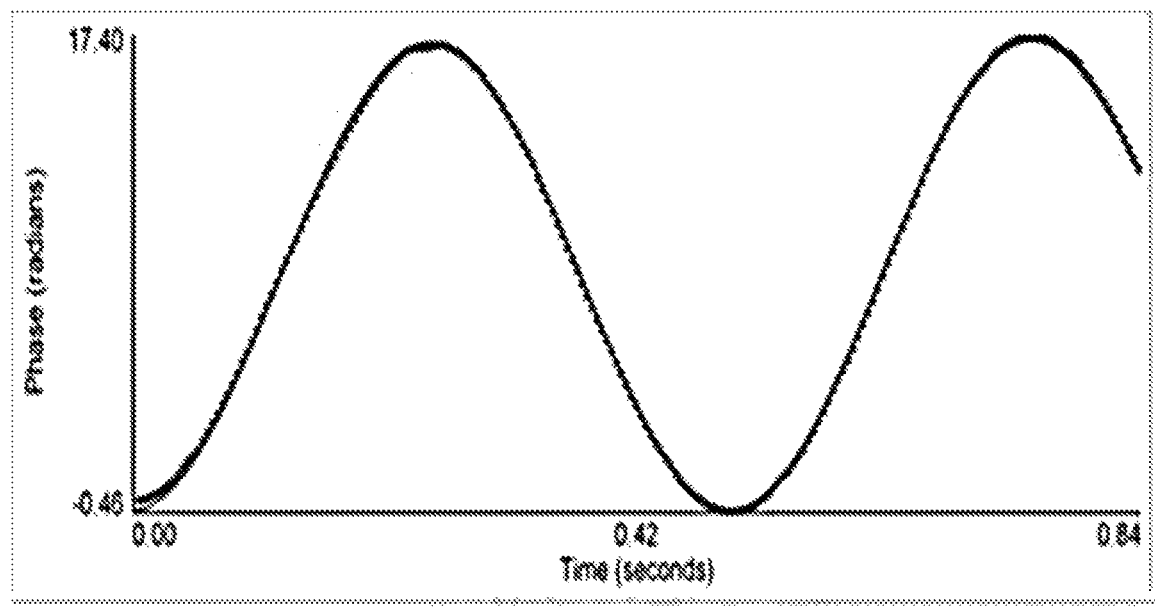

PTX-nanorods were synthesized by silica coating of pre-formed PTX nanocrystals. As shown in FIG. 20, PTX nanocrystals were generated by first dissolving PTX and Pluronic F127 in chloroform at 1:5 (w/w) ratio.[7] The organic solvent was then evaporated and placed under vacuum for 15 minutes. The thin film of PTX and PluronicF127 was further hydrated in water and sonicated to form needle shaped nanocrystal (FIG. 25). To further stabilize the PTX nanocrystals and facilitate the uptake of particles into NSCs, we attempted to grow a uniform silica shell around the PTX nanocrystals. As shown in FIG. 20, silica precursors phenyltrimethoxy silane (PTMS) and tetraethyl orthosilicate (TEOS) were mixed with PTX nanocrystals and underwent hydrolysis for 3 hours. PTMS was chosen because phenyl groups had a higher affinity to the PTX nanocrystals. Aminopropyltriethoxy silane (APTES) was subsequently chosen as both silica precursor and mild base catalyst for precursor hydrolysis and condensation. APTES was added into the nanocrystal mixture and allowed to stir overnight for 16 hours. By varying the amount of silica precursors used (PTX kept constant), we were able to control silica shell growth of the nanorods (FIG. 26). With increasing concentration of silica precursors (2× and 4×), obvious spherical silica particles were formed due to the self nucleation of silica clusters at high precursor concentration. By decreasing the concentration of silica precursor, nanorods tended to fuse together before forming a stable silica layer (0.5×). Using the optimal concentration of PTMS (7.17 mM), TEOS (4.80 mM), and subsequent APTES (7.14 mM), a uniform silica layer could be formed on the exterior of the PTX nanocrystal. FIGS. 21A-21B shows representative TEM images of silica nanorods that are 357±103 nm in length and 75±9 nm in width. Since APTES was added, the amine groups on the exterior of the silica shell caused the surface to be positively charged resulting in a zeta potential of +36.65 mV (FIG. 27). The nanorods showed high stability with no obvious aggregation after incubated under room temperature for one day. Hydrodynamic size and zeta potential of PTX-NRs remained constant after one day of incubation (FIG. 27, 232.7 nm vs 267.4 nm and +36.65 mV vs+39.72 mV). This is distinct from uncoated PTX nanocrystal which aggregated within hours.[24] The PTX nanorods also exhibit high drug loading capacity. The PTX loading capacity was calculated to be 19.3% (weight of PTX divided by total weight of the nanorod). To test the release property of PTX nanorods, nanorods containing 40 µg PTX were suspended in 1 mL of DMEM medium with 10% FBS. PTX released in the supernatant was extracted at different time points. PTX was gradually released from the nanorods with 63.0% released within 72 hours (FIG. 21C). This was distinct from PTX-F127 (40 µg/mL) which dissolved immediately in DMEM medium with 10% FBS 40. The controlled release of PTX from nanorod is preferable for NSC loading to prevent premature killing of NSCs before they reach the tumor site.

Cytotoxicity of PTX Nanorods.

Figure 22A:
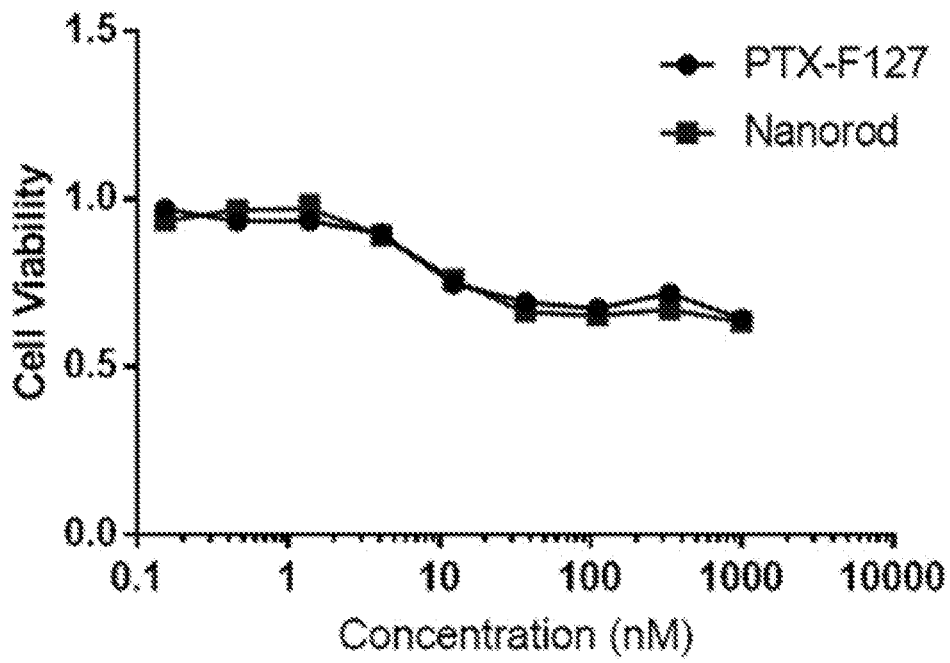
FIGS. 22A-22B. OVCAR-8 viability after FIG. 22A) 24 hours, FIG. 22B) 72 hours incubation with different concentration of PTX-F127 and PTX nanorod.
Figure 22B:
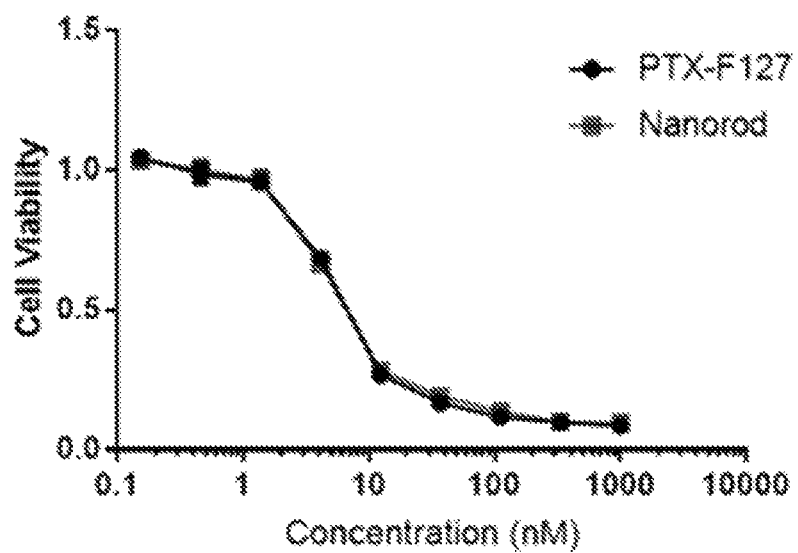
Figure 28A:
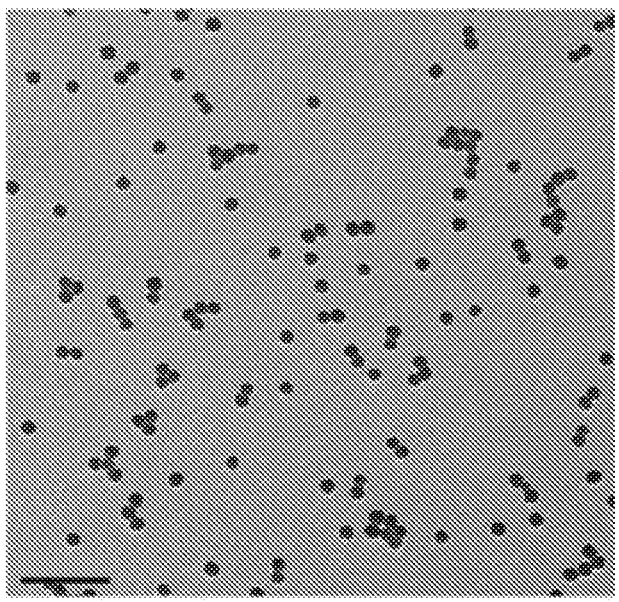
FIGS. 28A-28B.
Figure 28B:
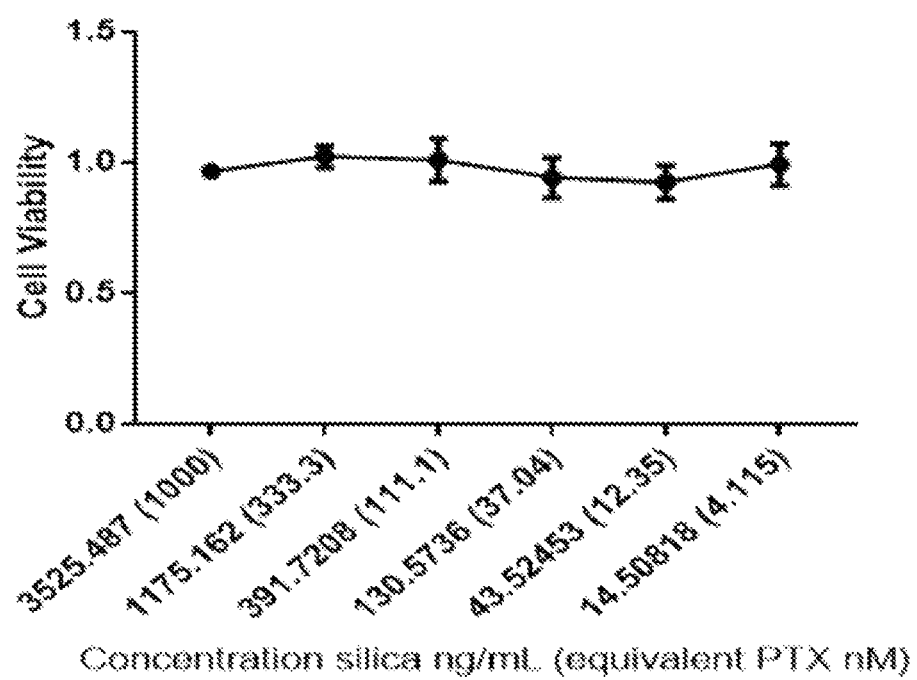

To determine whether the silica coating will affect the efficacy of PTX, we used OVCAR-8 cells, a model ovarian cancer cell line, to test the toxicity of PTX nanocrystal and PTX nanorod. OVCAR-8 viability was measured by MTS assay after incubating with different concentrations of PTX nanocrystal and PTX nanorod (FIGS. 22A-22B). After silica coating, NSCs treated with PTX nanorods maintained similar viability to NSCs treated with PTX-F127. The $IC_{50}$ of cells treated with either PTX nanorods or PTX-F127 were 7.7 nM and 7.8 nM, respectively and showed significant killing after 72 hours incubation. To exclude the possibility that the silica coating itself was toxic, we synthesized empty silica nanoparticles with the same PTMS/TEOS/APTES ratio but at 4× initial concentration (FIG. 28A) (1× and 2× did not form any silica particles). OVCAR-8 cells were incubated with different concentrations of silica particles for 72 hours and the cell viability remained high even at the highest concentration (3525.487 ng/mL equivalent to the same amount of silica content of PTX nanorod with 1000 nM PTX concentration, FIG. 28B).

NSC Loading of PTX Nanorods.

Figure 23A:
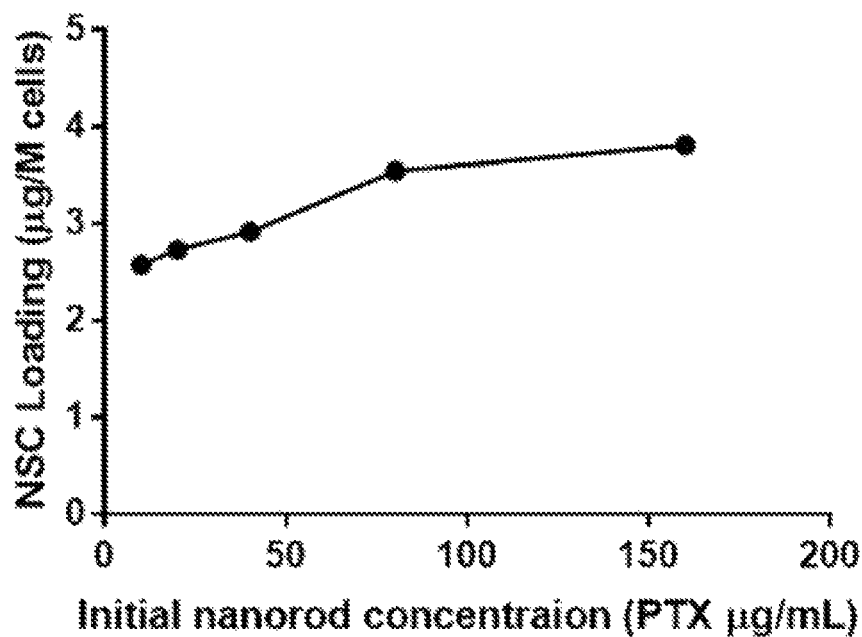
FIGS. 23A-23E.
Figure 23B:
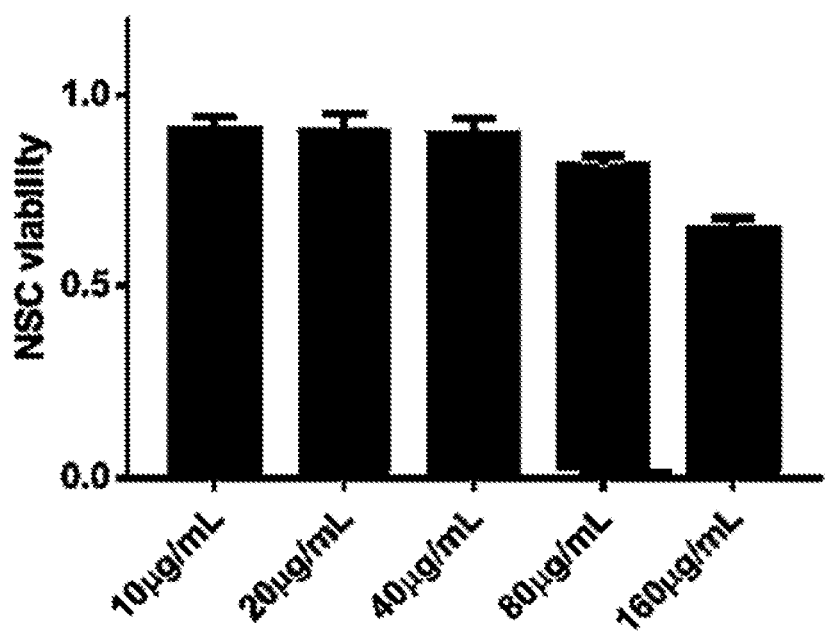
Figure 23C:
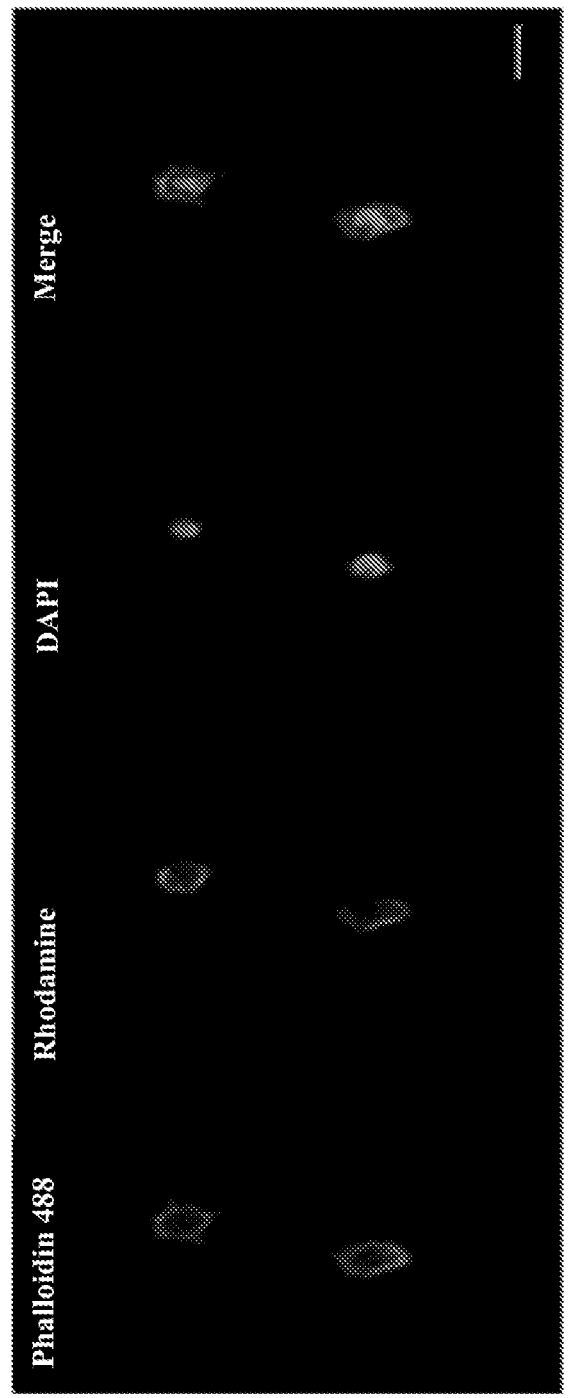
Figure 23D:
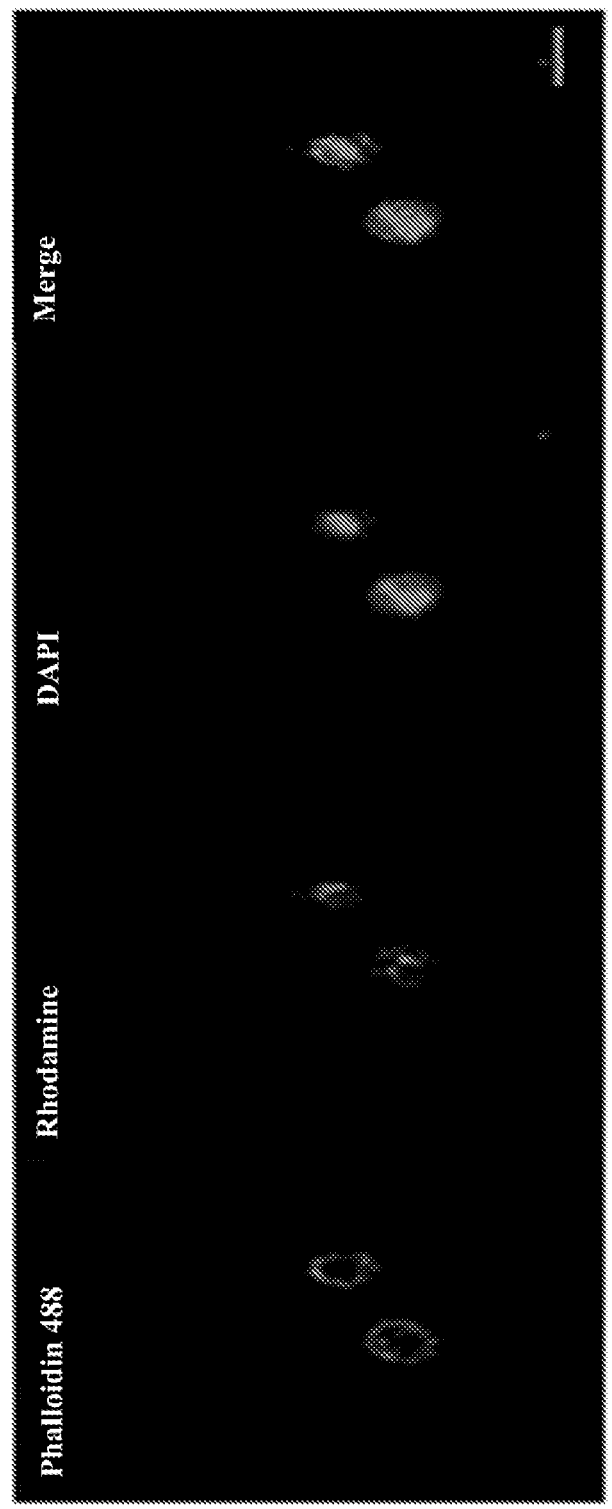
Figure 23E:
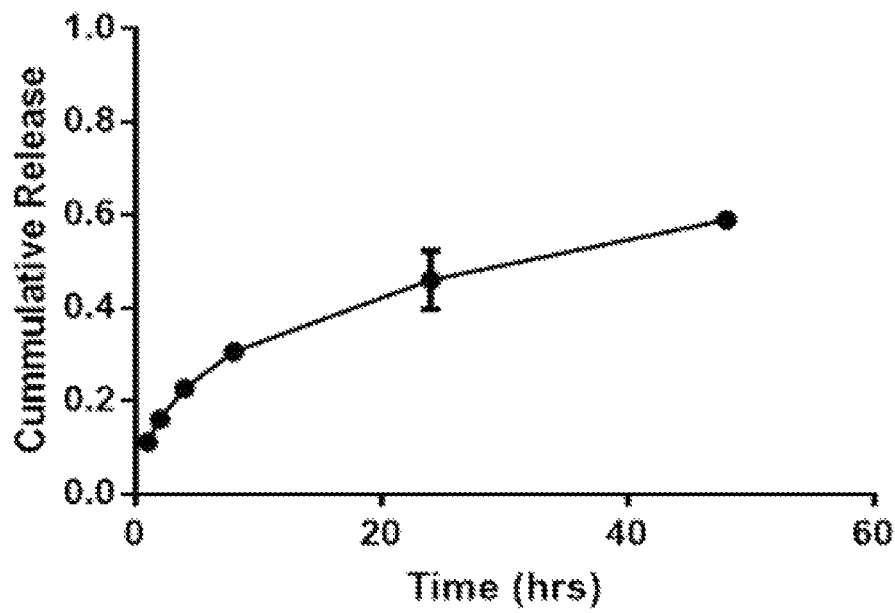

After demonstrating that nanorods have excellent PTX loading capacity and controlled release property, we investigated the loading efficiency of PTX-NRs onto NSCs. Here, we incubated NSCs with PTX nanorods at 25 μg/mL for 1 hour and measured the PTX uptake amount in the NSCs using HPLC. Loading of PTX to NSC reached 3.16 μg per million NSCs for PTX nanorods, while only 0.26 μg of PTX could be loaded to NSCs using PTX-F127 nanocrystals. Lastly, NSCs were loaded with Abraxane, however, no measurable PTX signal was detected by HPLC. We further measured NSC uptake of PTX under different initial incubating concentrations. FIG. 23A demonstrates that by increasing PTX nanorod concentrations from 10 μg/mL to 160 μg/mL, PTX loading into NSCs increased from 2.57 μg per one million NSCs to 3.81 μg per one million NSCs. Despite higher loading of PTX on NSCs, viability of PTX-loaded NSCs was reduced within 24 hours (FIG. 23B). Thus, we choose 25 μg/mL as the PTX nanorod loading concentration for further study. We further studied the uptake of PTX nanorods into cells using confocal microscopy. NSCs were treated with PTX nanorods labeled with sulfo-Rhodamine for 1 hour and underwent washing to clear excess PTX-nanorods that were not uptaken by cells or adhered to the cell surface. NSCs were fixed with paraformaldehyde and stained with phalloidin 488 for F-actin and DAPI for nuclei at different time points. As is shown in FIG. 23C, after 1 hour incubation, PTX nanorods were mostly attached on the surface of the NSCs, however, a small population of nanorods were starting to be internalized by the NSCs. After 4 hours, all the nanorods had been completely internalized within NSCs (FIG. 23D). This suggested that the cell loading of PTX nanorods is robust and are internalized within 4 hours without significant loss of nanorods after the initial loading. We further extracted PTX released from NSC/nanorod hybrids in the cell culture medium at different time points and measured the PTX concentration by HPLC. As shown in FIG. 23, PTX was gradually released from the nanorods after internalization with 58.9% of PTX released in 48 hours, which is slightly faster than then release of PTX nanorod in the cell culture medium alone (~50% PTX). The increase in silica degradation rate and release kinetics can be attributed to the acidic endosomal microenvironment.

NSC Migration and NSC/OVCAR-8 Coculture.

Figure 24A:
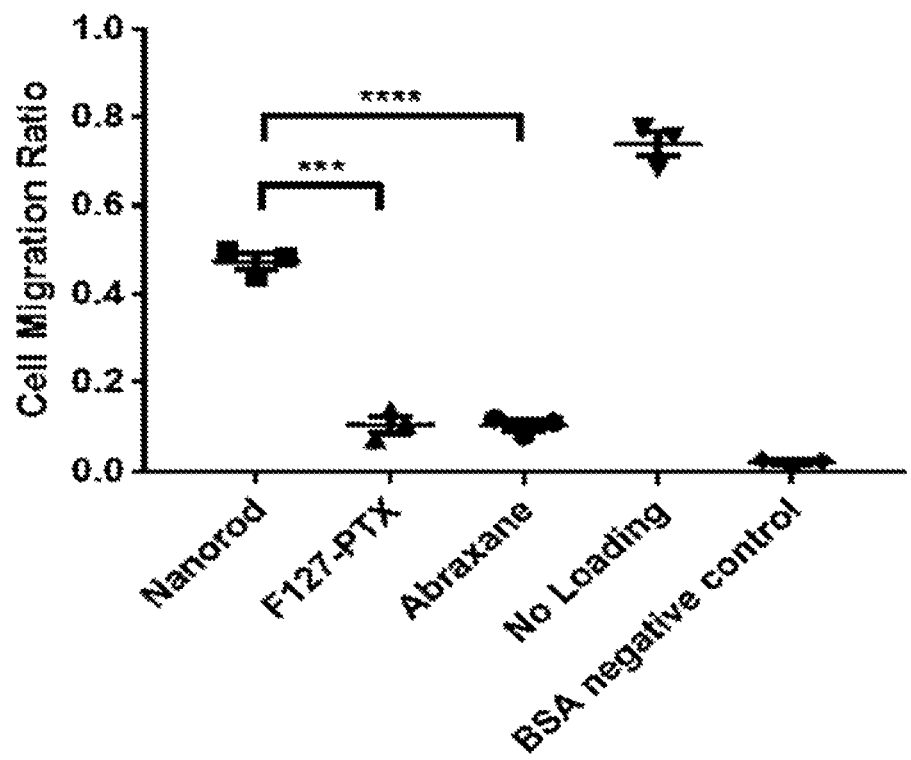
FIGS. 24A-24B.
Figure 24B:
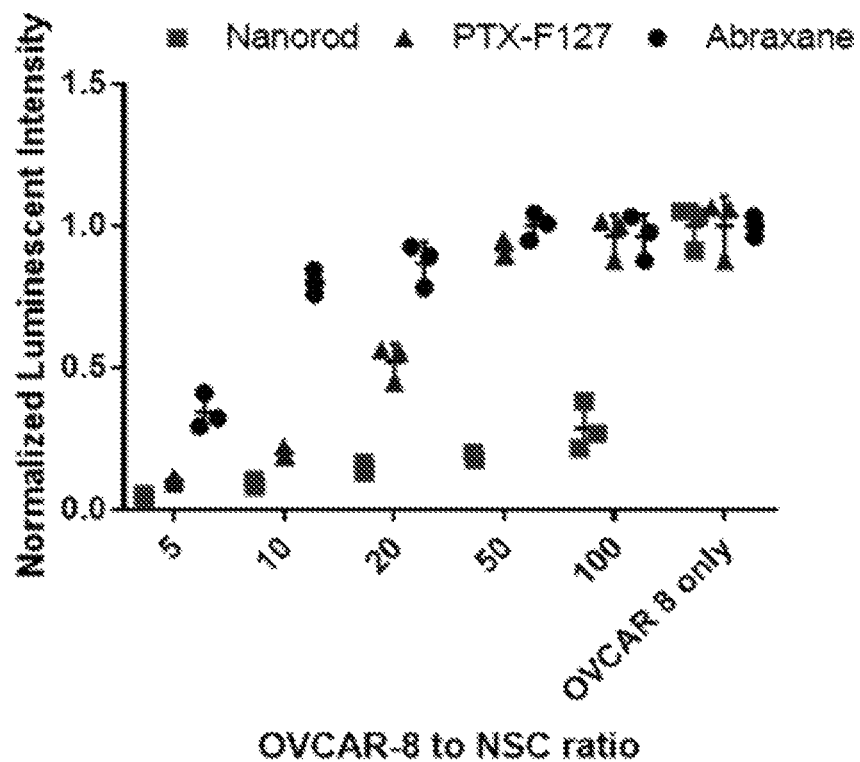
Figure 25A:
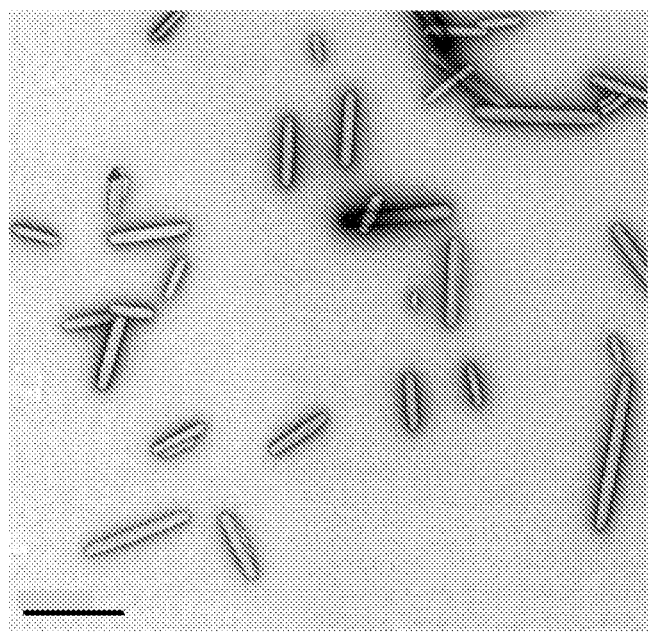
FIGS. 25A-25D. TEM image of PTX nanocrystal prepared at PTX to F127 ratio of FIG. 25A) 1:1.
Figure 25B:
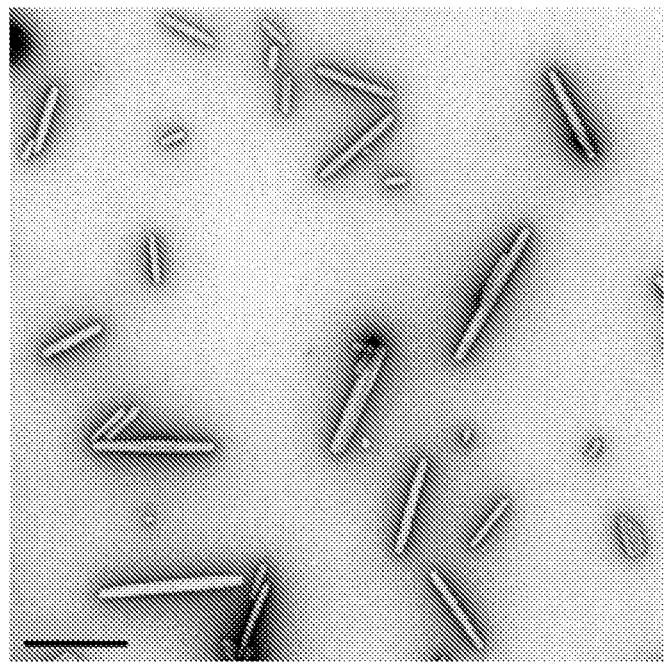
Figure 25C:
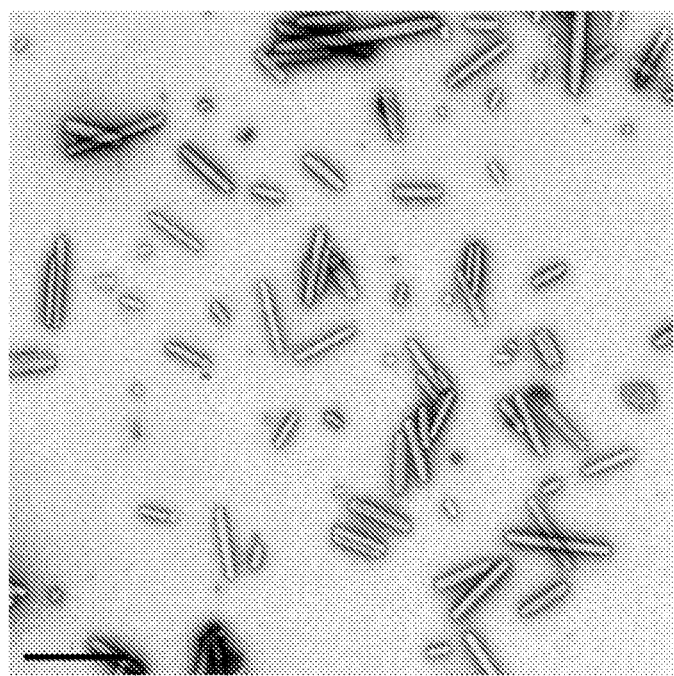
Figure 25D:
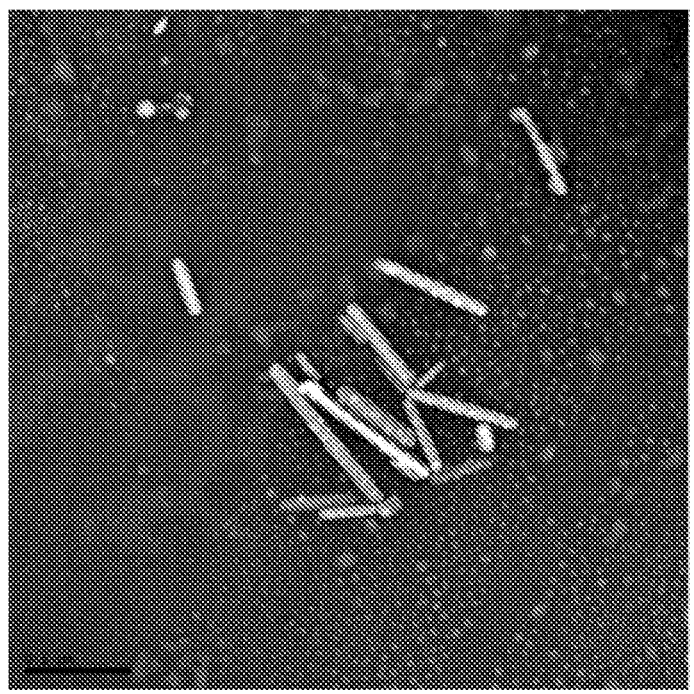

PTX is a potent microtubule stabilizer, which inhibits the migration of NSCs. Therefore, the migration capability of NSCs loaded with PTX nanorods was investigated using the Boyden Chamber migration assay. In this assay, migration was evaluated over 4 h because that is representative of the time it would take for them to reach the ovarian tumors when injected by IP. Untreated NSCs and NSCs incubated with different PTX formulation were seeded on a membrane placed above either 5% BSA (negative control) or SKOV-3 tumor-conditioned media as model ovarian tumor condition media. U87 glioma tumor-conditioned media was used as a known positive control for NSCs and 5% BSA media as a negative control. After 4 h, cells that had migrated to the bottom of the membrane were quantified and the migration ratio was calculated as cells migrated vs cells seeded. As is shown in FIG. 24A, after loading with PTX nanorods, the NSCs did show a reduction in migration compared to the NSC only control (47.5% vs 73.9%). However, NSCs incubated with free drug (PTX-F127 nanocrystal and Abraxane) showed more than four times reduction in the migration ratio (10.5% and 10.4% respectively), which is comparable to the BSA negative control (2.1%). This result suggested that the silica coating of PTX nanocrystal limited the direct contact of NSCs with free PTX, which further prove the great potential to use PTX nanorod as a PTX delivery vehicle to load NSCs for ovarian tumor specific chemotherapy. We further tested the tumor killing potential in vitro of NSCs/PTX nanorods by co-culturing OVCAR-8 cells with drug-loaded NSCs. NSCs were first incubated with PTX nanorods or PTX-F127 nanocrystals for 1 hour and then washed and trypsinized from 6-well plates. After cell counting, various amounts of drug loaded NSCs were plated onto 96-well plates with pre-cultured OVCAR-8 cells. The OVCAR-8 viability was determined by measuring the luciferase activity after 72 hours and the luminescent intensity of luciferase was normalized using untreated OVCAR-8 control. FIG. 24B demonstrates the excellent killing of OVCAR-8 by NSCs loaded with PTX-nanorods even at low amounts of NSCs/nanorod added. When the OVCAR-8:NSC ratio was increased to 100, the OVCAR-8 cells only had a viability of 36% after 72 hours. However, the NSCs/nanocrystal were significantly less effective for OVCAR-8 killing. OVCAR-8 cells could survive when NSCs/nanocrystal number dropped to a ratio of 50. This is consistent with the PTX loading results, that nanorods are 12 times more capable to be loaded to NSCs than PTX-F127 nanocrystals.

Conclusions.

Here, we synthesized novel PTX nanorods by coating PTX-F127 nanocrystals with a uniform silica layer. This PTX nanorod has very high drug loading capacity with gradual release of 60% PTX within 72 hours and no decrease of ovarian cancer cell proliferation inhibition compared with free drug. The PTX nanorod were able to be loaded into NSCs and the silica coating greatly preserved the migration capability of NSCs compared to PTX or PTX-F127 nanocrystals. Then PTX nanorod loaded NSCs showed great OVCAR-8 cell killing with low NSCs to OVCAR-8 ratio needed. To the best of our knowledge, this work represents the first demonstration that PTX nanoformulation could be loaded into NSCs for potential ovarian tumor targeted delivery.

Materials and Methods

Materials.

All organic and inorganic compounds and solvents were purchased from Sigma-Aldrich. Paclitaxel (PTX) was purchased from Ark Pharm. Abaraxane was purchased from Celegene. Alexa Fluor 488® phalloidin and -,6-diamidino-2-phenylindole (DAPI) were purchased from ThermoFisher Scientific. OVCAR-8, SKOV-3 and the clonal human HB1.F3 neural stem cell (NSC) were used.

Instrumentation.

Dynamic light scattering (DLS) and (potential (ZP) measurements were performed on a Brookhaven 90 Plus/BI-MAS Instrument (Brookhaven Instruments). DLS measurements were obtained by performing 5 runs at 30 s per run, and the ZP values were obtained by measuring 10 runs involving 30 cycles per run.

TEM images were obtained with an FEI Tecnai T12 transmission electron microscope at an accelerating voltage of 120 keV, and images were taken with a Gatan Ultrascan 2K CCD camera. NPs dispersed in water at an optimal concentration were drop-cast onto glow-discharged, 300 mesh carbon—Formvar coated grids and allowed to dry before imaging. High-resolution TEM characterization was obtained with a JEOL JEM-2100F at an acceleration voltage of 200 kV equipped with Gatan Orius Camera. Confocal microscopic images were taken on a Zeiss LSM700 confocal microscope at 63×. HPLC analysis was performed by Agilent 1100 Series with UV detector at 220 nm. Standard curve was made by measuring the area under PTX peak at different PTX concentration.

Synthesis of PTX-F127 Nanocrystal and PTX Nanorod.

Paclitaxel (4 mg) and Pluronic F127 (20 mg) were both measured out and combined in a scintillation vial. Chloroform (1 mL) was added to the scintillation vial and vortexed to completely solubilize PTX and Pluronic F127. A steady stream of nitrogen was used to evaporate the chloroform. This formed a nice dry film on the bottom of the vial. In order to ensure the vial was placed in a vacuum for 10 min, followed by adding 14 mL MilliQ $H_2O$ (14 mL). Qsonica cup sonicator (amplitude=100) was used to sonicate the mixture to form the nanosuspension. Pulse-on time was 5 minutes and pulse-off time was set to 10 minutes and this was repeated two more times for a total of 45 minutes of process time. To verify formation of nanocrystals, the solution was imaged by TEM. Four µL of the solution were removed and placed on a 300-mesh copper grid. After 30 seconds, it was blotted off and stained with 2% uranyl acetate. After 30 seconds, uranyl acetate was blotted off and allowed to dry. After sonication, TEOS (15 µL, 67.2 µmoles) and PTMS (18.75 µL, 100.4 µmoles) was added to the nanosuspension to get a final concentration of 4.80 mM (TEOS) and 7.17 mM (PTMS) and stirred for 4 hours. APTES (70 µL) was diluted with 37.5 µL of milliQ $H_2O$ and immediately added to the mixture to get a final concentration of 7.14 mM. The mixture was allowed to stir overnight (16 hours). The PTX nanorods were centrifuged at 20,000×g for 10 minutes and washed with milliQ $H_2O$ three times. Other concentration of silica precursor was also explored (0.5×, 2× and 4×) to optimize the synthesis of PTX nanorod. Empty silica nanoparticles were synthesized with similar method, except no PTX was added to the initial mixture and 4×TEOS/PTMS/APTES concentration was used.

Quantification of PTX in PTX Nanorod and PTX Released from Nanorod.

PTX nanorods (10 µL) were dissolved using hydrofluoric acid (2 µL, 48%) for 15 minutes and neutralized with sodium bicarbonate (3 mg) and calcium chloride (2 mg). Another 90 µL acetonitrile was added to the mixture and filtered by 0.4 µm syringe filter for HPLC analysis. PTX nanorods were freeze-dry by lyophilizer (Labconco) and weighed by balance. PTX loading capacity was calculated by weight of PTX/weight of the PTX nanorod. For PTX release study, PTX nanorod containing 40 µg PTX was suspended in 1 mL of DMEM cell culture medium with 10% fatal bovine serum (FBS). At different time point, the suspension was centrifuged at 10000 g and the supernatant was extracted by 1 mL of ethyl acetate. The extracts were dried under vacuum and dissolved in 100 µL acetonitrile for HPLC analysis.

Cell Culture.

All cells were cultured and maintained at 37° C. in a humidified incubator (Thermo Electron Corporation) containing 5% $CO_2$. Neural stem cells and OVCAR-8 cells were cultured in Dulbecco's modified Eagle's medium (DMEM; Invitrogen) supplemented with 10% fetal bovine serum (Gemini Bio), 1% L-glutamine (Invitrogen), and 1% penicillin-streptomycin (Invitrogen). SKOV-3 cells were cultured in RPMI 1640 medium (Gibco) supplemented with 10% fetal bovine serum (Gemini Bio), 1% L-glutamine (Invitrogen), and 1% penicillin-streptomycin (Invitrogen). When the cells reached 80% confluency, they were passaged using a 0.25% trypsin-ethylenediaminetetraacetic (trypsinEDTA) acid solution (Invitrogen); media was changed every 2-3 days. SKOV-3 cells were used to generate ovarian tumor-conditioned media by replacing culture media with serum-free media when cells were 80-100% confluent, followed by a 48 h incubation period.

Viability of OVACAR-8 Treated with Various Concentrations of PTX Nanorod.

OVCAR-8 cells were seeded in 96-well plates (4000 cells/well, 100 µL medium). They were incubated at 37° C. for 16 hours before treatment. All dilutions of PTX-F127 nanocrystal and PTX nanorod were done in media. After treatment, cells were incubated for 24 and 72 hours. At each time point 20 µL of MTS solution (Promega) was added to each well and cell viability was measured by microplate reader at 490 nm absorbance wavelength after incubated at 37° C. for two hours.

NSCs Loading with Nanorod, PTX Release and Viability.

NSCs loading with PTX nanorod was achieved by incubating NSCs (500K cells/well in 6-well plates) for 1 h with a suspension of nanorods in PBS at 37° C. Any unloaded nanorods were removed by repetitive PBS washing 3 times. The nanorod-loaded NSCs were then trypsinized and pelleted via centrifugation. The cell pellet was further ruptured using hydrofluoric acid and neutralized by sodium bicarbonate and calcium chloride. Acetonitrile was added to ruptured cells and filtered by 0.4 µm syringe filter for HPLC analysis to determine PTX loading in NSCs. To measure PTX released from nanorod-loaded NSCs, cell pellets were suspended in 1 mL of medium and the supernatant was collected at different time points. PTX was extracted using 1 mL of ethyl acetate. The extracts were dried under vacuum and dissolved in 100 µL acetonitrile for HPLC analysis. To determine the NSCs viability after loading, nanorod-loaded NSCs (4000 cells/well) were plated onto 96-well plates and viability was measured after 24 hours by MTS assay.

Microscopic Imaging of Internalization of NPs.

Suspensions of NSC/nanorod were fixed in 4% paraformaldehyde, rinsed in 0.1% Tween—PBS, and then stained for 15 minutes at room temperature in the dark with a PBS solution containing AlexaFluor 488-conjugated phalloidin (1:200 dilution) and DAPI (1 µg/mL) to stain cellular filamentous actin and nuclei, respectively. Cells were pelleted, rinsed, and then encapsulated within 1% (weight/volume) low-melting-point agarose (Sigma) to stabilize the cells for imaging. The agarose suspension (200 L) was placed on a glass slide with which a coverslip was used to create a thin gel layer that was polymerized upon exposure to 4° C. for 10 min. Images were acquired using a confocal microscope (Zeiss, Oberkochen, Germany) equipped with a 63× magnification water immersion objective.

Migration of NSCs.

NSCs' migration capability was measured using the in vitro transwell Boyden chamber assay. NSCs were incubated with PTX nanorods, PTX-F127 nanocrystals and Abraxane 25 µg/mL PTX in PBS for 1 hour. In a 24-well tissue culture plate 500 µL of target media (either containing only BSA as a negative control, or derived from the culture of SKOV-3 cells) was added to each well. At a density of 1×10$^5$ cells/well, PTX loaded NSCs in DMEM and 5% w/v BSA were placed in the transwell chambers and incubated at 37° C. for 4 hours. After the incubation period, the transwell chambers were placed in a new 24-well tissue culture plate containing accutase and incubated 10 mins at 37° C. Detached cells were then transferred to a 96-well v-bottom plate, centrifuged at 1,500 rpm for 5 mins, and resuspended in 1:1 media to ViaCount. NSC migration to conditioned media of PTX treated and nontreated cells was assessed using Guava EasyCyte technology.

Tumor Killing Effect In Vitro by Co-Culturing PTX Loaded NSCs and OVCAR-8.

OVCAR-8 cells were seeded in 96-well plates (4000 cells/well). They were incubated at 37° C. for 16 hours before treatment. NSCs were loaded with PTX nanorods, PTX-F127 nanocrystals and Abraxane as previously described. After a 1 hour incubation period, NSCs were repetitively washed 3 times by PBS to remove unloaded PTX nanorods, PTX-F127 nanocrystals or Abraxane and were detached with trypsin-EDTA. PTX loaded NSCs were transferred to the wells containing OVCAR-8 cells at ratios of 1:5, 1:10, 1:20, 1:50, and 1:100 by using serial dilutions. Each condition and ratio was done in triplicates. Cells were co-cultured for 72 hours and then OVCAR-8 viability was determined by adding 10 µL D-luciferin solution (3 mg/mL) to each well and measuring luciferase luminescent intensity by microplate reader.

Figure 29A:
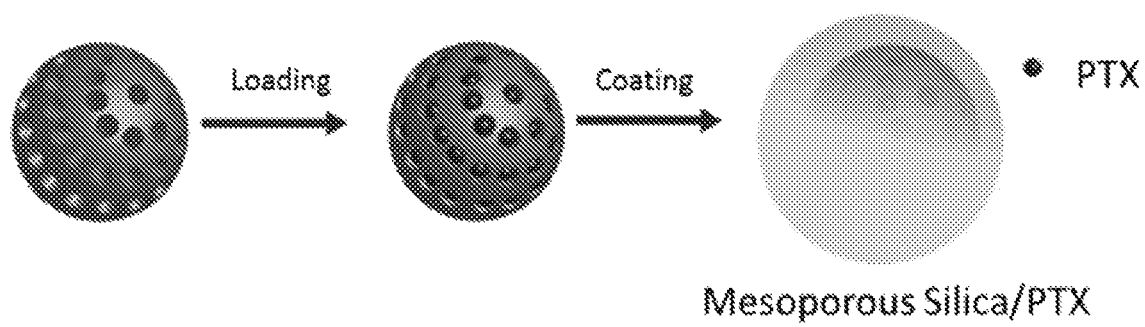
FIGS. 29A-29B. Drug loading approaches.
Figure 29B:
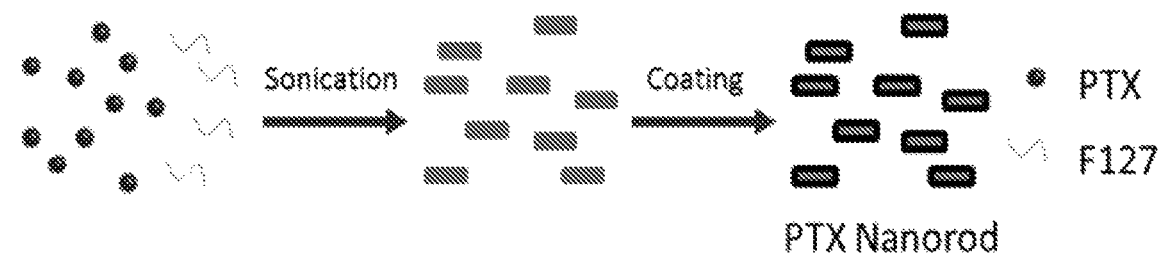

Example 5. Comparison of PTX-Nanorod Against Mesoporous Silica Nanoparticles (MSN) Loaded with PTX FIGS. 29A-29B show different drug loading approaches. In the FIG. 29A, loading of a mesoporous silica nanoparticle (MSN) with paclitaxel (PTX). FIG. 29B shows PTX nanorod formation. The PTX loading capacity by HPLC was calculated by weight of PTX (measured by HPLC) divided by total weight of the nanoparticle (measured by weighing lyophilized nanoparticle). The PTX loading capacity by TGA was calculated by net weight loss (PTX loaded particle final weight minus unloaded particle final weigh measured by TGA) divided by the total weight of PTX loaded nanoparticle (by TGA).

Figure 30A:
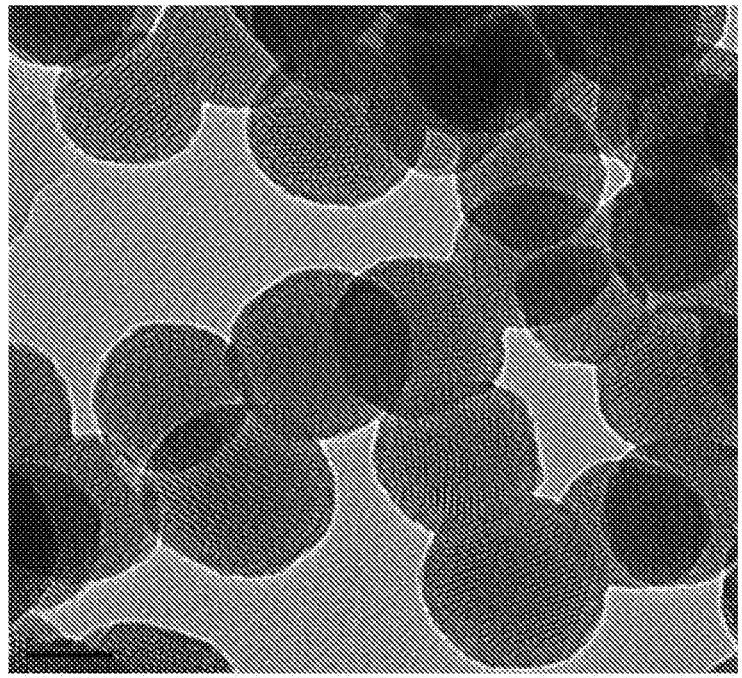
FIGS. 30A-30B. MSN characterization (FIG. 30A) before loading of PTX and (FIG. 30B) after loading of PTX and coating of MSN. Loading capacity of PTX from HLPC: 5.0%, from TGA: 5.3%. Size before loading: 90-110 nm, Zeta potential before loading: −34.27 mV. Size after loading and coating: 115-127 nm, Zeta potential after loading and coating: +38.19 mV.
Figure 30B:
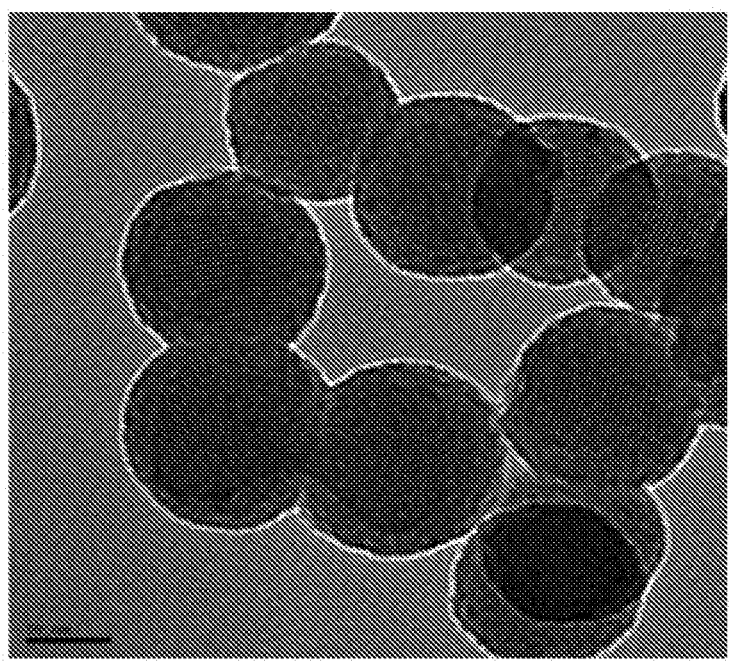
Figure 31:
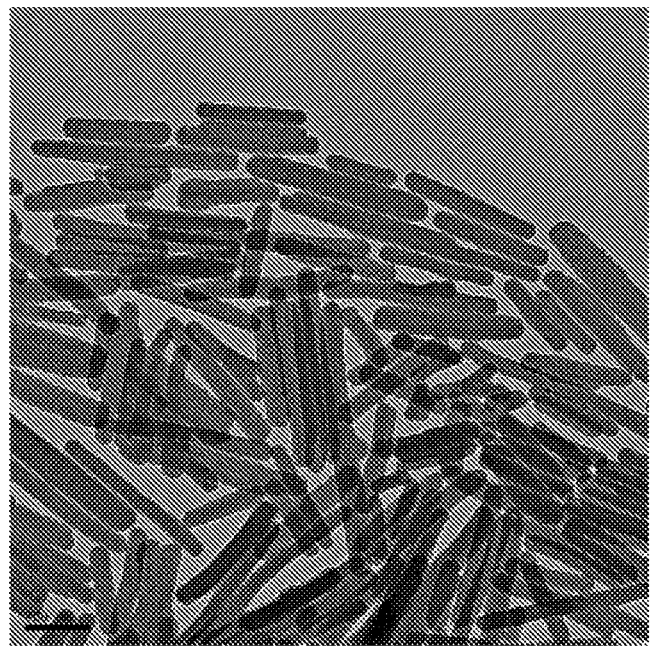
FIG. 31. Nanorod characterization. Images of nanorods at 2 different magnifications (top: 11000×; bottom: 26000×). Length: 397.1±107.1 nm, width: 70±8.2 nm, shell thickness: 36 nm, Zeta potential: +14.05 mV. Loading capacity of PTX from HPLC: 19.5%, from TGA: 21.3%
Figure 31:
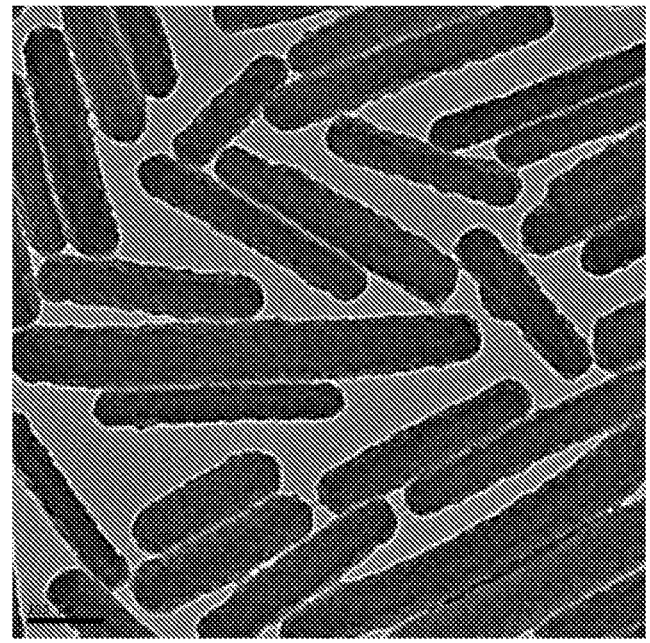

TEM images were obtained with an FEI Tecnai T12 transmission electron microscope at an accelerating voltage of 120 keV, and images were taken with a Gatan Ultrascan 2K CCD camera (FIGS. 30A-30B and FIG. 31). NPs dispersed in water at an optimal concentration were drop-cast onto glow-discharged, 300 mesh carbon—Formvar coated grids and allowed to dry before imaging. High-resolution TEM characterization was obtained with a JEOL JEM-2100F at an acceleration voltage of 200 kV equipped with Gatan Orius Camera. Size of nanoparticles were determined by measuring the length, width or diameters on the TEM imaging by image J with at least 20 particles in the view.

Dynamic light scattering (DLS) and (potential (ZP) measurements were performed on a Brookhaven 90 Plus/BI-MAS Instrument (Brookhaven Instruments). DLS measurements were obtained by performing 5 runs at 30 s per run, and the ZP values were obtained by measuring 10 runs involving 30 cycles per run (FIG. 31).

Figure 32A:
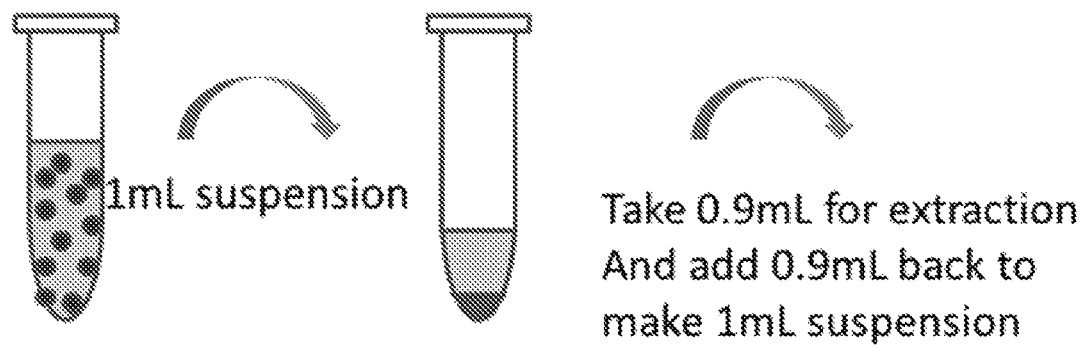
FIGS. 32A-32B. Release of PTX from nanorods and MSNs in DMEM with 10% FBS.
Figure 32A:
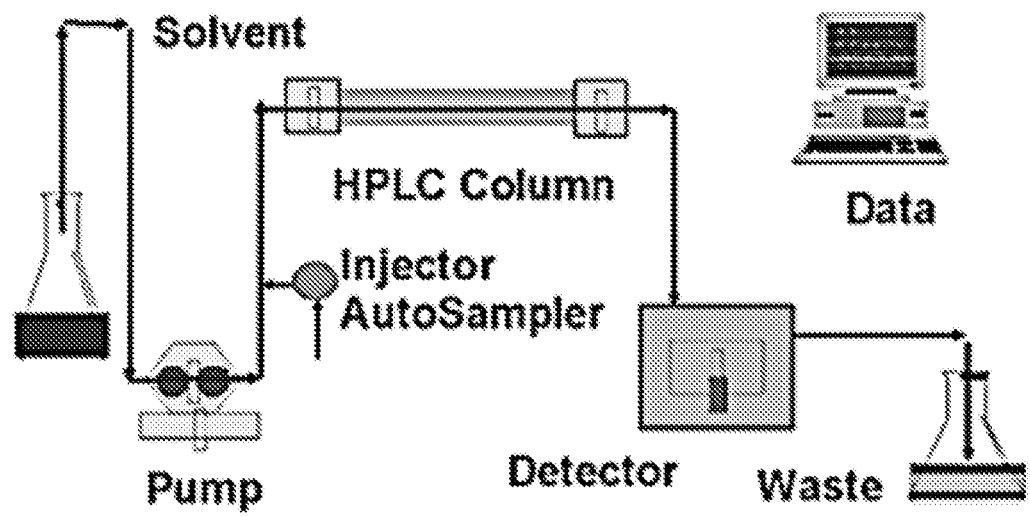
Figure 32B:
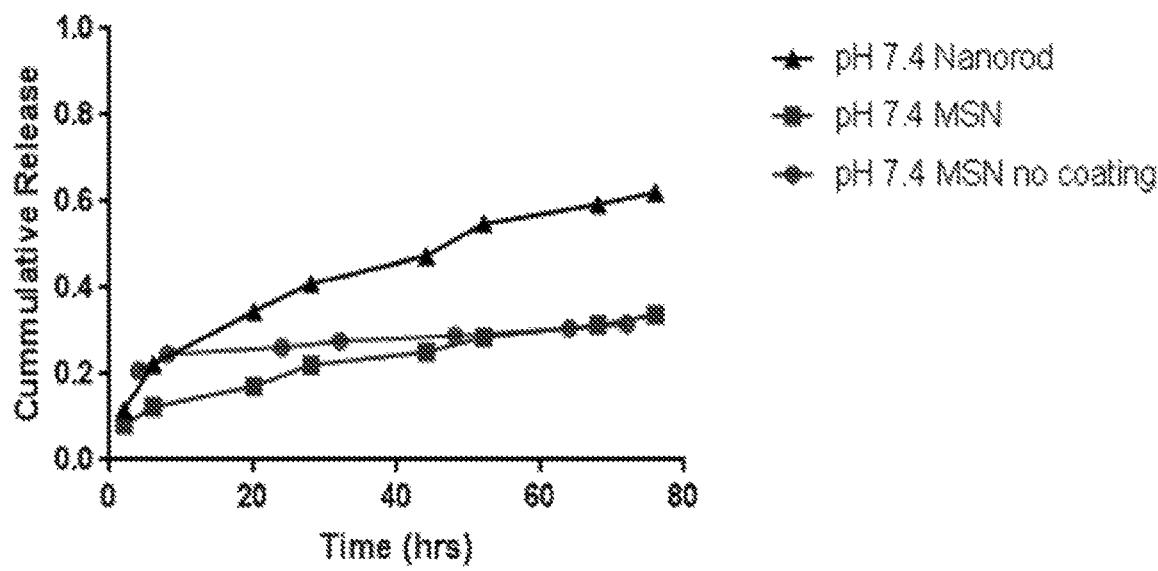
Figure 33A:
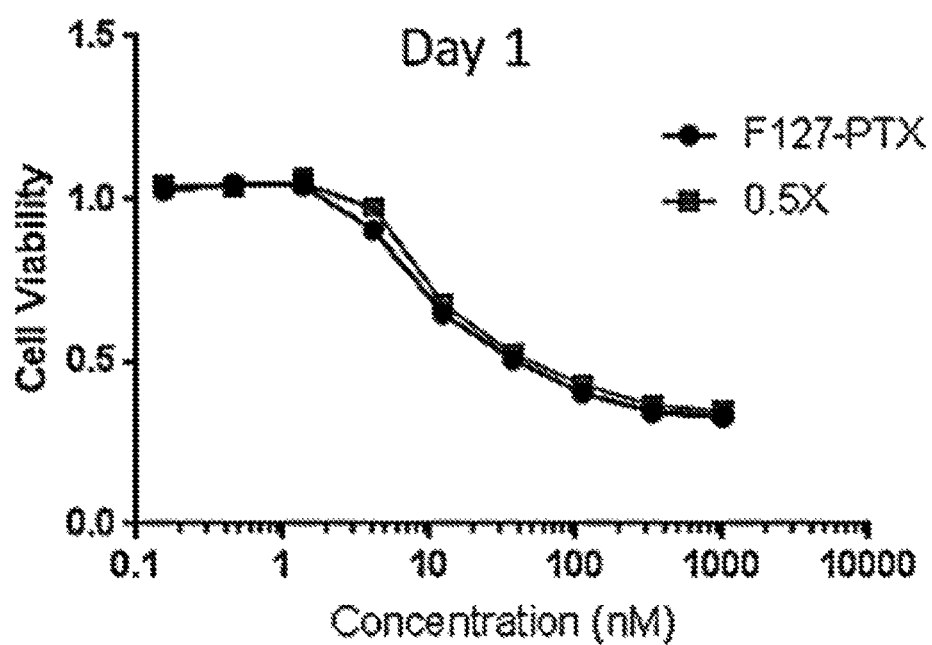
FIGS. 33A-33D. Ovcar-8 viability study.
Figure 33B:
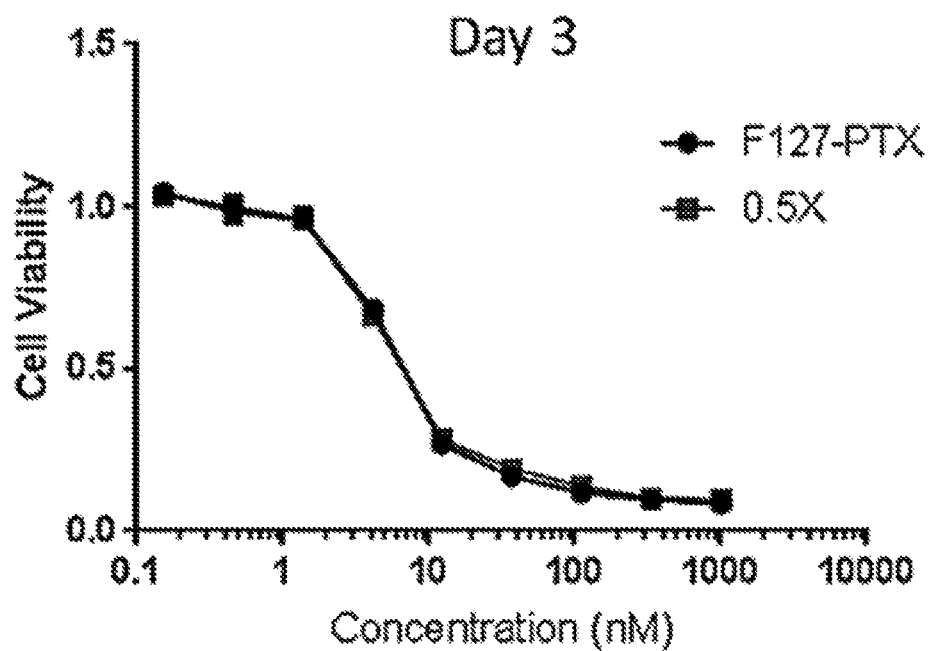
Figure 33C:
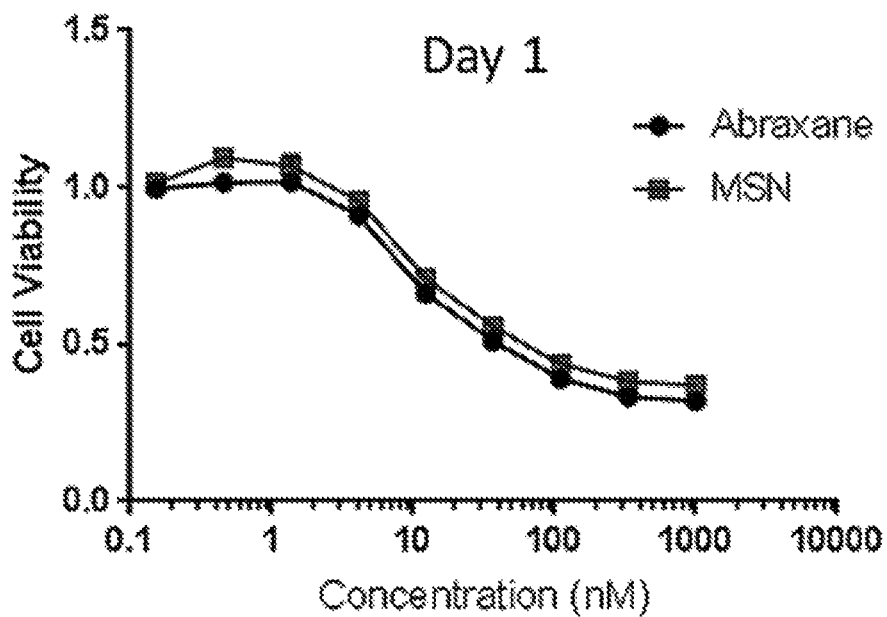
Figure 33D:
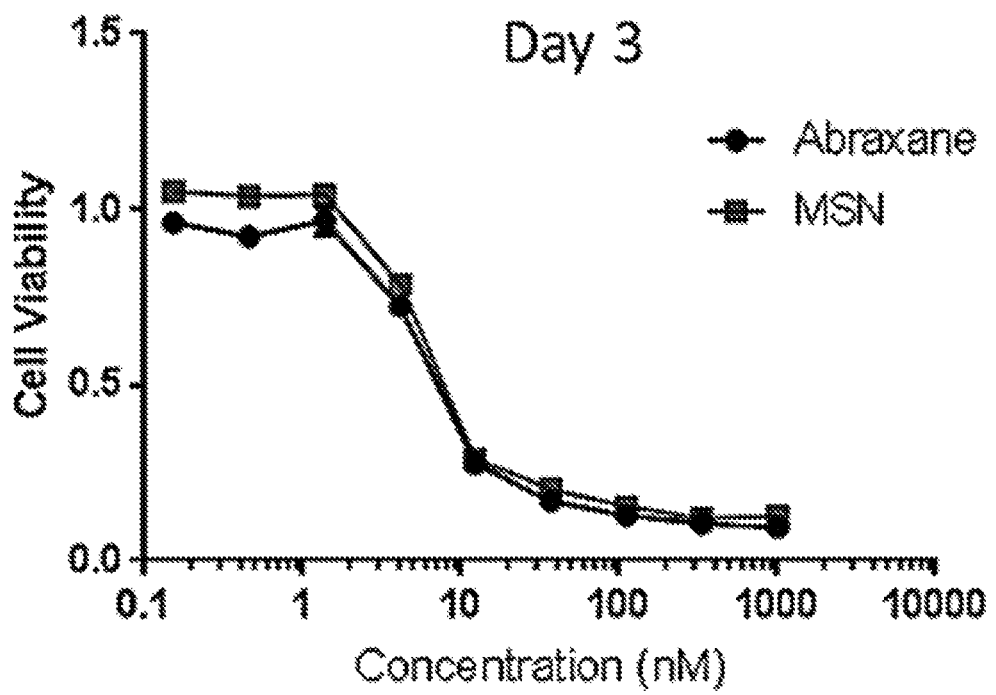

For PTX release study, PTX nanorods containing 40 µg PTX were suspended in 1 mL of DMEM cell culture medium with 10% fetal bovine serum (FBS). At different time point, the suspension was centrifuged at 10000 g and the supernatant was extracted by 1 mL of ethyl acetate. The extracts were dried under vacuum and dissolved in 100 µL acetonitrile for HPLC analysis. See FIGS. 32A-32B.

To determine OVCAR-8 cell viability, OVCAR-8 cells were seeded in 96-well plates (4000 cells/well, 100 µL medium). Cells were incubated at 37° C. for 16 hours before treatment as indicated. All dilutions of PTX-F127 nanocrystal and PTX nanorod were done in media. After treatment, cells were incubated for 24 and 72 hours. At each time point 20 µL of MTS solution (Promega) was added to each well and cell viability was measured by microplate reader at 490 nm absorbance wavelength after incubated at 37° C. for two hours (FIGS. 33A-33D).

Figure 34A:
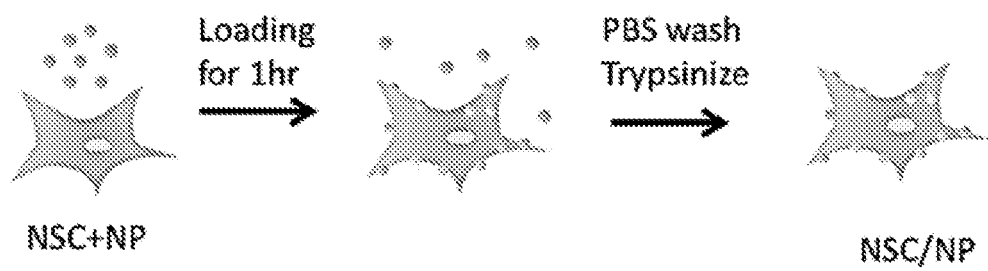
FIGS. 34A-34C.

For studies involving neural stem cell (NSC) drug loading, viability, and migration, NSC loading with PTX nanorod was achieved by incubating NSCs (500K cells/well in 6 well plate) for 1 h with a suspension of nanorods in PBS at 37° C. Any unloaded nanorods were removed by repetitive PBS washing for 3 times. The nanorod-loaded NSCs were then trypsinized and pelleted via centrifugation. Cell number was counted by hemocytometer under microscope. The cell pellet was further ruptured in hydrofluoric acid and neutralized by sodium bicarbonate and calcium chloride. Acetonitrile was added to ruptured cells and filtered by 0.4 µm syringe filter for HPLC analysis to determine PTX loading in NSCs (FIG. 34A, Table 3).

TABLE 3

PTX concentration with NSC, amount of loading per 1M cells, number of cells collected, and number of cells seeded for each drug formulation.

| | Nanorod | F127-PTX | MSN | Abraxane |
|---|---|---|---|---|
| PTX concentration with NSC (nM) | 28009 | 29224 | 30556 | 30315 |
| Loading µg/1M cells | 3.16 | 0.26 | 4.60 | 0 |
| Number of cells collected (K cells) | 465 | 670 | 400 | 450 |
| Number of cells seeded (K cells) | 500 | 500 | 500 | 500 |

Figure 34B:
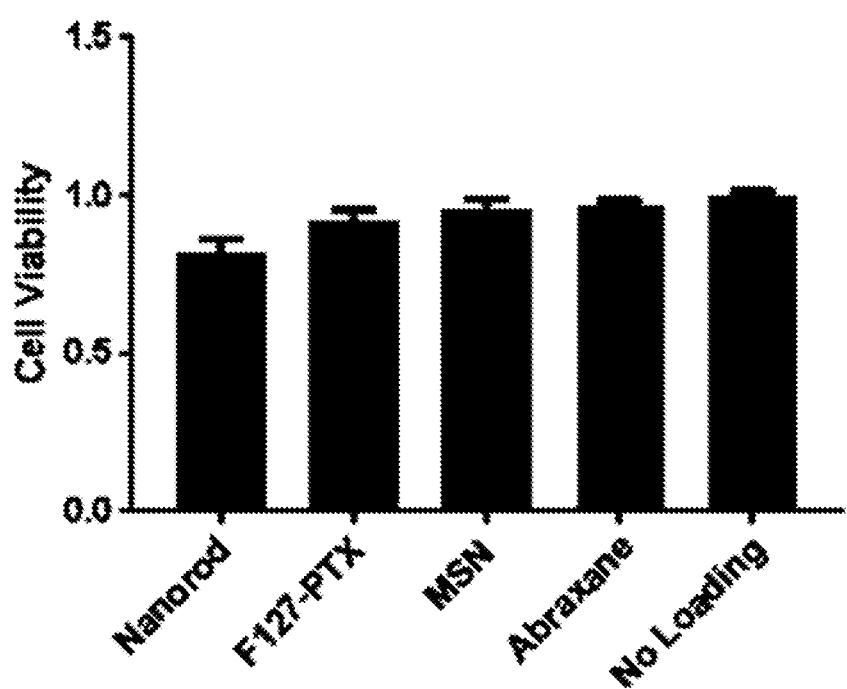

To determine NSC viability after loading, drug-loaded NSCs, including nanorod-loaded NSCs (4000 cells/well), were plated into 96-well plates and viability was measured after 24 hours by MTS assay (FIG. 34B).

Figure 34C:
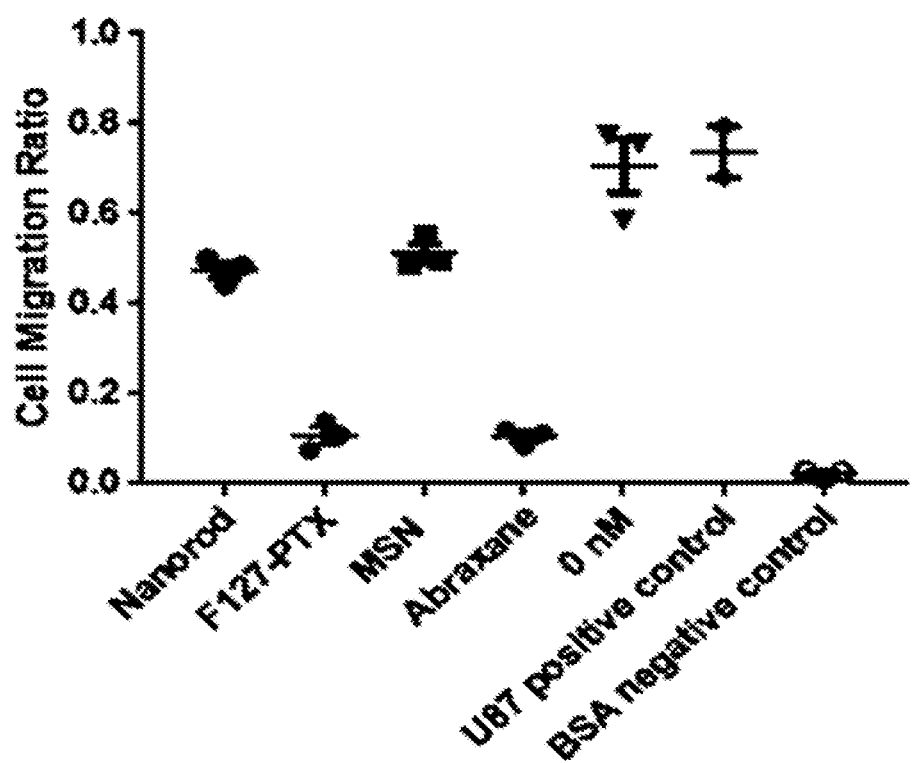

NSCs migration capability was measured by in vitro transwell Boyden chamber assay. NSCs were incubated with PTX nanorod, PTX-F127 nanocrystal and Abraxane at PTX concentration of 25 µg/mL in PBS for 1 hour. In a 24-well tissue culture plate 500 µL of target media (either containing only BSA as a negative control, or derived from the culture of SKOV-3 cells) was added to each well. At a density of 1×10$^5$ cells/well, PTX loaded NSCs in DMEM and 5% w/v BSA were placed in the transwell chambers and incubated at 37° C. for 4 hours. After the incubation period, the transwell chambers were placed in a new 24-well tissue culture plate containing accutase and incubated 10 mins at 37° C. Detached cells were then transferred to a 96 well v-bottom plate, centrifuged at 1,500 rpm for 5 mins, and resuspended in 1:1 media to ViaCount. NSC migration to conditioned media of PTX treated and nontreated cells was assessed using Guava EasyCyte technology. U87 tumor condition medium was also used as a positive control (FIG. 34C).

Figure 35A:
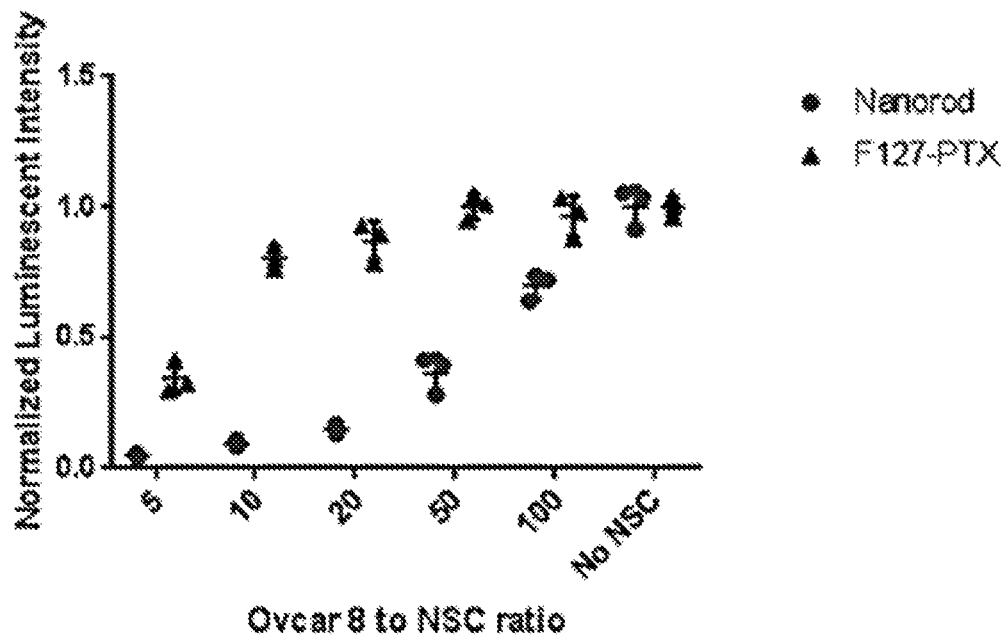
FIGS. 35A-35B. Results of Ovcar-8/NSC co-culture for 3 days.
Figure 35B:
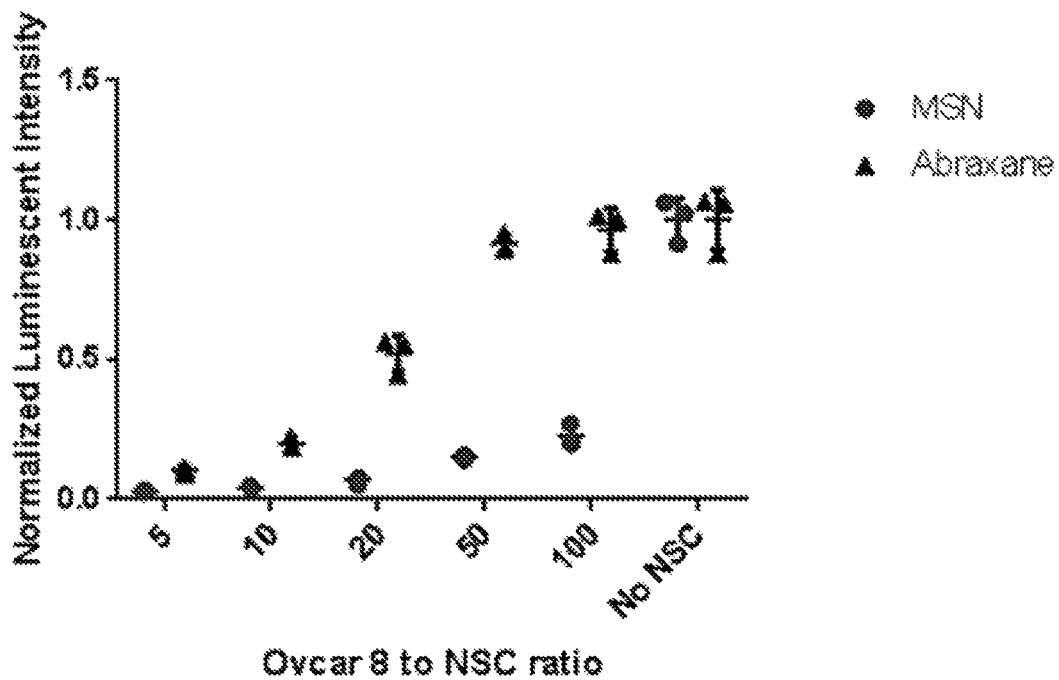
Figure 36:
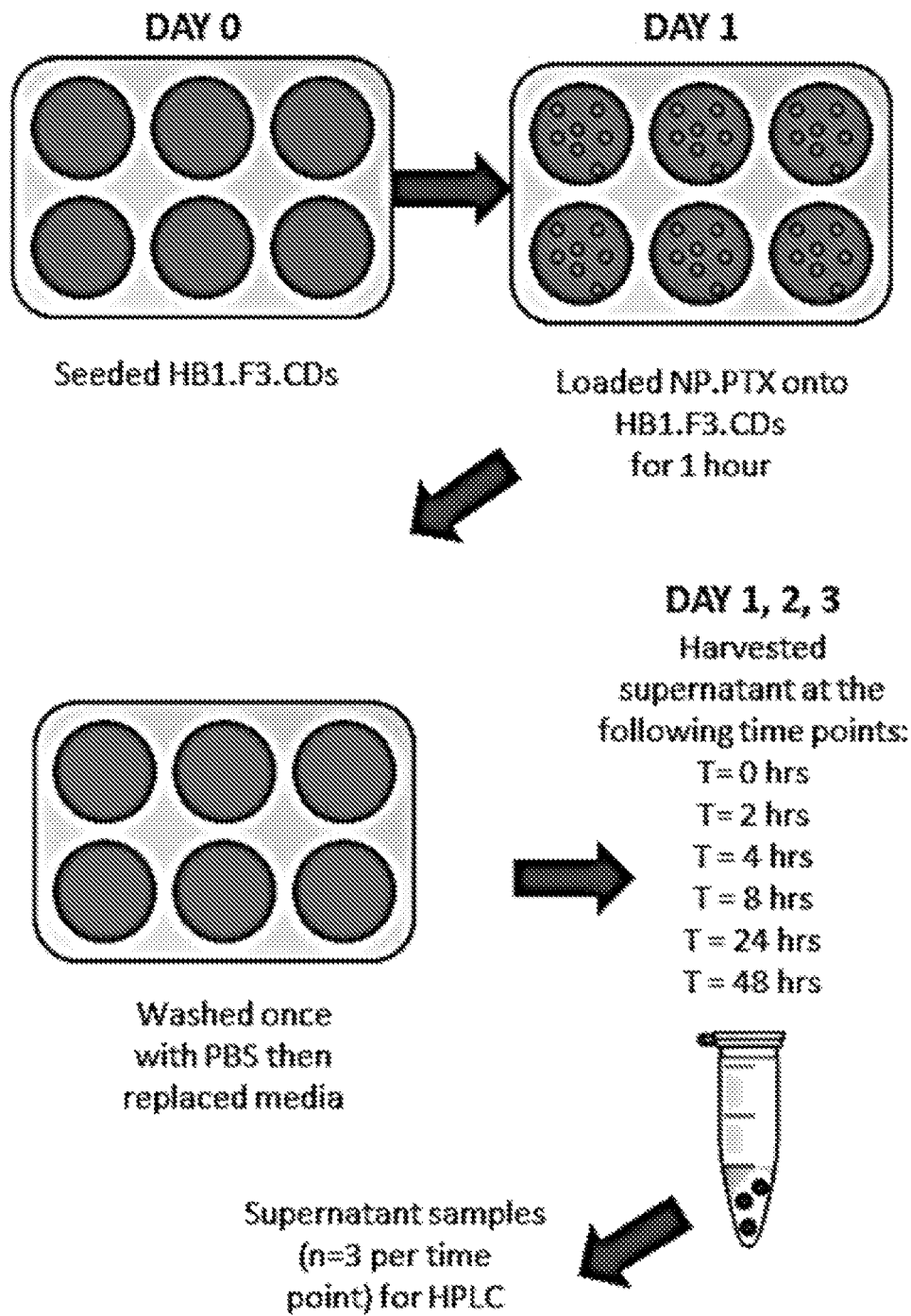
FIG. 36. Experimental design for testing nanoparticle PTX release profiles in cells.
Figure 37A:
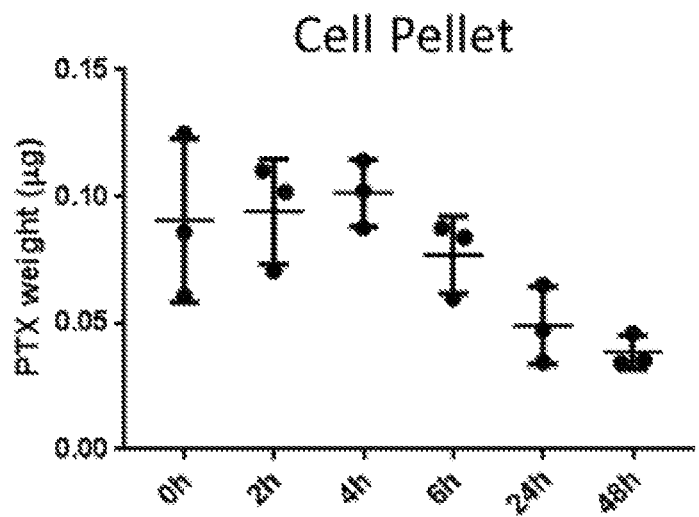
FIGS. 37A-37D. PTX release from Neural stem cells (NSC) including PTX nanorods (NSC.NP (Nanorod)).
Figure 37B:
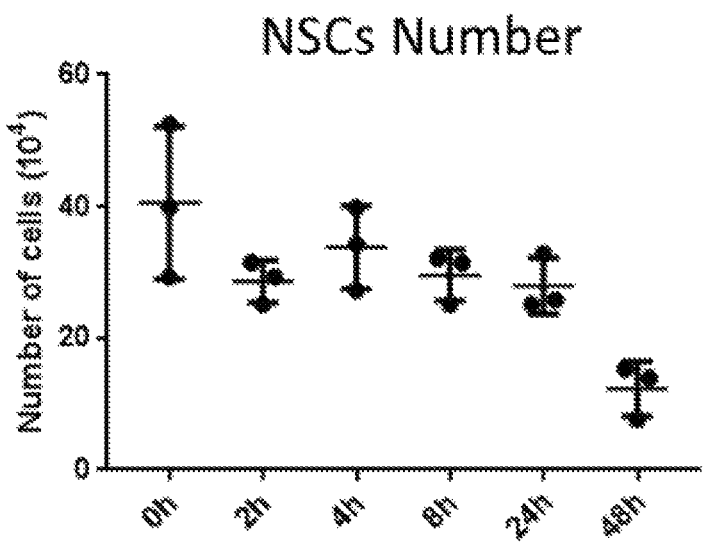
Figure 37C:
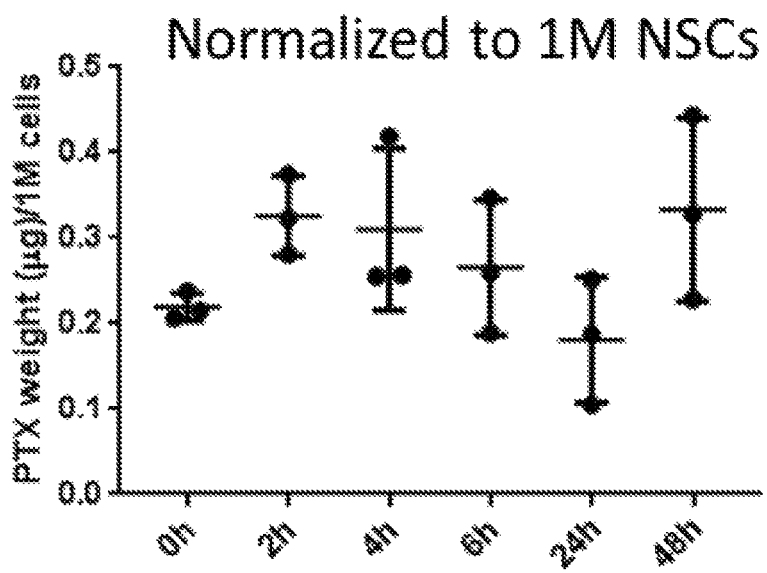
Figure 37D:
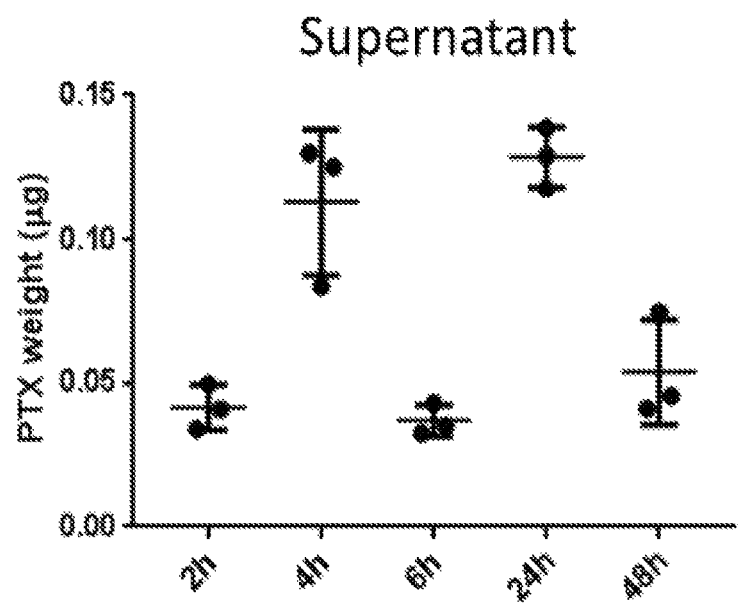
Figure 38A:
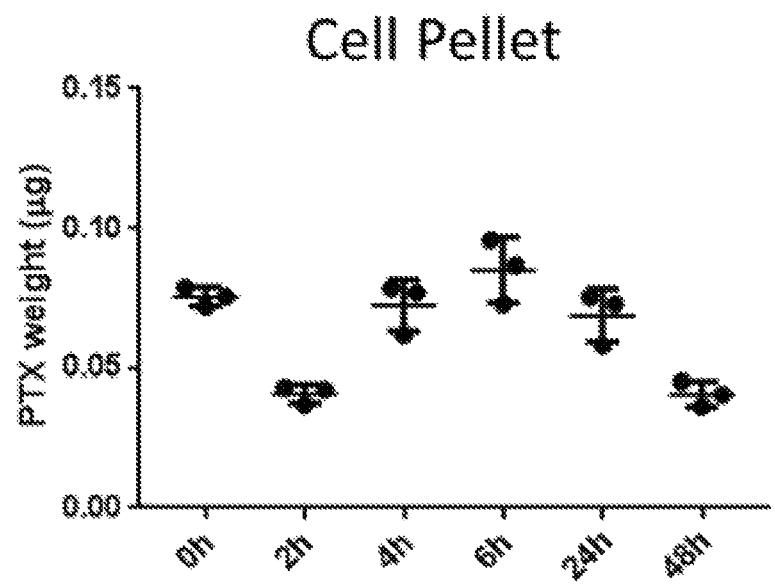
FIG. 38A-38D. PTX release from Neural stem cells (NSC) including PTX loaded mesoporous silica nanoparticles (MSN).
Figure 38B:
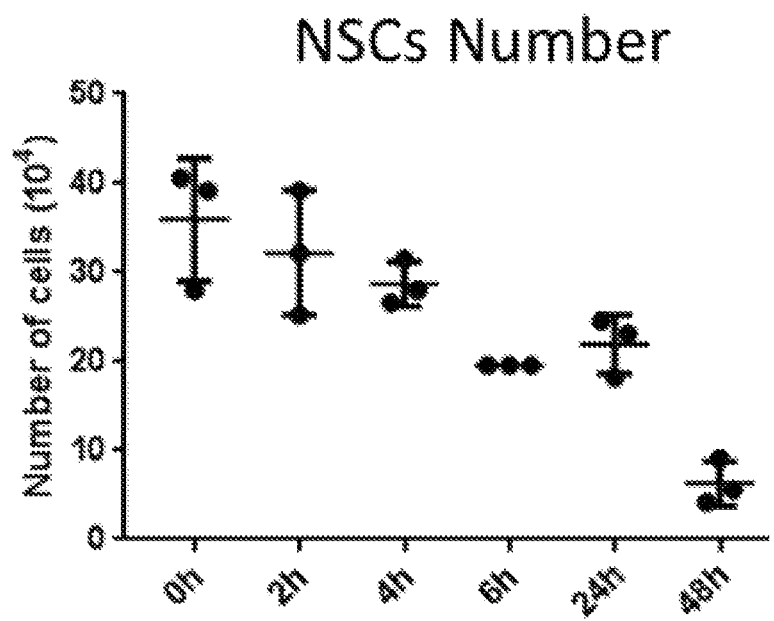
Figure 38C:
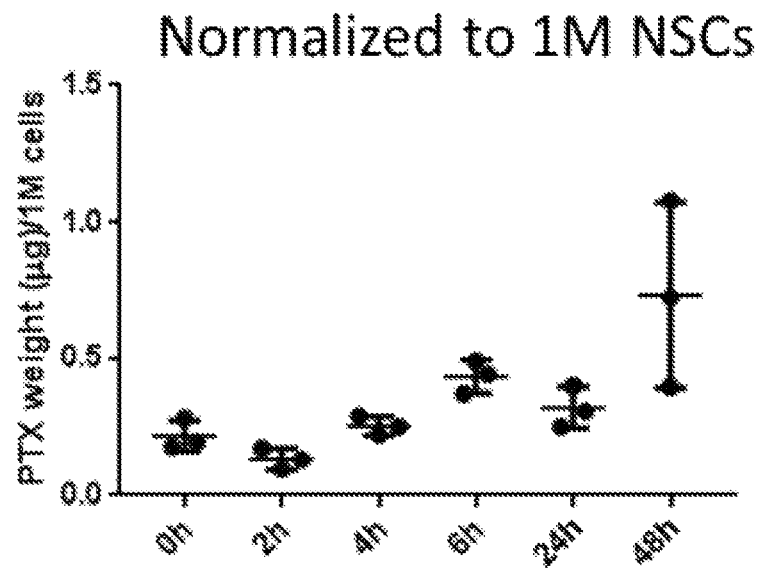
Figure 38D:
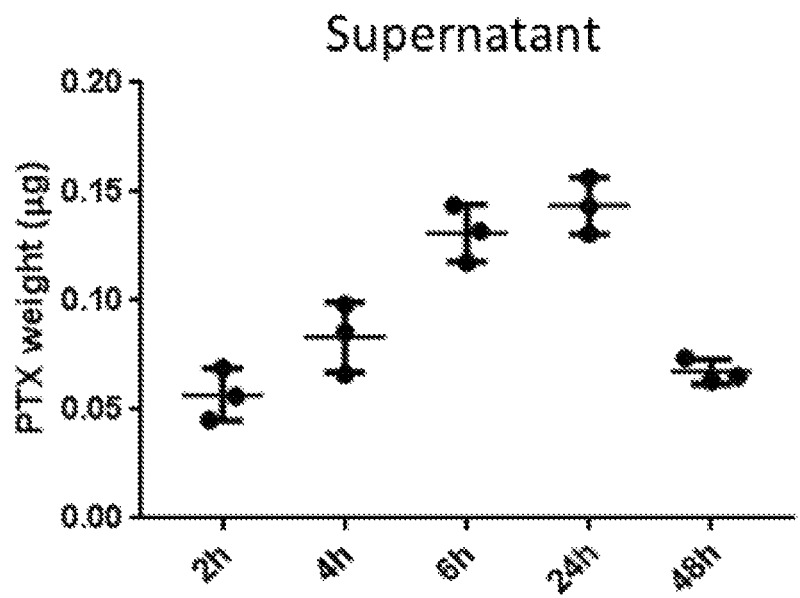

OVCAR-8 cells were seeded in 96-well plates (4000 cells/well). Cells were incubated at 37° C. for 16 hours before treatment. NSCs were loaded with PTX nanorod, PTX-F127 nanocrystal and Abraxane as previously described. After 1 hour incubation period, NSCs were repetitively washed 3 times by PBS to remove unloaded PTX nanorod, PTX-F127 nanocrystal or Abraxane and were detached with trypsinEDTA. PTX loaded NSCs were transferred to the wells containing OVCAR-8 cells at ratios of 1:5, 1:10, 1:20, 1:50, and 1:100 by using serial dilutions. Each condition and ratio was done in triplicates. Cells were co-cultured for 72 hours and then OVCAR-8 viability was determined by adding 10 µL D-luciferin solution (3 mg/mL) to each well and measuring luciferase luminescent intensity by microplate reader (FIGS. 35A-35B).

To measure PTX released from nanorod-loaded NSCs and MSN loaded NSCs, both cell pellets and supernatant were collected after cell loading with PTX nanorods or MSNs at different time point (FIGS. 36, 37A-37D, and 38A-38D). HPLC was used to measure the PTX in the cell pellet and supernatant as described above.

Figure 40:
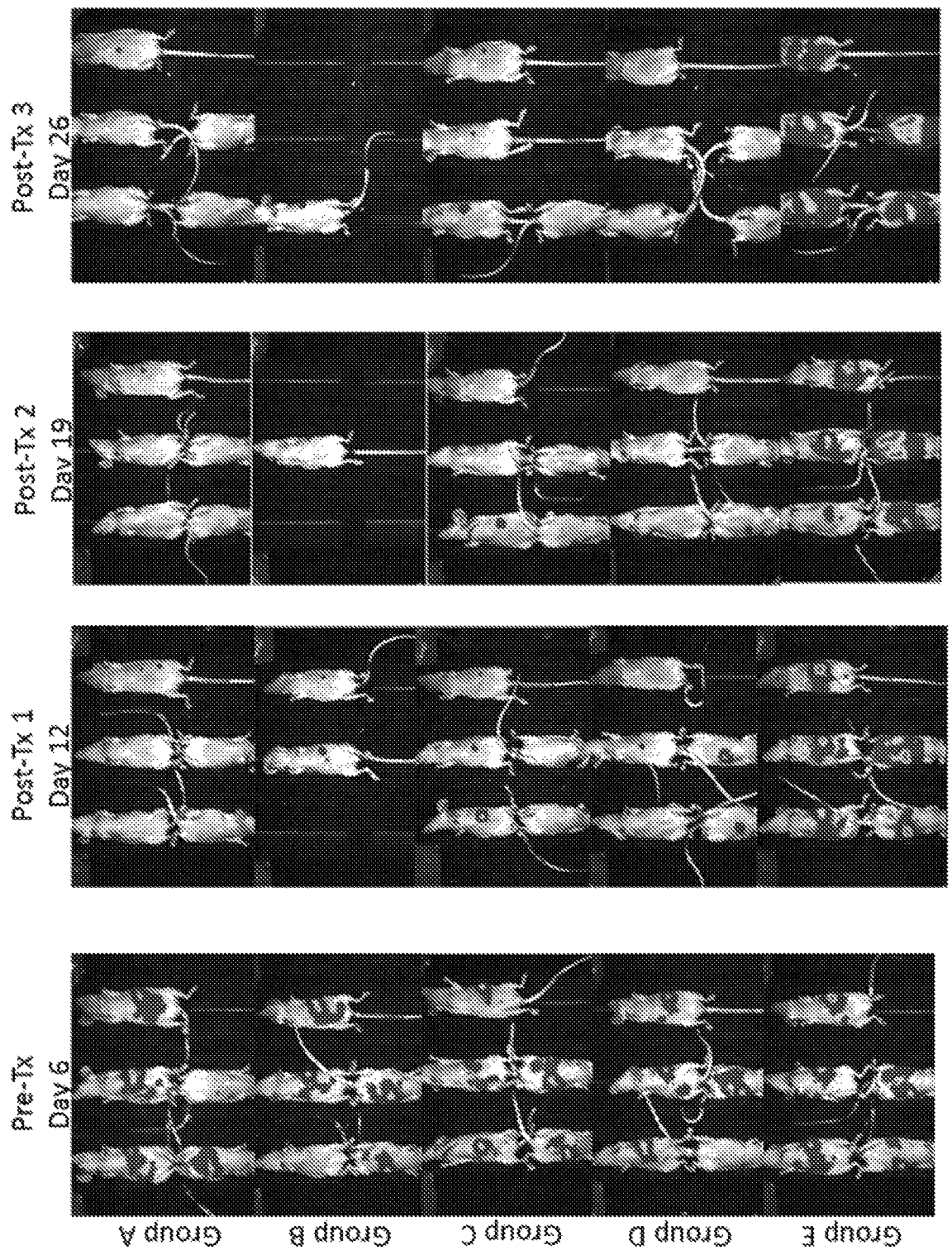
FIG. 40. Amix imaging of tumor implant across days following treatment specific to each group.
Figure 41:
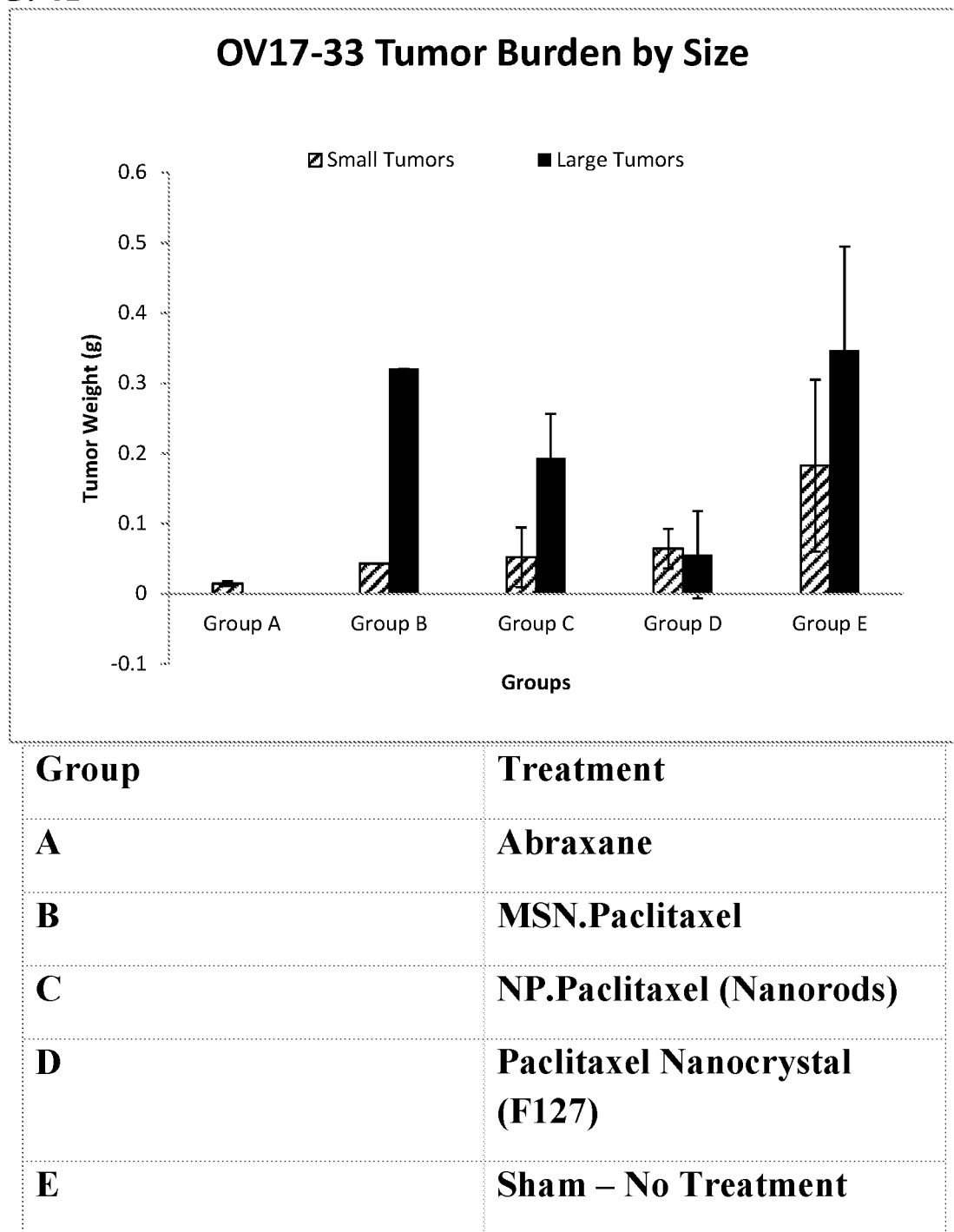
FIG. 41. Tumor burden analysis following treatment as described per Group.
Figure 42:
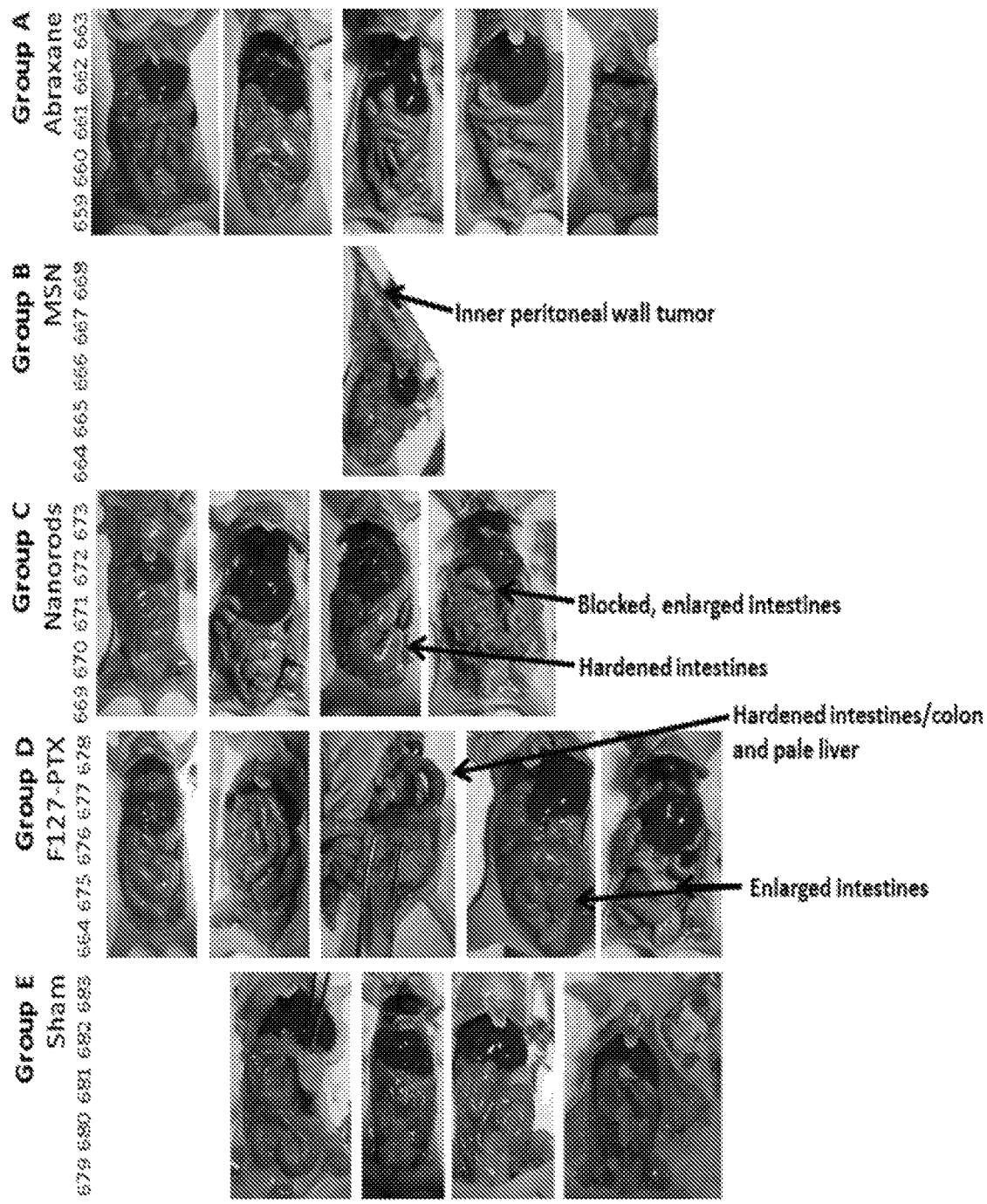
FIG. 42. Necroscopy observations of tumor burden following treatment. Group A showed tiny microscopic tumors (if any), most were small and free floating (easy to remove). Group B showed numerous tumors in lower fat, inner peritoneal wall, stomach and liver. Pale/discolored kidneys. Group C showed large and small tumors, on omentum, intestines, mesentery. Yellow tumors (#669) Blocked, enlarged (#670 & 671), hardened intestines (#672). Group D showed large and small tumors, on liver, hardened intestines/colon and pale liver (#676). Enlarged intestines (#677 & 678). Group E showed large and small tumors, all throughout the peritoneum, stomach/pancreas tumors, lower fat, etc.

To assess efficacy in vivo, 2 M OVCAR-8 cells were intraperitoneally injected into Nude mice on day 0. The tumor was allowed to grow for 7 days and mice were ip injected at 40 mg/kg in terms of PTX according to the indicated group twice a week for a total of 3 weeks (day 8, 12, 15, 17, 21, 24 injections). Mice were sacrificed on day 28 and all the tumors were collected and weighed. Amix imaging was taken by measuring luciferase signals from mice after ip injection of D-Luciferin 10 min before imaging on day 6, 12, 19, and 26. Treatment results can be seen in FIG. 40. Four mice of Group B (MSN) died during treatment and one mouse of Group C (PTX nanorod) died during treatment. Further assessment and results of treatment can be seen in FIGS. 41 and 42.

REFERENCES

References for Examples 1-3

(1) Lengyel, E. *The American Journal of Pathology* 2010, 177, 1053.
(2) Group, U. S. C. S. W.; Atlanta: U.S. Department of Health and Human Services, C. f. D. C. a. P. a. N. C. I., Ed. 2016.
(3) Webber, K.; Friedlander, M. *Best Practice& Research Clinical Obstetrics & Gynaecology*.
(4) Bookman, M. A. *Annals of Oncology* 2016, 27, i58.
(5) Spencer, C. M.; Faulds, D. *Drugs* 1994, 48, 794.
(6) Yardley, D. A. *Journal of controlled release: official journal of the Controlled Release Society* 2013, 170, 365.
(7) Singla, A. K.; Garg, A.; Aggarwal, D. *International Journal of Pharmaceutics* 2002, 235, 179.
(8) Ma, P.; Mumper, R. J. *Journal of nanomedicine & nanotechnology* 2013, 4, 1000164.
(9) Merlot, A. M.; Kalinowski, D. S.; Richardson, D. R. *Frontiers in Physiology* 2014, 5, 299.
(10) Nehate, C.; Jain, S.; Saneja, A.; Khare, V.; Alam, N.; Dubey, R. D.; Gupta, P. N. *Current drug delivery* 2014, 11, 666.
(11) Surapaneni, M. S.; Das, S. K.; Das, N. G. *ISRN pharmacology* 2012, 2012, 623139.
(12) Yamamoto, Y.; Kawano, I.; Iwase, H. *OncoTargets and therapy* 2011, 4, 123.
(13) Maeda, H. *Advances in enzyme regulation* 2001, 41, 189.
(14) Steichen, S. D.; Caldorera-Moore, M.; Peppas, N. A. *European journal of pharmaceutical sciences: official journal of the European Federation for Pharmaceutical Sciences* 2013, 48, 416.
(15) Jones, A.; Harris, A. L. *The cancer journal from Scientific American* 1998, 4, 209.
(16) Haley, B.; Frenkel, E. *Urologic oncology* 2008, 26, 57.
(17) Brannon-Peppas, L.; Blanchette, J. O. *Advanced drug delivery reviews* 2004, 56, 1649.
(18) Prabhakar, U.; Maeda, H.; Jain, R. K.; Sevick-Muraca, E. M.; Zamboni, W.; Farokhzad, O. C.; Barry, S. T.; Gabizon, A.; Grodzinski, P.; Blakey, D. C. *Cancer research* 2013, 73, 2412.
(19) Matsumura, Y.; Maeda, H. *Cancer research* 1986, 46, 6387.
(20) Akbarzadeh, A.; Rezaei-Sadabady, R.; Davaran, S.; Joo, S. W.; Zarghami, N.; Hanifehpour, Y.; Samiei, M.; Kouhi, M.; Nejati-Koshki, K. *Nanoscale Research Letters* 2013, 8, 102.
(21) Lasic, D. D. *Trends in biotechnology* 1998, 16, 307.
(22) Kedar, U.; Phutane, P.; Shidhaye, S.; Kadam, V. *Nanomedicine: Nanotechnology, Biology and Medicine* 2010, 6, 714.
(23) Liechty, W. B.; Peppas, N. A. *European journal of pharmaceutics and biopharmaceutics: official journal of Arbeitsgemeinschaft fur Pharmazeutische Verfahrenstechnik e.V* 2012, 80, 241.
(24) Oerlemans, C.; Bult, W.; Bos, M.; Storm, G.; Nijsen, J. F. W.; Hennink, W. E. *Pharmaceutical Research* 2010, 27, 2569.
(25) Anselmo, A. C.; Mitragotri, S. *Bioengineering & Translational Medicine* 2016, 1, 10.
(26) Lee, K. S.; Chung, H. C.; Im, S. A.; Park, Y. H.; Kim, C. S.; Kim, S. B.; Rha, S. Y.; Lee, M. Y.; Ro, J. *Breast cancer research and treatment* 2008, 108, 241.
(27) Kamaly, N.; Yameen, B.; Wu, J.; Farokhzad, O. C. *Chemical reviews* 2016, 116, 2602.
(28) Danhier, F.; Ansorena, E.; Silva, J. M.; Coco, R.; Le Breton, A.; Preat, V. *Journal of Controlled Release* 2012, 161, 505.
(29) Makadia, H. K.; Siegel, S. J. *Polymers* 2011, 3, 1377.
(30) Bobo, D.; Robinson, K. J.; Islam, J.; Thurecht, K. J.; Corrie, S. R. *Pharm Res* 2016, 33, 2373.
(31) Liberman, A.; Mendez, N.; Trogler, W. C.; Kummel, A. C. *Surface science reports* 2014, 69, 132.
(32) Tang, L.; Cheng, J. *Nano today* 2013, 8, 290.
(33) Tang, F.; Li, L.; Chen, D. *Advanced Materials* 2012, 24, 1504.
(34) Ehlerding, E. B.; Chen, F.; Cai, W. *Advanced Science* 2016, 3, 1500223.
(35) Lu, Y.; Chen, Y.; Gemeinhart, R. A.; Wu, W.; Li, T. *Nanomedicine (London, England)* 2015, 10, 2537.
(36) Kim, S. C.; Kim, D. W.; Shim, Y. H.; Bang, J. S.; Oh, H. S.; Wan Kim, S.; Seo, M. H. *Journal of controlled release: official journal of the Controlled Release Society* 2001, 72, 191.
(37) Kim, T.-Y.; Kim, D.-W.; Chung, J.-Y.; Shin, S. G.; Kim, S.-C.; Heo, D. S.; Kim, N. K.; Bang, Y.-J. *Clinical Cancer Research* 2004, 10, 3708.
(38) Deng, J.; Huang, L.; Liu, F. *Int J Pharm* 2010, 390, 242.
(39) Li, Y.; Wu, Z.; He, W.; Qin, C.; Yao, J.; Zhou, J.; Yin, L. *Molecular pharmaceutics* 2015, 12, 1485.
(40) Huang, B.; Abraham, W. D.; Zheng, Y.; Bustamante López, S. C.; Luo, S. S.; Irvine, D. J. *Science Translational Medicine* 2015, 7, 291ra94.
(41) Stephan, M. T.; Moon, J. J.; Um, S. H.; Bershteyn, A.; Irvine, D. J. *Nature medicine* 2010, 16, 1035.

(42) Choi, M.-R.; Stanton-Maxey, K. J.; Stanley, J. K.; Levin, C. S.; Bardhan, R.; Akin, D.; Badve, S.; Sturgis, J.; Robinson, J. P.; Bashir, R.; Halas, N. J.; Clare, S. E. *Nano Letters* 2007, 7, 3759.

(43) Li, L.; Guan, Y.; Liu, H.; Hao, N.; Liu, T.; Meng, X.; Fu, C.; Li, Y.; Qu, Q.; Zhang, Y.; Ji, S.; Chen, L.; Chen, D.; Tang, F. *ACS nano* 2011, 5, 7462.

(44) Mooney, R.; Weng, Y.; Garcia, E.; Bhojane, S.; Smith-Powell, L.; Kim, S. U.; Annala, A. J.; Aboody, K. S.; Berlin, J. M. *Journal of Controlled Release* 2014, 191, 82.

(45) Cheng, Y.; Morshed, R.; Cheng, S.-H.; Tobias, A.; Auffinger, B.; Wainwright, D. A.; Zhang, L.; Yunis, C.; Han, Y.; Chen, C.-T.; Lo, L.-W.; Aboody, K. S.; Ahmed, A. U.; Lesniak, M. S. *Small (Weinheim an der Bergstrasse, Germany)* 2013, 9, 4123.

(46) Liu, X.; Wu, F.; Tian, Y.; Wu, M.; Zhou, Q.; Jiang, S.; Niu, Z. *Scientific Reports* 2016, 6, 24567.

(47) Alakhova, D. Y.; Kabanov, A. V. *Molecular pharmaceutics* 2014, 11, 2566.

References for Example 4

(1) Stewart, S. L., Harewood, R., Matz, M., Rim, S. H., Sabatino, S. A., Ward, K. C., and Weir, H. K. (2017) Disparities in ovarian cancer survival in the United States (2001-2009): Findings from the CONCORD-2 study. *Cancer* 123 Suppl 24, 5138-5159.

(2) Lengyel, E. (2010) Ovarian cancer development and metastasis. *Am J Pathol* 177, 1053-1064.

(3) Vergote, I., Trope, C. G., Amant, F., Kristensen, G. B., Ehlen, T., Johnson, N., Verheijen, R. H. M., van der Burg, M. E. L., Lacave, A. J., Panici, P. B., Kenter, G. G., Casado, A., Mendiola, C., Coens, C., Verleye, L., Stuart, G. C. E., Pecorelli, S., Reed, N. S., European Organization for Research and Treatment of Cancer-Gynaecological Cancer Group, and NCIC Clinical Trials Group. (2010) Neoadjuvant chemotherapy or primary surgery in stage IIIC or IV ovarian cancer. *N Engl J Med* 363, 943-953.

(4) Ko, S. Y., and Naora, H. (2014) Therapeutic strategies for targeting the ovarian tumor stroma. *World J Clin Cases* 2, 194-200.

(5) Stoeckle, E., Bourdarias, L., Guyon, F., Croce, S., Brouste, V., Thomas, L., and Floquet, A. (2014) Progress in survival outcomes in patients with advanced ovarian cancer treated by neo-adjuvant platinum/taxane-based chemotherapy and late interval debulking surgery. *Ann Surg Oncol* 21, 629-636.

(6) Cao, P., Mooney, R., Tirughana, R., Abidi, W., Aramburo, S., Flores, L., Gilchrist, M., Nwokafor, U., Haber, T., Tiet, P., Annala, A. J., Han, E., Dellinger, T., Aboody, K. S., and Berlin, J. M. (2017) Intraperitoneal Administration of Neural Stem Cell-Nanoparticle Conjugates Targets Chemotherapy to Ovarian Tumors. *Bioconjug Chem* 28, 1767-1776.

(7) Deng, J., Huang, L., and Liu, F. (2010) Understanding the structure and stability of paclitaxel nanocrystals. *Int J Pharm* 390, 242-249.

(8) Surapaneni, M. S., Das, S. K., and Das, N. G. (2012) Designing Paclitaxel drug delivery systems aimed at improved patient outcomes: current status and challenges. *ISRN Pharmacol* 2012, 623139.

(9) Ma, P., and Mumper, R. J. (2013) Paclitaxel Nano-Delivery Systems: A Comprehensive Review. *J Nanomed Nanotechnol* 4, 1000164.

(10) Yardley, D. A. (2013) nab-Paclitaxel mechanisms of action and delivery. *J Control Release* 170, 365-372.

(11) Nyman, D. W., Campbell, K. J., Hersh, E., Long, K., Richardson, K., Trieu, V., Desai, N., Hawkins, M. J., and Von Hoff, D. D. (2005) Phase I and pharmacokinetics trial of ABI-007, a novel nanoparticle formulation of paclitaxel in patients with advanced nonhematologic malignancies. *J Clin Oncol* 23, 7785-7793.

(12) Hennenfent, K. L., and Govindan, R. (2006) Novel formulations of taxanes: a review. Old wine in a new bottle? *Ann Oncol* 17, 735-749.

(13) Vishnu, P., and Roy, V. (2011) Safety and Efficacy of nab-Paclitaxel in the Treatment of Patients with Breast Cancer. *Breast Cancer (Auckl)* 5, 53-65.

(14) FDA Approval for Paclitaxel Albumin-stabilized Nanoparticle Formulation-National Cancer Institute.

(15) Kundranda, M. N., and Niu, J. (2015) Albumin-bound paclitaxel in solid tumors: clinical development and future directions. *Drug Des Devel Ther* 9, 3767-3777.

(16) Nichols, J. W., and Bae, Y. H. (2014) EPR: Evidence and fallacy. *J Control Release* 190, 451-464.

(17) Bi, Y., Hao, F., Yan, G., Teng, L., Lee, R. J., and Xie, J. (2016) Actively targeted nanoparticles for drug delivery to tumor. *Curr Drug Metab* 17, 763-782.

(18) Tiet, P., and Berlin, J. M. (2017) Exploiting homing abilities of cell carriers: Targeted delivery of nanoparticles for cancer therapy. *Biochem Pharmacol* 145, 18-26.

(19) Zhao, D., Najbauer, J., Annala, A. J., Garcia, E., Metz, M. Z., Gutova, M., Polewski, M. D., Gilchrist, M., Glackin, C. A., Kim, S. U., and Aboody, K. S. (2012) Human neural stem cell tropism to metastatic breast cancer. *Stem Cells* 30, 314-325.

(20) Aboody, K. S., Najbauer, J., and Danks, M. K. (2008) Stem and progenitor cell-mediated tumor selective gene therapy. *Gene Ther* 15, 739-752.

(21) Aboody, K. S., Najbauer, J., Metz, M. Z., D'Apuzzo, M., Gutova, M., Annala, A. J., Synold, T. W., Couture, L. A., Blanchard, S., Moats, R. A., Garcia, E., Aramburo, S., Valenzuela, V. V., Frank, R. T., Barish, M. E., Brown, C. E., Kim, S. U., Badie, B., and Portnow, J. (2013) Neural stem cell-mediated enzyme/prodrug therapy for glioma: preclinical studies. *Sci Transl Med* 5, 184ra59.

(22) Zhao, D., Najbauer, J., Garcia, E., Metz, M. Z., Gutova, M., Glackin, C. A., Kim, S. U., and Aboody, K. S. (2008) Neural stem cell tropism to glioma: critical role of tumor hypoxia. *Mol Cancer Res* 6, 1819-1829.

(23) Liu, F., Park, J.-Y., Zhang, Y., Conwell, C., Liu, Y., Bathula, S. R., and Huang, L. (2010) Targeted cancer therapy with novel high drug-loading nanocrystals. *J Pharm Sci* 99, 3542-3551.

(24) Liu, Y., Huang, L., and Liu, F. (2010) Paclitaxel nanocrystals for overcoming multidrug resistance in cancer. *Mol Pharm* 7, 863-869.

Additional Embodiments

The meaning of the defined terms in this Additional Embodiments section below will supersede the meaning of the identical defined terms in the definitions section above only for this Additional Embodiments section. For the avoidance of doubt, the meaning of the defined terms in the Definition section above will apply to all other sections of the present application. For the avoidance of doubt, any defined terms in the Definitions section above that do not have an alternative meaning in the present Additional Embodiments section below, will apply to the embodiments in the present Additional Embodiments section.

The term "alkyl," by itself or as part of another substituent, means, unless otherwise stated, a straight (i.e., unbranched) or branched non-cyclic carbon chain (or carbon), or combination thereof, which may be fully saturated, mono- or polyunsaturated and can include di- and multivalent radicals, having the number of carbon atoms designated (i.e., $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched non-cyclic chain, or combinations thereof, including at least one carbon atom and at least one heteroatom (e.g. O, N, P, Si, and S), and wherein the nitrogen and sulfur atoms may optionally be oxidized, and the nitrogen heteroatom may optionally be quaternized. The heteroatom(s) (e.g. O, N, P, S, and Si) may be placed at any interior position of the heteroalkyl group or at the position at which the alkyl group is attached to the remainder of the molecule. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH 2, —S(O)—CH$_3$, —CH$_2$—CH$_2$—S(O)$_2$—CH$_3$, —CH=CHO—CH$_3$, —Si(CH$_3$)$_3$, —CH$_2$—CH=N—OCH$_3$, —CH=CH—N(CH$_3$)—CH$_3$, —CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, non-aromatic cyclic versions of "alkyl" and "heteroalkyl," respectively, wherein the carbons making up the ring or rings do not necessarily need to be bonded to a hydrogen due to all carbon valencies participating in bonds with non-hydrogen atoms. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, 3-hydroxy-cyclobut-3-enyl-1,2, dione, 1H-1,2,4-triazolyl-5(4H)-one, 4H-1,2,4-triazolyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. A heterocycloalkyl moiety may include one ring heteroatom (e.g., O, N, S, Si, or P). A heterocycloalkyl moiety may include two optionally different ring heteroatoms (e.g., O, N, S, Si, or P). A heterocycloalkyl moiety may include three optionally different ring heteroatoms (e.g., O, N, S, Si, or P). A heterocycloalkyl moiety may include four optionally different ring heteroatoms (e.g., O, N, S, Si, or P). A heterocycloalkyl moiety may include five optionally different ring heteroatoms (e.g., O, N, S, Si, or P). A heterocycloalkyl moiety may include up to 8 optionally different ring heteroatoms (e.g., O, N, S, Si, or P).

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. Non-limiting examples of aryl and heteroaryl groups include pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene. A heteroaryl moiety may include one ring heteroatom (e.g., O, N, or S). A heteroaryl moiety may include two optionally different ring heteroatoms (e.g., O, N, or S). A heteroaryl moiety may include three optionally different ring heteroatoms (e.g., O, N, or S). A heteroaryl moiety may include four optionally different ring heteroatoms (e.g., O, N, or S). A heteroaryl moiety may include five optionally different ring heteroatoms (e.g., O, N, or S). An aryl moiety may have a single ring. An aryl moiety may have two optionally different rings. An aryl moiety may have three optionally different rings. An aryl moiety may have four optionally different rings. A heteroaryl moiety may have one ring. A heteroaryl moiety may have two optionally different rings. A heteroaryl moiety may have three optionally different rings. A heteroaryl moiety may have four optionally different rings. A heteroaryl moiety may have five optionally different rings.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substitutents described herein.

The term "oxo," as used herein, means an oxygen that is double bonded to a carbon atom.

The term "alkylsulfonyl," as used herein, means a moiety having the formula —S($O_2$)—R', where R' is a substituted or unsubstituted alkyl group as defined above. R' may have a specified number of carbons (e.g., "$C_1$-$C_4$ alkylsulfonyl").

Each of the above terms (e.g., "alkyl", "heteroalkyl", "cycloalkyl", "heterocycloalkyl", "aryl", and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —$CO_2$R', —CONR'R", —OC(O)N R'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C=(O)NR"NR'"R"", —CN, —$NO_2$, in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the invention includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —$CO_2$R', —CONR'R", —OC (O)NR'R", —NR"C(O)R', —NR'—C(O)NR"R'", —NR"C(O)$_2$R', —NR—C(NR'R"R'")=NR"", —NR—C(NR' R")=NR'", —S(O)R', —S(O)$_2$R', —S(O)$_2$NR'R", —NRSO$_2$R', —NR'NR"R'", —ONR'R", —NR'C=(O)NR"NR'"R"", —CN, —$NO_2$, —R', —$N_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R'", and R"" groups when more than one of these groups is present.

A "substituent group," as used herein, means a group selected from the following moieties:
(A) oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, unsubstituted heteroaryl, and
(B) alkyl, heteroalkyl, cycloalkyl, heterocycloalkyl, aryl, heteroaryl, substituted with at least one substituent selected from:
(i) oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, unsubstituted heteroaryl, and
(ii) alkyl, heteroalkyl, cycloalkyl, heterocycloalkyl, aryl, heteroaryl, substituted with at least one substituent selected from:
(a) oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, unsubstituted heteroaryl, and
(b) alkyl, heteroalkyl, cycloalkyl, heterocycloalkyl, aryl, heteroaryl, substituted with at least one substituent selected from: oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, unsubstituted heteroaryl.

As used herein, the term "bioconjugate" or "bioconjugate linker" refers to the resulting association between atoms or molecules of bioconjugate reactive groups. The association can be direct or indirect. For example, a conjugate between a first bioconjugate reactive group (e.g. —$NH_2$, —COOH, —N-hydroxysuccinimide, or -maleimide) and a second bioconjugate reactive group (e.g., sulfhydryl, sulfur-containing amino acid, amine, amine sidechain containing amino acid, or carboxylate) provided herein can be direct, e.g., by covalent bond or linker (e.g. a first linker of second linker), or indirect, e.g., by non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). In embodiments, bioconjugates or bioconjugate linkers are formed using bioconjugate chemistry (i.e. the association of two bioconjugate reactive groups) including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the first bioconjugate reactive group (e.g., maleimide moiety) is covalently attached to the second bioconjugate reactive group (e.g. a sulfhydryl). In embodiments, the first bioconjugate reactive group (e.g., haloacetyl moiety) is covalently attached to the second bioconjugate reactive group (e.g. a sulfhydryl). In embodiments, the first bioconjugate reactive group (e.g., pyridyl moiety) is covalently attached to the second bioconjugate reactive group (e.g. a sulfhydryl). In embodiments, the first bioconjugate reactive group (e.g., —N-hydroxysuccinimide moiety) is covalently attached to the second bioconjugate reactive group (e.g. an amine). In embodiments, the first bioconjugate reactive group (e.g., maleimide moiety) is covalently attached to the second bioconjugate reactive group (e.g. a sulfhydryl). In embodiments, the first bioconjugate reactive group (e.g., -sulfo-N-hydroxysuccinimide moiety) is covalently attached to the second bioconjugate reactive group (e.g. an amine). The term "haloacetyl," as used herein, refers to a functional group having the formula:

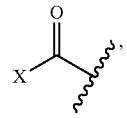

wherein X is a halogen.

A "detectable agent" or "detectable compound" is a composition detectable by appropriate means such as spectroscopic, photochemical, biochemical, immunochemical, chemical, magnetic resonance imaging, or other physical means. For example, useful detectable agents include $^{18}F$, $^{32}P$, $^{33}P$, $^{45}Ti$, $^{47}Sc$, $^{52}Fe$, $^{59}Fe$, $^{62}Cu$, $^{64}Cu$, $^{67}Cu$, $^{67}Ga$, $^{68}Ga$, $^{77}As$, $^{86}Y$, $^{90}Y$, $^{89}$r, $^{89}Zr$, $^{94}Tc$, $^{94}Tc$, $^{99m}Tc$, $^{99}Mo$, $^{105}Pd$, $^{105}Rh$, $^{111}Ag$, $^{111}In$, $^{123}I$, $^{124}I$, $^{125}I$, $^{131}I$, $^{142}Pr$, $^{143}Pr$, $^{149}Pm$, $^{153}Sm$, $^{154-1581}Gd$ $^{161}Tb$, $^{166}Dy$, $^{166}Ho$, $^{169}Er$, $^{175}Lu$, $^{177}Lu$, $^{186}Re$, $^{188}Re$, $^{189}Re$, $^{194}Ir$ $^{198}Au$, $^{199}Au$, $^{211}At$, $^{211}Pb$, $^{212}Bi$, $^{212}Pb$, $^{213}Bi$ $^{223}Ra$, $^{225}Ac$, Cr, V, Mn, Fe, Co, Ni, Cu, La, Ce, Pr, Nd, Pm, Sm, Eu, Gd, Tb, Dy, Ho, Er, Tm, Yb, Lu, 32P, fluorophore (e.g. fluorescent dyes), electron-dense reagents, enzymes (e.g., as commonly used in an ELISA), biotin, digoxigenin, paramagnetic molecules, paramagnetic nanoparticles, ultrasmall superparamagnetic iron oxide ("USPIO") nanoparticles, USPIO nanoparticle aggregates, superparamagnetic iron oxide ("SPIO") nanoparticles, SPIO nanoparticle aggregates, monochrystalline iron oxide nanoparticles, monochrystalline iron oxide, nanoparticle contrast agents, liposomes or other delivery vehicles containing Gadolinium chelate ("Gd-chelate") molecules, Gadolinium, radioisotopes, radionuclides (e.g. carbon-11, nitrogen-13, oxygen-15, fluorine-18, rubidium-82), fluorodeoxyglucose (e.g. fluorine-18 labeled), any gamma ray emitting radionuclides, positron-emitting radionuclide, radiolabeled glucose, radiolabeled water, radiolabeled ammonia, biocolloids, microbubbles (e.g. including microbubble shells including albumin, galactose, lipid, and/or polymers; microbubble gas core including air, heavy gas(es), perfluorcarbon, nitrogen, octafluoropropane, perflexane lipid microsphere, perflutren, etc.), iodinated contrast agents (e.g. iohexol, iodixanol, ioversol, iopamidol, ioxilan, iopromide, diatrizoate, metrizoate, ioxaglate), barium sulfate, thorium dioxide, gold, gold nanoparticles, gold nanoparticle aggregates, fluorophores, two-photon fluorophores, or haptens and proteins or other entities which can be made detectable, e.g., by incorporating a radiolabel into a peptide or antibody specifically reactive with a target peptide. A detectable moiety is a monovalent detectable agent or a detectable agent capable of forming a bond with another composition.

Radioactive substances (e.g., radioisotopes) that may be used as imaging and/or labeling agents in accordance with the embodiments of the disclosure include, but are not limited to, $^{18}$F, $^{32}$P, $^{33}$P, $^{45}$Ti, $^{47}$Sc, $^{52}$Fe, $^{59}$Fe, $^{62}$Cu, $^{64}$Cu, $^{67}$Cu, $^{67}$Ga, $^{68}$Ga, $^{77}$As, $^{86}$Y, $^{90}$Y.$^{89}$Sr, $^{89}$Zr, $^{94}$Tc, $^{94}$Tc, $^{99m}$Tc, $^{99}$Mo, $^{105}$Pd, $^{105}$Rh, $^{111}$Ag, $^{111}$In, $^{123}$I, $^{124}$I, $^{125}$I, $^{131}$I, $^{142}$Pr, $^{143}$Pr, $^{149}$Pm, $^{153}$Sm, $^{154\text{-}1581}$Gd, $^{161}$Tb, $^{166}$Dy, $^{166}$Ho, $^{169}$Er, $^{175}$Lu, $^{177}$Lu, $^{86}$Re, $^{188}$Re, $^{189}$Re, $^{194}$Ir, $^{198}$Au, $^{199}$Au, $^{211}$At, $^{211}$Pb, $^{212}$Bi, $^{212}$Pb, $^{213}$Bi, $^{223}$Ra and $^{225}$Ac. Paramagnetic ions that may be used as additional imaging agents in accordance with the embodiments of the disclosure include, but are not limited to, ions of transition and lanthanide metals (e.g. metals having atomic numbers of 21-29, 42, 43, 44, or 57-71). These metals include ions of Cr, V, Mn, Fe, Co, Ni, Cu, La, Ce, Pr, Nd, Pm, Sm, Eu, Gd, Tb, Dy, Ho, Er, Tm, Yb and Lu.

Useful bioconjugate reactive groups used for bioconjugate chemistries herein include, for example:
- (a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;
- (b) hydroxyl groups which can be converted to esters, ethers, aldehydes, etc.
- (c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;
- (d) dienophile groups which are capable of participating in Diels-Alder reactions such as, for example, maleimido or maleimide groups;
- (e) aldehyde or ketone groups such that subsequent derivatization is possible via formation of carbonyl derivatives such as, for example, imines, hydrazones, semicarbazones or oximes, or via such mechanisms as Grignard addition or alkyllithium addition;
- (f) sulfonyl halide groups for subsequent reaction with amines, for example, to form sulfonamides;
- (g) thiol groups, which can be converted to disulfides, reacted with acyl halides, or bonded to metals such as gold, or react with maleimides;
- (h) amine or sulfhydryl groups (e.g., present in cysteine), which can be, for example, acylated, alkylated or oxidized;
- (i) alkenes, which can undergo, for example, cycloadditions, acylation, Michael addition, etc;
- (j) epoxides, which can react with, for example, amines and hydroxyl compounds;
- (k) phosphoramidites and other standard functional groups useful in nucleic acid synthesis;
- (l) metal silicon oxide bonding; and
- (m) metal bonding to reactive phosphorus groups (e.g. phosphines) to form, for example, phosphate diester bonds.
- (n) azides coupled to alkynes using copper catalyzed cycloaddition click chemistry.
- (o) biotin conjugate can react with avidin or strepavidin to form a avidin-biotin complex or streptavidin-biotin complex.

The bioconjugate reactive groups can be chosen such that they do not participate in, or interfere with, the chemical stability of the conjugate described herein. Alternatively, a reactive functional group can be protected from participating in the crosslinking reaction by the presence of a protecting group. In embodiments, the bioconjugate comprises a molecular entity derived from the reaction of an unsaturated bond, such as a maleimide, and a sulfhydryl group.

Embodiment P 1

A nanoparticle obtainable by a process comprising:
- a. mixing an insoluble drug and an amphiphilic polymer in an organic solvent;
- b. removing said organic solvent, adding water, and sonicating the mixture to form a nanocrystal; and
- c. mixing tetraethyl orthosilicate (TEOS), phenyltrimethoxysilane (PTMS), and hydrolyzed aminopropyltriethoxy silane (APTES) with said nanocrystal to form a nanoparticle.

Embodiment P 2

The nanoparticle of embodiment P 1, further comprising isolating the nanoparticle following step (c).

Embodiment P 3

The nanoparticle of embodiment P 2, wherein the isolating of the nanoparticle comprises the use of a sucrose gradient solution.

Embodiment P 4

The nanoparticle of any one of embodiments P 1 to P 3, wherein the organic solvent comprises chloroform, dichloromethane, methanol, ethanol, tetrahydrofuran, or dioxane.

Embodiment P 5

The nanoparticle of any one of embodiments P 1 to P 3, wherein the organic solvent comprises chloroform.

Embodiment P 6

The nanoparticle of embodiment 1, wherein in step (b) the reaction is sonicating for at least a total of 25 total minutes.

Embodiment P 7

The nanoparticle of any one of embodiments P 1 to P 6, wherein the mass ratio of insoluble drug to amphiphilic polymer is about 1 to 1 to about 1 to 20.

Embodiment P 8

The nanoparticle of any one of embodiments P 1 to P 6, wherein the mass ratio of insoluble drug to amphiphilic polymer is about 1 to 1 to about 1 to 10.

Embodiment P 9

The nanoparticle of any one of embodiments P 1 to P 6, wherein the mass ratio of insoluble drug to amphiphilic polymer is about 1 to 1 to about 1 to 5.

Embodiment P 10

The nanoparticle of anyone of embodiments P1 to P 6, wherein the mass ratio of insoluble drug to amphiphilic polymer is about 1 to 1 or 1 to 5.

Embodiment P 11

The nanoparticle of any one of embodiments P 1 to P 6, wherein the mass ratio of insoluble drug to amphiphilic polymer is about 1 to 5.

Embodiment P 12

The nanoparticle of any one of embodiments P 1 to P 11, wherein the insoluble drug has a solubility of less than about 10 µg/mL in water.

Embodiment P 13

The nanoparticle of any one of embodiments P 1 to P 11, wherein the insoluble drug has a solubility of less than about 0.1 µg/mL in water.

Embodiment P 14

The nanoparticle of any one of embodiments P 1 to P 13, wherein the insoluble drug is a macrolide, steroid, or terpene.

Embodiment P 15

The nanoparticle of any one of embodiments P 1 to P 13, wherein the insoluble drug is a taxane.

Embodiment P 16

The nanoparticle of any one of embodiments P 1 to P 13, wherein the insoluble drug is paclitaxel.

Embodiment P 17

The nanoparticle of any one of embodiments P 1 to P 16, wherein the longest dimension of the nanoparticle is from about 10 nm to about 1000 nm.

Embodiment P 18

The nanoparticle of any one of embodiments P 1 to P 16, wherein the longest dimension of the nanoparticle is from about 60 nm to about 940 nm.

Embodiment P 19

The nanoparticle of any one of embodiments P 1 to P 16, wherein the longest dimension of the nanoparticle is from about 100 nm to about 500 nm.

Embodiment P 20

A method of making a nanoparticle comprising:
a. mixing a hydrophobic drug and an amphiphilic polymer in an organic solvent;
b. removing said organic solvent, adding water, and sonicating the mixture to form a nanocrystal; and
c. mixing tetraethyl orthosilicate (TEOS), phenyltrimethoxysilane (PTMS), and hydrolyzed aminopropyltriethoxy silane (APTES) with said nanocrystal to form a nanoparticle.

Embodiment P 21

The method of embodiment P 20, further comprising isolating the nanoparticle following step (c).

Embodiment P 22

The method of embodiment P 21, wherein the isolating of the nanoparticle comprises the use of a sucrose gradient solution.

Embodiment P 23

A cell comprising the nanoparticle of any one of embodiments P 1 to P 19.

Embodiment P 24

The cell of embodiment P 23, wherein the cell is a neural stem cell.

Embodiment P 25

A nanoparticle-cell construct comprising a monovalent nanoparticle of any one of embodiments P 1 to P 19, covalently attached to a protein through a covalent linker, said covalent linker having the formula:

$$\text{-L}^2\text{-X}^1\text{-L}^1\text{-X}^2\text{-L}^3\text{-;} \qquad \text{(Ia)}$$

or $$\text{-L}^2\text{-X}^2\text{-L}^3\text{-;} \qquad \text{(Ib)}$$

wherein,
$X^1$ and $X^2$ are independently a bioconjugate linker or a bond, wherein at least one of $X^1$ or $X^2$ is a bioconjugate linker;
$L^1$ is independently a polymeric linker;
$L^2$ is independently a bond, $-NR^{1a}-$, $-O-$, $-S-$, $-C(O)-$, $-C(O)O-$, $-S(O)-$, $-S(O)_2-$, $-NR^{1a}C(O)-$, $-C(O)NR^{1b}-$, $-C(O)(CH_2)_{z1}-$, $-NR^{1a}C(O)O-$, $-NR^{1a}C(O)NR^{1b}-$, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$L^3$ is independently a bond, $-NR^{2a}-$, $-O-$, $-S-$, $-C(O)-$, $-C(O)O-$, $-S(O)-$, $-S(O)_2-$, $-NR^{2a}C(O)-$, $-C(O)NR^{2b}-$, $-C(O)(CH_2)_{z2}-$, $-NR^{2a}C(O)O-$, $-NR^{2a}C(O)NR^{2b}-$, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$R^{1a}$, $R^{2a}$, $R^{1b}$, and $R^{2b}$ are independently hydrogen, halogen, $-CF_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)OH$, $-NHOH$, $-OCF_3$, $-OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and the symbols z1 and z2 are independently an integer from 1 to 10.

Embodiment P 26

The nanoparticle-cell construct of embodiment P 25, wherein the protein is a cell surface protein.

Embodiment P 27

The nanoparticle-cell construct of embodiment P 25 or P 26, wherein the protein comprises a sulfur-containing amino acid.

Embodiment P 28

The nanoparticle-cell construct of any one of embodiments P 25 to P 27, wherein $X^2$ has the formula:

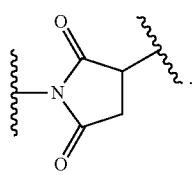 [SMILES: *C1CC(=O)N(*)C1=O]

Embodiment P 29

The nanoparticle-cell construct of any one of embodiments P 25 to P 27, wherein $X^2$ has the formula:

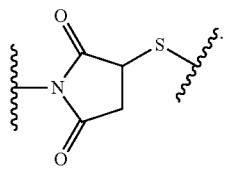 [SMILES: *SC1CC(=O)N(*)C1=O]

Embodiment P 30

The nanoparticle-cell construct of any one of embodiments P 25 to P 29, wherein $L^1$ is a branched polymeric linker.

Embodiment P 31

The nanoparticle-cell construct of any one of embodiments P 25 to P 29, wherein $L^1$ is polyethylene glycol with an average molecular weight of 400 g/mol, 484 g/mol, 1000 g/mol, 1450 g/mol, 1500 g/mol, 2000 g/mol, or 5000 g/mol.

Embodiment P 32

The nanoparticle-cell construct of any one of embodiments P 25 to P 29, wherein $L^1$ is polyethylene glycol with an average molecular weight of 2000 g/mol.

Embodiment P 33

The nanoparticle-cell construct of any one of embodiments P 25 to P 32, wherein said nanoparticle is further covalently attached to one or more nanoparticle substituents.

Embodiment P 34

The nanoparticle-cell construct of embodiment P 33, wherein said nanoparticle substituent is:

$$-L^2-X^1-R^3; \quad (i)$$

$$-L^2-X^1-L-X^3; \quad (ii) \text{ or}$$

$$-L^2-X^3; \quad (iii)$$

wherein
$R^3$ is a polymeric moiety; and
$X^3$ is a bioconjugate reactive group.

Embodiment P 35

The nanoparticle-cell construct of embodiment P 34, wherein $R^3$ is a polyethylene glycol moiety.

Embodiment P 36

The nanoparticle-cell construct of embodiments P 34 or P 35, wherein the bioconjugate reactive group is $-NH_2$, $-COOH$,

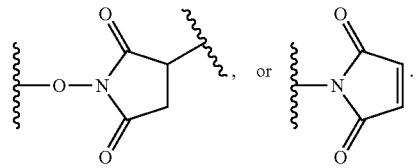 [SMILES: *ON1C(=O)CC(*)C1=O ; *N1C(=O)C=CC1=O]

Embodiment P 37

The nanoparticle-cell construct of any one of embodiments P 34 to P 36, comprising a plurality of nanoparticle substituents of the formula (i) and a plurality of nanoparticle substituents of the formula (ii) in a ratio of from about 50:50 to about 80:20.

Embodiment P 38

The nanoparticle-cell construct of anyone of embodiments P 34 to P 36, comprising a plurality of nanoparticle substituents of the formula (ii) and a plurality of nanoparticle substituents of the formula (iii) in a ratio of from about 50:50 to about 80:20.

Embodiment P 39

The nanoparticle-cell construct of anyone of embodiments P 34 to P 36, comprising a plurality of nanoparticle substituents of the formula (i) and a plurality of nanoparticle substituents of the formula (iii) in a ratio of from about 50:50 to about 80:20.

Embodiment P 40

A pharmaceutical composition comprising a pharmaceutically acceptable excipient and the nanoparticle of any one of embodiments P 1 to P 19, the cell of one of embodiments P 23 or P 24, or the nanoparticle-cell construct of any one of embodiments P 25 to P 39.

Embodiment P 41

A method of treating cancer in a subject in need of such treatment, said method comprising administering to the subject a therapeutically effective amount of the nanoparticle of any one of embodiments P 1 to P 19, the cell of one of embodiments P 23 or P 24, the pharmaceutical composition of embodiment P 40, or the nanoparticle-cell construct of any one of embodiments P 25 to P 39.

Embodiment P 42

The method of embodiment P 41, wherein the cancer is ovarian cancer, bladder cancer, head and neck cancer, brain cancer, breast cancer, lung cancer, cervical cancer, liver cancer, colorectal cancer, pancreatic cancer, glioblastoma, neuroblastoma, rhabdomyosarcoma, osteosarcoma, renal cancer, renal cell carcinoma, non-small cell lung cancer, uterine cancer, testicular cancer, anal cancer, bile duct cancer, biliary tract cancer, gastrointestinal carcinoid tumors, esophageal cancer, gall bladder cancer, appendix cancer, small intestine cancer, stomach (gastric) cancer, urinary bladder cancer, genitourinary tract cancer, endometrial cancer, nasopharyngeal cancer, head and neck squamous cell carcinoma, or prostate cancer.

Embodiment P 43

The method of embodiment P 41, wherein the cancer is ovarian cancer.

Further Embodiments

Embodiment 1

A nanoparticle obtainable by a process comprising:
a. mixing an insoluble drug and an amphiphilic polymer in an organic solvent;
b. removing said organic solvent, adding water, and sonicating the mixture to form a nanocrystal; and
c. mixing tetraethyl orthosilicate (TEOS), phenyltrimethoxysilane (PTMS), and hydrolyzed aminopropyltriethoxy silane (APTES) with said nanocrystal to form a nanoparticle.

Embodiment 2

The nanoparticle of embodiment 1, further comprising isolating the nanoparticle following step (c).

Embodiment 3

The nanoparticle of embodiment 2, wherein the isolating of the nanoparticle comprises the use of a sucrose gradient solution.

Embodiment 4

The nanoparticle of any one of embodiments 1 to 3, wherein the organic solvent comprises chloroform, dichloromethane, methanol, ethanol, tetrahydrofuran, or dioxane.

Embodiment 5

The nanoparticle of any one of embodiments 1 to 3, wherein the organic solvent comprises chloroform.

Embodiment 6

The nanoparticle of embodiments 1 to 5, wherein the sonicating in step (b) is for at least a total of 25 total minutes.

Embodiment 7

The nanoparticle of any one of embodiments 1 to 6, wherein the mass ratio of insoluble drug to amphiphilic polymer is about 1 to 1 to about 1 to 20.

Embodiment 8

The nanoparticle of any one of embodiments 1 to 6, wherein the mass ratio of insoluble drug to amphiphilic polymer is about 1 to 1 to about 1 to 10.

Embodiment 9

The nanoparticle of any one of embodiments 1 to 6, wherein the mass ratio of insoluble drug to amphiphilic polymer is about 1 to 1 to about 1 to 5.

Embodiment 10

The nanoparticle of any one of embodiments 1 to 6, wherein the mass ratio of insoluble drug to amphiphilic polymer is about 1 to 1 or 1 to 5.

Embodiment 11

The nanoparticle of any one of embodiments 1 to 6, wherein the mass ratio of insoluble drug to amphiphilic polymer is about 1 to 5.

Embodiment 12

The nanoparticle of any one of embodiments 1 to 11, wherein the insoluble drug has a solubility of less than about 10 μg/mL in water.

Embodiment 13

The nanoparticle of any one of embodiments 1 to 11, wherein the insoluble drug has a solubility of less than about 0.1 µg/mL in water.

Embodiment 14

The nanoparticle of any one of embodiments 1 to 13, wherein the insoluble drug is a macrolide, steroid, or terpene.

Embodiment 15

The nanoparticle of any one of embodiments 1 to 13, wherein the insoluble drug is a taxane.

Embodiment 16

The nanoparticle of any one of embodiments 1 to 13, wherein the insoluble drug is paclitaxel.

Embodiment 17

The nanoparticle of any one of embodiments 1 to 16, wherein the longest dimension of the nanoparticle is from about 10 nm to about 1000 nm.

Embodiment 18

The nanoparticle of any one of embodiments 1 to 16, wherein the longest dimension of the nanoparticle is from about 60 nm to about 940 nm.

Embodiment 19

The nanoparticle of any one of embodiments 1 to 16, wherein the longest dimension of the nanoparticle is from about 100 nm to about 500 nm.

Embodiment 20

A method of making a nanoparticle comprising:
a. mixing a hydrophobic drug and an amphiphilic polymer in an organic solvent;
b. removing said organic solvent, adding water, and sonicating the mixture to form a nanocrystal; and
c. mixing tetraethyl orthosilicate (TEOS), phenyltrimethoxysilane (PTMS), and hydrolyzed aminopropyltriethoxy silane (APTES) with said nanocrystal to form a nanoparticle.

Embodiment 21

The method of embodiment 20, further comprising isolating the nanoparticle following step (c).

Embodiment 22

The method of embodiment 21, wherein the isolating of the nanoparticle comprises the use of a sucrose gradient solution.

Embodiment 23

A cell comprising the nanoparticle of any one of embodiments 1 to 19.

Embodiment 24

The cell of embodiment 23, wherein the cell is a neural stem cell.

Embodiment 25

A nanoparticle-cell construct comprising a monovalent nanoparticle of any one of embodiments 1 to 19, covalently attached to a protein through a covalent linker, said covalent linker having the formula:

$$-L^2-X^1-L^1-X^2-L^3-; \qquad \text{(Ia)}$$

or $$-L^2-X^2-L^3-; \qquad \text{(Ib)}$$

wherein, $X^1$ and $X^2$ are independently a bioconjugate linker or a bond, wherein at least one of $X^1$ or $X^2$ is a bioconjugate linker;

$L^1$ is independently a polymeric linker;

$L^2$ is independently a bond, $-NR^{1a}-$, $-O-$, $-S-$, $-C(O)-$, $-C(O)O-$, $-S(O)-$, $-S(O)_2-$, $-NR^{1a}C(O)-$, $-C(O)NR^{1b}-$, $-C(O)(CH_2)_{z1}-$, $-NR^{1a}C(O)O-$, $-NR^{1a}C(O)NR^{1b}-$, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$L^3$ is independently a bond, $-NR^{2a}-$, $-O-$, $-S-$, $-C(O)-$, $-C(O)O-$, $-S(O)-$, $-S(O)_2-$, $-NR^{2a}C(O)-$, $-C(O)NR^{2b}-$, $-C(O)(CH_2)_{z2}-$, $-NR^{2a}C(O)O-$, $-NR^{2a}C(O)NR^{2b}-$, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$R^{1a}$, $R^{2a}$, $R^{1b}$, and $R^{2b}$ are independently hydrogen, halogen, $-CF_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)OH$, $-NHOH$, $-OCF_3$, $-OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and the symbols z1 and z2 are independently an integer from 1 to 10.

Embodiment 26

The nanoparticle-cell construct of embodiment 25, wherein the protein is a cell surface protein.

Embodiment 27

The nanoparticle-cell construct of embodiment 25 or 26, wherein the protein comprises a sulfur-containing amino acid.

Embodiment 28

The nanoparticle-cell construct of any one of embodiments 25 to 27, wherein $X^2$ has the formula:

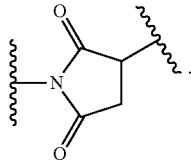 [SMILES: *C1CC(=O)N(*)C1=O]

Embodiment 29

The nanoparticle-cell construct of any one of embodiments 25 to 27, wherein $X^2$ has the formula:

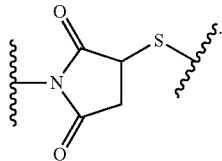 [SMILES: *SC1CC(=O)N(*)C1=O]

Embodiment 30

The nanoparticle-cell construct of any one of embodiments 25 to 29, wherein $L^1$ is a branched polymeric linker.

Embodiment 31

The nanoparticle-cell construct of any one of embodiments 25 to 29, wherein $L^1$ is polyethylene glycol with an average molecular weight of 400 g/mol, 484 g/mol, 1000 g/mol, 1450 g/mol, 1500 g/mol, 2000 g/mol, or 5000 g/mol.

Embodiment 32

The nanoparticle-cell construct of any one of embodiments 25 to 29, wherein $L^1$ is polyethylene glycol with an average molecular weight of 2000 g/mol.

Embodiment 33

The nanoparticle-cell construct of any one of embodiments 25 to 32, wherein said nanoparticle is further covalently attached to one or more nanoparticle substituents.

Embodiment 34

The nanoparticle-cell construct of embodiment 33, wherein said nanoparticle substituent is independently:

-$L^2$-$X^1$—$R^3$;                  (i)

-$L^2$-$X^1$-$L^1$-$X^3$;            (ii) or

-$L^2$-$X^3$;                        (iii)

wherein
$R^3$ is a polymeric moiety; and
$X^3$ is a bioconjugate reactive group.

Embodiment 35

The nanoparticle-cell construct of embodiment 34, wherein $R^3$ is a polyethylene glycol moiety.

Embodiment 36

The nanoparticle-cell construct of embodiments 34 or 35, wherein the bioconjugate reactive group is —$NH_2$, —COOH,

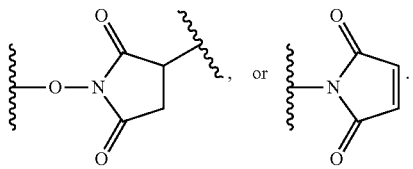 [SMILES: *ON1C(=O)CC(*)C1=O ; *N1C(=O)C=CC1=O]

Embodiment 37

The nanoparticle-cell construct of any one of embodiments 34 to 36, comprising a plurality of nanoparticle substituents of the formula (i) and a plurality of nanoparticle substituents of the formula (ii) in a ratio of from about 50:50 to about 80:20.

Embodiment 38

The nanoparticle-cell construct of any one of embodiments 34 to 36, comprising a plurality of nanoparticle substituents of the formula (ii) and a plurality of nanoparticle substituents of the formula (iii) in a ratio of from about 50:50 to about 80:20.

Embodiment 39

The nanoparticle-cell construct of any one of embodiments 34 to 36, comprising a plurality of nanoparticle substituents of the formula (i) and a plurality of nanoparticle substituents of the formula (iii) in a ratio of from about 50:50 to about 80:20.

Embodiment 40

A pharmaceutical composition comprising a pharmaceutically acceptable excipient and the nanoparticle of any one of embodiments 1 to 19, the cell of one of embodiments 23 or 24, or the nanoparticle-cell construct of any one of embodiments 25 to 39.

Embodiment 41

A method of treating cancer in a subject in need of such treatment, said method comprising administering to the subject a therapeutically effective amount of the nanoparticle of any one of embodiments 1 to 19, the cell of one of embodiments 23 or 24, the pharmaceutical composition of embodiment 40, or the nanoparticle-cell construct of any one of embodiments 25 to 39.

Embodiment 42

The method of embodiment 41, wherein the cancer is ovarian cancer, bladder cancer, head and neck cancer, brain cancer, breast cancer, lung cancer, cervical cancer, liver cancer, colorectal cancer, pancreatic cancer, glioblastoma, neuroblastoma, rhabdomyosarcoma, osteosarcoma, renal cancer, renal cell carcinoma, non-small cell lung cancer, uterine cancer, testicular cancer, anal cancer, bile duct cancer, biliary tract cancer, gastrointestinal carcinoid tumors, esophageal cancer, gall bladder cancer, appendix cancer, small intestine cancer, stomach (gastric) cancer, urinary bladder cancer, genitourinary tract cancer, endometrial cancer, nasopharyngeal cancer, head and neck squamous cell carcinoma, or prostate cancer.

Embodiment 43

The method of embodiment 41, wherein the cancer is ovarian cancer.

Embodiment 44

A nanoparticle comprising an insoluble drug nanocrystal, wherein said insoluble drug nanocrystal is enclosed within a silica layer.

Embodiment 45

The nanoparticle of embodiment 44, wherein said insoluble drug nanocrystal is a macrolide nanocrystal, steroid nanocrystal, or terpene nanocrystal.

Embodiment 46

The nanoparticle of embodiment 44, wherein said insoluble drug nanocrystal is a taxane nanocrystal.

Embodiment 47

The nanoparticle of embodiment 44, wherein said insoluble drug nanocrystal is a paclitaxel nanocrystal.

Embodiment 48

The nanoparticle of any one of embodiments 44 to 47, wherein said silica layer is from about 1 nm to about 100 nm thick.

Embodiment 49

The nanoparticle of any one of embodiments 44 to 47, wherein said silica layer is from about 20 nm to about 60 nm thick.

Embodiment 50

The nanoparticle of any one of embodiments 44 to 47, wherein said silica layer is from about 20 nm to about 40 nm thick.

Embodiment 51

The nanoparticle of any one of embodiments 44 to 50, wherein said nanoparticle has a length less than or equal to 1000 microns.

Embodiment 52

The nanoparticle of any one of embodiments 44 to 51, wherein said nanoparticle has a length from about 100 nm to about 600 nm.

Embodiment 53

The nanoparticle of any one of embodiments 44 to 52, wherein said nanoparticle has a length from about 250 nm to about 450 nm.

Embodiment 54

The nanoparticle of any one of embodiments 44-53, wherein said nanoparticle has a width from about 40 nm to about 100 nm.

Embodiment 55

The nanoparticle of any one of embodiments 44 to 54, wherein said nanoparticle has a width from about 50 nm to about 90 nm.

Embodiment 56

The nanoparticle of any one of embodiments 44 to 55, wherein said nanoparticle has a zeta potential from about 10 mV to about 60 mV.

Embodiment 57

The nanoparticle of any one of embodiments 44 to 56, wherein said nanoparticle has a zeta potential from about 10 mV to about 45 mV.

Embodiment 58

The nanoparticle of any one of embodiments 44 to 57, wherein said nanoparticle comprises at least 5 wt % of said insoluble drug nanocrystal.

Embodiment 59

The nanoparticle of any one of embodiments 44 to 58, wherein said nanoparticle comprises at least 10 wt % of said insoluble drug nanocrystal.

Embodiment 60

A cell comprising the nanoparticle of any one of embodiments 44 to 59.

Embodiment 61

The cell of embodiment 60, wherein the cell is a neural stem cell.

What is claimed is:
1. A nanoparticle obtainable by a process comprising:
a. mixing an insoluble drug and an amphiphilic polymer in an organic solvent;
b. removing said organic solvent, adding water, and sonicating the mixture to form a nanocrystal; and
c. mixing tetraethyl orthosilicate (TEOS), phenyltrimethoxysilane (PTMS), and hydrolyzed aminopropyltriethoxy silane (APTES) with said nanocrystal to form a nanoparticle.
2. The nanoparticle of claim 1, wherein the mass ratio of insoluble drug to amphiphilic polymer is from about 1 to 1 to about 1 to 20.
3. The nanoparticle of claim 1, wherein the insoluble drug has a solubility of less than about 10 µg/mL in water.

4. The nanoparticle of claim 1, wherein the insoluble drug is a macrolide, steroid, or terpene.

5. The nanoparticle of claim 1, wherein the insoluble drug is a taxane.

6. The nanoparticle of claim 1, wherein the insoluble drug is paclitaxel.

7. The nanoparticle of claim 1, wherein the longest dimension of the nanoparticle is from about 10 nm to about 1000 nm.

8. A cell comprising the nanoparticle of claim 1.

9. A nanoparticle-cell construct comprising a monovalent nanoparticle of claim 1, covalently attached to a protein through a covalent linker, said covalent linker having the formula:

$$-L^2-X^1-L^1-X^2-L^3-; \quad \text{(Ia) or}$$

$$-L^2-X^2-L^3-; \quad \text{(b)}$$

wherein, $X^1$ and $X^2$ are independently a bioconjugate linker or a bond, wherein at least one of $X^1$ or $X^2$ is a bioconjugate linker;

$L^1$ is independently a polymeric linker;

$L^2$ is independently a bond, —NR$^{1a}$—, —O—, —S—, —C(O)—, —C(O)O—, —S(O)—, —S(O)$_2$—, —NR$^{1a}$C(O)—, —C(O)NR$^{1b}$—, —C(O)(CH$_2$)$_{z1}$—, —NR$^{1a}$C(O)O—, —NR$^{1a}$C(O)NR$^{1b}$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$L^3$ is independently a bond, —NR$^{2a}$—, —O—, —S—, —C(O)—, —C(O)O—, —S(O)—, —S(O)$_2$—, —NR$^{2a}$C(O)—, —C(O)NR$^{2b}$—, —C(O)(CH$_2$)$_{z2}$—, —NR$^{2a}$C(O)O—, —NR$^{2a}$C(O)NR$^{2b}$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$R^{1a}$, $R^{2a}$, $R^{1b}$, and $R^{2b}$ are independently hydrogen, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —OCF$_3$, —OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and the symbols z1 and z2 are independently an integer from 1 to 10.

10. The nanoparticle-cell construct of claim 9, wherein the protein is a cell surface protein.

11. The nanoparticle-cell construct of claim 9, wherein said nanoparticle is further covalently attached to one or more nanoparticle substituents.

12. The nanoparticle-cell construct of claim 9, wherein said nanoparticle substituent further covalently attached is independently:

$$-L^2-X^1-R^3; \quad \text{(i)}$$

$$-L^2-X^1-L^1-X^3; \quad \text{(ii) or}$$

$$-L^2-X^3; \quad \text{(iii)}$$

wherein $R^3$ is a polymeric moiety; and $X^3$ is a bioconjugate reactive group.

13. A pharmaceutical composition comprising a pharmaceutically acceptable excipient and the nanoparticle of claim 1.

14. A nanoparticle comprising an insoluble drug nanocrystal, wherein said insoluble drug nanocrystal is enclosed within a silica layer and wherein said insoluble drug nanocrystal is a macrolide nanocrystal, steroid nanocrystal, or terpene nanocrystal, and wherein the nanoparticle is not mesoporous.

15. The nanoparticle of claim 14, wherein said insoluble drug nanocrystal is a taxane nanocrystal.

16. The nanoparticle of claim 14, wherein said insoluble drug nanocrystal is a paclitaxel nanocrystal.

17. A cell comprising the nanoparticle of claim 14.

18. The nanoparticle of claim 14, wherein the silica layer is from about 1 nm to about 100 nm thick.

* * * * *

UNITED STATES PATENT AND TRADEMARK OFFICE
CERTIFICATE OF CORRECTION

PATENT NO. : 11,191,745 B2
APPLICATION NO. : 16/483212
DATED : December 7, 2021
INVENTOR(S) : Pamela Tiet and Jacob Berlin Page 1 of 1

It is certified that error appears in the above-identified patent and that said Letters Patent is hereby corrected as shown below:

In the Specification

At Column 1, Line 19, delete "grant R01 CA97359" and insert the following -- R01 CA197359 --

Signed and Sealed this
Second Day of September, 2025

Coke Morgan Stewart
*Acting Director of the United States Patent and Trademark Office*